(12) United States Patent
Genieser

(10) Patent No.: US 9,487,553 B2
(45) Date of Patent: Nov. 8, 2016

(54) BORANOPHOSPHATE ANALOGUES OF CYCLIC NUCLEOTIDES

(75) Inventor: Hans-Gottfried Genieser, Lemwerder (DE)

(73) Assignee: BIOLOG LIFE SCIENCE INSTITUTE FORSCHUNGSLABOR UND BIOCHEMICA-VERTRIEB GMBH, Bremen (DE)

( * ) Notice: Subject to any disclaimer, the term of this patent is extended or adjusted under 35 U.S.C. 154(b) by 189 days.

(21) Appl. No.: 14/008,337

(22) PCT Filed: Mar. 27, 2012

(86) PCT No.: PCT/EP2012/055389
§ 371 (c)(1),
(2), (4) Date: Dec. 5, 2013

(87) PCT Pub. No.: WO2012/130829
PCT Pub. Date: Oct. 4, 2012

(65) Prior Publication Data
US 2014/0088033 A1    Mar. 27, 2014

(30) Foreign Application Priority Data
Mar. 29, 2011 (EP) .................................. 11160317

(51) Int. Cl.
  *C07H 23/00*  (2006.01)
  *C07F 9/6574*  (2006.01)
  *G01N 33/50*  (2006.01)
  *C12Q 1/48*  (2006.01)

(52) U.S. Cl.
  CPC ........... *C07H 23/00* (2013.01); *C07F 9/65744* (2013.01); *C12Q 1/485* (2013.01); *G01N 33/502* (2013.01)

(58) Field of Classification Search
None
See application file for complete search history.

(56) References Cited

PUBLICATIONS

Li et al., Chemical Communications, 2002, 2890-2891.*
Jinlai Lin et al:"Novel 3',5'-Cyclic Nucleotide Analogue: Adenosine 3',5'-Cyclic Boranomonophosphate", Organic Letters, vol. 3, No. 6, 2001, pp. 795-797, XP055001165, ISSN: 1523-7060, DOI: 10.1021/ol0003230 cited in the application compound 4c p. 797, col. 2, last paragraph.
Ping Li et al: "Synthesis of nucleoside 3',5'-cyclic boranophosphorothioate, a new type of cyclic nucleotide.", Chemical Communications, vol. No. 23, 2002, pp. 2890-2891, XP055001178, ISSN: 1359-7345, DOI:10.1039/b207350a * Scheme 2 * compounds 13a,b p. 2890, col. 1, paragraph 1.
International Search Report and Written Opinion under Rule 43 PCT attached to the Search Report, International Application No. PCT/EP/2012/055389.

* cited by examiner

*Primary Examiner* — Traviss C McIntosh, III
(74) *Attorney, Agent, or Firm* — Polsinelli PC

(57) ABSTRACT

The present invention relates to novel boranophosphate analogues of cyclic nucleotides. The invention further relates to the use of such compounds as reagents for signal transduction research or as modulators of cyclic nucleotide-regulated binding proteins and isoenzymes thereof, and/or as hydrolysis- and oxidation-resistant ligands for affinity chromatography, for antibody production or for diagnostic applications e.g. on chip surfaces and/or as additive for organ transplantation storage solutions.

18 Claims, 15 Drawing Sheets

A

B

C

BORANOPHOSPHATE ANALOGUES OF CYCLIC NUCLEOTIDES

CROSS-REFERENCE TO RELATED APPLICATIONS

This application is a national stage application (under 35 U.S.C. §371) of International Application No. PCT/EP2012/055389, filed Mar. 27, 2012, which claims benefit of European Application No. 111603317.1, filed Mar. 29, 2011, the entire contents of which are hereby incorporated by reference.

The present invention relates to novel boranophosphate analogues of cyclic nucleotides. The invention further relates to the use of such compounds as reagents for signal transduction research or as modulators of cyclic nucleotide-regulated binding proteins and isoenzymes thereof, and/or as hydrolysis- and oxidation-resistant ligands for affinity chromatography, for antibody production or for diagnostic applications e.g. on chip surfaces and/or as additive for organ transplantation storage solutions.

In addition to that the present invention relates to boranophosphate analogues of cyclic nucleotides as a medicament especially in the prophylaxis or the treatment of cyclic nucleotide-related diseases and a pharmaceutical composition, comprising a boranophosphate analogue of a cyclic nucleotide. Cyclic nucleotide analogues are well accepted tools, widely used in biochemistry research for modulation of second messenger signaling cascades in a broad variety of cellular systems.

In contrast to the natural signaling molecules, cyclic adenosine-3',5'-monophosphate (cyclic AMP, cAMP) and cyclic guanosine-3',5'-monophosphate (cyclic GMP, cGMP), their chemically modified analogues often show considerably higher lipophilicity resulting in improved diffusion into cells. Also, such structures can have improved or altered selectivity for the corresponding binding proteins and sometimes possess increased or even complete stability towards phosphodiesterases (J. P. Miller in H. Cramer & I. Schultz (Eds.) "Cyclic 3',5' Nucleotides; Mechanisms of Action", John Wiley and Sons, London; Vol. 5, 77-105 (1978)).

Since the cyclic phosphate group with its negative charge is the main essential motif, to be recognised by the quite conserved phosphate binding cassettes of typical cyclic nucleotide binding proteins, especially the nucleobase part of cyclic nucleotides can be widely modified without dramatic losses in biological activity.

Of course, however, such analogues influence specificity, e.g. between protein kinase A and G or the EPAC protein. Meanwhile nearly 2,000 different analogues of cyclic AMP, cyclic GMP and of the corresponding pyrimidine congeners cCMP, cUMP and cTMP have been described, and most of them are biologically active at at least one of the still increasing number of corresponding binding proteins. Nowadays, more than 130 cyclic nucleotide analogues are commercially available from Biolog LSI, Bremen, and have become important biochemical tools for signal transduction research.

Especially, the diastereoisomers of phosphorothioate-modified structures (J. P. Miller in H. Cramer & I. Schultz (Eds.) "Cyclic 3',5' Nucleotides; Mechanisms of Action", John Wiley and Sons, London; Vol. 5, 77-105 (1978)) with exocyclic axial and equatorial sulfur substitution at phosphorus have become extremely useful since both isomers often show opposed biological effects with their protein binding partners and possess higher lipophilicity.

Thus, whereas the Sp-isomer of cyclic adenosine-3',5'-monophosphorothioate (Sp-cAMPS) can mimic the natural messenger molecule at most cAMP binding sites, the corresponding structure with Rp-configuration (Rp-cAMPS) can have inhibitory potential, e.g. at protein kinase A. Other binding partners such as the Exchange Protein Directly Activated by Cyclic AMP (EPAC) (Rehmann et al., *J. Biol. Chem.*, 278, 38548-38556 (2003)) are activated by Sp-cAMPS, whereas Rp-cAMPS is more or less inactive here.

Other examples are the CAP protein (Scholübbers et al., *Eur. J. Biochem.*, 138, 101-109 (1984)), where Rp-cAMPS is a good activator while Sp-cAMPS has considerably reduced agonistic potential, and cyclic nucleotide gated ion channels (R. H. Kramer and G. R. Tibbs, *J. Neurosci.*, 16, 1285-1293 (1996)) with again different modulation potential.

With respect to degradation the phosphorothioate modification leads to reduced enzymatic hydrolysis (Sp-cAMPS) by phosphodiesterases (PDE) and can even result in total stability (Rp-cAMPS), depending on the PDE isozymes present.

Unfortunately, under oxidizing conditions, all phosphorothioates, regardless of Rp/Sp-configuration, tend to exchange sulfur against oxygen, resulting in a normal cyclic phosphate group that is still biologically active, but has lost all favourable properties such as increased lipophilicity and PDE-stability. Moreover, if equatorially (Rp-) modified cyclic phosphorothioates, which are often used to block protein kinase A-mediated signaling processes, are oxidized, the resulting agonistic cyclic phosphate inevitably disturbs any corresponding signal transduction studies and could produce un-interpretable or even false data. Another potential reaction under oxidising conditions is the dimerisation of phosphorothioates by forming disulfide bonds, which would result in total biological inactivation of such structures.

Oxidizing conditions can be formed by corresponding chemicals, e.g. peroxides or ozone etc., and by all kinds of energy rich radiation (e.g. bright sun light, UV, radioactivity) or electric discharge that results in ozone or active oxygen formation. In addition, oxidizing processes usually take place within cellular biosystems as well, where e.g. hydrogen peroxide or peroxynitrite are natural components to perform important biological tasks.

For medical purposes and for research purposes there is a growing need of further analogues of cyclic nucleotides having interesting characteristics. Since in biologically active systems as well as under research conditions there is very often the risk of oxidizing conditions, one interesting characteristic is an improved stability against oxidation. A problem in this regard is that biological systems are very complex so that specific characteristics of such new analogues cannot be predicted.

Therefore it has been an object of the present invention to provide cyclic nucleotide analogues that are improved regarding the oxidation stability compared to cyclic nucleotide analogues so far used e.g. for signal transduction research purposes in the field of medicine. Such novel cyclic nucleotide analogues preferably should show a good lipophilicity, especially preferably a comparable or better lipophilicity compared to that of sulfur modified cyclic nucleotide analogues. Preferably novel cyclic nucleotide analogues should have an improved PDE-stability (e.g. compared to the analogous sulfur modified compounds). Also, of course, such compounds preferably should be still biologically active and able to modulate typical cyclic nucleotide receptor proteins such as protein kinases, directly gated ion channels, GAF-domains of phosphodiesterases, the EPAC proteins, CAP proteins and/or other more specialized receptors, such as the chemoreceptor in the slime mould *Dictyostelium discoideum*.

Ideally, both, agonistic and antagonistic properties should be available, again comparable to the Rp- and Sp-phosphorothioate diastereomers.

This object is achieved by a compound having the structural formula (I) or (II)

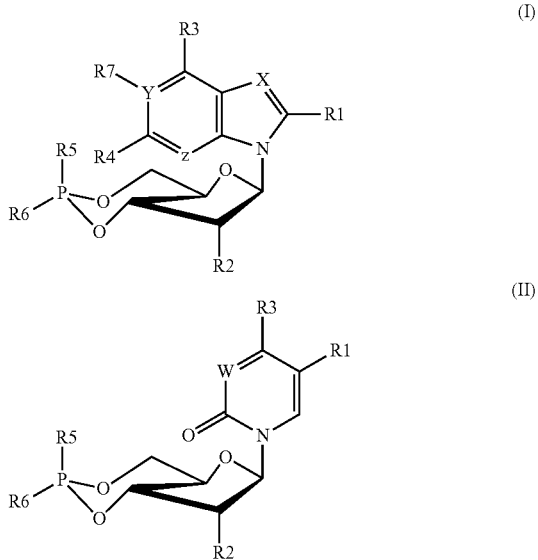

wherein:
W, X, Z can be independently from each other N or CH;
Y can be N or C
R1 can be independently H, halogen, azido, cyano, acyl, aracyl, nitro, alkyl, aryl, aralkyl, am ido-alkyl, am ido-aryl, am ido-aralkyl, NH-carbamoyl-alkyl, NH-carbamoyl-aryl, NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR8R9, SiR10R11R12 wherein R8, R9, R10, R11, R12 independently from each other can be H, alkyl, aryl, aralkyl;
R2 can be independently H, halogen, azido, acyl, aracyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR13R14, O—SiR15R16R17, wherein R13, R14, R15, R16, R17, independently from each other can be H, alkyl, aryl, aralkyl;
R3 can be independently H, halogen, azido, cyano, acyl, aracyl, nitro, alkyl, aryl, aralkyl, am ido-alkyl, am ido-aryl, am ido-aralkyl, NH-carbamoyl-alkyl, NH-carbamoyl-aryl, NH-carbamoyl-aralky, aralkyl-carbamoyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR18R19, SiR20R21R22, NH-carbamoylR23R24 wherein R18, R19, R20, R21, R22, R23, R24 independently from each other can be H, alkyl, aryl, aralkyl;
R4 can be independently H, halogen, azido, cyano, acyl, aracyl, nitro, alkyl, aryl, aralkyl, am ido-alkyl, am ido-aryl, am ido-aralkyl, NH-carbamoyl-alkyl, NH-carbamoyl-aryl, NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR25R26, SiR27R28R29 wherein R25, R26, R27, R28, R29 independently from each other can be H, alkyl, aryl, aralkyl;
R7 can be independently H, halogen (preferably chloro), amino, alkyl, nitro, N-oxide or absent, or can form together with R3, Y and the C bridging Y and R3 an imidazole ring which can be unsubstituted or substituted with alkyl, aryl or aralkyl or, can form together with R4 an imidazole ring which can be unsubstituted or substituted with alkyl, aryl or aralkyl;
and wherein
R5 is a borano ($BH_3$), methylborano, dimethylborano or cyanoborano ($BH_2CN$) group
and
R6 is H, azido, acyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, SH, S-alkyl, S-aryl, S-aralkyl, SeH, Se-alkyl, Se-aryl, Se-aralkyl, NR30R31, wherein R30, R31 independently from each other can be H, alkyl, aryl, aralkyl;
or
R5 is H, azido, acyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, SH, S-alkyl, S-aryl, S-aralkyl, SeH, Se-alkyl, Se-aryl, Se-aralkyl, NR32R33, wherein R32, R33 independently from each other can be H, alkyl, aryl, aralkyl;
and
R6 is a borano ($BH_3$), methylborano, dimethylborano or cyanoborano ($BH_2CN$) group
and salts, and/or hydrates thereof,
wherein the compound of formula (I) or (II) can optionally be isotopically or radioactively labeled, be labeled with a dye or be immobilized,
with the proviso that the compound of formula (I) or (II) is not
$N^6$-benzoyl-2'-tert.-butyldimethylsilyladenosine-3',5'-cyclic boranophosphate, cyanoethyl ester, Rp-/Sp-isomer,
2'-tert.-butyldimethylsilyladenosine-3',5'-cyclic boranophosphate, cyanoethyl ester, Rp-/Sp-isomer,
adenosine-3',5'-cyclic boranophosphate, Rp-/Sp-isomer,
thymidine-3',5'-cyclic cyanoboranophosphate, Rp-/Sp-isomer,
$N^6$-benzoyl-2'-tert.-butyldimethylsilyladenosine-3',5'-cyclic cyanoboranophosphate, Rp-/Sp-isomer,
2'-tert.-butyldimethylsilyladenosine-3',5'-cyclic cyanoboranophosphate, Rp-/Sp-isomer,
adenosine-3',5'-cyclic cyanoboranophosphate, Rp-/Sp-isomer,
5-fluoro-2'-deoxyuridine-3',5'-cyclic boranophosphate, 4-nitrophenyl ester, Rp-/Sp-isomer,
5-fluoro-2'-deoxyuridine-3',5'-cyclic boranophosphate, Rp-/Sp-isomer,
5-fluoro-2'-deoxyuridine-3',5'-cyclic boranophosphorothioate, Rp-/Sp-isomer,
thymidine-3',5'-cyclic boranophosphate, cyanoethyl ester, Rp-/Sp-isomer,
thymidine-3',5'-cyclic boranophosphate, 4-nitrophenyl ester, Rp-/Sp-isomer,
thymidine-3',5'-cyclic boranophosphate, Rp-/Sp-isomer,
thymidine-3',5'-cyclic boranophosphorothioate, Rp-/Sp-isomer.

Figure 1:
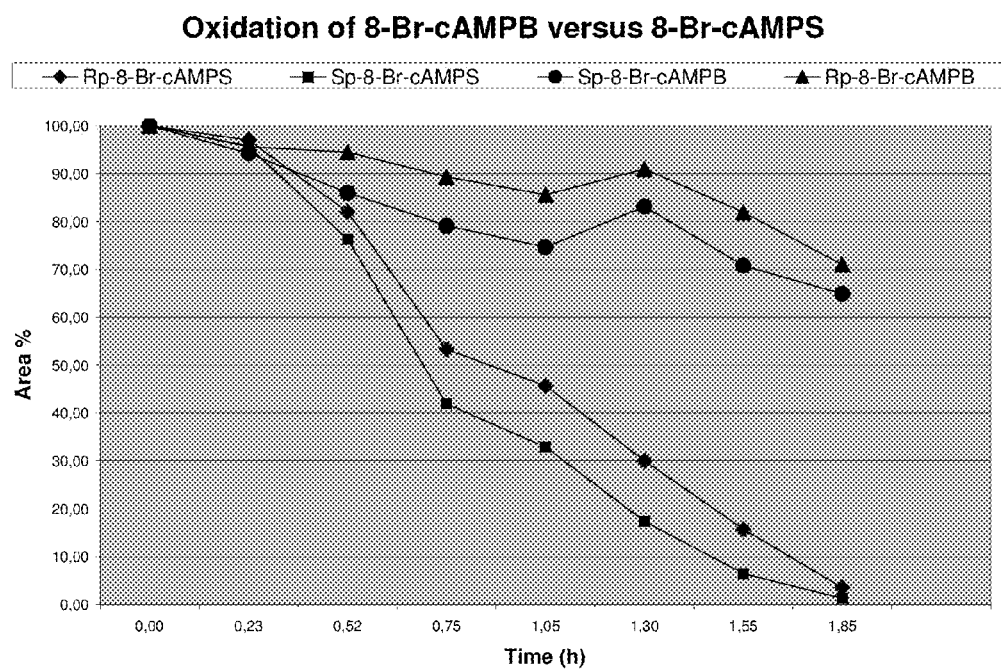
FIG. 1 depicts the result of the degradation example 1 with hydrogen peroxide. Oxidation of cyclic boranophosphates (Rp-8-Br-cAMPB; Sp-8-Br-cAMPB) versus cyclic phosphorothioates (Rp-8-Br-cAMPS; Sp-8-Br-cAMPS)

The binding situation with respect to phosphorus in a cyclic boranophosphate appears to be not precisely depictable and therefore the structural formulas shown in this description may deserve explanation.

When borane (BH$_3$) is added via the free electron pair of the tervalent phosphorus in a nucleoside-3',5'-cyclic phosphite ester, the resulting complexing bond is normally drawn by an arrow, pointing from phosphorus towards BH$_3$, and indicating that phosphorus is supposed to be still tervalent despite now having four different binding partners (compare Formula (III), which shows the association of a borano group to tervalent phosphorus in a cyclic phosphite ester). In this case a coordinate bond (also known as dipolar or dative covalent bond) is formed and borane serves as Lewis acid and phosphorus as Lewis base donating a pair of electrons.

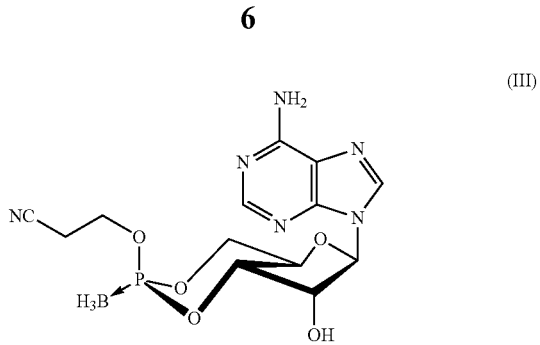

(III)

It is generally agreed that upon hydrolysis of the ester, phosphorus becomes pentavalent, in boranophosphate literature normally indicated by a double bond to oxygen and a permanent single bond to the borano group, which now carries a negative charge (compare formula (IV), which shows the usual depiction of a cyclic boranophosphate with pentavalent phosphorus and negatively charged borane).

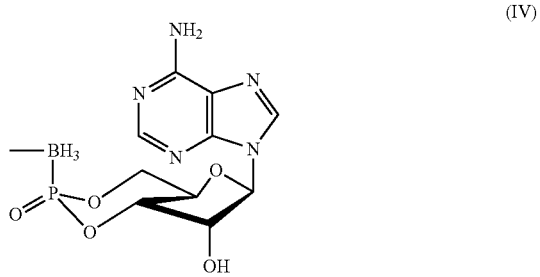

(IV)

This implies that the non dissociated molecule (free acid form) would carry a BH$_4$ group, with an additional bond to phosphorus, which in such a structural formula would make boron formally pentavalent as well.

In addition, according to literature, the negative charge is not really associated with the borane but rather shifted to phosphorus and it is probably more appropriate anyhow to assume a mesomeric situation such as described for cyclic AMP (compare formula (V), which shows the mesomeric distribution of the negative charge at a pentavalent phosphorus (cyclic AMP).

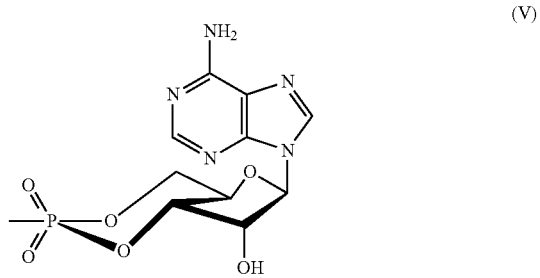

(V)

If a cyclic boranophosphate is further esterified (as for example compound 6 in Table 1), the phosphorus is supposed to be still pentavalent, but it is questionable whether it is appropriate to really draw a double bond to the borano group, indicating formally again a pentavalent boron.

Due to the indefinite electronic situation, which could give reason to ambiguous and disputable interpretations, it has been decided for the present specification to generally show a phosphorus with four single bond-like connections to its four binding partners within a cyclic boranophosphate or cyclic boranophosphite, indicating solely the type of binding or complexing partners without any commitment to the location of charges, the electronic and mesomeric nature and the valence situation at phosphorus, respectively (compare formulas (VI) and (VII), which show depiction principles used in the description of this invention).

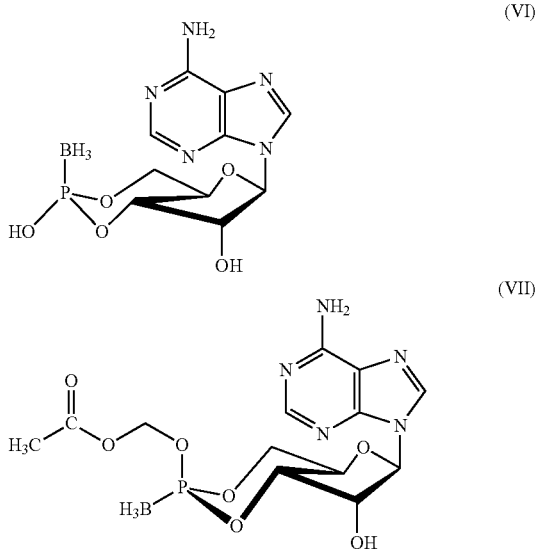

Listed below are the definitions of various terms and phrases used to describe the compounds of the present invention. These definitions apply to the terms as they are used throughout the specification.

Halogen refers to F, Cl, Br, and I.

Alkyl refers to an alkyl group, which is a substituted or unsubstituted, linear, branched or cyclic, saturated or unsaturated hydrocarbon moiety with 1 to 28, preferably with 1 to 20 carbon atoms, with or without heteroatoms, including, but not limited to, methyl, ethyl, propyl, isopropyl, butyl, sec.-butyl, tert.-butyl, and pentyl. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy. This definition deviates from commonly used definitions.

Preferred substituted alkyl moieties include, but are not limited to, dimethylaminocarbonyl, 19-amino-4,7,10,13,16-pentaoxanonadecylamino, acetoxymethyloxy, pivaloyloxymethyloxy, monosuccinyl, monosuccinyltyrosylmethylester, O-(8[tetramethylrhodaminyl]amino-3,6-dioxaoctylcarbamoyl).

Linear saturated hydrocarbon moieties (under the definition of "alkyl") refer preferably to a substituted or unsubstituted hydrocarbon moiety with 1 to 28, preferably with 1 to 20 carbon atoms, with or without heteroatoms, including, but not limited to, methyl, ethyl, propyl, butyl and pentyl. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Linear unsaturated hydrocarbon moieties (under the definition of "alkyl") refer preferably to a substituted or unsubstituted hydrocarbon moiety with 1 to 28, preferably with 1 to 20 carbon atoms, more preferably with 2 to 20 carbon atoms, with or without heteroatoms, including, but not limited to, ethylen, propylen, butylen and pentylen. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Branched saturated hydrocarbon moieties (under the definition of "alkyl") refer preferably to a substituted or unsubstituted hydrocarbon moiety with 1 to 28, preferably with 1 to 20 carbon atoms, with or without heteroatoms, including, but not limited to, isopropyl, sec.-butyl and tert.-butyl. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Branched unsaturated hydrocarbon moieties (under the definition of "alkyl") refer preferably to a substituted or unsubstituted hydrocarbon moiety with 1 to 28, preferably with 1 to 20 carbon atoms, more preferably with 3 to 20 carbon atoms, with or without heteroatoms. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Cyclic saturated hydrocarbon moieties (under the definition of "alkyl") refer preferably to a substituted or unsubstituted hydrocarbon moiety with 1 to 28, preferably with 1 to 20 carbon atoms, more preferably with 3 to 8 ring atoms, with or without heteroatoms, including, but not limited to, cyclopentyl, cyclohexyl, cycloheptyl, piperidino, piperazino. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Cyclic unsaturated hydrocarbon moieties (under the definition of "alkyl") refer preferably to a substituted or unsubstituted hydrocarbon moiety, more preferably to a non-aromatic moiety, with 1 to 28, preferably with 1 to 20 carbon atoms, more preferably with 3 to 8 ring atoms, with or without heteroatoms. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Aralkyl refers to an substituted or unsubstituted, linear, branched or cyclic, saturated or unsaturated hydrocarbon moiety with 1 to 28, preferably 1 to 20 carbon atoms, with or without heteroatoms, including, but not limited to, methyl, ethyl, propyl, isopropyl, butyl, sec.-butyl, tert.-butyl, pentyl, that connects to an unsubstituted or substituted aromatic or heteroaromatic hydrocarbon moiety, consisting of one or more aromatic or heteroaromatic rings with 3-8 ring atoms each. Substituents for both the alkyl and aryl part include, but are not limited to, one or more halogen atoms, haloalkyl groups, substituted or unsubstituted aryl groups, substituted or unsubstituted heteroaryl groups, amino, nitro, cyano, hydroxy, mercapto, carboxy, azido, methoxy, methylthio.

The above mentioned definitions of linear saturated, linear unsaturated, branched saturated, branched unsaturated, cyclic saturated and cyclic unsaturated apply for alkyl in aralkyl. The skilled person of course knows that the alkyl moiety under aralkyl is additionally substituted by one or more aromatic or heteroaromatic rings as defined above.

Aryl refers to an aryl group, which is an unsubstituted or substituted aromatic or heteroaromatic hydrocarbon moiety, consisting of one or more aromatic or heteroaromatic rings with 3-8 ring atoms each. Substituents include, but are not limited to, one or more halogen atoms, haloalkyl groups, substituted or unsubstituted aryl groups, substituted or unsubstituted heteroaryl groups, amino, nitro, cyano, hydroxy, mercapto, carboxy, azido, methoxy, methylthio.

Acyl refers to a —C(O)-alkyl group, wherein the alkyl group is as defined above.

Aracyl refers to a —C(O)-aryl group, wherein the aryl group is as defined above.

Carbamoyl refers to a —C(O)—NH$_2$ group, wherein the hydrogens can independently from each other be substituted with an alkyl group, aryl group or aralkyl group, wherein alkyl group, aryl group or aralkyl group are as defined above.

O-alkyl refers to an alkyl group, which is bound through an O-linkage, wherein the alkyl group is as defined above.

O-aryl refers to an aryl group, which is bound through an O-linkage, wherein the aryl group is as defined above.

O-aralkyl refers to an aralkyl group, which is bound through an O-linkage, wherein the aralkyl group is as defined above.

O-carbamoyl refers to a carbamoyl group, which is bound through an O-linkage, wherein the carbamoyl group is as defined above.

S-alkyl refers to an alkyl group, which is bound through a S-linkage, wherein the alkyl group is as defined above.

S-aryl refers to an aryl group, which is bound through a S-linkage, wherein the aryl group is as defined above.

S-aralkyl refers to an aralkyl group, which is bound through a S-linkage, wherein the aralkyl group is as defined above.

Se-alkyl refers to an alkyl group, which is bound through a Se-linkage, wherein the alkyl group is as defined above.

Se-aryl refers to an aryl group, which is bound through a Se-linkage, wherein the aryl group is as defined above.

Se-aralkyl refers to an aralkyl group, which is bound through a Se-linkage, wherein the aralkyl group is as defined above. NH-alkyl and N-bisalkyl refer to alkyl groups, which are bound through an N linkage, wherein the alkyl groups are as defined above.

NH-aryl and N-bisaryl refer to aryl groups, which are bound through an N linkage, wherein the aryl groups are as defined above.

NH-carbamoyl refers to a carbamoyl group, which is bound through an N-linkage, wherein the carbamoyl group is as defined above.

Amido-alkyl refers to an alkyl group, which is bound through a NH—C(O)— linkage, wherein the alkyl group is as defined above.

Amido-aryl refers to an aryl group, which is bound through a NH—C(O) linkage, wherein the aryl group is as defined above.

Amido-aralkyl refers to an aralkyl group, which is bound through a NH—C(O) linkage, wherein the aralkyl group is as defined above.

The person skilled in the art understands that many compounds that fall under formulas I and II as defined above have tautomeric forms. It has to be noted that according to this specification all tautomeric forms fall under formula I or II if at least one of the tautomers falls under formula I or II as defined above.

In the chair form of saturated six-membered rings, bonds to ring atoms, and the molecular entities attached to such bonds, are termed "axial" or "equatorial" according to whether they are located about the periphery of the ring ("equatorial"), or whether they are orientated above or below the approximate plane of the ring ("axial"). Due to the given stereochemistry of the cyclic phosphate ring, the axial position can only be above the approximate plane of the ring.

In natural cyclic nucleotide monophosphates (cNMP), both R5 and R6 are oxygen, and the double bond is "distributed or dislocated" between both atoms. In water at physiological pH, the compound has a negative charge between both oxygens, and a corresponding cation, such as H$^+$ or Na$^+$. The structural formula is therefore often written with one double bond to oxygen and one single bond to a hydroxyl group, while it is of no importance whether the double bond goes to the axial oxygen (R5) or the equatorial oxygen (R6).

The situation changes, however, if one of the oxygen atoms is exchanged for a different group, e.g. the borano group or another borano/modification of the present invention. The phosphorus atom is now chiral and has four different ligands resulting in two stereoisomeric forms, the axial and equatorial isomers. This is not explicitly indicated by O(H) and BH3 (BH4) in the definition of the respective R5 and R6. It means that R5 and R6 could be either O or BH3 or OH or BH4, depending on the location of the double bond. As described above, the binding situation in the cyclic boranophosphates is not precisely depictable. Therefore, it was decided not to depict the double bond in formula I and II at all. The same applies for formulas of single compounds in this text.

If the borano group is in the axial position (R5), the isomer may also be named the "Rp" isomer (from R/S nomenclature, and "p" for phosphorus), and if it is in the equatorial position (R6), the isomer may also be named the Sp-isomer. However, not all axial (equatorial) isomers will have a R(S) configuration, since this depends on the chemical nature of the substituents. Although the absolute configuration has not yet been determined for the cyclic boranophosphates described in this invention, the terms Rp and Sp are assigned to structures that behave biologically similar to the corresponding phosphorothioate congeners. For example, in order to be able to be activators of protein kinase A, cyclic phosphates need to have one exocyclic oxygen in the equatorial conformation in order to tolerate any modifications (e.g. S, BH3) at the axial position. A person skilled in the art understands that in formula I as well as in formula II, dependent on the meaning of the variables in the nucleobase moiety of the respective compound, there may exist tautomeric forms of the respective compound. In many cases only one of the tautomeric forms may be explicitly depictable by formula I or II. However, the person skilled in the art knows, that by depicting one of the tautomers under the respective formula, the other tautomer is disclosed at the same time.

The synthesis of nucleoside 3';5'-cyclic boranophosphorothiote, as an example of a new type of cyclic nucleotide, was described earlier by Li, P. and Ramsay Shaw, B., *Chemical Communications*, no. 23, 18 Nov. 2002 (2002-11-18), pages 2890-2891, to simply demonstrate accessibility of this class of compounds.

Interestingly, a first corresponding structure has been described earlier (Lin, J. L.; He, K. Ramsay Shaw, B., *Org. Lett.*, 3, 795-797 (2001)) to simply demonstrate accessibility of this class of compounds, and the authors considered it to be probably more stable against nucleases, a term that is rather broad and has been used by the group preferentially describing the increased stability of linear (non-cyclic) nucleoside 5'-boranophosphates towards various degrading enzymes. However, unexpectedly, it turned out that the new structures disclosed in this invention are obviously not metabolized by cyclic nucleotide-related phosphodiesterases at all, which is a clear improvement over the notorious sensitivity of phosphorothioates. Thus, the Sp-isomer of an otherwise unmodified cyclic nucleotide with phosphorothioate modification is slowly decomposed in presence of PDE type I, while a corresponding cyclic Rp-boranophosphate with comparable configuration also present in the mixture is not affected at all.

In addition, and much to the surprise of the inventor it turned out that cyclic nucleotide boranophosphate analogues are extraordinary stable towards oxidizing conditions, where the corresponding phosphorothioates inevitably will quickly decompose to form the oxygen-containing congeners, turning the kinase inhibiting equatorially modified Rp-diastereomers into powerful kinase activating structures, for example.

This increased stability was shown by the inventor for a broad variety of structural variations of cyclic boranophosphates including 2-, 6- and 8-modifications of the purine nucleobase and also for 2'-modifications at the ribose part, respectively, and this property is thus clearly independent from any modification at the nucleobase or the ribose moiety (compare examples below).

This was further confirmed by corresponding experiments with cyclic cytidine 3',5'-cyclic boranophosphate, a cyclic nucleotide with pyrimidine nucleobase (compare examples below).

Surprisingly it was found that cyclic nucleotides with boranophosphate modification according to the invention show a very good oxidation stability, especially compared to that with analogous phosphorothioate modifications.

A further advantage of the borano modified cyclic nucleotide analogues is, that even in case that oxidative degradation cannot be avoided completely for the compounds according to the invention, this oxidation does not produce biologically active cNMP agonists.

Compared to phosphorothioates, the new cyclic boranophosphate structures disclosed in the present invention have considerably higher lipophilicity, which can be monitored and determined by their extended retention times in reversed phase silica chromatography (Kraβ et al., *Anal. Chem.*, 69, 2575-2581 (1997).

Moreover, when the cyclic boranophosphates according to the invention are converted to their corresponding acetoxymethyl (AM) esters, surprisingly, the resulting compounds have considerably higher lipophilicity compared to AM esters prepared from cyclic nucleotides of otherwise comparable lipophilicity.

Higher lipophilicity means correspondingly improved membrane permeability and helps these structures to act in biological systems at much lower applicable concentrations.

The cyclic boranophosphates according to this invention exist as diastereomeric pairs, with either axial (Rp) or equatorial (Sp) orientation of the $BH_3$ group related to phosphorus. However, according to CIP rules the R/S nomenclature is reversed compared to phosphorothioate modification.

Since the electronic environment at the cyclic phosphate moiety is completely different compared to the situation with the natural signaling molecules cAMP and cGMP or to phosphorothioate modifications thereof, biological effects in respect to corresponding binding proteins were unpredictable. For example, compared to a phosphorothioate modification, the borano group does not have any free electron pairs which could interact by hydrogen bonding within a protein binding pocket and it is considerably more hydrophobic.

In addition, the localisation of the negative charge should definitely be different compared to natural phosphates or phosphorothioates.

However, surprisingly, measurements with isolated cyclic nucleotide receptor proteins point to the fact that the 3',5'-cyclic boranophosphate isomers of various nucleosides according to the invention behave strikingly similar to their phosphorothioate congeners, with respect to their orientation of the phosphate within the cNMP binding pocket and hence to their biological effects.

That means that despite its undisputed different electronic properties the cyclic boranophosphate moiety according to the invention behave surprisingly very similar to the already known phosphorothioate modification, and this holds also true for any modification in the nucleobase or ribose part of cNMP analogues described so far.

Thus, for example, activation assays with protein kinase A demonstrate that a Rp-isomer of a boranophosphate analogue of cAMP activates the receptor while the corresponding Sp-isomer is an inhibitor. Also, boranophosphate analogues of cGMP described in this invention activate and inhibit protein kinase G, respectively.

In addition, experiments with a cAMP activated ion channel (olfactory type) prove that the cyclic boranophosphates according to the invention can mimic the parent messenger molecule cyclic AMP.

Finally, surprisingly also the EPAC protein accepts cyclic boranophosphates according to the invention as activators.

Summing up, boranophosphate-modified cyclic nucleotides, according to the invention, are valuable molecular probes for the modulation of the signaling pathways of the second messenger cyclic AMP and cyclic GMP, respectively, as well as ligands in all forms of chromatography. Their biological activity depends on the diastereomeric configuration at phosphorus, and is thus strikingly comparable to the widely used phosphorothioate analogues in this respect.

However, in contrast to phosphorothioate-modified cyclic nucleotides, cyclic boranophosphates described in this invention are much more stable towards oxidation and enzymatic degradation by phosphodiesterases, respectively, and possess considerably increased lipophilicity.

According the invention it is preferred that R1 is selected from group consisting of H, halogen, azido, nitro, alkyl, aryl, OH, O-alkyl, O-aryl, SH, S-alkyl, S-aryl, S-aralkyl, S-benzyl, amino, NH-alkyl, NH-benzyl, NH-aryl, Se-aryl, and NR8R9 and SiR10R11R12 wherein R8, R9, R10, R11, R12 are alkyl.

According to the invention it is further preferred that R1 is selected from the group consisting of H, F, Cl, Br, I, azido, nitro, 2-furyl, 3-furyl, 2-bromo-5-furyl, 2-thienyl, 3-thienyl, allyl, trifluoromethyl, phenyl, OH, methoxy, ethoxy, n-propoxy, n-butoxy, benzyloxy, 4-methylbenzyloxy, 4-methoxybenzyloxy, 4-fluorobenzyloxy, 4-chlorobenzyloxy, 4-bromobenzyloxy, phenyloxy, SH, methylthio, ethylthio, n-propylthio, n-butylthio, n-pentylthio, n-hexylthio, isopropylthio, 2-hydroxyethylthio, 2-aminoethylthio, 2-carboxyethylthio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, cyclohexylthio, benzylthio, 4-azidobenzylthio, phenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 4-nitrophenylthio, 2-aminophenylthio, 3-aminophenylthio, 4-aminophenylthio, phenylethylamino, 3-phenyl-propylamino, 2-methoxyphenylthio, 3-methoxyphenylthio, 4-methoxyphenylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,3-dichlorophenylthio, 2,4-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio, 2,6-dichlorophenylthio, 4-isopropyloxyphenylthio, 4-methylthiophenylthio, 4-azidophenylthio, 4-methylcumarinyl, naphtyl-2-thio, 4-azidophenacylthio, benzimidazolyl-2-thiobenzothiazolylthio, pyridinylthio, amino, methylamino, n-hexylamino, 2-aminoethylamino, 6-aminohexylamino, 5-amino-3-oxopentylamino, 8-amino-3,6-dioxaoctylamino, 19-amino-4,7,10,13,16-pentaoxanonadecylamino, 17-amino-9-aza-heptadecylamino, 2-carboxyethylamino, 4-(N-methylanthranoyl)aminobutylamino, cyclopropylamino, cyclopentylamino, cyclohexylamino, dimethylamino, diethylamino, morpholino, piperidino, piperazino, benzylamino, 4-azidobenzylamino, anilino, 4-azidoanilino and phenylseleno.

According to the invention it is especially preferred that R1 is selected from the group consisting of H, F, Cl, Br, azido, nitro, 2-furyl, allyl, trifluoromethyl, phenyl, OH, methoxy, benzyloxy, phenyloxy, SH, methylthio, n-hexylthio, 2-hydroxyethylthio, 2-aminoethylthio, 2-(N-(7-nitrobenz-2-oxa-1,3-diazol-4-yl)amino)ethylthio, (4-bromo-2, 3-dioxobutyl)thio, [2-[(fluoresceinylthioureido)amino] ethyl]thio, phenylthio, benzylthio, 4-azidobenzylthio, 4-chlorophenylthio, 4-nitrophenylthio, 2-aminophenylthio, 4-methoxyphenylthio, 4-methylphenylthio, 2,3,5,6-tetrafluorophenylthio, 4-hydroxyphenylthio, 2,4-dichlorophenylthio, 4-azidophenylthio, 4-methylcumarinyl, 4-azidophenacylthio, 4-isopropylphenylthio, pyridinylthio, amino, methylamino, n-hexylamino, 6-aminohexylamino, 5-amino-3-oxopentylamino, 8-amino-3,6-dioxaoctylamino, 17-amino-9-aza-heptadecylamino, 19-amino-4,7,10,13,16-pentaoxanonadecylamino, 4-(N-methylanthranoyl)aminobutylamino, cyclohexylamino, dimethylamino, diethylamino, morpholino, piperidino, piperazino, benzylamino, 4-azidobenzylamino, anilino, 4-azidoanilino and phenylseleno.

According to the invention it is even more preferred that R1 is selected from the group consisting of H, F, Cl, Br, azido, 2-furyl, allyl, phenyl, OH, SH, 2-aminoethylthio, [2-[(fluoresceinylthioureido)amino]ethyl]thio, benzylthio, 4-azidobenzylthio, 4-chlorophenylthio, 2-aminophenylthio, 4-methoxyphenylthio, 4-hydroxyphenylthio, 4-azidophenylthio, amino, methylamino, n-hexylamino, 6-aminohexylamino, 19-amino-4,7,10,13,16-pentaoxanonadecylamino, diethylamino, piperidino and 4-azidoanilino.

According to the invention it is in addition to the above further preferred that R1 is selected from the group consisting of H, F, Cl, Br, azido, 2-furyl, phenyl, OH, SH, 2-aminoethylthio, benzylthio, 4-chlorophenylthio, methylamino, 6-aminohexylamino and piperidino.

According to the invention it is most preferred that R1 is selected from the group consisting of H, Br, azido, OH, 2-aminoethylthio, benzylthio, 4-chlorophenylthio, 6-aminohexylamino and piperidino.

In addition to the above or independent to the above it is preferred that according the invention that R2 is selected from group consisting of H, halogen, azido, amino, alkylamino, O-carbamoyl-alkyl, O-carbamoyl-aryl, O-carbamoyl-aralkyl, OH, O-alkyl, O-aryl, O-aralkyl, O-acyl, O-aracyl, SH, S-alkyl and OSiR15R16R17 wherein R15, R16 and R17 are alkyl.

According to the invention it is further preferred that R2 is selected from the group consisting of H, F, Cl, Br, amino, alkylamino, O-(2-aminoethylcarbamoyl), O-(3-aminopropylcarbamoyl), O-(4-amino-n-butylcarbamoyl), O-(6-aminohexylcarbamoyl), 0-(8-amino-3,6-dioxaoctylaminocarbamoyl), O-(19-amino-4,7,10,13,16-pentaoxanonadecylaminocarbamoyl), O-(17-amino-9-aza-heptadecylaminocarbamoyl), O-(6-carboxyhexylcarbamoyl), OH, methyloxy, ethyloxy, n-propyloxy, n-butyloxy, isobutyloxy, methoxyethyloxy, acyloxymethyloxy, 4-nitrobenzyloxymethyloxy, benzyloxy, O-acetyl, O-propionyl, O-n-butyryl, O-isobutyryl, O-n-hexanoyl, O-n-octanoyl, O-succinyl, O-anthraniloyl, O—(N-methylanthraniloyl), O-benzoyl, O-(4-benzoylbenzoyl), O-triflyl, O-toluolsulfonyl, O-dansyl, methylthio, O-trimethylsilyl, O-triethylsilyl, O-tert. butyldimethylsilyl and O-triisopropylsilyloxymethyl.

According to the invention it is especially preferred that R2 is selected from the group consisting of H, F, O-(2-aminoethylcarbamoyl), O-(6-aminohexylcarbamoyl), O-(8-amino-3,6-dioxaoctylaminocarbamoyl), O-(6-carboxyhexylcarbamoyl), OH, O-methyl, O-ethyl, O-n-propyl, O-n-butyl, O-n-butyryl, O-n-octanoyl, O-succinyl, O-anthraniloyl, O—(N-methylanthraniloyl), O-(4-benzoylbenzoyl), O-triflyl, O-dansyl, methylthio, O-trim ethylsilyl and O-triethylsilyl.

According to the invention it is even more preferred that R2 is selected from the group consisting of H, O-(2-aminoethylcarbamoyl), O-(6-aminohexylcarbamoyl), O-(8-amino-3,6-dioxaoctylaminocarbamoyl), OH, O-methyl, O-ethyl, O-n-butyryl, O-succinyl, O-anthraniloyl, O—(N-methylanthraniloyl), O-dansyl, O-(4-benzoylbenzoyl), methylthio and O-trimethylsilyl.

According to the invention it is in addition to the above further preferred that R2 is selected from the group consisting of H, O-(2-aminoethylcarbamoyl), O-(6-aminohexylcarbamoyl), OH, O-methyl, O-n-butyryl, O-succinyl, O—(N-methylanthraniloyl), O-dansyl and O-trimethylsilyl.

According to the invention it is most preferred that R2 is selected from the group consisting of H, O-(2-aminoethylcarbamoyl), O-(6-aminohexylcarbamoyl), OH, O-methyl, O-n-butyryl, O-succinyl and O—(N-methylanthraniloyl).

In addition to the above or independent to the above it is preferred that according the invention that R3 is selected from group consisting of H, halogen, azido, acyl, aracyl, nitro, alkyl, aryl, aralkyl, amido-alkyl, amido-aryl, amido-aralkyl, amino, NH-alkyl, NH-aryl, NH-aralkyl, NH-carbamoyl-alkyl, NH-carbamoyl-aryl, NH-carbamoyl-aralky, aralkyl-carbamoyl, OH, O-alkyl, O-aryl, O-aralkyl, O-acyl, O-aracyl, SH, S-alkyl, S-aryl, S-aralkyl, S-acyl, S-aracyl, NR18R19 and SiR2OR21R22 wherein R18, R19, R20, R21 and R22 are alkyl.

According to the invention it is further preferred that R3 is selected from the group consisting of H, F, Cl, Br, I, azido, acetyl, butyryl, benzoyl, nitro, methyl, ethyl, n-propyl, trifluoromethyl, 2-furyl, 2-thienyl, phenyl, benzyl, amidomethyl, amidoethyl, amido-n-propyl, amido-n-butyl, amidoisobutyl, benzoyl, 4-benzoylbenzoyl, amino, NH-methyl, NH-ethyl, NH-n-propyl, NH-tert.-butyl, NH-(2-aminoethyl), NH-n-(6-aminohexyl), NH-(8-amino-3,6-dioxaoctyl), NH-(6-carboxy-n-hexyl), NH-cyclohexyl, N,N-dimethyl, N,N-diethyl, N,N-di-n-propyl, N,N-diisopropyl, N-piperidinyl, N-piperazinyl, NH-benzyl, NH-phenyl, NH-4-azidophenyl, NH-phenylethyl, NH-phenylpropyl, NH-tert.-butylcarbamoyl, NH-phenylcarbamoyl, OH, methyloxy, ethyloxy, propyloxy, n-hexyloxy, 6-amino-n-hexyloxy, phenyloxy, benzyloxy, methylcarbonyloxy, benzoyloxy, SH, methylthio, ethylthio, propylthio, n-hexylthio, 6-amino-n-hexylthio, 4-bromo-2,3-dioxobutylthio, phenylthio, benzylthio, trimethylsilyl, triethylsilyl and tert. butyldimethylsilyl.

According to the invention it is especially preferred that R3 is selected from the group consisting of H, F, Cl, Br, I, azido, nitro, methyl, 2-furyl, 2-thienyl, phenyl, benzyl, amidoethyl, amido-n-propyl, amido-n-butyl, amidoisobutyl, benzoyl, 4-benzoylbenzoyl, amino, NH-methyl, NH-tert.-butyl, NH-(2-aminoethyl), NH-n-(6-aminohexyl), NH-(8-amino-3,6-dioxaoctyl), NH-(6-carboxy-n-hexyl), N,N-dimethyl, N,N-diethyl, N,N-di-n-propyl, N,N-diisopropyl, N-piperidinyl, N-piperazinyl, NH-benzyl, NH-phenyl, NH-tert.-butylcarbamoyl, NH-phenylcarbamoyl; OH, methyloxy, n-hexyloxy, 6-amino-n-hexyloxy, phenyloxy, benzyloxy, SH, ethylthio, 2-aminoethylthio, n-hexylthio, 6-amino-n-hexylthio, 4-bromo-2,3-dioxobutylthio, phenylthio, benzylthio, trimethylsilyl and triethylsilyl.

According to the invention it is even more preferred that R3 is selected from the group consisting of H, F, Cl, Br, I, nitro, 2-furyl, phenyl, benzyl, amidoethyl, amido-n-butyl, amidoisobutyl, benzoyl, 4-benzoylbenzoyl, amino, NH-methyl, NH-tert.-butyl, NH-(2-aminoethyl), NH-n-(6-aminohexyl), NH-(8-amino-3,6-dioxaoctyl), NH-(6-carboxy-n-hexyl), N,N-dimethyl, N,N-diethyl, N,N-di-n-propyl, N,N-diisopropyl, NH-tert-butyl, NH-benzyl, NH-phenyl, NH-tert-butylcarbamoyl, OH, O-methyl, O-(6-amino-n-hexyl), SH, ethylthio, 6-amino-n-hexylthio, phenylthio, benzylthio and trimethylsilyl.

According to the invention it is in addition to the above further preferred that R3 is selected from the group consisting of H, F, Cl, nitro, phenyl, amido-n-butyl, amidoisobutyl, benzoyl, 4-benzoylbenzoyl, amino, NH-tert.-butyl, NH-(2-aminoethyl), NH-n-(6-aminohexyl), N,N-dimethyl, N,N-di-n-propyl, N,N-diisopropyl, NH-benzyl, NH-phenyl, NH-tert-butylcarbamoyl, OH, 6-amino-n-hexyloxy, SH, ethylthio, 6-amino-n-hexylthio, phenylthio and benzylthio.

According to the invention it is most preferred that R3 is selected from the group consisting of H, Cl, amido-n-butyl, benzoyl, amino, NH-(2-aminoethyl), NH-n-(6-aminohexyl), N,N-dimethyl, NH-benzyl, NH-phenyl, NH-tert.-butylcarbamoyl, OH, 6-amino-n-hexyloxy, SH, 6-amino-n-hexylthio, phenylthio and benzylthio.

In addition to the above or independent to the above it is preferred that according the invention hat R4 is selected from group consisting of H, halogen, azido, acyl, aracyl, nitro, alkyl, aryl, aralkyl, amido-alkyl, amido-aryl, amido-aralkyl, NH-carbamoyl-alkyl, NH-carbamoyl-aryl, NH-carbamoyl-aralky, OH, O-alkyl, O-aryl, O-aralkyl, SH, S-alkyl, S-aryl, S-aralkyl, amino, alkylamino, NR25R26 and SiR27R28R29 wherein R25, R26, R27, R28, R29 are alkyl.

According to the invention it is further preferred that R4 is selected from the group consisting of H, F, Cl, Br, I, nitro, methyl, ethyl, n-propyl, n-hexyl, 6-amino-n-hexyl, trifluoromethyl, phenyl, 4-N,N-dimethylaminophenyl, benzyl, 4-azidobenzyl, amido-n-butyl, amidoisobutyl, amido(6-amino-n-hexyl), amidobenzoyl, OH, methyloxy, n-hexyloxy, phenyloxy, benzyloxy, SH, methylthio, ethylthio, 6-amino-n-hexylthio, phenylthio, 4-azidophenylthio, benzylthio, 4-azidobenzylthio, amino, methylamino, 2-aminoethylamino, n-hexylamino, 6-amino-n-hexylamino, 8-amino-3,6-dioxaoctylamino, dimethylamino, piperidino, piperazino, trimethylsilyl, triethylsilyl and tert. butyldimethylsilyl.

According to the invention it is especially preferred that R4 is selected from the group consisting of H, F, Cl, Br, I, methyl, n-hexyl, 6-amino-n-hexyl, phenyl, benzyl, amido-n-butyl, amidoisobutyl, amido(6-amino-n-hexyl), amidobenzoyl, OH, SH, methylthio, ethylthio, 6-amino-n-hexylthio, phenylthio, benzylthio, 4-azidobenzylthio, amino, methylamino, 2-aminoethylamino, 6-amino-n-hexylamino, 8-amino-3,6-dioxaoctylamino, dimethylamino, piperidino, piperazino, trimethylsilyl and tert. butyldimethylsilyl.

According to the invention it is even more preferred that R4 is selected from the group consisting of H, F, Cl, phenyl, benzyl, amido-n-butyl, amidoisobutyl, amido(6-amino-n-hexyl), amidobenzoyl, OH, SH, methylthio, 2-aminoethylthio, 6-amino-n-hexylthio, phenylthio, benzylthio, 4-azidobenzylthio, 4-bromo-2,3-dioxobutylthio, amino, methylamino, 2-aminoethylamino, 6-amino-n-hexylamino, 8-amino-3,6-dioxaoctylamino, dimethylamino, piperidino, piperazino, trimethylsilyl and tert. butyldimethylsilyl.

According to the invention it is in addition to the above further preferred that R4 is selected from the group consisting of H, F, Cl, methyl, amido-n-butyl, amido(6-amino-n-hexyl), OH, SH, methylthio, 2-aminoethylthio, 6-amino-n-hexylthio, amino, methylamino, 2-aminoethylamino, 6-amino-n-hexylamino and dimethylamino.

According to the invention it is most preferred that R4 is selected from the group consisting of H, Cl, amido-n-butyl, OH, SH, methylthio, 2-aminoethylthio, 6-amino-n-hexylthio, amino, methylamino, 2-aminoethylamino, 6-amino-n-hexylamino and dimethylamino.

In addition to the above or independent to the above it is preferred that according the invention that R5 or R6 (in case R5 or R6 is not the borano modification) is selected from group consisting of H, acyl, alkyl, aryl, aralkyl, OH, O-alkyl, O-aryl, O-aralkyl, O-acyl, SH, S-alkyl, S-aryl, S-aralkyl, amino, NH-alkyl, H-aryl, N-aralkyl and NR30R31, wherein R30, R31 are alkyl.

According to the invention it is further preferred that R5 or R6 (in case R5 or R6 is not the borano modification) is selected from the group consisting of H, methyl, ethyl, phenyl, benzyl, OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, acetyloxy, propionyloxy, benzoyloxy, SH, methylthio, acetoxymethylthio, cyanoethylthio, phenylthio, benzylthio, amino, methylamino, dimethylamino, piperidino, anilino and benzylamino.

According to the invention it is especially preferred that R5 or R6 (in case R5 or R6 is not the borano modification) is selected from the group consisting of H, methyl, ethyl, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, SH, methylthio, acetoxymethylthio, cyanoethylthio, phenylthio, benzylthio, amino, methylamino, dimethylamino, piperidino, anilino and benzylamino.

According to the invention it is even more preferred that R5 or R6 (in case R5 or R6 is not the borano modification) is selected from the group consisting of H, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, benzyloxy, SH, methylthio, acetoxymethylthio, methylamino, dimethylamino, piperidino and anilino.

According to the invention it is in addition to the above further preferred that R5 or R6 (in case R5 or R6 is not the borano modification) is selected from the group consisting of OH, cyanoethyloxy, acetoxymethyloxy, pivaloyloxymethyloxy, methoxymethyloxy, propionyloxymethyloxy, butyryloxymethyloxy, SH, acetoxymethylthio, methylamino, dimethylamino and piperidino.

According to the invention it is most preferred that R5 or R6 (in case R5 or R6 is not the borano modification) is selected from the group consisting of OH, cyanoethyloxy, acetoxymethyloxy and pivaloyloxymethyloxy.

In addition to the above or independent to the above it is preferred that according the invention that R7 is selected from group consisting of H, halogen, alkyl, nitro, N-oxide and absent.

According to the invention it is in addition to the above further preferred that R7 is selected from the group consisting of Cl, methyl and absent.

According to the invention it is most preferred that R7 is selected from the group consisting of Cl, methyl and absent.

It has to be noted that according to the invention one of R5 and R6 has to be a borano modification selected from the group consisting of borano ($BH_3$), methylborano, dimethylborano and cyanoborano ($BH_2CN$) group.

More preferred one of R5 or R6 according to the invention is selected from the group consisting of borano ($BH_3$) and cyanoborano ($BH_2CN$) group.

And most preferred one of R5 and R6 is borano ($BH_3$).

It has to be noted that there are some cNMP borano phosphate analogues excluded from the invention. Some of them may already have been mentioned in the state of the art. However, it has to be noted that the superior stability against oxidation of the respective borano phosphate analogues has not been known so far. On the other hand it cannot be excluded that there have been mentioned in the state of the art further compounds that may be comprised in formula I or formula II. However, if the disclosure of such compounds does not give any hint on the present invention i.e. the superior stability against oxidation of the compounds according to the inventions such incidentally mentioned compounds will be disclaimed from the invention, too. The above compounds defined be the preferred residues (or more preferred and so on) have respectively improved properties in the sense of the invention. Especially there is an increasing oxidation stability. In addition to that they prefer to have similar properties as analogous thio modifications regarding protein kinases A and G, PDE, EPAC and other or all of the above mentioned enzymes.

Especially preferred according to the invention are the compounds of table 1. It has to be noted that in table 1 in the chemical structure there is only the Rp isomer or the Sp isomer depicted. However, the person skilled in the art exactly knows how to depict the respective other isomer. It has further to be noted that in case of doubt the chemical structure as depicted in the formula is the valid one.

TABLE 1

Structures of novel compounds according to the invention.

| Compound | # | Chemical structure |
|---|---|---|
| 8-Bromoadenosine-3',5'-cyclic boranophosphate, Rp-isomer | 001 | 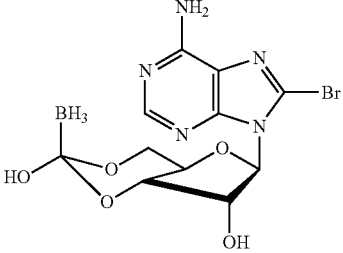<br>Rp-8-Br-cAMPB (001) |
| 8-Bromoadenosine-3',5'-cyclic boranophosphate, Sp-isomer | 002 | |
| 8-Bromoadenosine-3',5'-cyclic boranophosphate, 2-cyanoethyl ester, Rp-isomer | 003 | 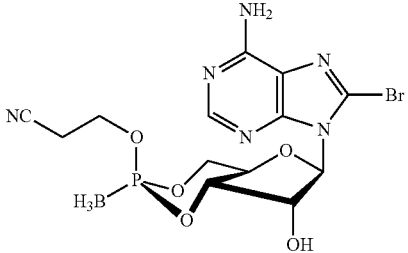<br>Sp-8-Br-cAMPB-CE (004) |
| 8-Bromoadenosine-3',5'-cyclic boranophosphate, 2-cyanoethyl ester, Sp-isomer | 004 | |
| 8-Bromoadenosine-3',5'-cyclic boranophosphate, Rp-isomer, acetoxymethyl ester | 005 | 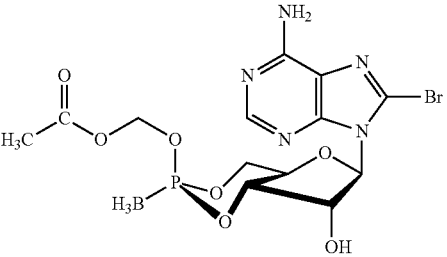<br>Sp-8-Br-cAMPB-AM (006) |
| 8-Bromoadenosine-3',5'-cyclic boranophosphate, Sp-isomer, acetoxymethyl ester | 006 | |

TABLE 1-continued

Structures of novel compounds according to the invention.

| Compound | # | Chemical structure |
|---|---|---|
| 8-Bromo-2'-O-(imidazoylcarbamoyl) adenosine-3',5'-cyclic boranophosphate, Rp-Isomer | 007 | |
| 8-Bromo-2'-O-(imidazoylcarbamoyl) adenosine-3',5'-cyclic boranophosphate, Sp-Isomer | 008 | 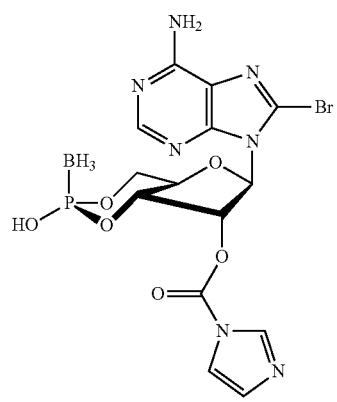 Rp-8-Br-2'-IC-cAMPB (007) |
| 8-Bromo-2'-O-(N-methylanthraniloyl)- adenosine-3',5'-cyclic boranophosphate, Rp-isomer | 009 | |
| 8-Bromo-2'-O-(N-methylanthraniloyl)- adenosine-3',5'-cyclic boranophosphate, Sp-isomer | 010 | 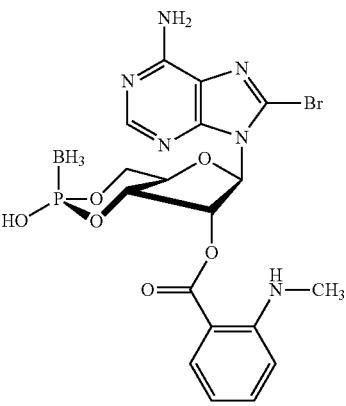 Rp-8-Br-2'-MANT-cAMPB (009) |
| 8-Bromo-2'-O-monosuccinyladenosine- 3',5'-cyclic boranophosphate, Rp-isomer | 011 | |
| 8-Bromo-2'-O-monosuccinyladenosine- 3',5'-cyclic boranophosphate, Sp-isomer | 012 | 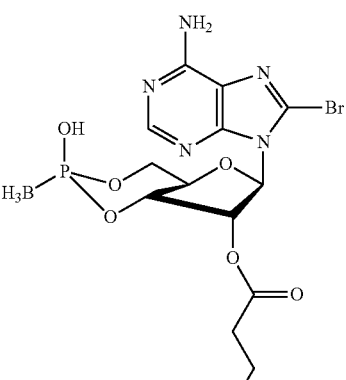 Sp-8-Br-2'-O-MS-cAMPB (012) |

TABLE 1-continued

Structures of novel compounds according to the invention.

| Compound | # | Chemical structure |
|---|---|---|
| 8-Chloroadenosine-3',5'-cyclic boranophosphate, Rp-isomer | 013 | Rp-8-Cl-cAMPB (013) |
| 8-Chloroadenosine-3',5'-cyclic boranophosphate, Sp-isomer | 014 | |
| 8-Hydroxyadenosine-3',5'-cyclic boranophosphate, Rp-isomer | 015 | Rp-8-OH-cAMPB (015) |
| 8-Hydroxyadenosine-3',5'-cyclic boranophosphate, Sp-isomer | 016 | |
| 8-Thioadenosine-3',5'-cyclic boranophosphate, Rp-isomer | 017 | Rp-8-SH-cAMPB (017) |
| 8-Thioadenosine-3',5'-cyclic boranophosphate, Sp-isomer | 018 | |
| 8-Azidoadenosine-3',5'-cyclic boranophosphate, Rp-isomer | 019 | Sp-8-N$_3$-cAMPB (020) |
| 8-Azidoadenosine-3',5'-cyclic boranophosphate, Sp-isomer | 020 | |
| 8-Aminoadenosine-3',5'-cyclic boranophosphate, Rp-isomer | 021 | Rp-8-NH$_2$-cAMPB (021) |
| 8-Aminoadenosine-3',5'-cyclic boranophosphate, Sp-isomer | 022 | |

TABLE 1-continued

Structures of novel compounds according to the invention.

| Compound | # | Chemical structure |
|---|---|---|
| 8-(2-Aminoethylamino)adenosine-3',5'-cyclic boranophosphate, Rp-isomer | 023 | |
| 8-(2-Aminoethylamino)adenosine-3',5'-cyclic boranophosphate, Sp-isomer | 024 | 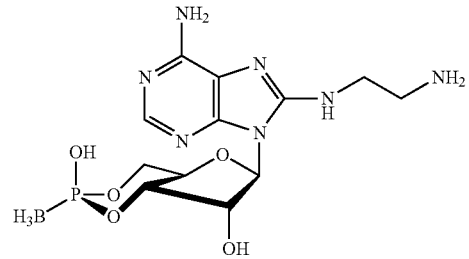<br>Sp-8-AEA-cAMPB (024) |
| 8-(6-Aminohexylamino)adenosine-3',5'-cyclic boranophosphate, Rp-isomer | 025 | |
| 8-(6-Aminohexylamino)adenosine-3',5'-cyclic boranophosphate, Sp-isomer | 026 | 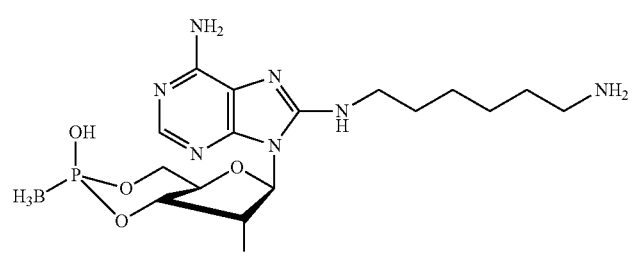<br>Sp-8-AHA-cAMPB (026) |
| 8-(6-Aminohexylamino)adenosine-3',5'-cyclic boranophosphate, Rp-isomer, immobilized to agarose | 027 | |
| 8-(6-Aminohexylamino)adenosine-3',5'-cyclic boranophosphate, Sp-isomer, immobilized to agarose | 028 | 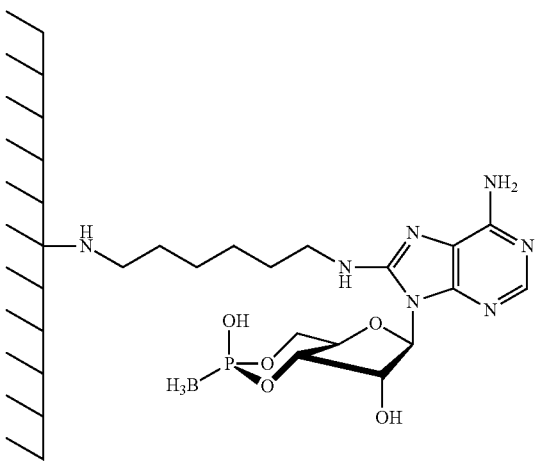<br>Sp-8-AHA-cAMPB Agarose (028) |
| 8-(19-Amino-4,7,10,13,16-penta-oxanonadecylamino)adenosine-3',5'-cyclic boranophosphate, Rp-isomer | 029 | |
| 8-(19-Amino-4,7,10,13,16-penta-oxanonadecylamino)adenosine-3',5'-cyclic boranophosphate, Sp-isomer | 030 | 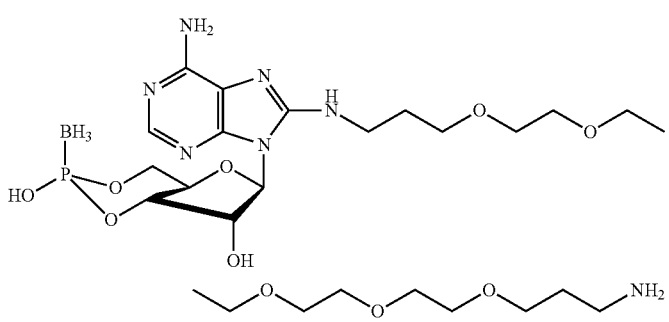<br>Rp-8-APONA-cAMPB (029) |

TABLE 1-continued

Structures of novel compounds according to the invention.

| Compound | # | Chemical structure |
|---|---|---|
| 8-Diethylaminoadenosine-3',5'-cyclic boranophosphate, Rp-isomer | 031 | 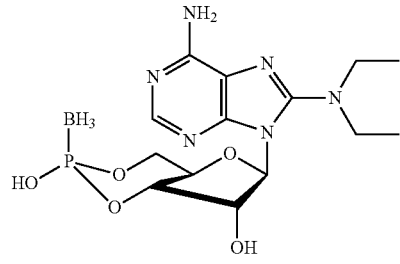<br>Rp-8-DEA-cAMPB (031) |
| 8-Diethylaminoadenosine-3',5'-cyclic boranophosphate, Sp-isomer | 032 | |
| 8-Cyclopentylaminoadenosine-3',5'-cyclic boranophosphate, Rp-isomer | 033 | 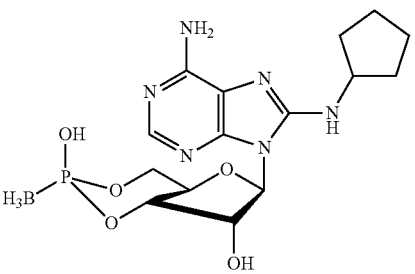<br>Sp-8-CP-cAMPB (034) |
| 8-Cyclopentylaminoadenosine-3',5'-cyclic boranophosphate, Sp-isomer | 034 | |
| 8-Piperidinoadenosine-3',5'-cyclic boranophosphate, Rp-isomer | 035 | 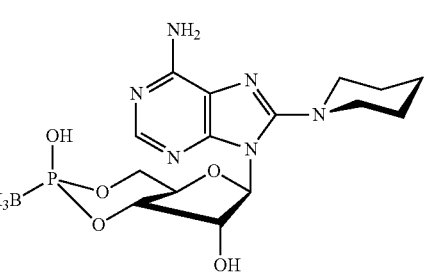<br>Sp-8-PIP-cAMPB (036) |
| 8-Piperidinoadenosine-3',5'-cyclic boranophosphate, Sp-isomer | 036 | |
| 8-Piperazinoadenosine-3',5'-cyclic boranophosphate, Rp-isomer | 037 | 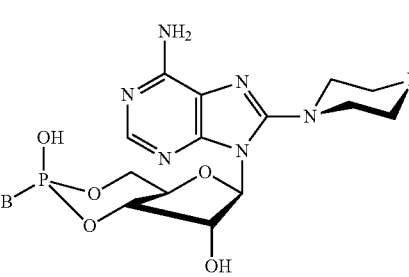<br>Sp-8-PIAZ-cAMPB (038) |
| 8-Piperazinoadenosine-3',5'-cyclic boranophosphate, Sp-isomer | 038 | |
| 8-Benzylaminoadenosine-3',5'-cyclic boranophosphate, Rp-isomer | 039 | 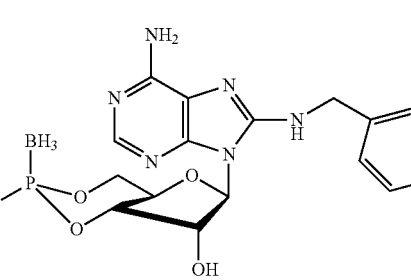<br>Rp-8-BnA-cAMPB (039) |
| 8-Benzylaminoadenosine-3',5'-cyclic boranophosphate, Sp-isomer | 040 | |

TABLE 1-continued

Structures of novel compounds according to the invention.

| Compound | # | Chemical structure |
|---|---|---|
| 8-Ethyloxyadenosine-3',5'-cyclic boranophosphate, Rp-isomer | 041 | 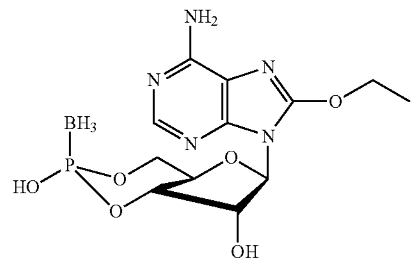 |
| 8-Ethyloxyadenosine-3',5'-cyclic boranophosphate, Sp-isomer | 042 | Rp-8-EtO-cAMPB (041) |
| 8-Phenoxyadenosine-3',5'-cyclic boranophosphate, Rp-isomer | 043 | 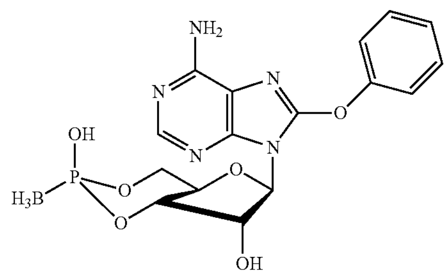 |
| 8-Phenoxyadenosine-3',5'-cyclic boranophosphate, Sp-isomer | 044 | Sp-8-PheO-cAMPB (044) |
| 8-Benzyloxyadenosine-3',5'-cyclic boranophosphate, Rp-isomer | 045 | 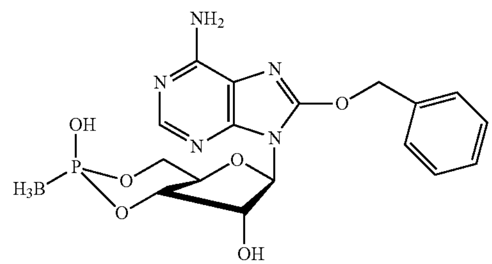 |
| 8-Benzyloxyadenosine-3',5'-cyclic boranophosphate, Sp-isomer | 046 | Sp-8-BnO-cAMPB (046) |
| 8-n-Hexylthioadenosine-3',5'-cyclic boranophosphate, Rp-isomer | 047 | 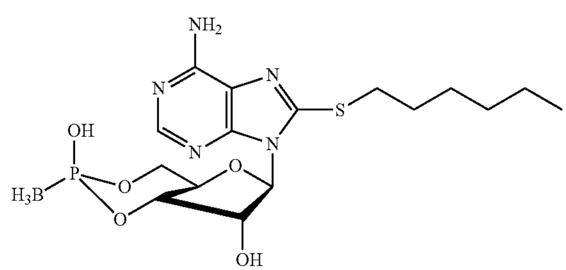 |
| 8-n-Hexylthioadenosine-3',5'-cyclic boranophosphate, Sp-isomer | 048 | Sp-8-HT-cAMPB (048) |
| 8-(2-Aminoethylthio)adenosine-3',5'-cyclic boranophosphate, Rp-isomer | 049 | 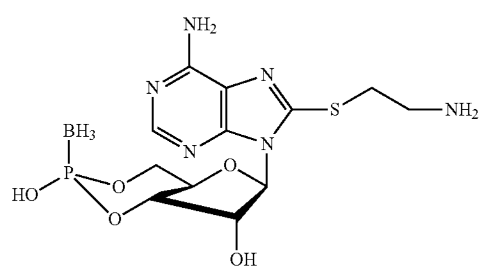 |
| 8-(2-Aminoethylthio)adenosine-3',5'-cyclic boranophosphate, Sp-isomer | 050 | Rp-8-AET-cAMPB (049) |

TABLE 1-continued

Structures of novel compounds according to the invention.

| Compound | # | Chemical structure |
|---|---|---|
| 8-(2-Aminophenylthio)adenosine-3',5'-cyclic boranophosphate, Rp-isomer | 051 | 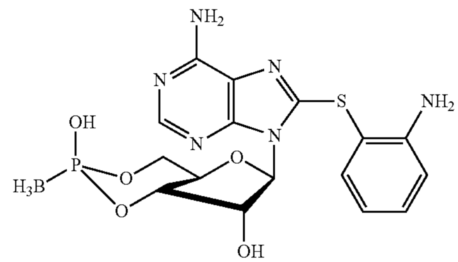 |
| 8-(2-Aminophenylthio)adenosine-3',5'-cyclic boranophosphate, Sp-isomer | 052 | Sp-8-APT-cAMPB (052) 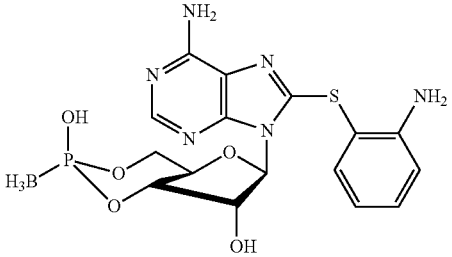 |
| 8-(4-Chlorophenylthio)adenosine-3',5'-cyclic boranophosphate, Rp-isomer | 053 | 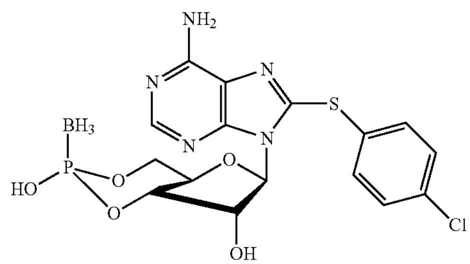 |
| 8-(4-Chlorophenylthio)adenosine-3',5'-cyclic boranophosphate, Sp-isomer | 054 | Rp-8-pCPT-cAMPB (053) 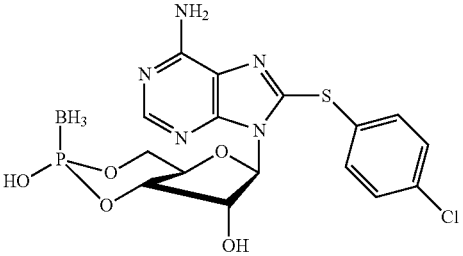 |
| 8-(2-Naphtylthio)adenosine-3',5'-cyclic boranophosphate, Rp-isomer | 055 | 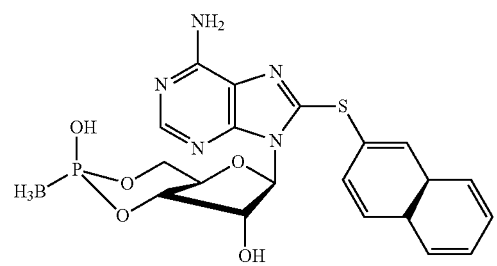 |
| 8-(2-Naphtylthio)adenosine-3',5'-cyclic boranophosphate, Sp-isomer | 056 | Sp-8-NT-cAMPB (056) 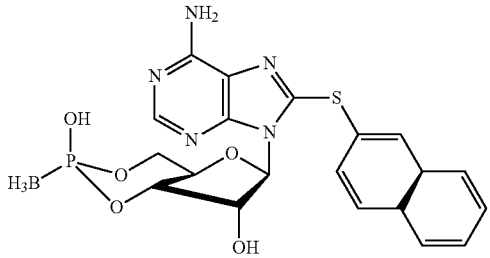 |
| 8-(2-Furyl)adenosine-3',5'-cyclic boranophosphate, Rp-isomer | 057 | 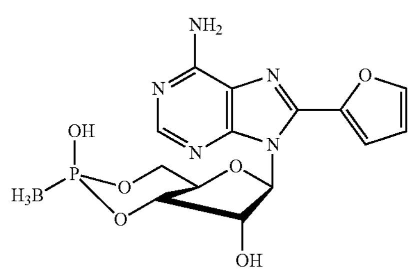 |
| 8-(2-Furyl)adenosine-3',5'-cyclic boranophosphate, Sp-isomer | 058 | Sp-8-Furyl-cAMPB (058) 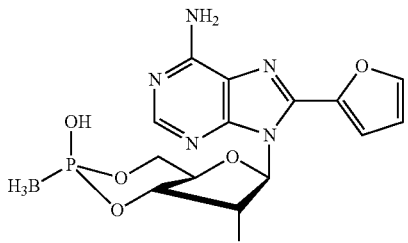 |
| 8-(2-Furyl)adenosine-3',5'-cyclic boranophosphate, Rp-isomer, pivaloyloxymethyl ester | 059 | 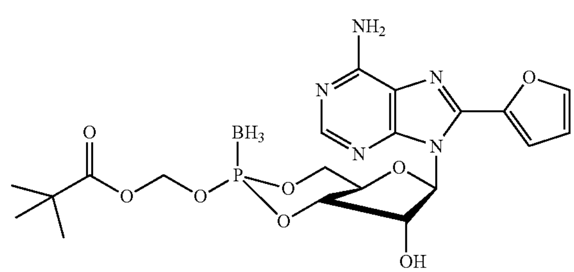 |
| 8-(2-Furyl)adenosine-3',5'-cyclic boranophosphate, Sp-isomer, pivaloyloxymethyl ester | 060 | Rp-8-Furyl-cAMPB-POM (059) 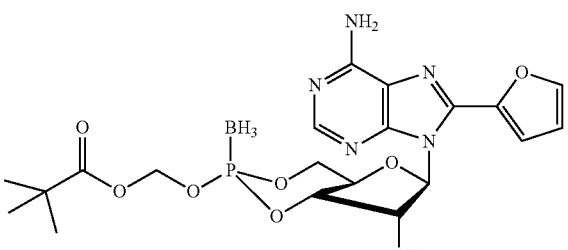 |

TABLE 1-continued

Structures of novel compounds according to the invention.

| Compound | # | Chemical structure |
|---|---|---|
| 8-Phenyladenosine-3',5'-cyclic boranophosphate, Rp-isomer | 061 | 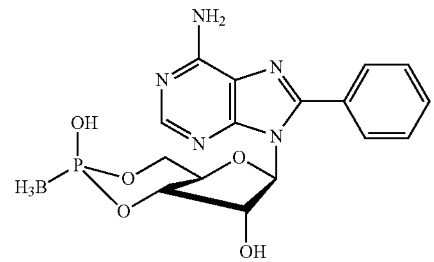 |
| 8-Phenyladenosine-3',5'-cyclic boranophosphate, Sp-isomer | 062 | 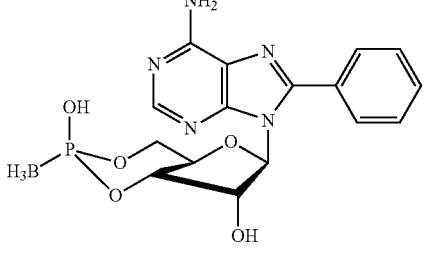 Sp-8-Phe-cAMPB (062) |
| 8-Phenyladenosine-3',5'-cyclic boranophosphate, Rp-isomer, acetoxymethyl ester | 063 | 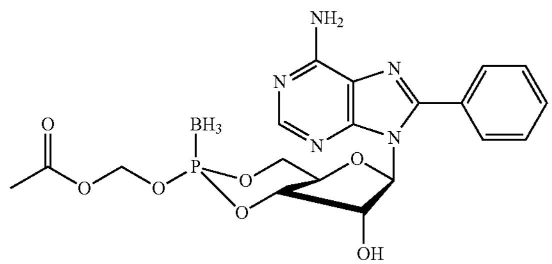 |
| 8-Phenyladenosine-3',5'-cyclic boranophosphate, Sp-isomer, acetoxymethyl ester | 064 | 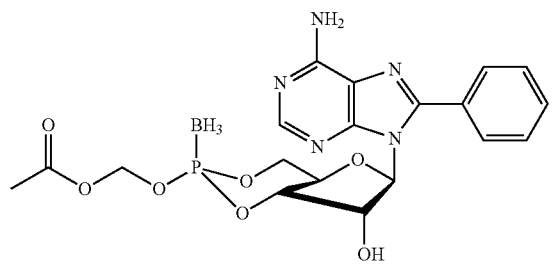 Rp-8-Phe-cAMPB-AM (063) |
| 8-Bromo-2'-O-methyladenosine-3',5'-cyclic boranophosphate, Rp-isomer | 065 | 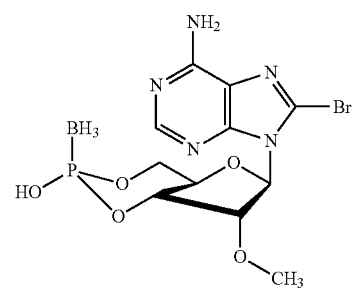 |
| 8-Bromo-2'-O-methyladenosine-3',5'-cyclic boranophosphate, Sp-isomer | 066 | 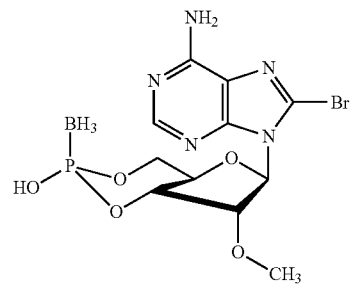 Rp-8-Br-2'-O—Me-cAMPB (065) |
| 8-Bromo-2'-O-methyladenosine-3',5'-cyclic boranophosphate, 2-cyanoethyl ester, Rp-isomer | 067 | 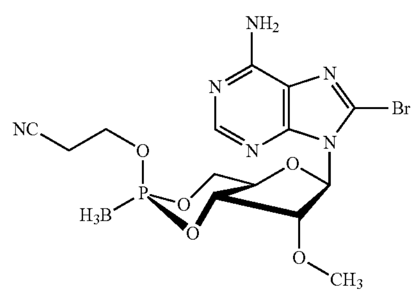 |
| 8-Bromo-2'-O-methyladenosine-3',5'-cyclic boranophosphate, 2-cyanoethyl ester, Sp-isomer | 068 | 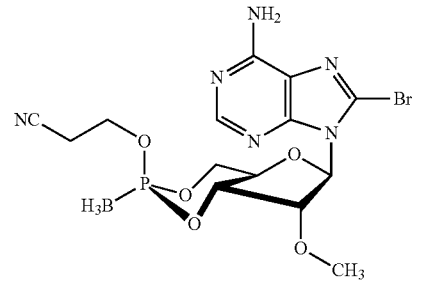 Sp-8-Br-2'-O—Me-cAMPB-CE (68) |
| 8-Hydroxy-2'-O-methyladenosine-3',5'-cyclic boranophosphate, Rp-isomer | 069 | 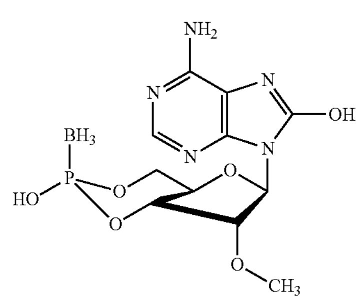 |
| 8-Hydroxy-2'-O-methyladenosine-3',5'-cyclic boranophosphate, Sp-isomer | 070 | 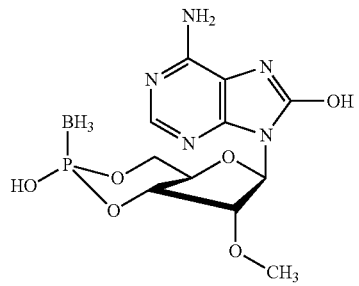 Rp-8-OH-2'-O—Me-cAMPB (69) |

TABLE 1-continued

Structures of novel compounds according to the invention.

| Compound | # | Chemical structure |
|---|---|---|
| 8-Benzylthio-2'-O-methyladenosine-3',5'-cyclic boranophosphate, Rp-isomer | 071 | Rp-8-BT-2'-O—Me-cAMPB (071) |
| 8-Benzylthio-2'-O-methyladenosine-3',5'-cyclic boranophosphate, Sp-isomer | 072 | |
| 8-Benzylthio-2'-O-methyladenosine-3',5'-cyclic boranophosphate, Rp-isomer, acetoxymethyl ester | 073 | Rp-8-BT-2'-O—Me-cAMPB (074) |
| 8-Benzylthio-2'-O-methyladenosine-3',5'-cyclic boranophosphate, Sp-isomer, acetoxymethyl ester | 074 | |
| 8-(4-Chlorophenylthio)-2'-O-methyladenosine-3',5'-cyclic boranophosphate, Rp-isomer | 075 | Rp-8-pCPT-2'-O—Me-cAMPB (075) |
| 8-(4-Chlorophenylthio)-2'-O-methyladenosine-3',5'-cyclic boranophosphate, Sp-isomer | 076 | |
| 8-(4-Chlorophenylthio)-2'-O-methyl-adenosine-3',5'-cyclic boranophosphate, Rp-isomer, acetoxymethyl ester | 077 | Sp-8-pCPT-2'-O—Me-cAMPB (078) |
| 8-(4-Chlorophenylthio)-2'-O-methyl-adenosine-3',5'-cyclic boranophosphate, Sp-isomer, acetoxymethyl ester | 078 | |

TABLE 1-continued

Structures of novel compounds according to the invention.

| Compound | # | Chemical structure |
| --- | --- | --- |
| 8-(4-Methoxyphenylthio)-2'-O-methyladenosine-3',5'-cyclic boranophosphate, Rp-Isomer | 079 | 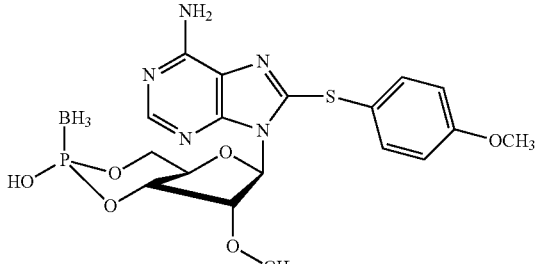<br>Rp-8-pMeOPT-2'-O—Me-cAMPB (079) |
| 8-(4-Methoxyphenylthio)-2'-O-methyladenosine-3',5'-cyclic boranophosphate, Sp-Isomer | 080 | |
| 8-(4-Methoxyphenylthio)-2'-O-methyl-adenosine-3',5'-cyclic boranophosphate, Rp-isomer, acetoxymethyl ester | 081 | 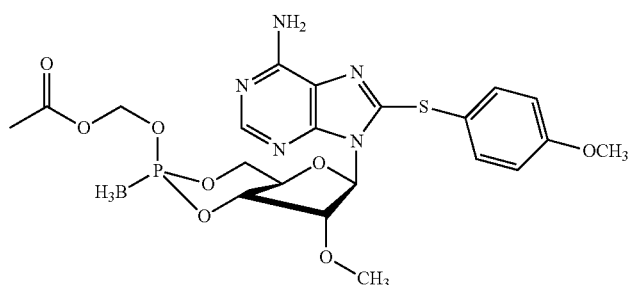<br>Sp-8-pMeOPT-2'-O—Me-cAMPB-AM (082) |
| 8-(4-Methoxyphenylthio)-2'-O-methyl-adenosine-3',5'-cyclic boranophosphate, Sp-isomer, acetoxymethyl ester | 082 | |
| 8-(6-Aminohexylamino)-2'-O-methyl-adenosine-3',5'-cyclic boranophosphate, Rp-isomer; immobilised to agarose | 083 | 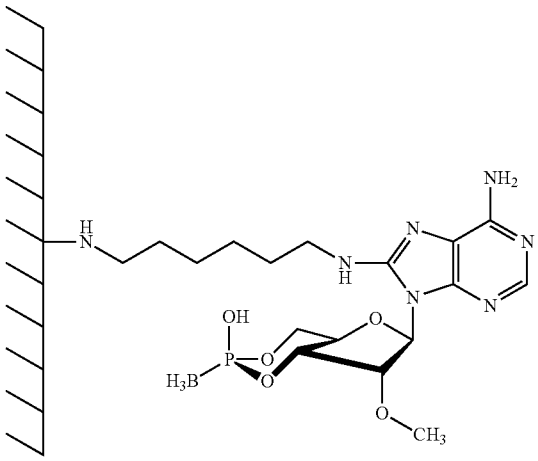<br>Sp-8-AHA-2'-O—Me-cAMPB-Agarose (084) |
| 8-(6-Aminohexylamino)-2'-O-methyl-adenosine-3',5'-cyclic boranophosphate, Sp-isomer; immobilised to agarose | 084 | |
| 2'-O-Methyladenosine-3',5'-cyclic boranophosphate, Rp-isomer | 085 | 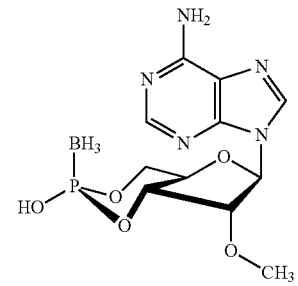<br>Rp-2'-O—Me-cAMPB (085) |
| 2'-O-Methyladenosine-3',5'-cyclic boranophosphate, Sp-isomer | 086 | |

TABLE 1-continued

Structures of novel compounds according to the invention.

| Compound | # | Chemical structure |
|---|---|---|
| 2'-O-Methyladenosine-3',5'-cyclic boranophosphate, 2-cyanoethylester, Rp-isomer | 087 | |
| 2'-O-Methyladenosine-3',5'-cyclic boranophosphate, 2-cyanoethylester, Sp-isomer | 088 | Sp-2'-O—Me-cAMPB-CE (088) |
| 2'-O-Methylinosine-3',5'-cyclic boranophosphate, Rp-isomer | 089 | |
| 2'-O-Methylinosine-3',5'-cyclic boranophosphate, Sp-isomer | 090 | Rp-2'-O—Me-cIMPB (089) |
| 2'-O-Methyl-$N^6$-monobutyryladenosine-3',5'-cyclic boranophosphate, Rp-isomer | 091 | |
| 2'-O-Methyl-$N^6$-monobutyryladenosine-3',5'-cyclic boranophosphate, Sp-isomer | 092 | Rp-2'-O—Me-6-MB-cAMPB (091) |
| Adenosine-3',5'-cyclic boranophosphate, Rp-isomer, acetoxymethyl ester | 093 | |
| Adenosine-3',5'-cyclic boranophosphate, Sp-isomer, acetoxymethyl ester | 094 | Sp-cAMPB-AM (094) |

TABLE 1-continued

Structures of novel compounds according to the invention.

| Compound | # | Chemical structure |
|---|---|---|
| N$^6$-Monobutyryladenosine-3',5'-cyclic boranophosphate, Rp-isomer | 095 | Rp-6-MB-cAMPB (095) |
| N$^6$-Monobutyryladenosine-3',5'-cyclic boranophosphate, Sp-isomer | 096 | |
| N$^6$-,2'-O-Dibutyryladenosine-3',5'-cyclic boranophosphate, Rp-isomer | 097 | Rp-DB-cAMPB (097) |
| N$^6$-,2'-O-Dibutyryladenosine-3',5'-cyclic boranophosphate, Sp-isomer | 098 | |
| N$^6$-,2'-O-Dibutyryladenosine-3',5'-cyclic boranophosphate, Rp-isomer, acetoxymethyl ester | 099 | Sp-DB-cAMPB-AM (100) |
| N$^6$-,2'-O-Dibutyryladenosine-3',5'-cyclic boranophosphate, Sp-isomer, acetoxymethyl ester | 100 | |
| N$^6$-Mono-tert. butylcarbamoyladenosine-3',5'-cyclic boranophosphate, Rp-isomer | 101 | Rp-6-MBC-cAMPB (101) |
| N$^6$-Mono-tert. butylcarbamoyladenosine-3',5'-cyclic boranophosphate, Sp-isomer | 102 | |

TABLE 1-continued

Structures of novel compounds according to the invention.

| Compound | # | Chemical structure |
|---|---|---|
| N⁶-Benzoyladenosine-3',5'-cyclic boranophosphate, Rp-isomer | 103 | 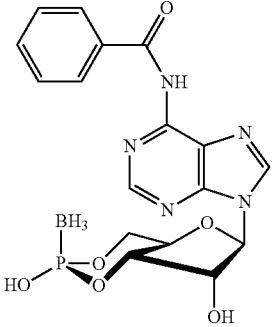 Rp-6-Bnz-cAMPB (103) |
| N⁶-Benzoyladenosine-3',5'-cyclic boranophosphate, Sp-isomer | 104 | |
| N⁶-Benzoyladenosine-3',5'-cyclic boranophosphate, Rp-isomer, acetoxymethyl ester | 105 | 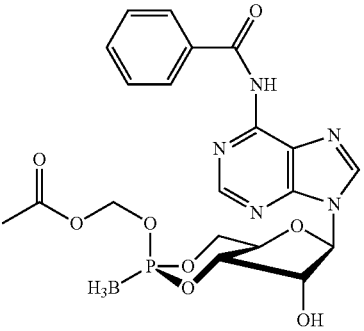 Sp-6-Bnz-cAMPB-AM (106) |
| N⁶-Benzoyladenosine-3',5'-cyclic boranophosphate, Sp-isomer, acetoxymethyl ester | 106 | |
| 2'-O-(N-Methylanthraniloyl)adenosine-3',5'-cyclic boranophosphate, Rp-isomer | 107 | 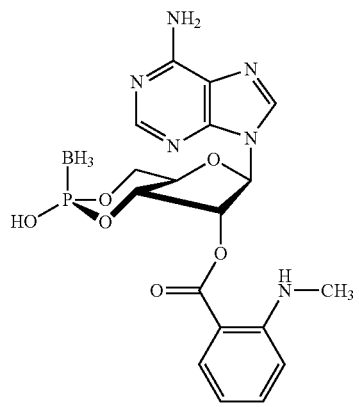 Rp-2'-MANT-cAMPB (107) |
| 2'-O-N-(Methylanthraniloyl)adenosine-3',5'-cyclic boranophosphate, Sp-isomer | 108 | |

TABLE 1-continued

Structures of novel compounds according to the invention.

| Compound | # | Chemical structure |
|---|---|---|
| 2'-O-([Fluoresceinyl]aminohexyl-carbamoyl)adenosine-3',5'-cyclic boranophosphate, Rp-isomer | 109 | 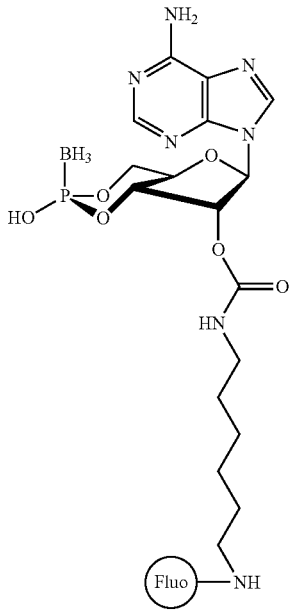 Rp-2'-Fluo-AHC-cAMPB (109) |
| 2'-O-([Fluoresceinyl]aminohexyl-carbamoyl)adenosine-3',5'-cyclic boranophosphate, Sp-isomer | 110 | |
| 2'-O-Monosuccinyladenosine-3',5'-cyclic boranophosphate, Rp-isomer | 111 | 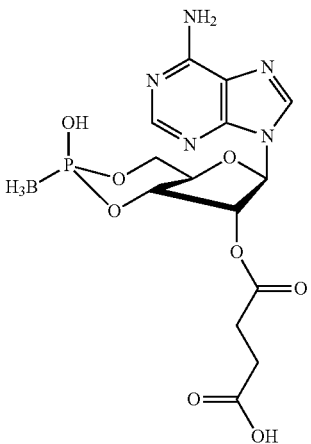 Sp-2'-O-MS-cAMPB (112) |
| 2'-O-Monosuccinyladenosine-3',5'-cyclic boranophosphate, Sp-isomer | 112 | |
| 2'-O-Monosuccinyladenosine-3',5'-cyclic boranophosphate, Rp-isomer, tyrosylmethylester | 113 | 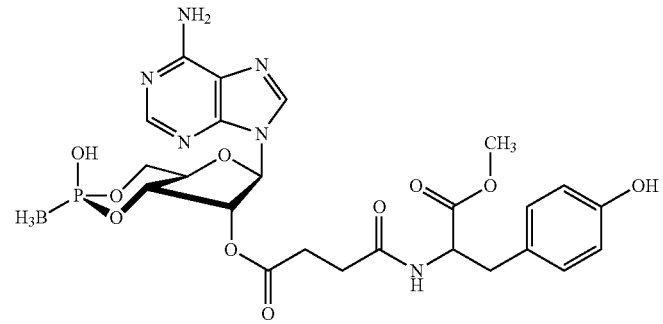 Sp-2'-O-MS-TME-cAMPB (114) |
| 2'-O-Monosuccinyladenosine-3',5'-cyclic boranophosphate, Sp-isomer, tyrosylmethylester | 114 | |

TABLE 1-continued

Structures of novel compounds according to the invention.

| Compound | # | Chemical structure |
|---|---|---|
| 2'-O-(2-Aminoethylcarbamoyl)-adenosine-3',5'-cyclic boranophosphate, Rp-isomer | 115 | |
| 2'-O-(2-Aminoethyl carbamoyl)-adenosine-3',5'-cyclic boranophosphate, Sp-isomer | 116 | Rp-2'-AEC-cAMPB (115) |
| 2'-O-(6-Aminohexylcarbamoyl)-adenosine-3',5'-cyclic boranophosphate, Rp-isomer | 117 | |
| 2'-O-(6-Aminohexylcarbamoyl)-adenosine-3',5'-cyclic boranophosphate, Sp-isomer | 118 | Rp-2'-AHC-cAMPB (117) |

TABLE 1-continued

Structures of novel compounds according to the invention.

| Compound | # | Chemical structure |
|---|---|---|
| 2'-O-(6-Aminohexylcarbamoyl)-adenosine-3',5'-cyclic boranophosphate, Rp-isomer; immobilised to agarose | 119 | 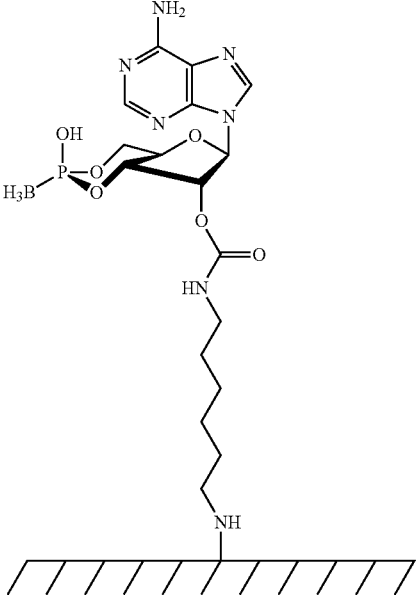<br>Sp-2'-AHC-cAMPB-Agarose (120) |
| 2'-O-(6-Aminohexylcarbamoyl)-adenosine-3',5'-cyclic boranophosphate, Sp-isomer; immobilised to agarose | 120 | |
| 2'-Deoxyadenosine-3',5'-cyclic boranophosphate, Rp-isomer | 121 | 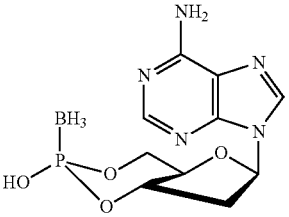<br>Rp-cdAMPB (121) |
| 2'-Deoxyadenosine-3',5'-cyclic boranophosphate, Sp-isomer | 122 | |
| 2'-Deoxyadenosine-3',5'-cyclic boranophosphate, Rp-isomer, acetoxymethyl ester | 123 | 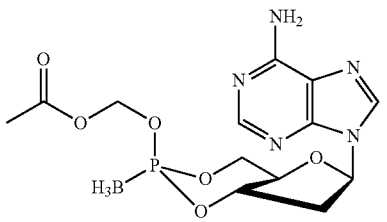<br>Sp-cdAMPB-AM (124) |
| 2'-Deoxyadenosine-3',5'-cyclic boranophosphate, Sp-isomer, acetoxymethyl ester | 124 | |
| 2'-Amino-2'-deoxyadenosine-3',5'-cyclic boranophosphate, Rp-isomer | 125 | 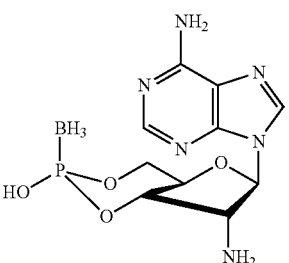<br>Rp-2'-NH$_2$-cAMPB (125) |
| 2'-Amino-2'-deoxyadenosine-3',5'-cyclic boranophosphate, Sp-isomer | 126 | |

TABLE 1-continued

Structures of novel compounds according to the invention.

| Compound | # | Chemical structure |
|---|---|---|
| 2'-Fluoro-2'-deoxyadenosine-3',5'-cyclic boranophosphate, Rp-isomer | 127 | |
| 2'-Fluoro-2'-deoxyadenosine-3',5'-cyclic boranophosphate, Sp-isomer | 128 | 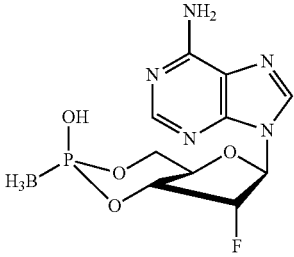 Sp-2'-F-cAMPB (128) |
| 6-Chloropurine-1-β-D-ribofuranoside-3',5'-cyclic boranophosphate, Rp-isomer | 129 | |
| 6-Chloropurine-1-β-D-ribofuranoside-3',5'-cyclic boranophosphate, Sp-isomer | 130 | 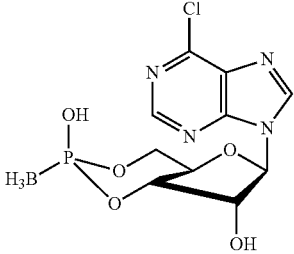 Sp-6-Cl-cPuMPB (130) |
| 6-Chloropurine-1-β-D-ribofuranoside-3',5'-cyclic boranophosphate, 2-cyanoethylester, Rp-isomer | 131 | |
| 6-Chloropurine-1-β-D-ribofuranoside-3',5'-cyclic boranophosphate, 2-cyanoethylester, Sp-isomer | 132 | 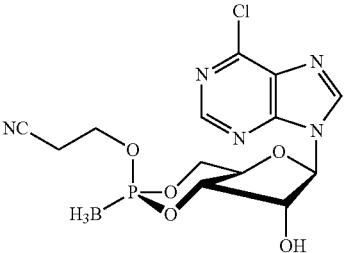 Sp-6-Cl-cPuMP-CE (132) |
| 6-Chloropurine-1-β-D-2'-O-trimethylsilylribofuranoside-3',5'-cyclic boranophosphate, Rp-isomer | 133 | |
| 6-Chloropurine-1-β-D-2'-O-trimethylsilylribofuranoside-3',5'-cyclic boranophosphate, Sp-isomer | 134 | 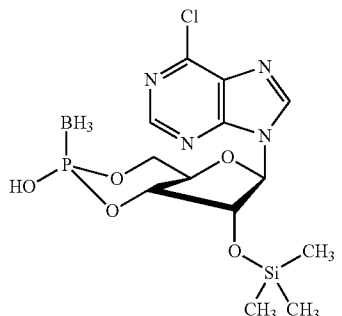 Rp-6-Cl-2'-TMS-cPuMPB (133) |

TABLE 1-continued

Structures of novel compounds according to the invention.

| Compound | # | Chemical structure |
|---|---|---|
| 6-Chloropurine-1-β-D-2'-O-(imidazolylcarbamoyl)ribofuranoside-3',5'-cyclic boranophosphate, Rp-isomer | 135 | |
| 6-Chloropurine-1-β-D-2'-O-(imidazolylcarbamoyl)ribofuranoside-3',5'-cyclic boranophosphate, Sp-isomer | 136 | |

Rp-6-Cl-2'-IC-cPuMPB (135)

| 6-Chloropurine-1-β-D-2'-O-(6-aminohexylcarbamoyl)ribofuranoside-3',5'-cyclic boranophosphate, Rp-isomer | 137 | |
| 6-Chloropurine-1-β-D-2'-O-(6-aminohexylcarbamoyl)ribofuranoside-3',5'-cyclic boranophosphate, Sp-isomer | 138 | |

Rp-2'-AHC-6-Cl-cPuMPB (137)

| Inosine-3',5'-cyclic boranophosphate, Rp-isomer | 139 | |
| Inosine-3',5'-cyclic boranophosphate, Sp-isomer | 140 | |

Sp-cIMPB (140)

TABLE 1-continued

Structures of novel compounds according to the invention.

| Compound | # | Chemical structure |
|---|---|---|
| 6-Methoxypurine-1-β-D-ribofuranoside-3',5'-cyclic boranophosphate, Rp-isomer | 141 | 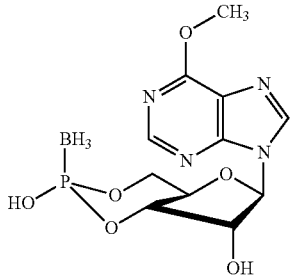<br>Rp-6-MeO-cPuMPB (141) |
| 6-Methoxypurine-1-β-D-ribofuranoside-3',5'-cyclic boranophosphate, Sp-isomer | 142 | |
| 6-Benzyloxypurine-1-β-D-ribofuranosyl-3',5'-cyclic boranophosphate, Rp-isomer | 143 | 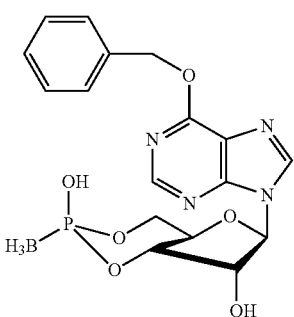<br>Sp-6-BnO-cPuMPB (144) |
| 6-Benzyloxypurine-1-β-D-ribofuranosyl-3',5'-cyclic boranophosphate, Sp-isomer | 144 | |
| $N^6$-(2-Aminoethyl)adenosine-3',5'-cyclic boranophosphate, Rp-isomer | 145 | 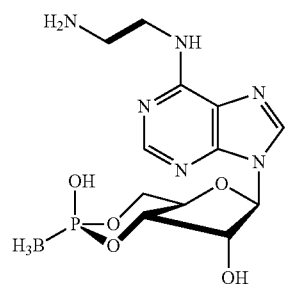<br>Sp-6-AE-cAMPB (146) |
| $N^6$-(2-Aminoethyl)adenosine-3',5'-cyclic boranophosphate, Sp-isomer | 146 | |
| $N^6$-(2-Aminoethyl)adenosine-3',5'-cyclic boranophosphate, Rp-isomer; immobilised to agarose | 147 | 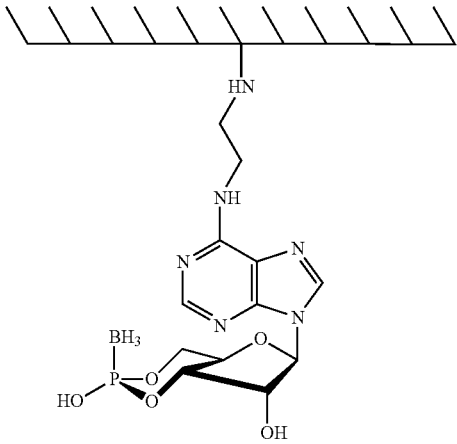<br>Rp-6-AE-cAMPB-Agarose (147) |
| $N^6$-(2-Aminoethyl)adenosine-3',5'-cyclic boranophosphate, Sp-isomer; immobilised to agarose | 148 | |

TABLE 1-continued

Structures of novel compounds according to the invention.

| Compound | # | Chemical structure |
|---|---|---|
| N⁶-(6-Aminohexyl)adenosine-3',5'-cyclic boranophosphate, Rp-isomer | 149 | |
| N⁶-(6-Aminohexyl)adenosine-3',5'-cyclic boranophosphate, Sp-isomer | 150 | Sp-6-AH-cAMPB (150) |
| N⁶,N⁶-Dimethyladenosine-3',5'-cyclic boranophosphate, Rp-isomer | 151 | |
| N⁶,N⁶-Dimethyladenosine-3',5'-cyclic boranophosphate, Sp-isomer | 152 | Rp-6-DMA-cAMPB (151) |
| N⁶,N⁶-Di-n-propyladenosine-3',5'-cyclic boranophosphate, Rp-isomer | 153 | |
| N⁶,N⁶-Di-n-propyladenosine-3',5'-cyclic boranophosphate, Sp-isomer | 154 | Rp-6-DPA-cAMPB (153) |
| N⁶,N⁶-Di-n-propyladenosine-3',5'-cyclic boranophosphate, Rp-isomer, acetoxymethyl ester | 155 | |
| N⁶,N⁶-Di-n-propyladenosine-3',5'-cyclic boranophosphate, Sp-isomer, acetoxymethyl ester | 156 | Sp-6-DPA-cAMPB (156) |

TABLE 1-continued

Structures of novel compounds according to the invention.

| Compound | # | Chemical structure |
| --- | --- | --- |
| N6-Cycloheptyladenosine-3',5'-cyclic boranophosphate, Rp-isomer | 157 | 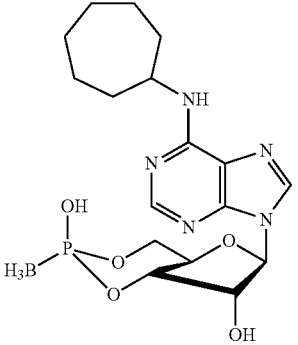<br>Sp-6-CH-cAMPB (158) |
| N6-Cycloheptyladenosine-3',5'-cyclic boranophosphate, Sp-isomer | 158 | |
| N6-Benzyladenosine-3',5'-cyclic boranophosphate, Rp-isomer | 159 | 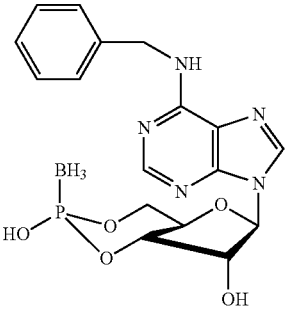<br>Rp-6-Bn-cAMPB (159) |
| N6-Benzyladenosine-3',5'-cyclic boranophosphate, Sp-isomer | 160 | |
| N6-Benzyladenosine-3',5'-cyclic boranophosphate, Rp-isomer, acetoxymethyl ester | 161 | 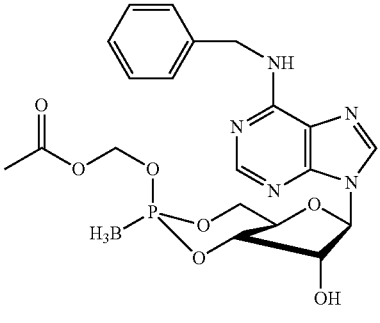<br>Sp-6-Bn-cAMPB-AM (162) |
| N6-Benzyladenosine-3',5'-cyclic boranophosphate, Sp-isomer, acetoxymethyl ester | 162 | |
| N6-Phenyladenosine-3',5'-cyclic boranophosphate, Rp-isomer | 163 | 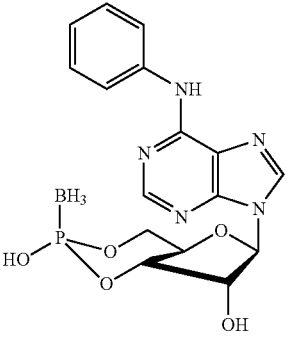<br>Rp-6-Phe-cAMPB (163) |
| N6-Phenyladenosine-3',5'-cyclic boranophosphate, Sp-isomer | 164 | |

TABLE 1-continued

Structures of novel compounds according to the invention.

| Compound | # | Chemical structure |
|---|---|---|
| 8-(4-Chlorophenylthio)-N⁶-phenyl-adenosine-3',5'-cyclic boranophosphate, Rp-isomer | 165 | |
| 8-(4-Chlorophenylthio)-N⁶-phenyl-adenosine-3',5'-cyclic boranophosphate, Sp-isomer | 166 | Sp-8-pCPT-6-Phe-cAMPB (166) |
| 6-Thiopurine-1-β-D-ribo-furanoside-3',5'-cyclic boranophosphate, Rp-isomer | 167 | |
| 6-Thiopurine-1-β-D-ribo-furanoside-3',5'-cyclic boranophosphate, Sp-isomer | 168 | Rp-8-SH-cPuMPB (167) |
| 6-Thiopurine-1-β-D-ribofuranoside-3',5'-cyclic boranophosphate, 2-cyanoethylester, Rp-isomer | 169 | |
| 6-Thiopurine-1-β-D-ribofuranoside-3',5'-cyclic boranophosphate, 2-cyanoethylester, Sp-isomer | 170 | Rp-6-SH-cPuMPB-CE (169) |
| 6-(2-Aminoethylthio)purine-1-β-D-ribofuranosyl-3',5'-cyclic boranophosphate, Rp-isomer | 171 | |
| 6-(2-Aminoethylthio)purine-1-β-D-ribofuranosyl-3',5'-cyclic boranophosphate, Sp-isomer | 172 | Rp-6-AET-cPuMPB (171) |

TABLE 1-continued

Structures of novel compounds according to the invention.

| Compound | # | Chemical structure |
|---|---|---|
| 6-Phenylthiopurine-1-β-D-ribofuranoside-3',5'-cyclic boranophosphate, Rp-isomer | 173 | 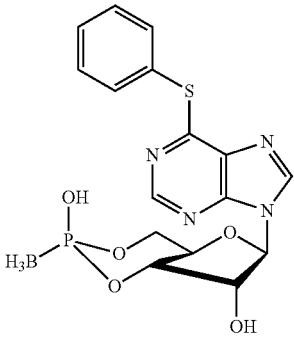 Sp-6-PT-cPuMPB (174) |
| 6-Phenylthiopurine-1-β-D-ribofuranoside-3',5'-cyclic boranophosphate, Sp-isomer | 174 | |
| 6-Phenylpurine-1-β-D-ribofuranoside-3',5'-cyclic boranophosphate, Rp-isomer | 175 | 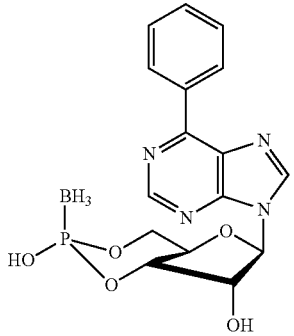 Rp-6-Phe-cPuMPB (175) |
| 6-Phenylpurine-1-β-D-ribofuranoside-3',5'-cyclic boranophosphate, Sp-isomer | 176 | |
| 6-(N,N-Dimethylaminocarbonyl)purine-1-β-D-ribofuranoside-3',5'-cyclic boranophosphate, Rp-isomer | 177 | 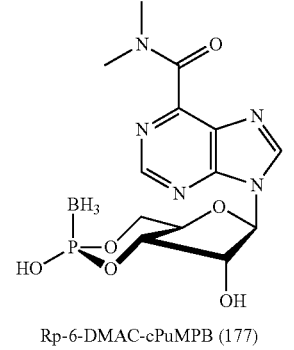 Rp-6-DMAC-cPuMPB (177) |
| 6-(N,N-Dimethylaminocarbonyl)purine-1-β-D-ribofuranoside-3',5'-cyclic boranophosphate, Sp-isomer | 178 | |
| 6-Azidopurine-1-β-D-ribofuranoside-3',5'-cyclic borano-phosphate, Rp-isomer | 179 | 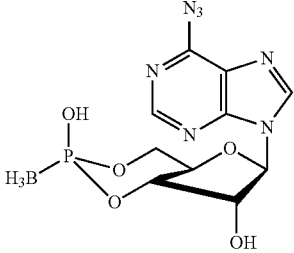 Sp-6-N$_3$-cPuMPB (180) |
| 6-Azidopurine-1-β-D-ribofuranoside-3',5'-cyclic borano-phosphate, Sp-isomer | 180 | |

TABLE 1-continued

Structures of novel compounds according to the invention.

| Compound | # | Chemical structure |
|---|---|---|
| Purine-1-β-D-ribofuranoside-3',5'-cyclic boranophosphate, Rp-isomer | 181 | 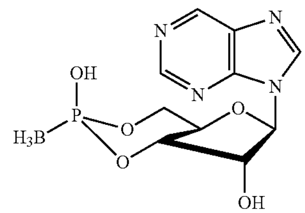 |
| Purine-1-β-D-ribofuranoside-3',5'-cyclic boranophosphate, Sp-isomer | 182 | Sp-cPuMPB (182) |
| 2-Chloroadenosine-3',5'-cyclic boranophosphate, Rp-isomer | 183 | 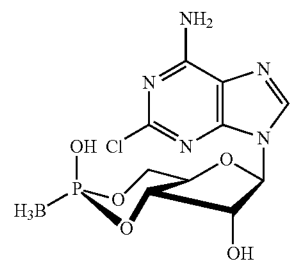 |
| 2-Chloroadenosine-3',5'-cyclic boranophosphate, Sp-isomer | 184 | Sp-2-Cl-cAMPB (184) |
| 2-Chloroadenosine-3',5'-cyclic boranophosphate, 2-cyanoethyl ester, Rp-isomer | 185 | 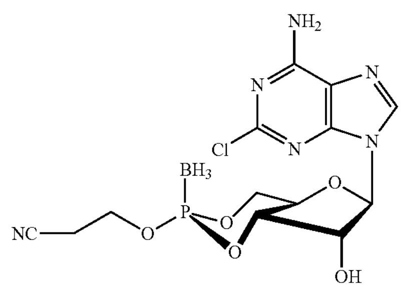 |
| 2-Chloroadenosine-3',5'-cyclic boranophosphate, 2-cyanoethyl ester, Sp-isomer | 186 | Rp-2-Cl-cAMPB-CE (185) |
| 2-(2-Aminoethylamino)adenosine-3',5'-cyclic boranophosphate, Rp-isomer | 187 | 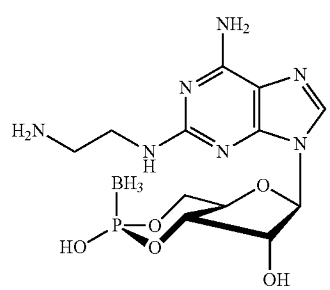 |
| 2-(2-Aminoethylamino)adenosine-3',5'-cyclic boranophosphate, Sp-isomer | 188 | Rp-2-AEA-cAMPB (187) |
| 2-(6-Aminohexyl)adenosine-3',5'-cyclic boranophosphate, Rp-isomer | 189 | 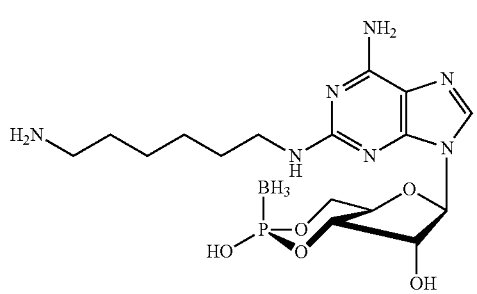 |
| 2-(6-Aminohexyl)adenosine-3',5'-cyclic boranophosphate, Sp-isomer | 190 | Rp-2-AHA-cAMPB (189) |

TABLE 1-continued

Structures of novel compounds according to the invention.

| Compound | # | Chemical structure |
|---|---|---|
| 2-(6-Aminohexylamino)-adenosine-3',5'-cyclic boranophosphate, Rp-isomer; immobilised to agarose | 191 | 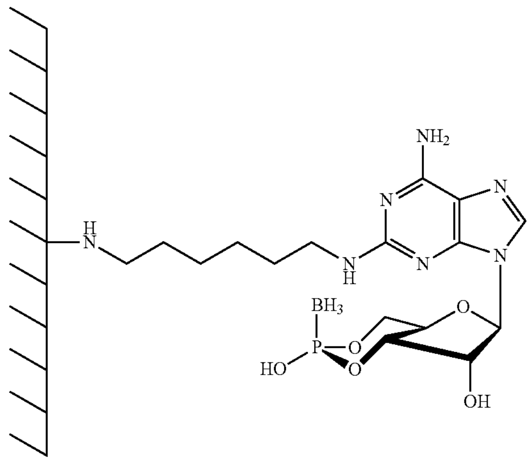 |
| 2-(6-Aminohexylamino)-adenosine-3',5'-cyclic boranophosphate, Sp-isomer; immobilised to agarose | 192 | Rp-2-AHA-cAMPB-Agarose (191) |
| 2-N,N-Diethylaminoadenosine-3',5'-cyclic boranophosphate, Rp-isomer | 193 | 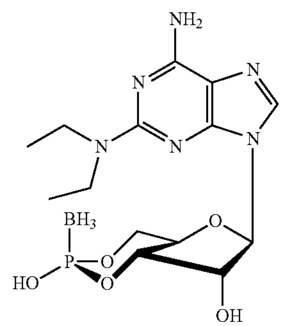 |
| 2-N,N-Diethylaminoadenosine-3',5'-cyclic boranophosphate, Sp-isomer | 194 | Rp-2-DEA-cAMPB (193) |
| 2-Thioadenosine-3',5'-cyclic boranophosphate, Rp-isomer | 195 | 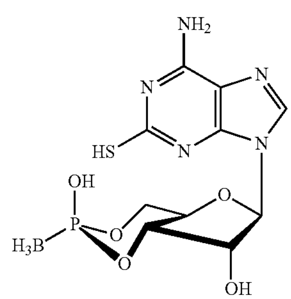 |
| 2-Thioadenosine-3',5'-cyclic boranophosphate, Sp-isomer | 196 | Sp-2-SH-cAMPB (196) |
| 2-(2-Hydroxyethylthioadenosine-3',5'-cyclic boranophosphate, Rp-isomer 2- | 197 | 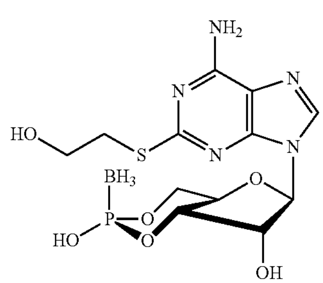 |
| 2-(2-Hydroxyethylthioadenosine-3',5'-cyclic boranophosphate, Sp-isomer- | 198 | Rp-2-HET-cAMPB (197) |

TABLE 1-continued

Structures of novel compounds according to the invention.

| Compound | # | Chemical structure |
|---|---|---|
| 2-Chloro-8-methylaminoadenosine-3',5'-cyclic boranophosphate, Rp-isomer | 199 | 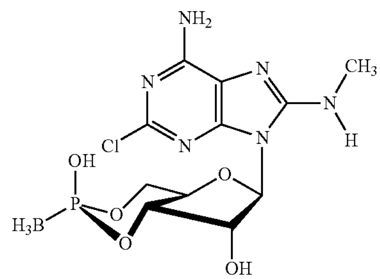 |
| 2-Chloro-8-methylaminoadenosine-3',5'-cyclic boranophosphate, Sp-isomer | 200 | Sp-2-Cl-8-MA-cAMPB (200) |
| 2-Chloro-8-hexylaminoadenosine-3',5'-cyclic boranophosphate, Rp-isomer | 201 | 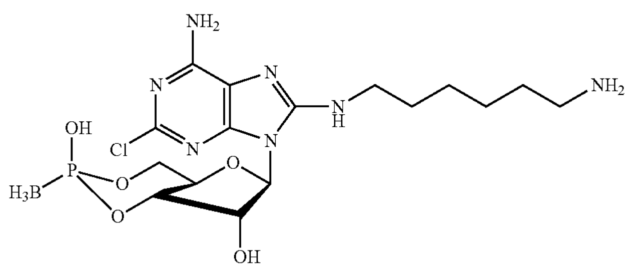 |
| 2-Chloro-8-hexylaminoadenosine-3',5'-cyclic boranophosphate, Sp-isomer | 202 | Sp-2-Cl-8-AHA-cAMPB (202) |
| Guanosine-3',5'-cyclic boranophosphate, Rp-isomer | 203 | 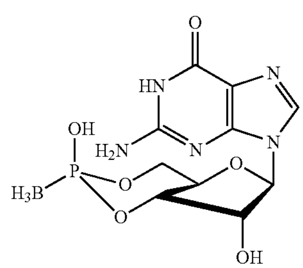 |
| Guanosine-3',5'-cyclic boranophosphate, Sp-isomer | 204 | Sp-cGMPB (204) |
| Guanosine-3',5'-cyclic boranophosphate, Rp-isomer, acetoxymethyl ester | 205 | 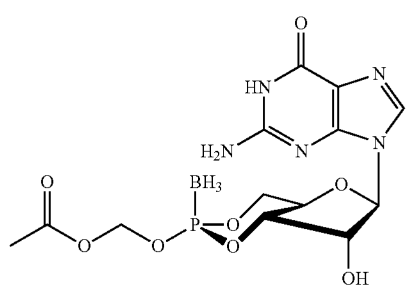 |
| Guanosine-3',5'-cyclic boranophosphate, Sp-isomer, acetoxymethyl ester | 206 | Rp-cGMPB-AM (205) |

TABLE 1-continued

Structures of novel compounds according to the invention.

| Compound | # | Chemical structure |
|---|---|---|
| 2'-O-Monosuccinylguanosine-3',5'-cyclic boranophosphate, Rp-isomer | 207 | |
| 2'-O-Monosuccinylguanosine-3',5'-cyclic boranophosphate, Sp-isomer | 208 | Sp-2'-O-MS-cGMPB (208) |
| 2'-O-Monosuccinylguanosine-3',5'-cyclic boranophosphate, Rp-isomer, tyrosylmethylester | 209 | |
| 2'-O-Monosuccinylguanosine-3',5'-cyclic boranophosphate, Sp-isomer, tyrosylmethylester | 210 | Rp-2'-O-MS-TME-cGMPB (209) |
| 2'-O-(2-Aminoethylcarbamoyl)guanosine-3',5'-cyclic boranophosphate, Rp-isomer | 211 | |
| 2'-O-(2-Aminoethylcarbamoyl)guanosine-3',5'-cyclic boranophosphate, Sp-isomer | 212 | Sp-2'-AEC-cGMPB (212) |

TABLE 1-continued

Structures of novel compounds according to the invention.

| Compound | # | Chemical structure |
|---|---|---|
| 2'-O-(6-Aminohexylcarbamoyl)guanosine-3',5'-cyclic boranophosphate, Rp-isomer | 213 | 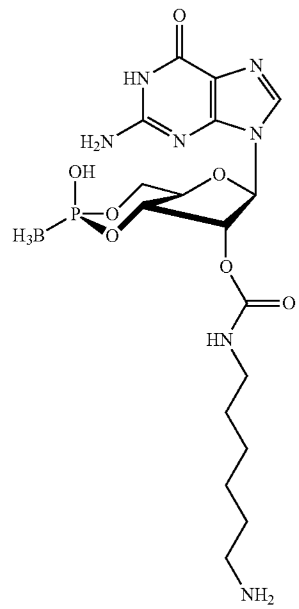 |
| 2'-O-(6-Aminohexylcarbamoyl)guanosine-3',5'-cyclic boranophosphate, Sp-isomer | 214 | Sp-2'-AHC-cGMPB (214) |
| 2'-O-([Fluoresceinyl]aminohexyl-carbamoyl)guanosine-3',5'-cyclic boranophosphate, Rp-isomer | 215 | 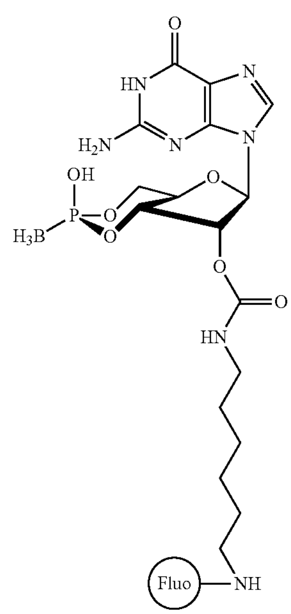 |
| 2'-O-([Fluoresceinyl]aminohexyl-carbamoyl)guanosine-3',5'-cyclic boranophosphate, Sp-isomer | 216 | Sp-2'-Fluo-AHC-cGMPB (216) |

TABLE 1-continued

Structures of novel compounds according to the invention.

| Compound | # | Chemical structure |
|---|---|---|
| 2'-O-(6-Aminohexylcarbamoyl)guanosine-3',5'-cyclic boranophosphate, Rp-isomer; immobilised to agarose | 217 | 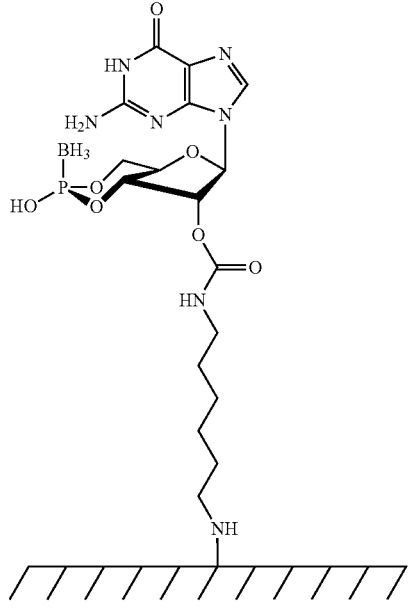 Rp-2'-AHC-cAMPB-Agarose (217) |
| 2'-O-(6-Aminohexylcarbamoyl)guanosine-3',5'-cyclic boranophosphate, Sp-isomer; immobilised to agarose | 218 | |
| 8-Bromoguanosine-3',5'-cyclic boranophosphate, Rp-isomer | 219 |  Sp-8-Br-cGMPB (220) |
| 8-Bromoguanosine-3',5'-cyclic boranophosphate, Sp-isomer | 220 | |
| 8-Bromoguanosine-3',5'-cyclic boranophosphate, 2-cyanoethyl ester, Rp-isomer | 221 |  Sp-8-Br-cGMPB-CE (222) |
| 8-Bromoguanosine-3',5'-cyclic boranophosphate, 2-cyanoethyl ester, Sp-isomer | 222 | |

TABLE 1-continued

Structures of novel compounds according to the invention.

| Compound | # | Chemical structure |
|---|---|---|
| 8-Bromo-2'-O-(imidazoylcarbamoyl)-guanosine-3',5'-cyclic boranophosphate, Rp-isomer | 223 | |
| 8-Bromo-2'-O-(imidazoylcarbamoyl)-guanosine-3',5'-cyclic boranophosphate, Sp-isomer | 224 | Rp-8-Br-2'-IC-cGMPB (223) |
| 2'-O-(8-Amino-3,6-dioxaoctylcarbamoyl)-8-bromoguanosine-3',5'-cyclic boranophosphate, Rp-isomer | 225 | |
| 2'-O-(8-Amino-3,6-dioxaoctylcarbamoyl)-8-bromoguanosine-3',5'-cyclic boranophosphate, Sp-isomer | 226 | Sp-2'-ADOC-8-Br-cGMPB (226) |
| 2'-O-(8-Amino-3,6-dioxaoctylcarbamoyl)-8-bromoguanosine-3',5'-cyclic boranophosphate, Rp-isomer, immobilised to agarose | 227 | |
| 2'-O-(8-Amino-3,6-dioxaoctylcarbamoyl)-8-bromoguanosine-3',5'-cyclic boranophosphate, Sp-isomer, immobilised to agarose | 228 | Sp-2'-ADOC-8-Br-cGMPB-Agarose (228) |

TABLE 1-continued

Structures of novel compounds according to the invention.

| Compound | # | Chemical structure |
|---|---|---|
| 2'-O-(8-[Tetramethylrhodaminyl]amino-3,6-dioxaoctylcarbamoyl)-8-bromo-guanosine-3',5'-cyclic boranophosphate, Rp-isomer | 229 | 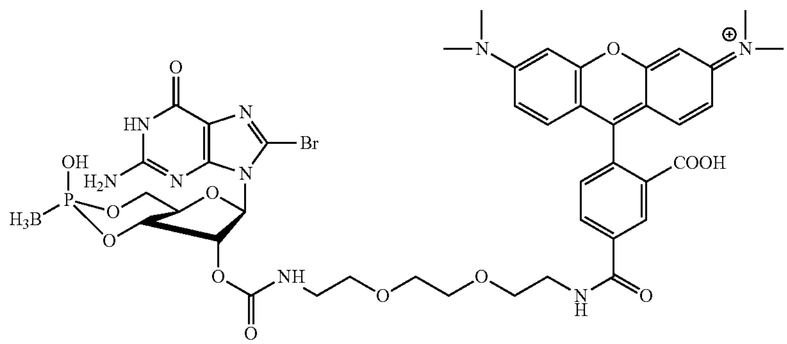 |
| 2'-O-(8-[Tetramethylrhodaminyl]amino-3,6-dioxaoctylcarbamoyl)-8-bromo-guanosine-3',5'-cyclic boranophosphate, Sp-isomer | 230 | Sp-2'-TAMRA-ADOC-8-Br-cGMPB (230) |
| 2'-O-N-(Methylanthraniloyl)guanosine-3',5'-cyclic boranophosphate, Rp-isomer | 231 | 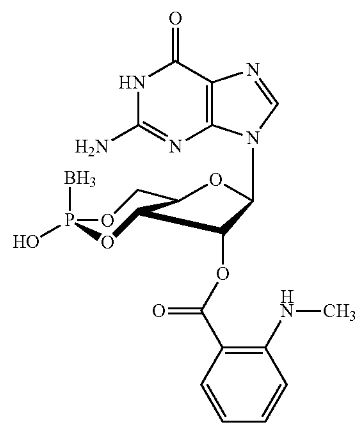 |
| 2'-O-(N-Methylanthraniloyl)guanosine-3',5'-cyclic boranophosphate, Sp-isomer | 232 | Rp-2'-MANT-cGMPB (231) |
| 8-Nitroguanosine-3',5'-cyclic boranophosphate, Rp-isomer | 233 | 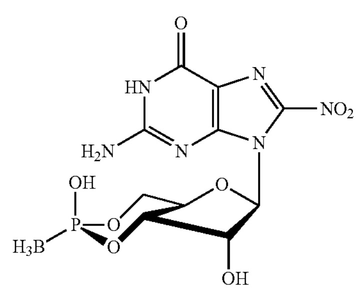 |
| 8-Nitroguanosine-3',5'-cyclic boranophosphate, Sp-isomer | 234 | Sp-8-NO$_2$-cGMPB (234) |
| 8-(2-Aminoethylthio)guanosine-3',5'-cyclic boranophosphate, Rp-isomer | 235 | 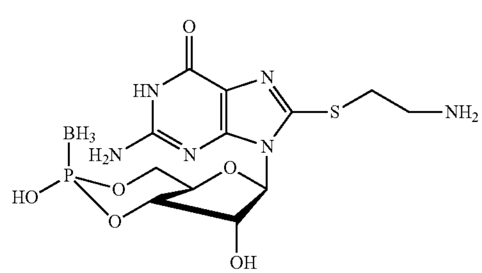 |
| 8-(2-Aminoethylthio)guanosine-3',5'-cyclic boranophosphate, Sp-isomer | 236 | Rp-8-AET-cGMPB (235) |

TABLE 1-continued

Structures of novel compounds according to the invention.

| Compound | # | Chemical structure |
|---|---|---|
| 8-(2-Aminoethylthio)guanosine-3',5'-cyclic boranophosphate, Rp-isomer; immobilised to agarose | 237 | 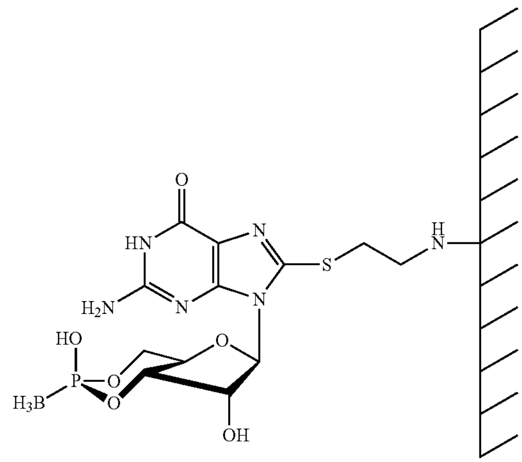 |
| 8-(2-Aminoethylthio)guanosine-3',5'-cyclic boranophosphate, Sp-isomer; immobilised to agarose | 238 | Sp-8-AET-cGMPB-Agarose (238) |
| 8-(6-Aminohexylamino)guanosine-3',5'-cyclic boranophosphate, Rp-isomer | 239 | 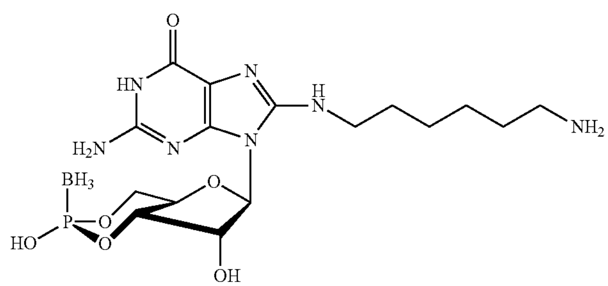 |
| 8-(6-Aminohexylamino)guanosine-3',5'-cyclic boranophosphate, Sp-isomer | 240 | Rp-8-AHA-cGMPB (239) |
| 8-(4-Chlorophenylthio)guanosine-3',5'-cyclic boranophosphate, Rp-isomer | 241 | 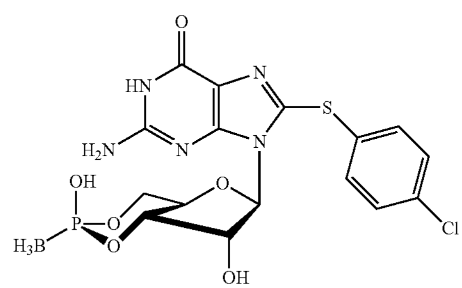 |
| 8-(4-Chlorophenylthio)guanosine-3',5'-cyclic boranophosphate, Sp-isomer | 242 | Sp-8-pCPT-cGMPB (242) |
| 8-(4-Chlorophenylthio)guanosine-3',5'-cyclic boranophosphate, Rp-isomer, acetoxymethyl ester | 243 | 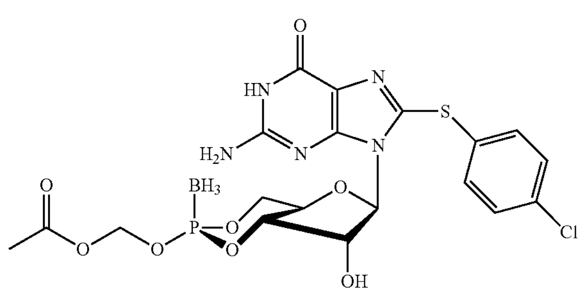 |
| 8-(4-Chlorophenylthio)guanosine-3',5'-cyclic boranophosphate, Sp-isomer, acetoxymethyl ester | 244 | Rp-8-pCPT-cGMPB-AM (243) |

TABLE 1-continued

Structures of novel compounds according to the invention.

| Compound | # | Chemical structure |
|---|---|---|
| 2-(6-Aminohexyl)guanosine-3',5'-cyclic boranophosphate, Rp-isomer; immobilised to agarose | 245 | Rp-2-AH-cGMPB-Agarose (245) |
| 2-(6-Aminohexyl)guanosine-3',5'-cyclic boranophosphate, Sp-isomer; immobilised to agarose | 246 | |
| 8-Phenylguanosine-3',5'-cyclic boranophosphate, Rp-isomer | 247 | Sp-8-Phe-cGMPB (248) |
| 8-Phenylguanosine-3',5'-cyclic boranophosphate, Sp-isomer | 248 | |
| 2-Aminopurine-1-β-D-ribofuranoside-3',5'-cyclic boranophosphate, Rp-isomer | 249 | Rp-2-NH$_2$-cPuMPB (249) |
| 2-Aminopurine-1-β-D-ribofuranoside-3',5'-cyclic boranophosphate, Sp-isomer | 250 | |
| Xanthosine-3',5'-cyclic boranophosphate, Rp-isomer | 251 | Rp-cXMPB (251) |
| Xanthosine-3',5'-cyclic boranophosphate, Sp-isomer | 252 | |

TABLE 1-continued

Structures of novel compounds according to the invention.

| Compound | # | Chemical structure |
|---|---|---|
| Xanthosine-3',5'-cyclic boranophosphate, Rp-isomer, acetoxymethyl ester | 253 | 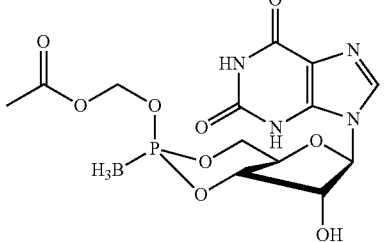<br>Sp-cXMPB-AM (254) |
| Xanthosine-3',5'-cyclic boranophosphate, Sp-isomer, acetoxymethyl ester | 254 | |
| 2'-Deoxyguanosine-3',5'-cyclic boranophosphate, Rp-isomer | 255 | 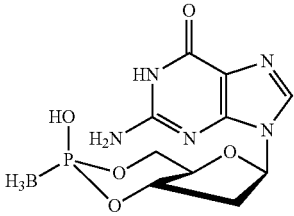<br>Sp-cdGMPB (256) |
| 2'-Deoxyguanosine-3',5'-cyclic boranophosphate, Sp-isomer | 256 | |
| 2'-Deoxyguanosine-3',5'-cyclic borano-phosphate, Rp-isomer, acetoxymethyl ester | 257 | 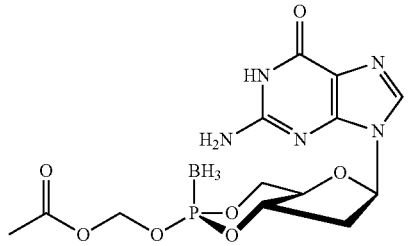<br>Rp-cdGMP-AM (257) |
| 2'-Deoxyguanosine-3',5'-cyclic borano-phosphate, Sp-isomer, acetoxymethyl ester | 258 | |
| Cytidine-3',5'-cyclic boranophosphate, Rp-isomer | 259 | 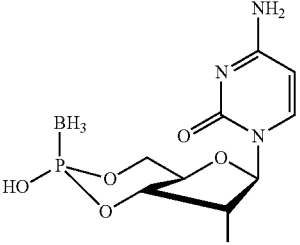<br>Rp-cCMPB (259) |
| Cytidine-3',5'-cyclic boranophosphate, Sp-isomer | 260 | |
| Cytidine-3',5'-cyclic boranophosphate, 2-cyanoethyl ester, Rp-isomer | 261 | 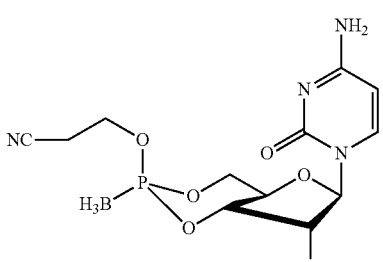<br>Sp-cCMPB-CE (262) |
| Cytidine-3',5'-cyclic boranophosphate, 2-cyanoethyl ester, Sp-isomer | 262 | |

TABLE 1-continued

Structures of novel compounds according to the invention.

| Compound | # | Chemical structure |
|---|---|---|
| Cytidine-3',5'-cyclic boranophosphate, Rp-isomer, acetoxymethyl ester | 263 | |
| Cytidine-3',5'-cyclic boranophosphate, Sp-isomer, acetoxymethyl ester | 264 | Rp-cCMPB-AM (263) |
| 2'-O-(Imidazolylcarbamoyl)cytidine-3',5'-cyclic boranophosphate, Rp-isomer | 265 | |
| 2'-O-(Imidazolylcarbamoyl)cytidine-3',5'-cyclic boranophosphate, Sp-isomer | 266 | Sp-2'-IC-cCMPB (266) |
| 2'-O-(4-Aminobutylaminocarbamoyl)-cytidine-3',5'-cyclic boranophosphate, Rp-isomer | 267 | |
| 2'-O-(4-Aminobutylaminocarbamoyl)-cytidine-3',5'-cyclic boranophosphate, Sp-isomer | 268 | Rp-2'-ABC-cCMPB (267) |

TABLE 1-continued

Structures of novel compounds according to the invention.

| Compound | # | Chemical structure |
|---|---|---|
| 2'-O-(4-Aminobutylaminocarbamoyl)-cytidine-3',5'-cyclic boranophosphate, Rp-isomer; immobilised to agarose | 269 | 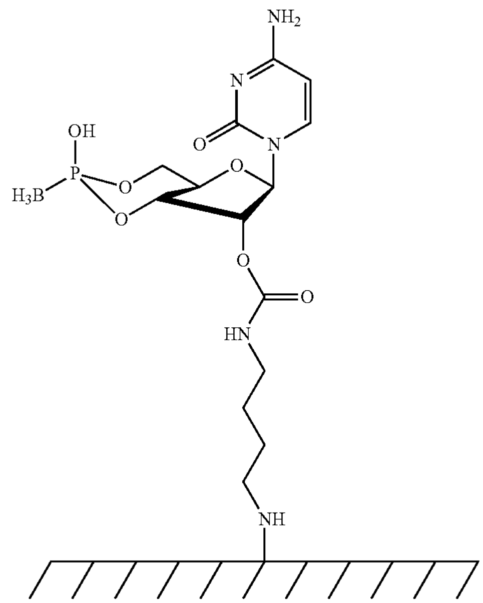 |
| 2'-O-(4-Aminobutylaminocarbamoyl)-cytidine-3',5'-cyclic boranophosphate, Sp-isomer; immobilised to agarose | 270 | 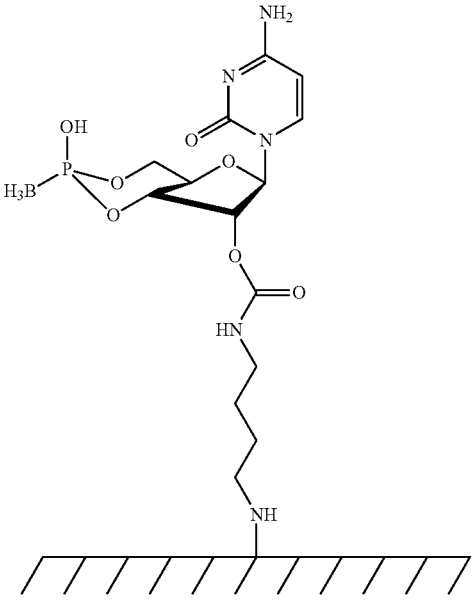<br>Sp-2'-ABC-cCMPB-Agarose (270) |
| 2'-(N-Methylanthraniloyl)cytidine-3',5'-cyclic boranophosphate, Rp-isomer | 271 | 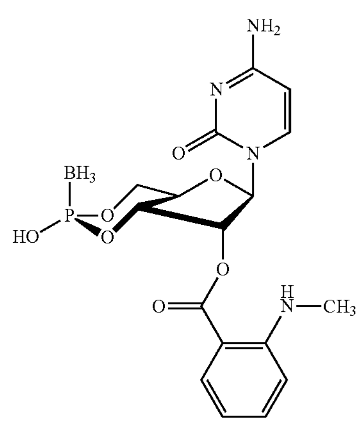 |
| 2'-(N-Methylanthraniloyl)cytidine-3',5'-cyclic boranophosphate, Sp-isomer | 272 | 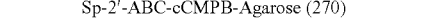<br>Rp-2'-MANT-cCMPB (271) |

TABLE 1-continued

Structures of novel compounds according to the invention.

| Compound | # | Chemical structure |
|---|---|---|
| 2'-O-(6-Carboxypentylcarbamoyl)cytidine-3',5'-cyclic boranophosphate, Rp-isomer | 273 | 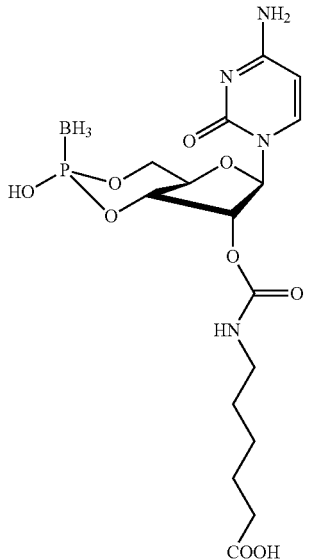<br>Rp-2'-CPC-cCMPB (273) |
| 2'-O-(6-Carboxypentylcarbamoyl)cytidine-3',5'-cyclic boranophosphate, Sp-isomer | 274 | |
| Uridine-3',5'-cyclic boranophosphate, Rp-isomer | 275 | 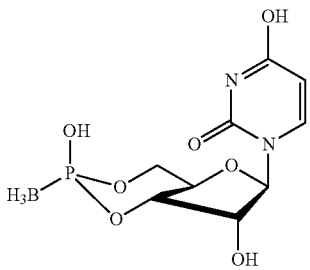<br>Sp-cUMPB (276) |
| Uridine-3',5'-cyclic boranophosphate, Sp-isomer | 276 | |
| Uridine-3',5'-cyclic boranophosphate, Rp-isomer, acetoxymethyl ester | 277 | 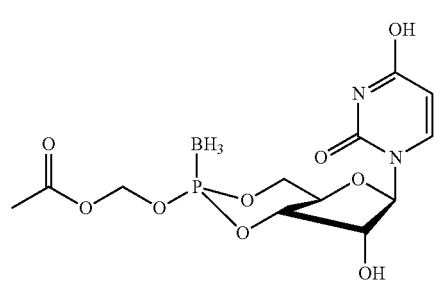<br>Rp-cUMPB-AM (277) |
| Uridine-3',5'-cyclic boranophosphate, Sp-isomer, acetoxymethyl ester | 278 | |
| 7-Deazaadenosine-3',5'-cyclic boranophosphate, Rp-isomer | 279 | 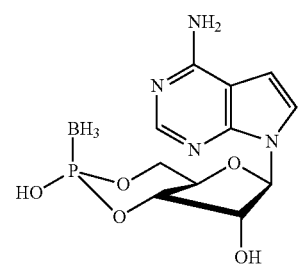<br>Rp-7-CH-cAMPB (279) |
| 7-Deazaadenosine-3',5'-cyclic boranophosphate, Sp-isomer | 280 | |

TABLE 1-continued

Structures of novel compounds according to the invention.

| Compound | # | Chemical structure |
|---|---|---|
| 7-Deazaadenosine-3',5'-cyclic borano-phosphate, Rp-isomer, acetoxymethyl ester | 281 | 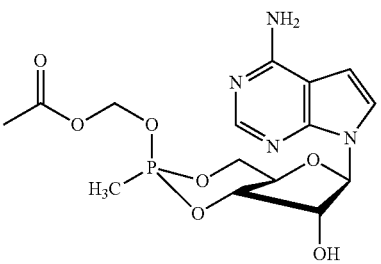 |
| 7-Deazaadenosine-3',5'-cyclic borano-phosphate, Sp-isomer, acetoxymethyl ester | 282 | Sp-7-CH-cAMPB-AM (282) |
| 7-Deazaguanosine-3',5'-cyclic boranophosphate, Rp-isomer | 283 | 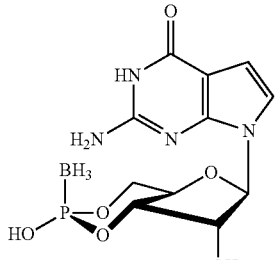 |
| 7-Deazaguanosine-3',5'-cyclic boranophosphate, Sp-isomer | 284 | Rp-7-CH-cGMPB (283) |
| Adenosine-1-N-oxide-3',5'-cyclic boranophosphate, Rp-isomer | 285 | 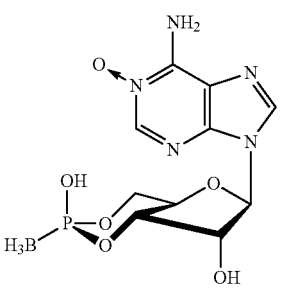 |
| Adenosine-1-N-oxide-3',5'-cyclic boranophosphate, Sp-isomer | 286 | Sp-1-NO-cAMPB (286) |
| 1,N$^6$-Ethenoadenosine-3',5'-cyclic boranophosphate, Rp-isomer | 287 | 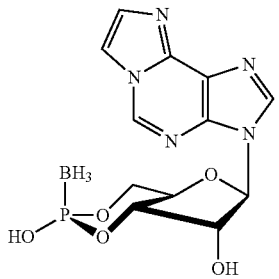 |
| 1,N$^6$-Ethenoadenosine-3',5'-cyclic boranophosphate, Sp-isomer | 288 | Rp-ε-cAMPB (287) |

TABLE 1-continued

Structures of novel compounds according to the invention.

| Compound | # | Chemical structure |
|---|---|---|
| 1,N6-Ethenoadenosine-3',5'-cyclic boranophosphate, Rp-isomer, acetoxymethyl ester | 289 | 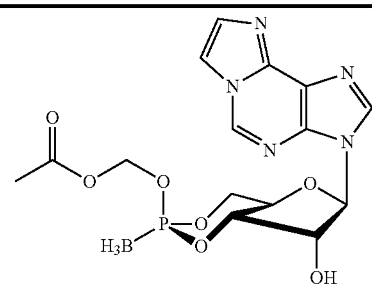 |
| 1,N6-Ethenoadenosine-3',5'-cyclic boranophosphate, Sp-isomer, acetoxymethyl ester | 290 | Sp-ε-cAMPB-AM (290) |
| 8-Azido-1,N6-ethenoadenosine-3',5'-cyclic boranophosphate, Rp-isomer | 291 | 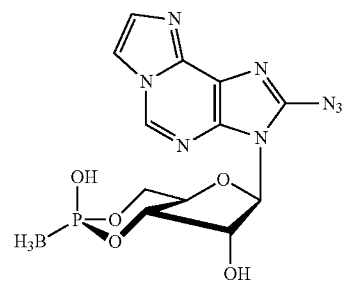 |
| 8-Azido-1,N6-ethenoadenosine-3',5'-cyclic boranophosphate, Sp-isomer | 292 | Sp-8-N3-ε-cAMPB (292) |
| 8-Bromo-β-phenyl-1,N6-etheno-guanosine-3',5'-cyclic boranophosphate, Rp-isomer | 293 | 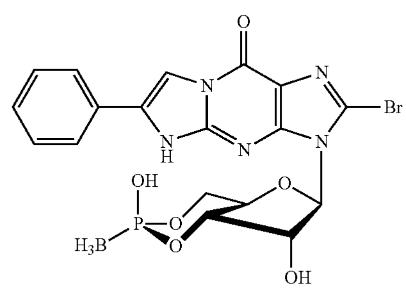 |
| 8-Bromo-β-phenyl-1,N6-etheno-guanosine-3',5'-cyclic boranophosphate, Sp-isomer | 294 | Sp-8-Br-PET-cGMPB (294) |
| 4-Nitrobenzimidazole-1-β-D-ribofuranoside-3',5'-cyclic boranophosphate, Rp-isomer | 295 | |
| 4-Nitrobenzimidazole-1-β-D-ribofuranoside-3',5'-cyclic boranophosphate, Sp-isomer | 296 | Rp-4-NO2-cBIMPB (295) |
| 5,6-Dimethylbenzimidazole-1-β-D-ribofuranoside-3',5'-cyclic boranophosphate, Rp-isomer | 297 | 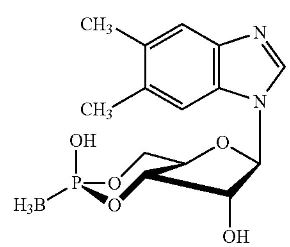 |
| 5,6-Dimethylbenzimidazole-1-β-D-ribofuranoside-3',5'-cyclic boranophosphate, Sp-isomer | 298 | Sp-5,6-DM-cBIMPB (298) |

TABLE 1-continued

Structures of novel compounds according to the invention.

| Compound | # | Chemical structure |
|---|---|---|
| 5,6-Dimethylbenzimidazole-1-β-D-ribofuranoside-3',5'-cyclic boranophosphate, Rp-isomer, acetoxymethyl ester | 299 | Rp-5,6-DM-cBIMPB (299) |
| Dimethylbenzimidazole-1-β-D-ribofuranoside-3',5'-cyclic boranophosphate, Sp-isomer, acetoxymethyl ester | 300 | |
| 5,6-Dichlorobenzimidazole-1-β-D-ribofuranoside-3',5'-cyclic boranophosphate, Rp-isomer | 301 | Sp-5,6-DCl-cBIMPB (302) |
| 5,6-Dichlorobenzimidazole-1-β-D-ribofuranoside-3',5'-cyclic boranophosphate, Sp-isomer | 302 | |
| 5,6-Dichlorobenzimidazole-1-β-D-ribofuranoside-3',5'-cyclic boranophosphate, Rp-isomer, acetoxymethyl ester | 303 | Rp-5,6-DCl-cBIMPB-AM (303) |
| 5,6-Dichlorobenzimidazole-1-β-D-ribofuranoside-3',5'-cyclic boranophosphate, Sp-isomer, acetoxymethyl ester | 304 | |
| 8-Bromo-2'-phenoxythiocarbonyl-adenosine-3',5'-cyclic boranophosphate, Rp-isomer | 305 | Sp-8-Br-2'-PTC-cAMPB (306) |
| 8-Bromo-2'-phenoxythiocarbonyl-adenosine-3',5'-cyclic boranophosphate, Sp-isomer | 306 | |

As will be clear to a skilled person, the compounds according to the present invention may further be labelled, according to well-known labelling techniques. For example, fluorescent dyes may be coupled to the compounds in order to, but not limited to, localize the intracellular distribution of cyclic nucleotide binding proteins in living cells by means of confocal microscopy, for fluorescence correlation spectrometry, for fluorescence energy transfer studies, or for determination of their concentration in living cells. The fluorescent dye is preferably coupled, optionally via a spacer, to positions 8 (R1) and/or 2' (R2) and/or 6 (R3) and/or 2 (R4) of the purine or pyrimidine nucleobase, since, according to the invention, substituents at these positions have been shown to be well accepted.

A spacer according to this invention refers to, but is not limited to, an aminoalkylamino moiety, or an aminoalkylthio moiety, or a thioalkylthio moiety, or a thioalkylcarboxy moiety, or an aminoalkylcarboxy moiety, or a thioureido-aminoalkylthio moiety, or an amino oligoethylene glycole amino moiety or an alkyl ester with 1 to 12 alkyl and 1 to 12 ethylene units, respectively.

A spacer according to this invention has endstanding reactive groups that allow for conjugation with various dyes, quantum dots, biotin, tyrosylmethyl ester or other labels, proteins, insoluble carriers and supports and can be, but are not limited to, a NH2-, SH—, OH—, COOH, N3, NHS-ester, halogen group Examples of suitable fluorescent dyes are, but are not limited to, fluorescein, anthraniloyl, N-methylanthraniloyl, dansyl or the nitro-benzofurazanyl (NBD) system, rhodamine-based dyes such as Texas Red or TAMRA, cyanine dyes such as Cy™3, Cy™5, Cy™7, EVOblue™10 EVOblue™30, EVOblue™90, EVOblue™100 (EVOblue™-family) the BODIPY™-family, Alexa Fluor™-family, DY-547, DY-647, coumarines, acridines, oxazones, phenalenones, fluorescent proteins such as GFP, BFP and YFP, and near and far infrared dyes.

As discussed above the biological effect of the compounds according to the invention can be dependent thereon if the borano modification it is in equatorial or in the axial position. Thus, only phosphorothioate-modified cyclic nucleotides with axial (Sp-) configuration activate protein kinase A. Hence, if a cyclic boranophosphate analogue is agonistic at protein kinase A, it needs to have the borano group in axial position as well, and—according to CIP rules—is Rp-configurated It is noted that all stereoisomeric forms of the compounds of the invention, i.e. axial and equatorial isomers, and Rp and Sp isomers, respectively, are embraced by the present invention, independent of whether it is possible to separate them.

Suitable examples of salts of the phosphate moiety of the compounds according to the invention are Li, Na, K, Ca, Mg or $NH_4$, and tetraalkylammonium, trialkylammonium, dialkylammonium, alkylammonium, e.g. tetrabutylammonium, triethylammonium, trimethylammonium, diethylammonium, octylammonium and cetyltrimethylammonium. Alternatively, the free acid (H) form of the boranophosphate moiety is a suitable form for the compounds according to the invention.

It should be understood that hydrates of the compounds are also within the scope of the present invention.

The invention is further illustrated by the following Examples and Figures, describing preferred embodiments of the present invention, which are, however, not intended to limit the invention in any way.

Instead of or additional to fluorescent dyes the compounds according to the inventions may be labelled with (radio) nuclides. The person skilled in the art knows many techniques and suitable isotopes that can be used for this.

Also, the increased stability of the cyclic boranophosphates disclosed in this invention makes them highly valuable tools for methods connected to immunisation and antibody production, and to form stable, enzyme-connected tracers for diverse immuno assays using horse reddish peroxidase, alkaline phosphatase or other.

As can be seen from the above, the compounds according to the invention are valuable tools for research purposes (in this manner research indicates the non-therapeutical use as described as follows). Accordingly, a part of the invention is the use of a compound according to the invention
- as a reagent for signal transductions research,
- as modulator of protein kinases A and G, of EPAC (exchange protein directly activated by cyclic AMP) isozymes, of CNG (cyclic nucleotide gated) ion channels, of CAP (catabolite activated protein) proteins, of cyclic nucleotide-responsive phosphodiesterases, of GAF (cGMP-specific phosphodiesterases, adenylyl cyclases and formate hydrogen lyase system activator) domains, of transporter systems and other cyclic nucleotide-regulated binding proteins and isozymes thereof,
- as immobilised, hydrolysis- and oxidation-resistant ligand for affinity chromatography, for antibody production and for diagnostic applications on chip surfaces,
- as additive for organ transplantation storage solutions.

Many of the uses according to the invention utilize the improved oxidative stability of the cyclic nucleotide analogues according to the invention. Since in most cases hydrolytic stability of the cNMP analogues according to the invention is improved, too (at least compared to the respective phosphorothioate analogue), this characteristic of the compounds according to the invention can utilized for many purposes, too. The same is valid for the improved enzymatic stability e.g. against PDE and/or the improved lipophilicity of the compounds according to the invention.

Since there are many reactions in the body that are triggered and/or influenced by cyclic monophosphate nucleotides in the body of humans or animals, a part of the invention is a compound according to the invention for use as a medicament. This also includes a pharmaceutical composition, comprising one or more compounds according to the invention and one or more pharmaceutical acceptable excipients. As stated above, the compounds according to the invention also comprise the salts and/or hydrates of the compounds falling under formula I or formula II.

The person skilled in the art knows, that the use in the field of the medicine especially as part of medicaments certainly only physiologically acceptable salts of the compounds according to the invention may be used.

Further part of the invention is the use of a compound according to the invention in the prophylaxis or the treatment of a cyclic nucleotide-related disease, preferably of cardiovascular diseases, cancer, diabetes, asthma, cystic fibrosis, dekubitus, adipositas, proliferative skin diseases, cellulite, erectile dysfunction, immunodeficiency, neurodegenerative diseases, spinal cord injuries and paralysis, kidney failure, alzheimer's disease, mood disorders, aging processes, gout, dental and periodontal diseases, as well as memory and learning disorders.

Further uses in this regard may be the use as immunostimulatory drug for stimulation and improvement of the function the immune system especially in immunodeficiencies such as HIV. Further uses of the compounds according to the invention may be the stimulation of reinervation in spinal cord injuries and paralysis which may be made in vivo or in in vitro.

The invention also relates to prodrugs of the compounds described in this invention, wherein known functional moieties are coupled to the compounds according to the invention, according to well known techniques. It is widely accepted that such structures can enhance membrane-permeability and potency of the mother-compound 10-1000 fold.

For example, the boranophosphate compounds according to the invention may be transformed into bioactivatable prodrugs. For example, bioactivatable protecting groups may be coupled to the cyclic phosphate moiety, leading to significantly increased lipophilicity and bioavailability of the compounds of the invention. Examples for bioactivatable protection groups of the cyclic phosphate are, but are not limited to, acetoxymethyl, propionyloxymethyl, butyryloxymethyl, pivaloyloxymethyl, acetoxyethyl, acetoxybutyl, acetoxyisobutyl. Examples of corresponding compounds according to the invention, but are not limited to, are the acetoxymethyl esters of Rp- and Sp-8-bromoadenosine-3',5'-cyclic boranophosphate (examples 3 and 4).

The compounds according to the present invention may also be transformed into chemically labile prodrugs according to well-known techniques. For example, alkyl or aryl groups as well as substituted alkyl or aryl groups may be coupled to the cyclic phosphate moiety, leading to significantly increased lipophilicity and bioavailability of the compounds of the invention. Examples for chemically labile protection groups of the cyclic phosphate, but not limited to, are methyl, ethyl, 2-cyanoethyl, propyl, benzyl, phenyl and PEGylation by polyethylene glycol and its ethers. These compounds are inactive per se, but extremely membrane-permeable, leading to strongly increased intracellular concentrations. Upon hydrolysis of the ester bond, the biologically active mother compounds are released.

The compounds according to the present invention may also be transformed into photolysable (so-called "caged") compounds according to well-known techniques. For example, caged groups may be coupled to the cyclic phosphate moiety, leading to compounds with significantly increased lipophilicity and bioavailability. Examples for caged groups of the cyclic phosphate, but are not limited to, are o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged).

The compounds according to the present invention can also be immobilized to insoluble supports, such as, but not limited to, agarose, dextran, cellulose, starch and other carbohydrate-based polymers, to synthetic polymers such as polacrylamide, polyethyleneimine, polystyrol and similar materials, to apatite, glass, silica, gold, graphene, fullerenes, carboranes, titania, zirconia or alumina, to the surface of a chip suitable for connection with various ligands, or encapsulated within nanocontainers for controlled delivery release purposes.

Preferably, such compounds of the present invention have extended modifications either at R1 or at R2 or at R3 or at R4 which represent a spacer, as already described in more detail above.

Examples, but not limited to, are the Sp-isomer of 8-(6-aminohexyl)aminoadenosine-3',5'-cyclic boranophosphate (example 11), the Sp-isomer of 2'-(8-[amino-2,6-dioxaoctyl] carbamoyl)guanosine-3',5'-cyclic boranophosphate (example 19), 8-bromo-2'-O-monosuccinyladenosine-3',5'-cyclic boranophosphate, Sp-isomer (example 21), 8-(aminoethylthio)guanosine-3',5'-cyclic boranophosphate, Sp-isomer (example 29), 8-(19-amino-4,7,10,13,16-pentaoxanonadecylamino) adenosine-3',5'-cyclic boranophosphate, Rp- and Sp-isomers (examples 30 & 31), $N^6$-(6-aminohexyl)adenosine-3',5'-cyclic boranophosphate, Rp- and Sp-isomer (examples 51 & 52) and the Rp- and Sp-isomers of $N^6$-(2-aminoethylthio)purine-1-β-D-ribofuranosyl-3',5'-cyclic boranophosphate (examples 53 & 54).

The invention is further illustrated by the following figures and examples describing preferred embodiments of the present invention which are, however, not intended to limit the invention in any way.

EXAMPLES 1) 8-Bromoadenosine-3',5'-cyclic boranophosphate, Rp-isomer (Rp-8-Br-cAMPB, #001)

Synthesis was performed according to Lin, J. L.; He, K.; Ramsay Shaw, B., Org. Lett., 3, 795-797 (2001), starting with 8-bromoadenosine (Biolog, Bremen/Germany). After addition of 1.1 equivalents of 2-cyanoethyl-(N,N,N',N'-tetraisopropylphosphorodiamidite (Sigma-Aldrich, Munich, Germany) in dimethylformamide, and without isolation of the intermediate 5'-phosphite, cyclisation with 1-H-tetrazole (Sigma-Aldrich) was performed. Subsequent addition of dimethylsulfide-borane complex (Sigma-Aldrich) gave both 2-cyanoethyl-protected diastereomers in good yields. After basic removal of the 2-cyanoethyl protecting group, the 8-Br-cAMPB isomers were separated by preparative column chromatography on reversed phase silica (RP-18, 15% acetonitrile, 20 mM triethylammonium formate buffer, pH 7). The slower eluting Rp-isomer was isolated, further purified by repeated chromatographic cycles with the same eluent system and finally transferred to the sodium form. Purity 99.4% by reversed phase HPLC (RP-18, 10μ, 15 Vol.-% acetonitrile, 20 mM triethylammonium formate buffer, pH 7, 2 ml/min., UV 264 nm), yield 21%.

$C_{10}H_{14}BBrN_5O_5P$; MW 405.94 (free acid)
UV: $\lambda_{max}$: 264 nm, ϵ17.000
HPLC: 7:74 min.
NMR: δ $^1$H, $D_2O$, 600 MHz: 8.27 ppm (s, 1H, H-2)
6.17 ppm (s, 1H, H-1')
5.38-5.41 ppm (m, 1H, H-3')
4.25-4.52 ppm (m, 4H, H-2', H-4', H-5' a, H-5' b)
0.5 ppm (br q, 3H, $BH_3$)
NMR: δ $^{31}$P, $D_2O$, 243 MHz: 96.2 ppm; $^2J_{P-B}$ 148 Hz
NMR: δ $^{11}$B, $D_2O$, 96 MHz: −40.5 ppm;
ESI-MS (+): m/z 608/610 [M+TEA+H]$^+$; 392/394 [M-$BH_3$+H]$^+$
ESI-MS (−): m/z 404/406 [M−H]$^-$→390 [M-$BH_3$-H]$^-$→212 [8-Br-A−H]$^-$ 2) 8-Bromoadenosine-3',5'-cyclic boranophosphate, Sp-isomer (Sp-8-Br-cAMPB, #002)

Synthesis was performed according to Lin, J. L.; He, K.; Ramsay Shaw, B., Org. Lett., 3, 795-797 (2001)starting with 8-bromoadenosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers. After basic removal of the 2-cyanoethyl protecting group, the 8-Br-cAMPB isomers were separated by preparative column chromatography on reversed phase silica (15 Vol.-% acetonitrile, 20 mM triethylammonium formate buffer, pH 7). The faster eluting Sp-isomer was isolated, further purified by repeated chromatographic cycles with the same eluent system and finally transferred to the sodium form. Purity 99.5% by reversed phase HPLC (RP-18, 10μ, 15 Vol.-% acetonitrile, 20 mM triethylammonium formate buffer, pH 7, 2 ml/min., UV 264 nm), yield 37%.

$C_{10}H_{14}BBrN_5O_5P$; MW 405.94 (free acid)
UV: $\lambda_{max}$: 264 nm, ϵ17.000
HPLC: 6:22 min.
NMR: δ $^1$H, $D_2O$, 600 MHz: 8.25 ppm (s, 1H, H-2)
6.13 ppm (s, 1H, H-1')
5.3-5.33 ppm (m, 1H, H-3')
4.15-4.49 ppm (m, 4H, H-2', H-4', H-5' a, H-5' b)
0.39 ppm (br d, 3H, $BH_3$)
NMR: δ $^{31}$P, $D_2O$, 243 MHz: 91.1 ppm; $^2J_{P-B}$ 155 Hz
NMR: δ $^{11}$B, $D_2O$, 96 MHz: −39.6 ppm;
ESI-MS (+): m/z 608/610 [M+TEA+H]$^+$; 392/394 [M-$BH_3$+H]$^+$ ESI-MS (−): m/z 404/406 [M−H]⁻→390 [M−BH₃−H]⁻→212 [8-Br-A−H]⁻

3) 8-Bromoadenosine-3',5'-cyclic boranophosphate, Rp-isomer; acetoxymethyl ester (Rp-8-Br-cAMPB-AM, #005)

1 µmol of Rp-8-bromoadenosine-3',5'-cyclic boranophosphate, sodium salt, (example 1) was dissolved in 20 µl of dimethylformamide and 0.5 µl diisopropylethylamine (Hünig's Base, Sigma-Aldrich) as well as 0.5 µl acetoxymethyl bromide (Sigma-Aldrich) were added. The progress of the reaction was followed by HPLC (RP-18, 10µ, 11 Vol.-% propanol-2, 20 mM triethylammonium formate buffer, pH 6.8, 1.5 ml/min., UV 264 nm). The product signal was isolated from preparative HPLC with a purity of 98.2%, yield 48.3%.

$C_{13}H_{18}BBrN_5O_7P$; MW 478.00
UV: $\lambda_{max}$: 264 nm; ϵ17.000
HPLC: 4:98 min.
ESI-MS (+): m/z 478/480 [M+H]⁺; 464/466 [M−BH₃+H]⁺; 214/216 [8-Br-A+H]⁺
ESI-MS (−): m/z 494/496 [M+H₂O−H]⁻; 404/406 [M−AM−H]⁻

4) 8-Bromoadenosine-3',5'-cyclic boranophosphate, Sp-isomer; acetoxymethyl ester (Sp-8-Br-cAMPB-AM, #006)

1 µmol of Sp-8-bromoadenosine-3',5'-cyclic boranophosphate, sodium salt, (example 2) was dissolved in 20 µl of dimethylformamide and 0.5 µl diisopropylethylamine (Hünig's Base, Sigma-Aldrich) as well as 0.5 µl acetoxymethyl bromide (Sigma-Aldrich) were added. The progress of the reaction was followed by HPLC (RP-18, 11 Vol.-% propanol-2, 20 mM triethylammonium formate buffer, pH 6.8, 1.5 ml/min., UV 264 nm). The product signal was isolated from preparative HPLC with a purity of 98.7%, yield 53.3%.

$C_{13}H_{18}BBrN_5O_7P$; MW 478.00
UV: $\lambda_{max}$: 264 nm; ϵ17.000
HPLC: 3:58 min.
ESI-MS (+): m/z 478/480 [M+H]⁺; 464/466 [M−BH₃+H]⁺
ESI-MS (−): m/z 476/478 [M−H]⁻; 404/406 [M−AM−H]⁻; 212/214 [8-Br-A−H]⁺

5) 8-Bromoguanosine-3',5'-cyclic boranophosphate, Rp-isomer (Rp-8-Br-cGMPB, #219)

Synthesis was performed according to Lin et al. Lin, J. L.; He, K.; Ramsay Shaw, B., Org. Lett., 3, 795-797 (2001), starting with 8-bromoguanosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of borane dimethylsulfide complex (Sigma-Aldrich) gave both 2-cyanoethyl-protected diastereomers. After basic removal of the 2-cyanoethyl protecting group, the 8-Br-cGMPB isomers were separated by preparative column chromatography on reversed phase silica (6 Vol.-% propanol-2, 100 mM TEAF, pH 7).

The slower eluting Rp-isomer was isolated, further purified by repeated chromatographic cycles to yield the sodium salt of Rp-8-Br-cGMPB with a purity of 99.6% (RP-18, 10µ, 6 Vol.-% propanol-2, 20 mM triethylammonium formate buffer, pH 7, 2 ml/min., UV 260 nm), yield 23.4%.

$C_{10}H_{14}BBrN_5O_6P$; MW 421.94
UV: $\lambda_{max}$: 260 nm; ϵ15.000
HPLC: 7:51 min.
NMR: δ ¹H, D₂O, 600 MHz: 6.03 ppm (s, 1H, H-1')
5.38-5.40 ppm (m, 1H, H-3')
4.99 ppm (d, 1H, H-2')
4.22-4.50 ppm (m, 4H, H-2', H-4', H-5' a, H-5' b)
0.5 ppm (br q, 3H, BH₃)
NMR: δ ³¹P, D₂O, 243 MHz: 95.9 ppm (q); ²$J_{P-B}$ 134 Hz
ESI-MS (+): m/z 523/525 [M+TEA+H]⁺→509 [M−BH₃+H]⁺
ESI-MS (−): m/z 420/422 [M−H]⁻→406 [M−BH₃−H]⁻→228 [8-Br-G−H]⁻

6) 8-Bromoguanosine-3',5'-cyclic boranophosphate, Sp-isomer (Sp-8-Br-cGMPB, #220)

Synthesis was performed according to Lin et al. Lin, J. L.; He, K.; Ramsay Shaw, B., Org. Lett., 3, 795-797 (2001), starting with 8-bromoguanosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate-5'-phosphite. Subsequent addition of borane dimethylsulfide complex (Sigma-Aldrich) gave both 2-cyanoethyl-protected diastereomers. After basic removal of the 2-cyanoethyl protecting group, the 8-Br-cGMPB isomers were separated by preparative column chromatography on reversed phase silica (6 Vol.-% IPA, 100 mM TEAF, pH 7).

The faster eluting Sp-isomer was isolated, further purified by repeated chromatographic cycles to yield the sodium salt of Sp-8-Br-cGMPB with a purity of 98.2% (RP-18, 10µ, 6 Vol.-% propanol-2, 20 mM triethylammonium formate buffer, pH 7, 2 ml/min., UV 260 nm), yield 28.9%.

$C_{10}H_{14}BBrN_5O_6P$; MW 421.94 (for free acid)
UV: $\lambda_{max}$: 260 nm; ϵ15.000
HPLC: 6:80 min.
NMR: δ ¹H, D₂O, 600 MHz: 5.96 ppm (s, 1H, H-1')
5.30 ppm (m, 1H, H-3')
4.98-4.99 ppm (d, 1H, H-2')
4.13-4.42 ppm (m, 4H, H-2', H-4', H-5' a, H-5' b)
0.5 ppm (br d, 3H, BH₃)
NMR: δ ³¹P, D₂O, 243 MHz: 91.1 ppm (q); ²$J_{P-B}$ 123 Hz
ESI-MS (+): m/z 523/525 [M+TEA+H]⁺→509 [M−BH₃+H]⁺
ESI-MS (−): m/z 420/422 [M−H]⁻→406 [M−BH₃−H]⁻→228 [8-Br-G−H]⁻

7) 2'-O-Methyladenosine-3',5'-cyclic boranophosphate, Rp-isomer (Rp-2'-O-Me-cAMPB, #085)

Synthesis was performed according to Lin, J. L.; He, K.; Ramsay Shaw, B., Org. Lett., 3, 795-797 (2001), starting with 2'-O-methyladenosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of borane dimethylsulfide complex (Sigma-Aldrich) gave both 2-cyanoethyl-protected diastereomers in good yields. After basic removal of the 2-cyanoethyl protecting group, the 2'-O-Me-cAMPB isomers were separated by preparative column chromatography on reversed phase silica (RP-18, 15 Vol.-% acetonitrile, 10 mM TEAF, pH 7).

The faster eluting Rp-isomer (28%) was isolated, further purified by repeated chromatographic cycles to yield the sodium salt of Rp-2'-O-Me-cAMPB with a purity of 97.5%.

$C_{11}H_{17}BN_5O_5P$; MW 341.07 (free acid)
UV: $\lambda_{max}$: 258 nm; $\epsilon$15.000
HPLC: 3:30 min.
ESI-MS (+): m/z 544 [M+2TEA+H]$^+$
ESI-MS (−): m/z 340 [M−H]$^-$→326 [M−BH$_3$—H]$^-$→134 [adenine-H]$^-$

8) 2'-O-Methyladenosine-3',5'-cyclic boranophosphate, Sp-isomer (Sp-2'-O-Me-cAMPB, #086)

Synthesis was performed according to Lin, J. L.; He, K.; Ramsay Shaw, B., Org. Lett., 3, 795-797 (2001), starting with 2'-O-methyladenosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers. After basic removal of the 2-cyanoethyl protecting group, the 2'-O-Me-cAMPB isomers were separated by preparative column chromatography on reversed phase silica (RP-18, 15 Vol.-% acetonitrile, 10 mM TEAF, pH 7).

The slower eluting Sp-isomer (32%) was isolated, further purified by repeated chromatographic cycles to yield the sodium salt of Sp-2'-O-Me-cAMPB with a purity of 92.0%.

$C_{11}H_{17}BN_5O_5P$; MW 341.07 (free acid)
UV: $\lambda_{max}$: 258 nm; $\epsilon$15.000
HPLC: 6:00 min.
ESI-MS (+): m/z 443 [M+TEA+H]$^+$; 544 [M+2TEA+H]$^+$
ESI-MS (−): m/z 340 [M−H]$^-$→326 [M−BH$_3$−H]$^-$→134 [adenine-H]$^-$

9) 8-(4-Chlorophenylthio)adenosine-3',5'-cyclic boranophosphate, Rp-isomer (Rp-8-pCPT-cAMPB, #053)

Rp-8-pCPT-cAMPB was prepared by nucleophilic substitution of the 8-bromo function of 1 µmol Rp-8-Br-cAMPB, sodium salt (example 1), with excessive 4-chlorothiophenol (Fluka, Buchs, Switzerland) and diisopropylethylamine (Hünig's base, Sigma-Aldrich) in 500 µl propanol-2 at 99° C. in a sealed plastic vial for 24 h.

The progress of the reaction was followed by HPLC (RP-18, 40 Vol.-% acetonitrile, 20 mM triethylammonium formate buffer, 1 ml/min., UV detection at 264 and 280 nm). Using the same eluent, Rp-8-pCPT-cAMPB was isolated and purified to 99.7% by preparative reversed phase chromatography as the corresponding triethyl ammonium salt, yield 92.8%.

$C_{16}H_{18}ClBN_5O_5PS$; MW 469.65 (free acid)
UV: $\lambda_{max}$: 280 nm; $\epsilon$17.000
HPLC: 2:10 min.
ESI-MS (+): m/z 672 [M+2TEA+H]$^+$
ESI-MS (−): m/z 468/470 [M−H]$^-$→454 [M−BH$_3$−H]$^-$→276 [8-pCPT-A−H]$^-$

10) 8-Cyclopentylaminoadenosine-3',5'-cyclic boranophosphate, Sp-isomer (Sp-cPA-cAMPB, #034)

Sp-8-cPA-cAMPB was prepared by nucleophilic substitution of the 8-bromo function of 1 µmol Sp-8-Br-cAMPB, sodium salt (example 2), with excessive cyclopentylamine (Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 264 and 278 nm). Using the same eluent, Sp-8-cPA-cAMPB was isolated and purified up to 99.1% by preparative reversed phase chromatography as the corresponding triethyl ammonium salt, yield 91.3%.

$C_{15}H_{24}BN_6O_5P$; MW 410.18 (free acid)
UV: $\lambda_{max}$: 278 nm; $\epsilon$17.000
HPLC: 5:61 min.
ESI-MS (+): m/z 433 [M+H]$^+$; 613 [M+2 TEA+H]$^+$
ESI-MS (−): m/z 409 [M−H]$^-$→395 [M-BH$_3$−H]$^-$→217 [8-cPA-A−H]$^-$

11) 8-(6-Aminohexylamino)adenosine-3',5'-cyclic boranophosphate, Sp-isomer (Sp-8-AHA-cAMPB, #026)

Sp-8-AHA-cAMPB was prepared by nucleophilic substitution of the 8-bromo function of 10 µmol Sp-8-Br-cAMPB, sodium salt (example 2), with excessive 1,6-diaminohexane (Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 258 and 275 nm). Using the same eluent, Sp-8-AHA-cAMPB was successfully isolated and purified (98.9%) by preparative reversed phase chromatography as the corresponding triethyl ammonium salt, yield 89.2%.

$C_{16}H_{29}BN_7O_5P$; MW 441.23 (free acid)
UV: $\lambda_{max}$: 275 nm; $\epsilon$17.000
HPLC: 1:40 min.
ESI-MS (+): m/z 543 [M+TEA+H]$^+$
ESI-MS (−): m/z 440 [M−H]$^-$→426 [M-BH$_3$−H]$^-$→248 [8-AHA-A−H]$^-$

12) 8-(6-Aminohexylamino)adenosine-3',5'-cyclic boranophosphate, Sp-isomer immobilized to Agarose (Sp-8-AHA-cAMPB-Agarose, #028)

6 µmol of Sp-8-AHA-cAMPB, triethylammonium salt (example 11) was coupled to 1 ml of N-hydroxysuccinimide-activated Sepharose Fast Flow (Pharmacia, Erlangen, Germany) in dry dimethylsulfoxide via the endstanding primary ω-amino group in position 8 of the adenine nucleobase. 7 µl of diisopropylethylamine (Hünig's base, Sigma-Aldrich) were added and the coupling progress was followed by HPLC (RP-18, 20 Vol.-% acetonitrile, 20 mM triethylammonium formate buffer, 1 ml/min., UV 275 nm), monitoring the decrease of the Sp-8-AHA-cAMPB signal at 1:40 min. After 1 h of gentle shaking at RT one equivalent of ethanolamine (Fluka) was added in order to block all non-reacted active sites. Subsequently, the gel was filtered off, washed with propanol-2 and phosphate buffer and stored in phosphate buffer containing 0.01% sodium azide (Fluka) for preservation.

Sp-8-AHA-cAMPB-Agarose ligand density: approx. 0.6 µmol/100 µl of settled gel.

13) 8-Benzylaminoadenosine-3',5'-cyclic boranophosphate, Rp-isomer (Rp-8-BnA-cAMPB, #039)

Rp-8-BnA-cAMPB was prepared by nucleophilic substitution of the 8-bromo function of 1 µmol Rp-8-Br-cAMPB, sodium salt (example 1), with excessive benzylamine (Fluka) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 258 and 275 nm). Using the same eluent, Rp-8-BnA-cAMPB was isolated and purified up to 99.7% by preparative reversed phase chromatography as the corresponding triethyl ammonium salt, yield 91%.

$C_{17}H_{22}BN_6O_5P$; MW 432.18 (free acid)
UV: $\lambda_{max}$: 275 nm
HPLC: 6:10 min.
ESI-MS (+): m/z 534 [M+TEA+H]$^+$
ESI-MS (−): m/z 431 [M−H]$^-$→417 [M−BH$_3$−H]$^-$→239 [8-BnA-A−H]$^-$

14) 8-Hexylthioadenosine-3',5'-cyclic boranophosphate, Sp-isomer (Sp-8-HT-cAMPB, #048)

Sp-8-HT-cAMPB was prepared by nucleophilic substitution of the 8-bromo function of 1 µmol Sp-8-Br-cAMPB, sodium salt (example 2), with excessive 1-hexanethiol (Fluka) and diisopropylethylamine (Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 258 and 283 nm). Using the same eluent, Sp-8-HT-cAMPB was isolated and purified by preparative reversed phase chromatography (99.8%) as the corresponding triethyl ammonium salt, yield 96.1%.

$C_{16}H_{27}BN_5O_5PS$; MW 443.27 (free acid)
UV: $\lambda_{max}$: 283 nm, ϵ20.000
HPLC: 6:22 min.
ESI-MS (+): m/z 545 [M+TEA+H]$^+$
ESI-MS (−): m/z 442 [M−H]$^-$→428 [M−BH$_3$−H]$^-$→250 [8-HT-A−H]$^-$

15) 8-Piperidinoadenosine-3',5'-cyclic boranophosphate, Sp-isomer (Sp-8-PIP-cAMPB, #036)

Sp-8-PIP-cAMPB was prepared by nucleophilic substitution of the 8-bromo function of 1 µmol Sp-8-Br-cAMPB, sodium salt (example 2), with excessive piperidine (Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 258 and 273 nm). Using the same eluent, Sp-8-PIP-cAMPB was isolated and purified by preparative reversed phase chromatography as the corresponding triethyl ammonium salt, yield 91.9%.

$C_{15}H_{24}BN_6O_5P$; MW 410.18 (free acid)
UV: $\lambda_{max}$: 273 nm, ϵ15.000
HPLC: 4:43 min., purity 99.5%
ESI-MS (+): m/z 512 [M+TEA+H]$^+$
ESI-MS (−): m/z 409 [M−H]$^-$→395 [M−BH$_3$−H]$^-$→217 [8-PIP-A−H]$^-$

16) 8-Benzyloxyadenosine-3',5'-cyclic boranophosphate, Sp-isomer (Sp-8-BnO-cAMPB, #046)

Sp-8-BnO-cAMPB was prepared by nucleophilic substitution of the 8-bromo function of 1 µmol Sp-8-Br-cAMPB, sodium salt (example 2), with excessive benzylalcohol (30 Fluka) and 10 µl diisopropylethylamine (Hünig's base, Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 1 ml/min., UV detection at 258 nm). Using the same eluent, Sp-8-BnO-cAMPB was isolated and purified (98.4%) by preparative reversed phase chromatography as the corresponding triethyl ammonium salt; yield 68.7%.

$C_{17}H_{21}BN_5O_6P$; MW 433.17 (free acid)
UV: $\lambda_{max}$: 258 nm, ϵ15.400
HPLC: 7:05 min.
ESI-MS (+): m/z 535 [M+TEA+H]$^+$
ESI-MS (−): m/z 432 [M−H]$^-$→418 [M−BH$_3$−H]$^-$→240 [8-BnO-A−H]$^-$

17) 8-Bromo-2'-O—N-methylanthraniloyladenosine-3',5'-cyclic boranophosphate, Rp-isomer (Rp-8-Br-2'-MANT-cAMPB, #009)

Rp-8-Br-2'-MANT-cAMPB was prepared by esterification of 1 µmol Rp-8-Br-cAMPB, sodium salt (example 1), with excessive (20 mg) N-methylisatoic acid anhydride (Sigma-Aldrich) in 300 µl water at RT in a sealed plastic vial for 2 h. From time to time pH was adjusted to 8.5 with aqueous sodium hydroxide.

The progress of the reaction was followed by HPLC (RP-18, 25 Vol.-% acetonitrile, 20 mM triethylammonium formate buffer, 1 ml/min., UV detection at 264 nm). Using the same eluent, the intensively blue fluorescent Rp-8-Br-2'-MANT-cAMPB was isolated and purified by preparative reversed phase chromatography as the corresponding triethyl ammonium salt, yield 79.8%, purity 99.3%.

$C_{18}H_{21}BBrN_6O_6P$; MW 539.09 (free acid)
UV: $\lambda_{max}$: 264/355 nm, ϵ17.000/5.300
$\lambda_{exc}$ 350 nm, $\lambda_{em}$ 445 nm
HPLC: 4:50 min.
ESI-MS (+): m/z 539/541 [M+H]$^+$
ESI-MS (−): m/z 537/539 [M−H]$^-$→523 [M−BH$_3$−H]$^-$→212 [8-Br-A−H]$^-$

18) 8-Bromo-2'-O-(imidazolylcarbamoyl)-guanosine-3',5'-cyclic boranophosphate, Sp-isomer (Sp-8-Br-2'-IC-cGMPB, #224)

10 µmol of Sp-8-Br-cGMPB, triethylammonium salt (example 6), was dissolved in 1 ml of dry dimethylformamide and 50 mg of carbonyldiimidazole (Sigma-Aldrich) were added. The progress of the reaction was followed by HPLC (RP-18, 25 Vol.-% acetonitrile, 20 mM triethylammonium formate buffer, 2 ml/min., UV detection at 260 nm). After completion of the reaction, the raw Sp-8-Br-2'-IC-cGMPB was isolated and purified to 95.7% by preparative reversed phase chromatography with the same eluent as the corresponding triethyl ammonium salt, yield 85.2%.

$C_{14}H_{16}BBrN_7O_7P$; MW 516.01 (free acid)
UV: $\lambda_{max}$: 260 nm, ϵ15.000
HPLC: 2:33 min.
ESI-MS (+): m/z 617/619 [M+TEA+H]$^+$
ESI-MS (−): m/z 514/516 [M−H]$^-$→500 [M−BH$_3$−H]$^-$→228 [8-BrG−H]$^-$

19) 2'-O-(8-Amino-3,6-dioxaoctylcarbamoyl)-8-bromoguanosine-3',5'-cyclic boranophosphate, Sp-isomer (Sp-2'-ADOC-8-Br-cGMPB, #226)

5 µmol of Sp-8-Br-2'-IC-cGMPB, triethylammonium salt (example 18), was dissolved in dry dimethylformamide and 20 µl of 1,8-diamino-3,6-dioxaoctane (Merck, Darmstadt, Germany) were added. The solution was stirred at RT while the coupling progress was followed by HPLC (RP-18, 15 Vol.-% acetonitrile, 20 mM triethylammonium formate buffer, 1 ml/min., UV 260 nm), monitoring the decrease of the Sp-8-Br-2'-IC-cGMPB signal at 6:47 min. After 0.5 h the starting material had disappeared and a new product signal had risen at 3:10 min.; yield 89%.

The raw Sp-2'-ADOC-8-Br-cGMPB was isolated and purified by preparative reversed phase chromatography as the corresponding triethyl ammonium salt, using 25 Vol.-% acetonitrile, 20 mM triethylammonium formate buffer at 1.5 ml/min., purity 997.4%.

$C_{17}H_{28}BBrN_7O_9P$; MW 596.14 (free acid)
UV: $\lambda_{max}$: 260 nm, $\epsilon$15.000
HPLC: 2:78 min.
ESI-MS (+): m/z 596/598 [M+H]$^+$→582 [M-BH$_3$+H]$^+$
ESI-MS (−): m/z 594/596 [M−H]$^-$→580 [M-BH$_3$−H]$^-$

20) 2'-O-(8-Amino-3,6-dioxaoctylcarbamoyl)-8-bromoguanosine-3',5'-cyclic boranophosphate, Sp-isomer immobilized to agarose (Sp-2'-ADOC-8-Br-cGMPB-Agarose, #228)

3 µmol of Sp-2'-ADOC-8-Br-cGMPB, triethylammonium salt (example 19), were immobilised to 0.5 ml (settled gel) of N-hydroxysuccinimide-activated Sepharose 4 Fast Flow (GE Healthcare, Erlangen, Germany) in dry dimethylsulfoxide via its endstanding primary ω-amino group in position 2' of the ribose moiety. 4 µl of diisopropylethylamine (Hünig's base, Sigma-Aldrich) were added and the coupling progress was followed by HPLC (RP-18, 25 Vol.-% acetonitrile, 20 mM triethylammonium formate buffer, 2 ml/min., UV 260 nm), by monitoring the decrease of the Sp-2'-ADOC-8-Br-cGMPB signal at 1:47 min. After 1.5 h of gentle shaking at RT 1 µl of ethanolamine (Sigma-Aldrich) were added in order to block all non reacted active sites. Subsequently, the gel was filtered off in a small glass filter funnel, washed with propanol-2 and phosphate buffer and stored in phosphate buffer containing 0.01% sodium azide (Fluka) for preservation.

21) 8-Bromo-2'-O-monosuccinyladenosine-3',5'-cyclic boranophosphate, Sp-isomer (Sp-8-Br-2'-MS-cAMPB, #012)

1 µmol of Sp-8-Br-cAMPB, sodium salt (example 2), was dissolved in 300 µl of dry dimethylformamide and 20 mg of succinic anhydride (Fluka) were added. The progress of the reaction was followed by HPLC (RP-18, 15 Vol.-% acetonitrile, 20 mM triethylammonium formate buffer, 1.5 ml/min., UV detection at 264 nm). After completion of the reaction, the triethyl ammonium salt Sp-8-Br-2'-MS-cAMPB was isolated and purified by preparative reversed phase chromatography to 98.6% using the same eluent, yield 65.9%.

$C_{14}H_{18}BBrN_5O_8P$; MW 506.01 (free acid)
UV: $\lambda_{max}$: 264 nm, $\epsilon$17.000
HPLC: 4:86 min.
ESI-MS (+): m/z 607/609 [M+TEA+H]$^+$
ESI-MS (−): m/z 504/506 [M−H]$^-$→404 [M-MS-H]$^-$→212 [8-Br-A−H]$^-$

22) 8-Thioadenosine-3',5'-cyclic boranophosphate, Rp-isomer (Rp-8-SH-cAMPB, #017)

Rp-8-SH-cAMPB was prepared by nucleophilic substitution of the 8-bromo function of 1 µmol Rp-8-Br-cAMPB, sodium salt (example 1), with a saturated solution of sodium hydrogen sulfide in 100 µl of dimethylformamide at RT in a sealed plastic vial for 5 h.

The progress of the reaction was followed by HPLC (RP-18, 15 Vol.-% acetonitrile, 20 mM triethylammonium formate buffer, 1.5 ml/min., UV detection at 264 and 295 nm). Using the same eluent, Rp-8-SH-cAMPB was isolated and purified (99.7%) by preparative reversed phase chromatography as the corresponding triethyl ammonium salt, yield 78.5%

$C_{10}H_{15}BN_5O_5PS$; MW 359.11 (free acid)
UV: $\lambda_{max}$: 297 nm, $\epsilon$23.700
HPLC: 2:95 min.
ESI-MS (+): m/z 461 [M+TEA+H]$^+$
ESI-MS (−): m/z 358 [M−H]$^-$→344[M-BH$_3$−H]$^-$→166 [8-SH-A−H]$^-$

23) 8-Azidoadenosine-3',5'-cyclic boranophosphate, Rp-isomer (Rp-8-N$_3$-cAMPB, #019)

Rp-8-N$_3$-cAMPB was prepared by nucleophilic substitution of the 8-bromo function of 1 µmol of Rp-8-Br-cAMPB, sodium salt (example 1), with excessive sodium azide (Fluka) in dimethylformamide at 99° C. in a sealed plastic vial for 0.5 h.

The progress of the reaction was followed by HPLC (RP-18, 15 Vol.-% acetonitrile, 20 mM triethylammonium formate buffer, 1.5 ml/min., UV detection at 264 and 280 nm). Using the same eluent, Rp-8-N$_3$-cAMPB was isolated and purified in the dark to >99% by preparative reversed phase chromatography to yield 88.8% as the corresponding triethyl ammonium salt.

$C_{10}H_{14}BN_8O_5P$; MW 368.01 (free acid)
UV: $\lambda_{max}$: 280 nm, $\epsilon$13.000
HPLC: 6:36 min.
ESI-MS (+): m/z 571 [M+2TEA+H]$^+$
ESI-MS (−): m/z 367 [M−H]$^-$→353 [M-BH$_3$−H]$^-$→175 [8-N$_3$-A−H]$^-$

24) 8-Azidoadenosine-3',5'-cyclic boranophosphate, Sp-isomer (Sp-8-N$_3$-cAMPB, #020)

Sp-8-N$_3$-cAMPB was prepared by nucleophilic substitution of the 8-bromo function of Sp-8-Br-cAMPB, sodium salt (example 2), with excessive sodium azide (Fluka) in dimethylformamide at 99° C. in a sealed plastic vial for 0.5 h.

The progress of the reaction was followed by HPLC (RP-18, 15 Vol.-% acetonitrile, 20 mM triethylammonium formate buffer, 1.5 ml/min., UV detection at 264 and 280 nm). Using the same eluent, Sp-8-N$_3$-cAMPB was isolated and purified in the dark to >99% by preparative reversed phase chromatography to yield 91.2% as the corresponding triethyl ammonium salt.

$C_{10}H_{14}BN_8O_5P$; MW 368.01 (free acid)
UV: $\lambda_{max}$: 280 nm, $\epsilon$13.000
HPLC: 4:20 min.
ESI-MS (+): m/z 571 [M+2TEA+H]$^+$
ESI-MS (−): m/z 367 [M−H]$^-$→353 [M-BH$_3$−H]$^-$→175 [8-N$_3$-A−H]$^-$

25) 8-Aminoadenosine-3',5'-cyclic boranophosphate, Rp-isomer (Rp-8-NH$_2$-cAMPB, #021)

Rp-8-NH$_2$-cAMPB was prepared by reduction of the 8-azido group of 1 µmol Rp-8-N$_3$-cAMPB, triethyl ammonium salt (example 23), with 5 mg dithiothreitol (Fluka) in 300 μl of dimethylformamide at RT in a sealed plastic vial for 30 min.

The progress of the reaction was followed by HPLC (RP-18, 15 Vol.-% acetonitrile, 20 mM triethylammonium formate buffer, 2 ml/min., UV detection at 273 nm). Using the same eluent, Rp-8-NH$_2$-cAMPB was isolated and purified by preparative reversed phase chromatography as the corresponding triethyl ammonium salt, yield 95.3%, purity 99.7%.

$C_{10}H_{16}BN_6O_5P$; MW 342.01 (free acid)
UV: $\lambda_{max}$: 273 nm, $\epsilon$16.400 (pH11)
HPLC: 1:66 min.
ESI-MS (+): m/z 545 [M+2TEA+H]$^+$; 444 [M+TEA+H]$^+$; 329 [M-BH$_3$+H]$^+$
ESI-MS (−): m/z 341 [M−H]$^-$→327 [M-BH$_3$−H]$^-$→149 [8-NH$_2$-A−H]$^-$

26) 8-Aminoadenosine-3',5'-cyclic boranophosphate, Sp-isomer (Sp-8-NH$_2$-cAMPB, #022)

Sp-8-NH$_2$-cAMPB was prepared by reduction of the 8-azido group of 1 μmol Sp-8-N$_3$-cAMPB, triethyl ammonium salt (example 24), with 5 mg dithiothreitol (Fluka) in 300 μl of dimethylformamide at RT in a sealed plastic vial for 30 min.

The progress of the reaction was followed by HPLC (RP-18, 15 Vol.-% acetonitrile, 20 mM triethylammonium formate buffer, 2 ml/min., UV detection at 273 nm). Using the same eluent, Sp-8-NH$_2$-cAMPB was isolated and purified by preparative reversed phase chromatography as the corresponding triethyl ammonium salt, yield 95.1%, purity 99.4%.

$C_{10}H_{16}BN_6O_5P$; MW 342.01 (free acid)
UV: $\lambda_{max}$: 273 nm, $\epsilon$16.400 (pH11)
HPLC: 1:65 min.
ESI-MS (+): m/z 545 [M+2TEA+H]$^+$; 444 [M+TEA+H]$^+$; 329 [M-BH$_3$+H]$^+$
ESI-MS (−): m/z 341 [M−H]$^-$→327 [M-BH$_3$−H]$^-$→149 [8-NH$_2$-A−H]$^-$

27) Guanosine-3',5'-cyclic boranophosphate, Rp-isomer (Rp-cGMPB, #203)

Rp-cGMPB was prepared by reductive dehalogenation of the 8-bromo function of Rp-8-Br-cGMPB, sodium salt (example 5, 10 μmol), with excessive cysteamine hydrochloride (10 mg, Sigma-Aldrich) in 100 μl of water at 99° C. in a sealed plastic vial for 0.5 h.

The progress of the reaction was followed by HPLC (RP-18, 10 Vol.-% acetonitrile, 20 mM triethylammonium formate buffer, 1.0 ml/min., UV detection at 260 nm). Using the same eluent, Rp-cGMPB was isolated and purified to 99.41% by preparative reversed phase chromatography as the corresponding triethyl ammonium salt, yield 62.3%.

$C_{10}H_{15}BN_5O_6P$; MW 343.04 (free acid)
UV: $\lambda_{max}$: 252 nm, $\epsilon$13.500
HPLC: 7:30 min.
ESI-MS (+): m/z 445 [M+TEA+H]$^+$→431 [M-BH$_3$+H]$^-$
ESI-MS (−): m/z 342 [M−H]$^-$→328 [M-BH$_3$−H]$^-$→150 [G−H]$^-$

28) Guanosine-3',5'-cyclic boranophosphate, Sp-isomer (Sp-cGMPB, #204)

Sp-cGMPB was prepared by reductive dehalogenation of the 8-bromo function of Sp-8-Br-cGMPB, sodium salt (example 6, 1 μmol), with excessive cysteamine hydrochloride (10 mg, Sigma-Aldrich) in 100 μl of water at 99° C. in a sealed plastic vial for 0.5 h.

The progress of the reaction was followed by HPLC (RP-18, 10 Vol.-% acetonitrile, 20 mM triethylammonium formate buffer, 1.0 ml/min., UV detection at 260 nm). Using the same eluent, Sp-cGMPB was isolated and purified to >99% HPLC by preparative reversed phase chromatography as the corresponding triethyl ammonium salt, yield 65.1%.

$C_{10}H_{15}BN_5O_6P$; MW 343.04 (free acid)
UV: $\lambda_{max}$: 252 nm, $\epsilon$13.500
HPLC: 6:45 min.
ESI-MS (+): m/z 445 [M+TEA+H]$^+$
ESI-MS (−): m/z 342 [M−H]$^-$→328 [M-BH$_3$−H]$^-$→150 [G−H]$^-$

29) 8-(Aminoethylthio)guanosine-3',5'-cyclic boranophosphate, Sp-isomer (Sp-8-AET-cGMPB, #236)

Sp-8-AET-cGMPB was prepared by nucleophilic substitution of the 8-bromo function of Sp-8-Br-cGMPB, sodium salt (example 6, 1 μmol), with excessive cysteamine hydrochloride (10 mg, Sigma-Aldrich) and diisopropylethylamine (Fluka) in 100 μl of water at 99° C. in a sealed plastic vial for 0.5 h.

The progress of the reaction was followed by HPLC (RP-18, 10 Vol.-% acetonitrile, 20 mM triethylammonium formate buffer, 1 ml/min., UV detection at 260 nm). Using the same eluent, Sp-8-AET-cGMPB was isolated and purified (99.8%) by preparative reversed phase chromatography as the corresponding triethyl ammonium salt, yield 88.9%.

$C_{12}H_{20}BN_6O_6PS$; MW 418.18 (free acid)
UV: $\lambda_{max}$: 277 nm, $\epsilon$14.000
HPLC: 7:84 min.
ESI-MS (+): m/z 419 [M+H]$^+$
ESI-MS (−): m/z 417 [M−H]$^-$→403 [M-BH$_3$−H]$^-$→225 [8-AET-G−H]$^-$

30) 8-(19-Amino-4,7,10,13,16-pentaoxanonadecylamino)adenosine-3',5'-cyclic boranophosphate, Rp-isomer (Rp-8-APONA-cAMPB, #029)

8-APONA-cAMPB was prepared by nucleophilic substitution of the 8-bromo function of 8-Br-cAMPB. A mixture of Rp- and Sp-8-Br-cAMPB (examples 1 & 2), 1 μmol each, was treated with 10 μl (excess) of 1,19-diamino-4,7,10,13,16-pentaoxanonadecane (Berry & Associates, Dexter, Mich., USA) in dimethylformamide at 99° C. in a sealed plastic vial for 1 h.

The progress of the reaction was followed by HPLC (RP-18, 15 Vol.-% acetonitrile, 20 mM triethylammonium formate buffer, 1 ml/min., UV detection at 264 and 275 nm). Using the same eluent, Rp-8-APONA-cAMPB was isolated and purified by preparative reversed phase chromatography to yield 89.9% as the corresponding triethyl ammonium salt with a purity of 99.1%.

$C_{24}H_{45}BN_7O_{10}P$; MW 633.45 (free acid)
UV: $\lambda_{max}$: 275 nm, $\epsilon$17.000
HPLC: 11:60 min.
ESI-MS (+): m/z 735 [M+TEA+H]$^+$
ESI-MS (−): m/z 632 [M−H]$^-$→618 [M-BH$_3$−H]$^-$→440 [8-APONA-A−H]$^-$

31) 8-(19-Amino-4,7,10,13,16-pentaoxanonadecylamino)adenosine-3',5'-cyclic boranophosphate, Sp-isomer (Sp-8-APONA-cAMPB, #030)

8-APONA-cAMPB was prepared by nucleophilic substitution of the 8-bromo function of 8-Br-cAMPB. A mixture of Rp- and Sp-8-Br-cAMPB (examples 1 & 2), 1 µmol each in dimethylformamide, was treated with 10 µl (excess) of 1,19-diamino-4,7,10,13,16-pentaoxanonadecane (Berry & Associates, Dexter, Mich., USA) at 99° C. in a sealed plastic vial for 1 h.

The progress of the reaction was followed by HPLC (RP-18, 15 Vol.-% acetonitrile, 20 mM triethylammonium formate buffer, 1 ml/min., UV detection at 264 and 275 nm). Using the same eluent, Sp-8-APONA-cAMPB was isolated and purified by preparative reversed phase chromatography to yield 88.2% as the corresponding triethyl ammonium salt with a purity of 99.4%.

$C_{24}H_{45}BN_7O_{10}P$; MW 633.45 (free acid)
UV: $\lambda_{max}$: 275 nm, ϵ17.000
HPLC: 10:03 min.
ESI-MS (+): m/z 735 [M+TEA+H]$^+$
ESI-MS (−): m/z 632 [M−H]$^-$→618 [M-BH$_3$−H]$^-$→440 [8-APONA-A−H]$^-$

32) 8-(Piperazino)adenosine-3',5'-cyclic boranophosphate, Sp-isomer (Sp-8-PIAZ-cAMPB, #038)

Sp-8-PIAZ-cAMPB was prepared by nucleophilic substitution of the 8-bromo function of 1 µmol Sp-8-Br-cAMPB, sodium salt (example 2), with excessive piperazine (Fluka) in 500 µl of dimethylformamide at 99° C. in a sealed plastic vial for 24 h.

The progress of the reaction was followed by HPLC (RP-18, 40 Vol.-% acetonitrile, 20 mM triethylammonium formate buffer, 1 ml/min., UV detection at 258 and 275 nm). Using the same eluent, Sp-8-PIAZ-cAMPB was isolated and purified by preparative reversed phase chromatography as the corresponding triethyl ammonium salt, yield 91%, purity 99.3%.

$C_{14}H_{23}BN_7O_5P$; MW 411.17 (free acid)
UV: $\lambda_{max}$: 275 nm, ϵ17.000
HPLC: 3:28 min.
ESI-MS (+): m/z 513 [M+TEA+H]$^+$
ESI-MS (−): m/z 410 [M−H]$^-$→396 [M-BH$_3$—H]$^-$→218 [8-PIAZ-A−H]$^-$

33) 8-(2-Aminophenylthio)adenosine-3',5'-cyclic boranophosphate, Sp-isomer (Sp-8-APT-cAMPB, #052)

Sp-8-APT-cAMPB was prepared by nucleophilic substitution of the 8-bromo function of 1 µmol Sp-8-Br-cAMPB, sodium salt (example 2), with excessive 2-aminothiophenol (Fluka) in 500 µl of dimethylformamide at 99° C. in a sealed plastic vial for 24 h.

The progress of the reaction was followed by HPLC (RP-18, 40 Vol.-% acetonitrile, 20 mM triethylammonium formate buffer, 1 ml/min., UV detection at 258 and 275 nm). Using the same eluent, Sp-8-APT-cAMPB was isolated and purified (99.7%) by preparative reversed phase chromatography as the corresponding triethyl ammonium salt, yield 83.4%.

$C_{16}H_{20}BN_6O_5PS$; MW 450.22 (free acid)
UV: $\lambda_{max}$: 275 nm, ϵ17.000
HPLC: 1:40 min.
ESI-MS (+): m/z 552 [M+TEA+H]$^+$
ESI-MS (−): m/z 449 [M−H]$^-$→435 [M-BH$_3$−H]$^-$→257 [8-APT-A−H]$^-$

34) 8-(2-Naphtylthio)adenosine-3',5'-cyclic boranophosphate, Sp-isomer (SP-8-NT-cAMPB, #056)

Sp-8-NT-cAMPB was prepared by nucleophilic substitution of the 8-bromo function of 1 µmol Sp-8-Br-cAMPB, sodium salt (example 2), with excessive 2-thionaphtol (Fluka) in 500 µl of dimethylformamide at 99° C. in a sealed plastic vial for 24 h.

The progress of the reaction was followed by HPLC (RP-18, 40 Vol.-% acetonitrile, 20 mM triethylammonium formate buffer, 1 ml/min., UV detection at 264 and 285 nm). Using the same eluent, Sp-8-NT-cAMPB was isolated and purified up to 99.8% (HPLC) by preparative reversed phase chromatography to yield 91.1% as the corresponding triethyl ammonium salt.

$C_{20}H_{21}BN_5O_5PS$; MW 485.27 (free acid)
UV: $\lambda_{max}$: 285 nm, ϵ16.000
HPLC: 3:14 min.
ESI-MS (+): m/z 587 [M+TEA+H]$^+$
ESI-MS (−): m/z 484 [M−H]$^-$→470 [M-BH$_3$−H]$^-$→292 [8-NT-A−H]$^-$

35) 8-Bromo-2'-O-methyladenosine-3',5'-cyclic boranophosphate, Rp-isomer (Rp-8-Br-2'-O-Me-cAMPB, #065)

Synthesis was performed according to Lin, J. L.; He, K.; Ramsay Shaw, B., Org. Lett., 3, 795-797 (2001), starting with 8-bromo-2'-O-methyladenosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers. After basic removal of the 2-cyanoethyl protecting group, the 8-Br-2'-O-Me-cAMPB isomers were separated by preparative column chromatography on reversed phase silica (RP-18, 25 Vol.-% acetonitrile, 20 mM triethylammonium formate buffer, 1 ml./min., pH 7). The faster eluting Rp-isomer was isolated, further purified up to 99.3% by repeated chromatographic cycles with the same eluent system and finally transferred to the sodium form. Overall yield: 22.5%.

$C_{11}H_{16}BBrN_5O_5P$; MW 419.97 (free acid)
UV: $\lambda_{max}$: 264 nm, ϵ17.000
HPLC: 3:45 min.
NMR: δ $^1$H, D$_2$O, 600 MHz: 8.27 ppm (s, 1H, H-2)
6.28 ppm (s, 1H, H-1')
5.5 ppm (m, 1H, H-3')
4.15-4.73 ppm (m, 4H, H-2', H-4', H-5'a, H-5'b)
3.54 ppm (d, 3H, 2'-O-Me)
0.5 ppm (br q, 3H, BH3)
NMR: δ $^{31}$P, D$_2$O, 243 MHz: 96.2 ppm; $^2J_{P-B}$ 138.5 Hz
ESI-MS (+): m/z 622/624 [M+2TEA+H]$^+$
ESI-MS (−): m/z 418/420 [M−H]$^-$→404 [M-BH$_3$−H]$^-$→212 [8-Br-A−H]$^-$

36) 8-Bromo-2'-O-methyladenosine-3',5'-cyclic boranophosphate, Sp-isomer (Sp-8-Br-2'-O-Me-cAMPB, #066)

Synthesis was performed according to Lin, J. L.; He, K.; Ramsay Shaw, B., Org. Lett., 3, 795-797 (2001), starting with 8-bromo-2'-O-methyladenosine. After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers. After basic removal of the 2-cyanoethyl protecting group, the 8-Br-cAMPB isomers were separated by preparative column chromatography on reversed phase silica (RP-18, 25 Vol.-% acetonitrile, 20 mM triethylammonium formate buffer, 1 ml/min., pH 7). The slower eluting Sp-isomer was isolated, further purified (99.4%) by repeated chromatographic cycles with the same eluent system and finally transferred to the sodium form. Overall yield: 29.1%.

$C_{11}H_{16}BBrN_5O_5P$; MW 419.97 (free acid)
UV: $\lambda_{max}$: 264 nm, $\epsilon$17.000
HPLC: 4:62 min.
NMR: δ $^1$H, $D_2O$, 600 MHz: 8.26 ppm (s, 1H, H-2)
6.24 ppm (s, 1H, H-1')
5.4 ppm (m, 1H, H-3')
4.17-4.82 ppm (m, 4H, H-2', H-4', H-5'a, H-5'b)
3.52 ppm (d, 3H, 2'-O-Me)
0.35 ppm (br d, 3H, BH3)
NMR: δ $^{31}$P, $D_2O$, 243 MHz: 91.2 ppm; $^2J_{P-B}$ 155.5 Hz
ESI-MS (+): m/z 622/624 [M+2TEA+H]$^+$
ESI-MS (−): m/z 418/420 [M−H]$^-$→404 [M−BH$_3$−H]$^-$→212 [8-Br-A−H]$^-$

37) 2'-O-Methylinosine-3',5'-cyclic boranophosphate, Rp-isomer (Rp-2'-O-Me-cIMPB, #089)

1 µmol of Rp-2'-O-Me-cAMPB, sodium salt (example 7), was dissolved in 500 µl of water, 10 mg of AMP deaminase (Deamizyme 50.000, Amano Enzyme Inc., Nagoya, Japan) were added and the vial was held at 36° C. for 36 hours. The progress of the reaction was followed by HPLC (RP-18, 15 Vol.-% acetonitrile, 100 mM TEAF, 1 ml/min., UV detection at 258 nm). The raw Rp-2'-O-Me-cIMPB was isolated and purified (99.7%) by preparative reversed phase chromatography as the corresponding triethyl ammonium salt, using the same eluent, yield 26.9%.

$C_{11}H_{16}BN_7O_7P$; MW 516.01 (free acid)
UV: $\lambda_{max}$: 249 nm, $\epsilon$12.000
HPLC: 2:04 min.
ESI-MS (+): m/z 444 [M+TEA+H]$^+$→343 [M−TEA+H]$^+$
ESI-MS (−): m/z 341 [M−H]$^-$→327 [M−BH$_3$−H]$^-$→135 [I−H]$^-$

38) 6-Chloropurine-1-β-D-ribofuranoside-3',5'-cyclic boranophosphate, Rp-isomer, 2-cyanoethylester (Rp-6-Cl-cPuMPB-CE, #131)

Synthesis was performed according to Lin, J. L.; He, K.; Ramsay Shaw, B., Org. Lett., 3, 795-797 (2001), starting with 6-chloropurine riboside (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers, which were isolated by preparative column chromatography on reversed phase silica (RP-18, 40 Vol.-% acetonitrile, 20 mM triethylammonium formate buffer, pH 7). The slower eluting Rp-isomer was isolated and further purified by reversed phase chromatography with the same eluent system, yield 32.3%.

$C_{12}H_{16}BClN_5O_5P$; MW 387.5
UV: $\lambda_{max}$: 263 nm, $\epsilon$8.900
HPLC: 3:42 min.
ESI-MS (+): m/z 523/525 [M+Na+TEA+H]$^+$
ESI-MS (−): m/z 345/347 [M−CN—H]$^-$→331 [M−BH$_3$−H]$^-$→153 [6-Cl—Pu−H]$^-$

39) 6-Chloropurine-1-β-D-ribofuranoside-3',5'-cyclic boranophosphate, Sp-isomer, 2-cyanoethylester (Sp-6-Cl-cPuMPB-CE, #132)

Synthesis was performed according to Lin, J. L.; He, K. Ramsay Shaw, B., Org. Lett., 3, 795-797 (2001), starting with 6-chloropurine riboside (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers, which were isolated by preparative column chromatography on reversed phase silica (RP-18, 40 Vol.-% acetonitrile, 20 mM triethylammonium formate buffer, pH 7). The faster eluting Sp-isomer was isolated and further purified by reversed phase chromatography with the same eluent system, yield 37.5%.

$C_{12}H_{16}BClN_5O_5P$; MW 387.5
UV: $\lambda_{max}$: 263 nm, $\epsilon$8.900
HPLC: 2:20 min.
ESI-MS (+): m/z 523/525 [M+Na+TEA+H]$^+$
ESI-MS (−): m/z 345/347 [M−CN—H]$^-$→331 [M−BH$_3$−H]$^-$→153 [6-Cl—Pu−H]$^-$

40) 6-Thiopurine-1-β-D-ribofuranoside-3',5'-cyclic boranophosphate, Rp-isomer, 2-cyanoethylester (Rp-6-SH-cPuMPB-CE, #169)

A solution of 10 µmol of Rp-6-Cl-cPuMPB-CE (example 38) in acetonitrile was treated with a saturated solution of sodium hydrogen sulfide (Fluka) in dimethylformamide at RT. After the green-blue colour of the sulfide had been decolorized, the quantitatively formed Rp-6-SH-cPuMPB-CE was isolated by preparative column chromatography on reversed phase silica (RP-18, 40 Vol.-% acetonitrile, 20 mM triethylammonium formate buffer, pH 7), purity 94.3%.

$C_{13}H_{17}BN_5O_5PS$; MW 397.2
UV: $\lambda_{max}$: 263 nm, $\epsilon$8.900
HPLC: 1:53 min.
ESI-MS (+): m/z 499 [M+TEA+H]$^+$
ESI-MS (−): m/z 396 [M−H]$^-$→382 [M−BH$_3$−H]$^-$→329 [M−BH$_3$—CE−H]$^-$
382 [M−BH$_3$−H]$^-$→151 [6-SH—Pu−H]$^-$

41) 6-Thiopurine-1-β-D-ribofuranoside-3',5'-cyclic boranophosphate, Rp-isomer (Rp-6-SH-cPuMPB, #167)

The reaction was performed as described at example 40, but the Rp-6-SH-cPuMPB-CE formed was allowed to stand 3 days at RT in slightly basic solution, while the cyanoethyl group was cleaved off to yield the free cyclic boranophosphate. Rp-6-SH-cPuMPB (99.4%) was isolated by preparative column chromatography on reversed phase silica (RP-18, 25 Vol.-% acetonitrile, 20 mM triethylammonium formate buffer, pH 7) as triethyl ammonium salt, yield 83.6%.

$C_{10}H_{14}BN_4O_5PS$; MW 344.1 (free acid)
UV: $\lambda_{max}$: 263 nm, $\epsilon$8.900
HPLC: 1:31 min.
ESI-MS (+): m/z 547 [M+2 TEA+H]$^+$
ESI-MS (−): m/z 343 [M−H]$^-$→329 [M−BH$_3$−H]$^-$→151 [6-SH—Pu−H]$^-$

42) 6-Chloropurine-1-β-D-ribofuranoside-3',5'-cyclic boranophosphate, Rp-isomer (Rp-6-Cl-cPuMPB, #129)

6-Chloropurine-1-β-D-ribofuranoside-3',5'-cyclic boranophosphate 2-cyanoethyl ester, Rp-isomer (example 38) was treated with base according to Lin, J. L.; He, K.; Ramsay Shaw, B., Org. Lett., 3, 795-797 (2001), but acetonitrile was used instead.

Rp-6-Cl-cPuMPB was isolated by preparative high pressure liquid chromatography on reversed phase silica (15 Vol.-% acetonitrile, 20 mM triethylammonium formate buffer, pH 7, 2 ml/min.), further purified by repeated chromatographic cycles with the same eluent system and finally transferred to the sodium form, yield 79.1%, purity 99.1%.

$C_{10}H_{13}BClN_4O_5P$; MW 346.5 (free acid)
UV: $\lambda_{max}$: 263 nm, ϵ8.900
HPLC: 7:25 min.
NMR: δ $^1H$, $D_2O$, 600 MHz: 8.85 ppm (s, 1H, H-8)
8.68 ppm (s, 1H, H-2)
6.30 ppm (s, 1H, H-1')
5.02 ppm (m, 1H, H-3')
4.39-4.58 ppm (m, 4H, H-2', H-4', H-5'a, H-5'b)
0.48 ppm (br q, 3H, BH3)
NMR: δ $^{31}P$, $D_2O$, 243 MHz: 96.1 ppm; $^2J_{P-B}$ 138.5 Hz
ESI-MS (+): m/z 448/450 [M+TEA+H]$^+$; 549/551 [M+2TEA+H]$^+$
ESI-MS (−): m/z 345/347 [M−H]$^-$→331 [M-BH$_3$−H]$^-$→153 [6-Cl—Pu−H]$^-$

43) 6-Chloropurine-1-β-D-ribofuranoside-3',5'-cyclic boranophosphate, Sp-isomer (Sp-6-Cl-cPuMPB, #130)

In order to remove the cyanoethyl group of 6-chloropurine-1-β-D-ribofuranoside-3',5'-cyclic boranophosphate 2-cyanoethyl ester, Sp-isomer, 2.5 mmol of Sp-6-Cl-cPuMPB-CE (example 39) were treated with base at RT according to Lin, J. L.; He, K.; Ramsay Shaw, B., Org. Lett., 3, 795-797 (2001), but acetonitrile was used instead.

The Sp-6-Cl-cPuMPB was isolated by preparative column chromatography on reversed phase silica (15 Vol.-% acetonitrile, 20 mM triethylammonium formate buffer, pH 7, 2 ml/min.), further purified by repeated chromatographic cycles with the same eluent system and finally transferred to the sodium form by ion exchange. Yield 81.3%, purity 98.8%.

$C_{10}H_{13}BClN_4O_5P$; MW 346.5 (free acid)
UV: $\lambda_{max}$: 263 nm, ϵ8.900
HPLC: 5:33 min.
NMR: δ $^1H$, $D_2O$, 600 MHz: 8.85 ppm (s, 1H, H-8)
8.68 ppm (s, 1H, H-2)
6.28 ppm (s, 1H, H-1')
4.95 ppm (m, 1H, H-3')
4.29-4.49 ppm (m, 4H, H-2', H-4', H-5'a, H-5'b)
0.4 ppm (br d, 3H, BH3)
NMR: δ $^1H$, $D_2O$, 243 MHz: 91.2 ppm; $^2J_{P-B}$ 160.4 Hz
ESI-MS (+): 549/551 [M+2 TEA+H]$^+$; 333/335 [M-BH$_3$+H]$^+$→155 [6-Cl—Pu+H]$^+$
ESI-MS (−): m/z 345/347 [M−H]$^-$→331 [M-BH$_3$−H]$^-$→153 [6-Cl—Pu−H]$^-$

44) 8-(4-Chlorophenylthio)-2'-O-methyladenosine-3',5'-cyclic boranophosphate, Rp-isomer (Rp-8-pCPT-2'-O-Me-cAMPB, #075)

Rp-8-pCPT-2'-O-Me-cAMPB was prepared by nucleophilic substitution of the 8-bromo function of 15 μmol Rp-8-Br-2'-O-Me-cAMPB, sodium salt (example 35), with two equivalents (30 μmol) of 4-chlorothiophenol (Fluka, Buchs, Switzerland) in aqueous isopropanol (20 Vol.-%) 85° C. in a sealed vial for 24 h. The pH was kept at 8-9 using 10 Vol.-% aqueous sodium hydroxide.

The progress of the reaction was followed by HPLC (RP-18, 40 Vol.-% acetonitrile, 20 mM triethylammonium formate buffer, 1 ml/min., UV detection at 264 and 282 nm). Rp-8-pCPT-2'-O-Me-cAMPB was isolated and purified up to 99.6% by preparative reversed phase chromatography with 15 Vol.-% acetonitrile as the corresponding sodium salt; yield: 87.3%.

$C_{17}H_{20}ClBN_5O_5PS$; MW 483.68 (free acid)
UV: $\lambda_{max}$: 282 nm, ϵ16.000
HPLC: 3:43 min.
ESI-MS (+): m/z 528/530 [M+2Na+H]$^+$
m/z 607/609 [M+TEA+Na+H]$^+$
m/z 686/688 [M+2TEA+H]$^+$
ESI-MS (−): m/z 482/484 [M−H]$^-$→468 [M-BH$_3$−H]$^-$→276 [8-pCPT-A−H]$^-$

45) 8-(4-Chlorophenylthio)-2'-O-methyladenosine-3',5'-cyclic boranophosphate, Sp-isomer (Sp-8-pCPT-2'-O-Me-cAMPB, #076))

Sp-8-pCPT-2'-O-Me-cAMPB was prepared by nucleophilic substitution of the 8-bromo function of 18 μmol Sp-8-Br-2'-O-Me-cAMPB, sodium salt (example 36), with excessive (10 mg) 4-chlorothiophenol (Fluka) in isopropanol/water at 85° C. at pH 8-9 in a sealed vial for 24 hours.

The progress of the reaction was followed by HPLC (RP-18, 40 Vol.-% acetonitrile, 20 mM triethylammonium formate buffer, 1 ml/min., UV detection at 264 and 282 nm). Using a similar eluent, Sp-8-pCPT-2'-O-Me-cAMPB was isolated and purified up to 99.7% by preparative reversed phase chromatography as the corresponding triethyl ammonium salt, yield: 90.1%.

$C_{17}H_{20}ClBN_5O_5PS$; MW 483.68 (free acid)
UV: $\lambda_{max}$: 282 nm, ϵ16.000
HPLC: 4:69 min.
ESI-MS (+): m/z 528/530 [M+2Na+H]$^+$
m/z 607/609 [M+TEA+Na+H]$^+$
m/z 686/688 [M+2TEA+H]$^+$
ESI-MS (−): m/z 482/484 [M−H]$^-$→468 [M-BH$_3$−H]$^-$→276 [8-pCPT-A−H]$^-$

46) 8-Benzylthio-2'-O-methyladenosine-3',5'-cyclic boranophosphate, Rp-isomer (Rp-8-BT-2'-O-Me-cAMPB, #071)

Rp-8-BT-2'-O-Me-cAMPB was prepared by nucleophilic substitution of the 8-bromo function of 18 μmol Rp-8-Br-2'-O-Me-cAMPB, sodium salt (example 35), with excessive (15 μl) benzylmercaptan (Fluka) in 5 ml propanol-2/water at 80° C. in a sealed vial for 24 h. NaOH was used to keep the pH at 8.

The progress of the reaction was followed by HPLC (RP-18, 40 Vol.-% acetonitrile, 20 mM triethylammonium formate buffer, 1 ml/min., UV detection at 264 and 283 nm). Using the same eluent, Rp-8-BT-2'-O-Me-cAMPB was isolated and purified by preparative reversed phase chromatography to yield 92% as the corresponding triethyl ammonium salt with a purity of 99.8%.

$C_{18}H_{23}BN_5O_5PS$; MW 463.26 (free acid)
UV: $\lambda_{max}$: 283 nm, ϵ17.100
HPLC: 2:83 min.
ESI-MS (+): m/z 508 [M+2Na+H]$^+$→494 [M-BH$_3$+H]$^+$ m/z 587 [M+Na+TEA+H]⁺→486[M+Na+H]⁺; 472 [M-BH₃+H]⁺
m/z 666 [M+2TEA+H]⁺→565[M+TEA+H]⁺
ESI-MS (−): m/z 462 [M−H]⁻→448 [M-BH₃−H]⁻→256 [8-BT-A−H]⁻

47) 8-Benzylthio-2'-O-methyladenosine-3',5'-cyclic boranophosphate, SP-isomer (Sp-8-BT-2'-O-Me-cAMPB, #072)

Sp-8-BT-2'-O-Me-cAMPB was prepared by nucleophilic substitution of the 8-bromo function of 11 µmol Sp-8-Br-2'-O-Me-cAMPB, sodium salt (example 36), with excessive (10 µl) benzylmercaptan (Fluka) in 5 ml propanol-2/water at 80° C. in a sealed vial for 24 h. NaOH was used to keep the pH at 8.

The progress of the reaction was followed by HPLC (RP-18, 40 Vol.-% acetonitrile, 20 mM triethylammonium formate buffer, 1 ml/min., UV detection at 264 and 283 nm). Using the same eluent, Sp-8-BT-2'-O-Me-cAMPB was isolated and purified by preparative reversed phase chromatography to yield 91.4% as the corresponding triethyl ammonium salt, purity: 99.4%.

$C_{18}H_{23}BN_5O_5PS$; MW 463.26 (free acid)
UV: $\lambda_{max}$: 283 nm, ϵ17.100
HPLC: 3:72 min.
ESI-MS (+): m/z 508 [M+2Na+H]⁺→494 [M-BH₃+H]⁺
m/z 587 [M+Na+TEA+H]⁺→486[M+Na+H]⁺, 472 [M-BH₃+H]⁺
m/z 666 [M+2TEA+H]⁺→565[M+TEA+H]⁺
ESI-MS (−): m/z 462 [M−H]⁻→448 [M-BH₃−H]⁻→256 [8-BT-A−H]⁻

48) 8-Hydroxy-2'-O-methyladenosine-3',5'-cyclic boranophosphate, Rp-isomer (Rp-8-OH-2'-O-Me-cAMPB, #069)

Rp-8-OH-2'-O-Me-cAMPB was prepared by nucleophilic substitution of the 8-bromo function of 1 µmol Rp-8-Br-2'-O-Me-cAMPB, sodium salt (example 35), with excessive water and diisopropylethylamine (Hünig's base, Sigma-Aldrich) at 99° C. in a sealed plastic vial for 24 h.

The progress of the reaction was followed by HPLC (RP-18, 15 Vol.-% acetonitrile, 20 mM triethylammonium formate buffer, 1 ml/min., UV detection at 264 nm). Using the same eluent, Rp-8-OH-2'-O-Me-cAMPB was isolated and purified (99.6%) by preparative reversed phase chromatography as the corresponding sodium salt, yield: 34%.

$C_{11}H_{17}BN_5O_6P$; MW 357.07 (free acid)
UV: $\lambda_{max}$: 268 nm, ϵ11.000
HPLC: 6:21 min.
ESI-MS (+): m/z 344 [M-BH₃+H]⁺→328 [M-BH₃—O+H]⁺; 152 [8-OH-A+H]⁺
ESI-MS (−): m/z 356 [M−H]⁻→342 [M-BH₃−H]⁻; 150 [8-OH-A−H]⁺

49) N⁶,N⁶-Dimethyladenosine-3',5'-cyclic boranophosphate, Rp-isomer (Rp-6-DM-cAMPB, #151)

Rp-6-DM-cAMPB and Sp-6-DM-cAMPB were prepared by nucleophilic substitution of the 6-chloro function of a mixture of Rp-6-Cl-cPuMPB and Sp-6-Cl-cPuMPB (examples 42, 43), 1 µmol each, with excessive dimethylamine (Merck) in water (Fluka) at 99° C. in a sealed plastic vial for 6 h.

The progress of the reaction was followed by HPLC (RP-18, 15 Vol.-% acetonitrile, 20 mM triethylammonium formate buffer, 2 ml/min., UV detection at 263 and 274 nm). Using the same eluent, Rp-6-DM-cAMPB was isolated and purified to >99% by preparative reversed phase chromatography as the corresponding triethyl ammonium salt, yield 90.9%.

$C_{12}H_{19}BN_5O_5P$; MW 355.1 (free acid)
UV: $\lambda_{max}$: 274 nm, ϵ12.000
HPLC: 12:19 min.
ESI-MS (+): m/z 457 [M+TEA+H]⁺
ESI-MS (−): m/z 354 [M−H]⁻→340 [M-BH₃−H]⁻→162 [6-DMA−H]⁻

50) N⁶,N⁶-Dimethyladenosine-3',5'-cyclic boranophosphate, Sp-isomer (Sp-6-DM-cAMPB, #152)

Rp-6-DM-cAMPB and Sp-6-DM-cAMPB were prepared by nucleophilic substitution of the 6-chloro function of a mixture of Rp-6-Cl-cPuMPB and Sp-6-Cl-cPuMPB (examples 42, 43), 1 µmol each, with excessive dimethylamine (Merck) in water (Fluka) at 99° C. in a sealed plastic vial for 6 h.

The progress of the reaction was followed by HPLC (RP-18, 15 Vol.-% acetonitrile, 20 mM triethylammonium formate buffer, 2 ml/min., UV detection at 263 and 274 nm). Using the same eluent, Sp-6-DM-cAMPB was isolated and purified to >99% by preparative reversed phase chromatography as the corresponding triethyl ammonium salt, yield 92.0%.

$C_{12}H_{19}BN_5O_5P$; MW 355.1 (free acid)
UV: $\lambda_{max}$: 274 nm, ϵ12.000
HPLC: 06:09 min.
ESI-MS (+): m/z 457 [M+H+TEA]⁺
ESI-MS (−): m/z 354 [M−H]⁻→340 [M-BH₃−H]⁻→162 [6-DMA−H]⁻

51) N⁶-(6-Aminohexyl)adenosine-3',5'-cyclic boranophosphate, Rp-isomer (Rp-6-AH-cAMPB, #149)

Rp-6-AH-cAMPB and Sp-6-AH-cAMPB were prepared by nucleophilic substitution of the 6-chloro function of a mixture of Rp-6-Cl-cPuMPB and Sp-6-Cl-cPuMPB (examples 42, 43), 1 µmol each with excessive 1,6-diaminohexane (Fluka) in water at 99° C. in a sealed plastic vial for 2 h.

The progress of the reaction was followed by HPLC (RP-18, 15 Vol.-% acetonitrile, 20 mM triethylammonium formate buffer, 2 ml/min., UV detection at 263 and 266 nm). Using the same eluent, Rp-6-AH-cAMPB was isolated and purified by preparative reversed phase chromatography as the corresponding triethyl ammonium salt (99.7%), yield 77.9%.

$C_{16}H_{28}BN_6O_5P$; MW 426.22 (free acid)
UV: $\lambda_{max}$: 266 nm, ϵ16.200
HPLC: 3:10 min.
ESI-MS (+): m/z 528 [M+TEA+H]⁺→427 [M+H]⁺→413 [M-BH₃+H]⁺
235 [6-AH-A+H]⁺
ESI-MS (−): m/z 425 [M−H]⁻→411 [M-BH₃−H]⁻→233 [6-HA-A−H]⁻

52) N⁶-(6-Aminohexyl)adenosine-3',5'-cyclic boranophosphate, Sp-isomer (Sp-6-AH-cAMPB, #150)

Rp-6-AH-cAMPB and Sp-6-AH-cAMPB were prepared by nucleophilic substitution of the 6-chloro function of a mixture of Rp-6-Cl-cPuMPB and Sp-6-Cl-cPuMPB (examples 42, 43), 1 µmol each, with excessive 1,6-diaminohexane (Fluka) in water at 99° C. in a sealed plastic vial for 2 h.

The progress of the reaction was followed by HPLC (RP-18, 15 Vol.-% acetonitrile, 20 mM triethylammonium formate buffer, 2 ml/min., UV detection at 263 and 266 nm). Using the same eluent, Sp-6-AH-cAMPB was isolated and purified by preparative reversed phase chromatography as the corresponding triethyl ammonium salt (99.3%), yield 80%.

$C_{16}H_{28}BN_6O_5P$; MW 426.22 (free acid)
UV: $\lambda_{max}$: 266 nm, ϵ16.200
HPLC: 2:53 min.
ESI-MS (+): m/z 528 [M+TEA+H]$^+$→427 [M+H]$^+$→413 [M-BH$_3$+H]$^+$
235 [6-AH-A+H]$^+$
ESI-MS (−): m/z 425 [M−H]$^-$→411 [M-BH$_3$−H]$^-$→233 [6-HA-A−H]$^-$

53) N$^6$-(2-Aminoethylthio)purine-1-β-D-ribofuranoside-3',5'-cyclic borano phosphate, Rp-isomer (Rp-6-AET-cPuMPB, #171)

Rp-6-AET-cPuMPB and Sp-6-AET-cAMPB were prepared by nucleophilic substitution of the 6-chloro function of a mixture of Rp-6-Cl-cPuMPB and Sp-6-Cl-cPuMPB (examples 42, 43), 1 µmol each, with excessive cysteamine hydrochloride (Fluka) in water at 99° C. in a sealed plastic vial for 2 h.

The progress of the reaction was followed by HPLC (RP-18, 15 Vol.-% acetonitrile, 20 mM triethylammonium formate buffer, 2 ml/min., UV detection at 263 and 290 nm). Using the same eluent, Rp-6-AET-cPuMPB was isolated and purified by preparative reversed phase chromatography to yield 94.6% as the corresponding triethyl ammonium salt, purity 99.4%.

$C_{12}H_{13}BN_5O_5PS$; MW 387.16 (free acid)
UV: $\lambda_{max}$: 290 nm, ϵ17.000
HPLC: 1:83 min.
ESI-MS (+): m/z 489 [M+TEA+H]$^+$
ESI-MS (−): m/z 386 [M−H]$^-$→372 [M-BH$_3$−H]$^-$→194 [6-AET-Pu−H]$^-$

54) N$^6$-(2-Aminoethylthio)purine-1-β-D-ribofuranoside-3',5'-cyclic boranophosphate, Sp-isomer (Sp-6-AET-cPuMPB, #172)

Rp-6-AET-cPuMPB and Sp-6-AET-cAMPB were prepared by nucleophilic substitution of the 6-chloro function of a mixture of Rp-6-Cl-cPuMPB and Sp-6-Cl-cPuMPB (examples 42, 43), 1 µmol each, with excessive cysteamine hydrochloride (Fluka) in water at 99° C. in a sealed plastic vial for 2 h.

The progress of the reaction was followed by HPLC (RP-18, 15 Vol.-% acetonitrile, 20 mM triethylammonium formate buffer, 2 ml/min., UV detection at 263 and 290 nm). Using the same eluent, Sp-6-AET-cPuMPB was isolated and purified by preparative reversed phase chromatography (98.9%) as the corresponding triethyl ammonium salt to yield 92.9%.

$C_{12}H_{19}BN_5O_5PS$; MW 387.16 (free acid)
UV: $\lambda_{max}$: 290 nm, ϵ17.000
HPLC: 1:72 min.
ESI-MS (+): m/z 489 [M+TEA+H]$^+$
ESI-MS (−): m/z 386 [M−H]$^-$→372[M-BH$_3$−H]$^-$→194 [6-AET-Pu−H]$^-$

55) N$^6$-Benzyladenosine-3',5'-cyclic boranophosphate, Rp-isomer (Rp-6-Bn-cAMPB, #159)

Rp-6-Bn-cAMPB and Sp-6-Bn-cAMPB were prepared in 90.2% and 92.4% yield by nucleophilic substitution of the 6-chloro function of a mixture of Rp-6-Cl-cPuMPB and Sp-6-Cl-cPuMPB (examples 42, 43), 1 µmol each, with excessive benzylamine (Fluka) in water/isopropanol at 99° C. in a sealed plastic vial for 1 h.

The progress of the reaction was followed by HPLC (RP-18, 40 Vol.-% acetonitrile, 20 mM triethylammonium formate buffer, 1 ml/min., UV detection at 263 and 269 nm). Using the same eluent, Rp-6-Bn-cAMPB was isolated and purified by preparative reversed phase chromatography as the corresponding triethyl ammonium salt, purity 99.8%.

$C_{17}H_{21}BN_5O_5P$; MW 417.17 (free acid)
UV: $\lambda_{max}$: 269 nm, ϵ20.500
HPLC: 2:97 min.
ESI-MS (+): m/z 519 [M+TEA+H]$^+$→404 [M-BH$_3$-TEA+H]$^+$→
226 [6-Bn-A+H]$^+$
ESI-MS (−): m/z 416 [M−H]$^-$→402 [M-BH$_3$−H]$^-$→224 [6-Bn-A−H]$^-$

56) N$^6$-Benzyladenosine-3',5'-cyclic boranophosphate, Sp-isomer (Sp-6-Bn-cAMPB, #160)

Rp-6-Bn-cAMPB and Sp-6-Bn-cAMPB were prepared in 90.2% and 92.4% yield by nucleophilic substitution of the 6-chloro function of a mixture of Rp-6-Cl-cPuMPB and Sp-6-Cl-cPuMPB (examples 42, 43), 1 µmol each, with excessive benzylamine (Fluka) in water/isopropanol at 99° C. in a sealed plastic vial for 1 h.

The progress of the reaction was followed by HPLC (RP-18, 40 Vol.-% acetonitrile, 20 mM triethylammonium formate buffer, 1 ml/min., UV detection at 263 and 269 nm). Using the same eluent, Sp-6-Bn-cAMPB was isolated and purified by preparative reversed phase chromatography as the corresponding triethyl ammonium salt, purity 99.7%.

$C_{17}H_{21}BN_5O_5P$; MW 417.17 (free acid)
UV: $\lambda_{max}$: 269 nm, ϵ20.500
HPLC: 2:74 min.
ESI-MS (+): m/z 519 [M+TEA+H]$^+$→404 [M-BH$_3$-TEA+H]$^+$→
226 [6-Bn-A+H]$^+$
ESI-MS (−): m/z 416 [M−H]$^-$→402 [M-BH$_3$−H]$^-$→224 [6-Bn-A−H]$^-$

57) N$^6$-Phenyladenosine-3',5'-cyclic boranophosphate, Rp-isomer (Rp-6-Phe-cAMPB, #163)

Rp-6-Phe-cAMPB and Sp-6-Phe-cAMPB were prepared by nucleophilic substitution of the 6-chloro function of a mixture of Rp-6-Cl-cPuMPB and Sp-6-Cl-cPuMPB (examples 42, 43), 1 µmol each, with excessive aniline (Fluka) in water/isopropanol at 99° C. in a sealed plastic vial for 4 h. The pH kept adjusted to 8.5.

The progress of the reaction was followed by HPLC (RP-18, 40 Vol.-% acetonitrile, 50 mM TEAF, 2 ml/min., UV detection at 263 and 288 nm). Using the same eluent, Rp-6-Phe-cAMPB was isolated and purified to a purity of 99.2% by preparative reversed phase chromatography as the corresponding triethyl ammonium salt; yield 74.3%.

$C_{16}H_{19}BN_5O_5P$; MW 403.14 (free acid)
UV: $\lambda_{max}$: 288 nm, ϵ20.800
HPLC: 2:18 min.

ESI-MS (+): m/z 606 [M+2TEA+H]⁺→404 [M-BH₃-2TEA+H]⁺→
212 [6-Phe-A+H]⁺
ESI-MS (−): m/z 402 [M−H]⁻→388 [M-BH₃−H]⁻→210 [6-Phe-A−H]⁻

58) N⁶-Phenyladenosine-3',5'-cyclic boranophosphate, Sp-isomer (Sp-6-Phe-cAMPB, #164)

Rp-6-Phe-cAMPB and Sp-6-Phe-cAMPB were prepared by nucleophilic substitution of the 6-chloro function of a mixture of Rp-6-Cl-cPuMPB and Sp-6-Cl-cPuMPB (examples 42, 43), 1 μmol each, with excessive aniline (Fluka) in water/isopropanol at 99° C. in a sealed plastic vial for 4 h. The pH kept adjusted to 8.5.

The progress of the reaction was followed by HPLC (RP-18, 40 Vol.-% acetonitrile, 50 mM TEAF, 2 ml/min., UV detection at 263 and 288 nm). Using the same eluent, Sp-6-Phe-cAMPB was isolated and purified by preparative reversed phase chromatography (99.7%) as the corresponding triethyl ammonium salt; yield 75.7%.

$C_{16}H_{19}BN_5O_5P$; MW 403.14 (free acid)
UV: $\lambda_{max}$: 288 nm, ε20.800
HPLC: 1:88 min.
ESI-MS (+): m/z 606 [M+2TEA+H]⁺→404 [M-BH₃-2TEA+H]⁺→
212 [6-Phe-A+H]⁺
ESI-MS (−): m/z 402 [M−H]⁻→388 [M-BH₃−H]⁻→210 [6-Phe-A−H]⁻

59) 6-Benzyloxypurine-1-β-D-ribofuranoside-3',5'-cyclic boranophosphate, Rp-isomer (Rp-6-BnO-cPuMPB, #143)

Rp-6-BnO-cPuMPB and Sp-6-BnO-cPuMPB were prepared by nucleophilic substitution of the 6-chloro function of a mixture of Rp-6-Cl-cPuMPB and Sp-6-Cl-cPuMPB (examples 42, 43), 1 μmol each, with 10 μl of diisopropylethylamine (Hünig's base, Sigma-Aldrich) and excessive benzylalcohol (Fluka) in water/isopropanol 1:1 at 99° C. in a sealed plastic vial for 5 h.

The progress of the reaction was followed by HPLC (RP-18, 30 Vol.-% acetonitrile, 20 mM triethylammonium formate buffer, 2 ml/min., UV detection at 263 and 250 nm). Using the same eluent, the slower eluting Rp-6-BnO-cPuMPB was isolated and purified by preparative reversed phase chromatography (99.6%) as the corresponding triethyl ammonium salt, yield 78.6%.

$C_{17}H_{20}BN_4O_6P$; MW 418.15 (free acid)
UV: $\lambda_{max}$: 250 nm, ε10.500
HPLC: 6:08 min.
ESI-MS (+): m/z 621 [M+2TEA+H]⁺→405 [M-BH₃-2TEA+H]⁺→
227 [6-BnO—Pu+H]⁺
ESI-MS (−): m/z 417 [M−H]⁻→403 [M-BH₃−H]⁻→225 [6-BnO—Pu−H]⁻

60) 6-Benzyloxypurine-1-β-D-ribofuranoside-3',5'-cyclic boranophosphate, Sp-isomer (Sp-6-BnO-cPuMPB, #144)

Rp-6-BnO-cPuMPB and Sp-6-BnO-cPuMPB were prepared by nucleophilic substitution of the 6-chloro function of a mixture of Rp-6-Cl-cPuMPB and Sp-6-Cl-cPuMPB (examples 42, 43), 1 μmol each, with 10 μl of diisopropylethylamine (Hünig's base, Sigma-Aldrich) and excessive benzylalcohol (Fluka) in water/isopropanol 1:1 at 99° C. in a sealed plastic vial for 5 h.

The progress of the reaction was followed by HPLC (RP-18, 30 Vol.-% acetonitrile, 20 mM triethylammonium formate buffer, 2 ml/min., UV detection at 263 and 250 nm). Using the same eluent, the faster eluting Sp-6-BnO-cPuMPB was isolated and purified by preparative reversed phase chromatography (99.7%) as the corresponding triethyl ammonium salt, yield 81.2%.

$C_{17}H_{20}BN_4O_6P$; MW 418.15 (free acid)
UV: $\lambda_{max}$: 250 nm, ε10.500
HPLC: 6:08 min.
ESI-MS (+): m/z 621 [M+2TEA+H]⁺→405 [M-BH₃-2TEA+H]⁺→
227 [6-BnO—Pu+H]⁺
ESI-MS (−): m/z 417 [M−H]⁻→403 [M-BH₃−H]⁻→225 [6-BnO—Pu−H]⁻

61) 6-Phenylthiopurine-1-β-D-ribofuranoside-3',5'-cyclic boranophosphate, Rp-isomer (Rp-6-PT-cPuMPB, #173)

Rp-6-PT-cPuMPB and Sp-6-PT-cPuMPB were prepared by nucleophilic substitution of the 6-chloro function of a mixture of Rp-6-Cl-cPuMPB and Sp-6-Cl-cPuMPB (examples 42, 43), 1 μmol each, with 10 μl of diisopropylethylamine (Hünig's base, Sigma-Aldrich) and excessive thiophenol (Fluka) in water/isopropanol 1:1 at 99° C. in a sealed plastic vial for 1 h.

The progress of the reaction was followed by HPLC (RP-18, 30 Vol.-% acetonitrile, 20 mM triethylammonium formate buffer, 2 ml/min., UV detection at 263 and 291 nm). Using the same eluent, the slower eluting Rp-6-PT-cPuMPB was isolated and purified by preparative reversed phase chromatography as the corresponding triethyl ammonium salt. Yield 93.3%, purity 99.8%.

$C_{16}H_{18}BN_4O_5PS$; MW 420.19 (free acid)
UV: $\lambda_{max}$: 291 nm, ε17.500
HPLC: 3:26 min.
ESI-MS (+): m/z 521 [M+TEA+H]⁺4406 [M-BH₃-TEA+H]⁺→
229 [6-PT-Pu+H]⁺
ESI-MS (−): m/z 419 [M−H]⁻→405 [M-BH₃−H]⁻→227 [6-PT-Pu−H]⁻

62) 6-Phenylthiopurine-1-β-D-ribofuranoside-3',5'-cyclic boranophosphate, Sp-isomer (Sp-6-PT-cPuMPB, #174)

Rp-6-PT-cPuMPB and Sp-6-PT-cPuMPB were prepared by nucleophilic substitution of the 6-chloro function of a mixture of Rp-6-Cl-cPuMPB and Sp-6-Cl-cPuMPB (examples 42, 43), 1 μmol each, with 10 μl of diisopropylethylamine (Hünig's base, Sigma-Aldrich) and excessive thiophenol (Fluka) in water/isopropanol 1:1 at 99° C. in a sealed plastic vial for 1 h.

The progress of the reaction was followed by HPLC (RP-18, 30 Vol.-% acetonitrile, 20 mM triethylammonium formate buffer, 2 ml/min., UV detection at 263 and 291 nm). Using the same eluent, the faster eluting Sp-6-PT-cPuMPB was isolated and purified by preparative reversed phase chromatography as the corresponding triethyl ammonium salt. Yield 95.1%, purity 99.7%.

$C_{16}H_{18}BN_4O_5PS$; MW 420.19 (free acid)
UV: $\lambda_{max}$: 291 nm, ε17.500
HPLC: 2:86 min.

ESI-MS (+): m/z 521 [M+TEA+H]⁺→406 [M-BH₃-TEA+H]⁺→
229 [6-PT-Pu+H]⁻
ESI-MS (−): m/z 419 [M−H]⁻→405 [M-BH₃−H]⁻→227 [6-PT-Pu−H]⁻

63) Purine-1-β-D-ribofuranoside-3',5'-cyclic boranophosphate, Rp-isomer (Rp-cPuMPB, #181)

Rp-cPuMPB and Sp-cPuMPB were prepared by catalytic dehalogenation of the 6-chloro function of a mixture of Rp-6-Cl-cPuMPB and Sp-6-Cl-cPuMPB (examples 42, 43), 1 µmol each, with a stream of hydrogen gas in water at RT in a plastic vial for 1 h, in the presence of 5% palladium on charcoal (Sigma).

The progress of the reaction was followed by HPLC (RP-18, 15 Vol.-% acetonitrile, 20 mM triethylammonium formate buffer, 2 ml/min., UV detection at 263 nm). Using the same eluent, the slower eluting Rp-cPuMPB was isolated and purified by preparative reversed phase chromatography (99.3%) as the corresponding triethyl ammonium salt, yield 42.1%.

$C_{10}H_{14}BN_4O_5P$; MW 312.03 (free acid)
UV: $\lambda_{max}$: 263 nm, $\epsilon$8.000
HPLC: 3:98 min.
ESI-MS (+): m/z 414 [M+TEA+H]⁺→299 [M-BH₃-TEA+H]⁺
ESI-MS (−): m/z 311 [M−H]⁻→297 [M-BH₃−H]⁻→119 [Pu−H]⁻

64) Purine-1-β-D-ribofuranoside-3',5'-cyclic boranophosphate, Sp-isomer (Sp-cPuMPB, #182)

Rp-cPuMPB and Sp-cPuMPB were prepared by catalytic dehalogenation of the 6-chloro function of a mixture of Rp-6-Cl-cPuMPB and Sp-6-Cl-cPuMPB (examples 42, 43), 1 µmol each, with a stream of hydrogen gas in water at RT in a plastic vial for 1 h, in the presence of 5% palladium on charcoal (Sigma).

The progress of the reaction was followed by HPLC (RP-18, 15 Vol.-% acetonitrile, 20 mM triethylammonium formate buffer, 2 ml/min., UV detection at 263 nm). Using the same eluent, the faster eluting Sp-cPuMPB was isolated and purified by preparative reversed phase chromatography as the corresponding triethyl ammonium salt, yield: 48.7%.

Sp-cPuMPB was also received as by-product from dehalogenation of Sp-6-Cl-cPuMPB under Stille conditions as described under example 93.

$C_{10}H_{14}BN_4O_5P$; MW 312.03 (free acid)
UV: $\lambda_{max}$: 263 nm, $\epsilon$8.000
HPLC: 3:28 min.
ESI-MS (+): m/z 414 [M+TEA+H]⁺→299 [M-BH₃-TEA+H]⁺
ESI-MS (−): m/z 311 [M−H]⁻→297 [M-BH₃−H]⁻→119 [Pu−H]⁻

65) Cytidine-3',5'-cyclic boranophosphate, Rp-isomer, 2-cyanoethylester (Rp-cCMPB-CE, #259)

Synthesis was performed according to Lin, J. L.; He, K.; Ramsay Shaw, B., Org. Lett., 3, 795-797 (2001), starting with cytidine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers, which were separated by preparative column chromatography on reversed phase silica (RP-18, 35 Vol.-% acetonitrile, 20 mM triethylammonium formate buffer, pH 7). The faster eluting Rp-isomer was isolated and further purified to 99.2% by reversed phase chromatography with the same eluent system; yield 22.2%.

$C_{12}H_{18}BN_4O_6P$; MW 356.08
UV: $\lambda_{max}$: 271 nm, $\epsilon$9.000
HPLC: 4:75 min.
ESI-MS (+): m/z 559 [M+2TEA+H]⁺→458 [M+TEA+H]⁺
ESI-MS (−): m/z 403 [M-CN+TEA−H]⁻→288 [M-BH₃−H]⁻

66) Cytidine-3',5'-cyclic boranophosphate, Sp-isomer, 2-cyanoethylester (SP-cCMPB-CE, #260)

Synthesis was performed according to Lin, J. L.; He, K.; Ramsay Shaw, B., Org. Lett., 3, 795-797 (2001), starting with cytidine (Biolog). After addition of 1.1 equivalents of 2-cyanoethyl-(N,N,N',N'-tetraisopropyl-phosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers, which were separated by preparative column chromatography on reversed phase silica (RP-18, 35 Vol.-% acetonitrile, 20 mM triethylammonium formate buffer, pH 7). The slower eluting Sp-isomer was isolated and further purified to 99.7% by reversed phase chromatography with the same eluent system; yield 19.5%.

$C_{12}H_{18}BN_4O_6P$; MW 356.08
UV: $\lambda_{max}$: 271 nm, $\epsilon$9.000
HPLC: 4:45 min.
ESI-MS (+): m/z 559 [M+2TEA+H]⁺→458 [M+TEA+H]⁺
ESI-MS (−): m/z 403 [M-CN+TEA−H]⁻→288 [M-BH₃−H]⁻

67) Cytidine-3',5'-cyclic boranophosphate, Rp-isomer (Rp-cCMPB, #259)

Cytidine-3',5'-cyclic boranophosphate 2-cyanoethyl ester, Rp-isomer (example 65) was treated with base according to Lin, J. L.; He, K.; Ramsay Shaw, B., Org. Lett., 3, 795-797 (2001), but acetonitrile was used as a solvent instead.

The faster eluting Rp-isomer of cCMPB was isolated by preparative high pressure liquid chromatography on reversed phase silica (10 Vol.-% acetonitrile, 50 mM TEAF, pH 7, 1 ml/min.), further purified by repeated chromatographic cycles (99.8%) with the same eluent system and finally transferred to the sodium form; yield 91.1%.

$C_9H_{15}BN_3O_6P$; MW 303.02 (free acid)
UV: $\lambda_{max}$: 271 nm, $\epsilon$9.000
HPLC: 3:66 min.
NMR: δ ¹H, D₂O, 500 MHz: 7.82 ppm (d, 1H, H-6)
6.21 ppm (d, 1H, H-5)
5.89 ppm (s, 1H, H-1')
4.33-4.7 ppm (m, 5H, H-2', H-3', H-4', H-5'a, H-5'b)
0.40 ppm (br q, 3H, BH3)
NMR: δ ³¹P, D₂O, 243 MHz: 96.0 ppm; $^2J_{P-B}$ 138.5 Hz
ESI-MS (+): m/z 405 [M+TEA+H]⁺
ESI-MS (−): m/z 302 [M−H]⁻→288 [M-BH₃−H]⁻→108 [C—H]⁻

68) Cytidine-3',5'-cyclic boranophosphate, Sp-isomer (Sp-cCMPB, #260)

Cytidine-3',5'-cyclic boranophosphate 2-cyanoethyl ester, Sp-isomer (example 66) was treated with base according to Lin, J. L.; He, K.; Ramsay Shaw, B., Org. Lett., 3, 795-797 (2001), but acetonitrile was used as a solvent instead.

The slower eluting Sp-cCMPB was isolated by preparative high pressure liquid chromatography on reversed phase silica (10 Vol.-% acetonitrile, 20 mM triethylammonium formate buffer, pH 7, 2 ml/min.), further purified (96.1%) by repeated chromatographic cycles with the same eluent system and finally transferred to the sodium form; yield 91.2%.

$C_9H_{15}BN_3O_6P$; MW 303.02 (free acid)
UV: $\lambda_{max}$: 271 nm, $\epsilon$9.000
HPLC: 5:45 min.
NMR: δ $^1$H, $D_2O$, 500 MHz: 7.57 ppm (d, 1H, H-6)
5.90 ppm (d, 1H, H-5)
5.73 ppm (s, 1H, H-1')
4.12-4.4 ppm (m, 5H, H-2', H-3', H-4', H-5'a, H-5'b)
0.35 ppm (br d, 3H, $BH_3$)
NMR: δ $^1$H, $D_2O$, 243 MHz: 91.2 ppm; $^2J_{P-B}$ 153.1 Hz
ESI-MS (+): m/z 405 [M+TEA+H]$^+$
ESI-MS (−): m/z 302 [M−H]$^-$→288 [M-BH$_3$−H]$^-$→108 [C—H]$^-$

69) 2-Chloroadenosine-3',5'-cyclic boranophosphate, Rp-& Sp-isomer, 2-cyanoethylester (Rp-/Sp-2-Cl-cAMPB-CE, #185/186)

Synthesis was performed according to Lin, J. L.; He, K.; Ramsay Shaw, B., Org. Lett., 3, 795-797 (2001), starting with 2-chloroadenosine (Biolog). After addition of 1.1 equivalents of 2-cyanoethyl-(N,N,N',N'-tetraisopropylphosphorodiamidite (Sigma-Aldrich) in dimethylformamide, cyclisation with 1-H-tetrazole (Sigma-Aldrich) was performed without isolation of the intermediate 5'-phosphite. Subsequent addition of dimethylsulfide-borane complex (Sigma-Aldrich) gave both 2-cyanoethyl-protected diastereomers, which were isolated unseparated (88.3%) by preparative column chromatography on reversed phase silica (RP-18, 50 Vol.-% acetonitrile, 20 mM triethylammonium formate buffer, pH 7, 2 ml/min.), yield 39.8%.

$C_{13}H_{17}BClN_6O_5P$; MW 414.6
UV: $\lambda_{max}$: 262 nm, $\epsilon$14.300
HPLC: 4:04 min.
ESI-MS (+): m/z 459/461 [M+2Na+H]$^+$; 437/439 [M+Na+H]$^+$
ESI-MS (−): m/z 413/415 [M−H]$^-$→399 [M-BH$_3$−H]$^-$→168 [2-Cl-A−H]$^-$

70) 2-Chloroadenosine-3',5'-cyclic boranophosphate, Rp-isomer (Rp-2-Cl-cAMPB, #183)

2-Chloroadenosine-3',5'-cyclic boranophosphate, Rp- and Sp-isomer, cyanoethylester (example 69) was treated with base according to Lin, J. L.; He, K.; Ramsay Shaw, B., Org. Lett., 3, 795-797 (2001), but acetonitrile was used as a solvent instead.

The faster eluting Rp-isomer of 2-Cl-cAMPB was isolated by preparative high pressure liquid chromatography on reversed phase silica (15% acetonitrile, 50 mM TEAF, pH 7, 2 ml/min.), further purified by repeated chromatographic cycles up to 99.3% with the same eluent system and finally transferred to the sodium form, yield: 90.3%.

$C_{10}H_{14}BClN_5O_5P$; MW 361.5 (free acid)
UV: $\lambda_{max}$: 262 nm, $\epsilon$14.300
HPLC: 3:73 min.
ESI-MS (+): m/z 564/566 [M+2TEA+H]$^+$
ESI-MS (−): m/z 360/362 [M−H]$^-$→346 [M-BH$_3$−H]$^-$→168 [2-Cl-A−H]$^-$
NMR: δ $^1$H, $D_2O$, 600 MHz: 8.21 ppm (s, 1H, H-8)
6.11 ppm (s, 1H, H-1')
4.73 ppm (m, 1H, H-3')
4.29-4.58 ppm (m, 4H, H-2', H-4', H-5'a, H-5'b)
0.5 ppm (br q, 3H, $BH_3$)
NMR: δ $^{31}$P, $D_2O$, 243 MHz: 96.1 ppm; $^2J_{P-B}$ 133.7 Hz

71) 2-Chloroadenosine-3',5'-cyclic boranophosphate, Sp-isomer (Sp-2-Cl-cAMPB, #184)

2-Chloroadenosine-3',5'-cyclic boranophosphate, Rp- and Sp-isomer, cyanoethylester (example 69) was treated with base according to Lin, J. L.; He, K.; Ramsay Shaw, B., Org. Lett., 3, 795-797 (2001), but acetonitrile was used as a solvent instead.

The slower eluting Sp-isomer of 2-Cl-cAMPB was isolated by preparative high pressure liquid chromatography on reversed phase silica (15 Vol.-% acetonitrile, 50 mM TEAF, pH 7, 2 ml/min.), further purified (99.8%) by repeated chromatographic cycles with the same eluent system and finally transferred to the sodium form; yield: 89.8%.

$C_{10}H_{14}BClN_5O_5P$; MW 361.5 (free acid)
UV: $\lambda_{max}$: 262 nm, $\epsilon$14.300
HPLC: 5:16 min.
ESI-MS (+): m/z 564/566 [M+2TEA+H]$^+$
ESI-MS (−): m/z 360/362 [M−H]$^-$→346 [M-BH$_3$−H]$^-$→168 [2-Cl-A−H]$^-$
NMR: δ $^1$H, $D_2O$, 600 MHz: 8.22 ppm (s, 1H, H-8)
6.09 ppm (s, 1H, H-1')
4.73 ppm (m, 1H, H-3')
4.24-4.57 ppm (m, 4H, H-2', H-4', H-5'a, H-5'b)
0.39 ppm (br d, 3H, $BH_3$)
NMR: δ $^{31}$P, $D_2O$, 243 MHz: 91.1 ppm; $^2J_{P-B}$ 143.4 Hz

72) 8-Hydroxy-2'-O-methyladenosine-3',5'-cyclic boranophosphate, Rp-isomer (Rp-8-OH-2'-O-Me-cAMPB, #069)

150 μmol of 8-Bromo-2'-O-methyladenosine-3',5'-cyclic boranophosphate, Rp-isomer (example 35) was dehalogenated by 200 mM aqueous triethylammonium buffer for one hour at 80° C.

The mixture containing Rp-2'-O-Me-cAMPB and Rp-8-OH-2'-O-Me-cAMPB in nearly equivalent amounts was separated by preparative high pressure liquid chromatography on reversed phase silica (9 Vol.-% acetonitrile, 20 mM triethylammonium formate buffer, pH 7). Rp-8-OH-2'-O-Me-cAMPB was isolated to yield 70 μmol (46.7%) with a purity of >99%.

$C_{11}H_{17}BN_5O_6P$; MW 357.1 (free acid)
UV: $\lambda_{max}$: 268 nm, $\epsilon$11.000
HPLC: 11:27 min.
ESI-MS (+): m/z 459 [M+TEA+H]$^+$; 560 [M+2TEA+H]$^+$
ESI-MS (−): m/z 356 [M−H]$^-$→342 [M-BH$_3$−H]$^-$→164 [8-OH-A−H]$^-$

73) 6-Chloropurine-2'-O-trimethylsilyl-1-β-D-ribofuranoside-3',5'-cyclic boranophosphate, Rp-isomer (Rp-6-Cl-2'-TMS-cPuMPB, #133)

To 1 μmol of Rp-6-Cl-cPuMPB (example 42) in a 1 ml plastic vial 300 μl of acetonitrile, 10 μl of hexamethyldisilazane (Fluka) and 10 μl of trimethylsilyl chloride (Fluka) were added and the closed vial was heated for one hour at 80° C.

Rp-6-Cl-2'-TMS-cPuMPB was nearly quantitatively formed and isolated by semipreparative high pressure liquid chromatography on reversed phase silica (25 Vol.-% acetonitrile, 20 mM triethylammonium formate buffer, pH 7, 263 nm), purity 87.8%.

$C_{13}H_{21}BClN_4O_5SiP$; MW 418.7 (free acid)
UV: $\lambda_{max}$: 263 nm, $\epsilon$8.900
HPLC: 15:89 min.
ESI-MS (+): m/z 520 $[M+H+TEA]^+ \rightarrow 506$ $[M+TEA-BH_3+H]^+$
ESI-MS (−): m/z 417 $[M-H]^- \rightarrow 403$ $[M-BH_3-H]^- \rightarrow 153$ $[6-Cl-Pu-H]^-$

74) 6-Methoxypurine-1-β-D-ribofuranoside-3',5'-cyclic boranophosphate, Rp-isomer (Rp-6-MeO-cPuMPB, #141)

To 1 μmol of Rp-6-Cl-cPuMPB (example 42) in a 1 ml plastic vial 500 μl of methanol and 20 μl of diisopropylethylamine (Hünig's base, Sigma-Aldrich) were added and the closed vial was heated for 12 h at 99° C.

Rp-6-MeO-cPuMPB was isolated in 99.5% purity by semipreparative high pressure liquid chromatography on reversed phase silica (20 Vol.-% acetonitrile, 20 mM triethylammonium formate buffer, pH 7, 252 nm, 1 ml/min.); yield 82.3%.

$C_{11}H_{16}BN_4O_6P$; MW 342.1 (free acid)
UV: $\lambda_{max}$: 252 nm, $\epsilon$11.800
HPLC: 4:47 min.
ESI-MS (+): m/z 545 $[M+2TEA+H]^+$
ESI-MS (−): m/z 341 $[M-H]^- \rightarrow 327$ $[M-BH_3-H]^- \rightarrow 149$ $[6-MeO-Pu-H]^-$

75) 8-Diethylaminoadenosine-3',5'-cyclic boranophosphate, Rp-isomer (Rp-8-DEA-cAMPB, #031)

To 1 μmol of Rp-8-Br-cAMPB (example 1) in a 1 ml plastic vial 50 μl of dimethylformamide and 20 μl of diethylamine (Sigma-Aldrich) were added and the closed vial was heated for 1 h at 99° C.

Rp-8-DEA-cAMPB was isolated in 92% yield by semipreparative high pressure liquid chromatography on reversed phase silica (20 Vol.-% acetonitrile, 20 mM triethylammonium formate buffer, pH 7, 276 nm), purity 99.7%.

$C_{14}H_{24}BN_6O_5P$; MW 398.17 (free acid)
UV: $\lambda_{max}$: 276 nm, $\epsilon$18.000
HPLC: 2:00 min.
ESI-MS (+): m/z 500 $[M+TEA+H]^+$
ESI-MS (−): m/z 397 $[M-H]^- \rightarrow 383$ $[M-BH_3-H]^- \rightarrow 205$ $[8-DEA-A-H]^-$

76) 8-(2-Furyl)adenosine-3',5'-cyclic boranophosphate, Sp-isomer (Sp-8-Furyl-cAMPB, #058)

Sp-8-Furyl-cAMPB was synthesized according to Andrei et al., *Org. Biomol. Chem.*, 5, 2070-2080 (2007).

Briefly, triphenylphosphine (Sigma-Aldrich) and palladium acetate (Sigma-Aldrich) were dissolved in dry dimethylformamide and heated for 15 min. at 50° C. to form an active red catalyst.

5 μmol of Sp-8-Br-cAMPB (example 1) and 7 μl of 2-(tri-n-butylstannyl)furane (Sigma-Aldrich) were dissolved in 50 μl of dimethylformamide, 5 μl of the freshly prepared catalyst were added and the whole mixture was heated for 1 h at 85° C.

Sp-8-Furyl-cAMPB was isolated with a purity of 95.8% as main reaction product from the dark brown solution by semipreparative high pressure liquid chromatography on reversed phase silica (20 Vol.-% acetonitrile, 20 mM triethylammonium formate buffer, pH 7, 1.5 ml/min., UV 302 nm) with a yield of 32.8%.

$C_{14}H_{18}BN_5O_6P$; MW 393.10 (free acid)
UV: $\lambda_{max}$: 302 nm, $\epsilon$11.000
HPLC: 3:28 min.
ESI-MS (+): m/z 517 $[M+Na+H]^+$; 899 $[M+4TEA+H]^+$
ESI-MS (−): m/z 392 $[M-H]^- \rightarrow 378$ $[M-BH_3-H]^- \rightarrow 200$ $[8-Furyl-A-H]^-$

77) 2'-O-Methyl-$N^6$-monobutyryladenosine-3',5'-cyclic boranophosphate, Rp-isomer (Rp-2'-O-Me-6-MB-cAMPB, #091)

To 1 μmol of Rp-2'-O-Me-cAMPB (example 7) in a 1 ml plastic vial 300 μl of dimethylformamide and 10 μl of butyric acid anhydride (Sigma-Aldrich) and 10 μl of ethyldiisopropylamine (Sigma-Aldrich) were added and the closed vial was heated for 1 h at 50° C.

The product signal was isolated by semipreparative high pressure liquid chromatography on reversed phase silica (25 Vol.-% acetonitrile, 20 mM triethylammonium formate buffer, pH 7, 1 ml/min., UV 273 nm); yield 78.4%, purity 99.8%.

$C_{15}H_{23}BN_5O_6P$; MW 411.16 (free acid)
UV: $\lambda_{max}$: 273 nm, $\epsilon$19.000
HPLC: 4:27 min.
ESI-MS (+): m/z 412 $[M+H]^+$; 513 $[M+TEA+H]^+$
ESI-MS (−): m/z 410 $[M-H]^- \rightarrow 204$ $[6-MB-A-H]^-$

78) $N^6$-Cycloheptyladenosine-3',5'-cyclic boranophosphate, Sp-isomer (Sp-6-CH-cAMPB, #158)

To 1 μmol of Sp-6-Cl-cPuMPB (example 43) in 100 μl of water 10 μl cycloheptylamine (Sigma-Aldrich) were added and the closed vial was heated for 1 h at 99° C.

The product signal was isolated by semipreparative high pressure liquid chromatography on reversed phase silica (25 Vol.-% acetonitrile, 20 mM triethylammonium formate buffer, pH 7, 2 ml/min., 280 nm) as triethylammonium salt, yield 89.4%, purity 99.6%.

$C_{17}H_{27}BN_5O_5P$; MW 423.22 (free acid)
UV: $\lambda_{max}$: 271 nm, $\epsilon$19.300
HPLC: 12:51 min.
ESI-MS (+): m/z 525 $[M+TEA+H]^+$
ESI-MS (−): m/z 422 $[M-H]^- \rightarrow 408$ $[M-BH_3-H]^- \rightarrow 230$ $[6-CH-A-H]^-$

79) 6-Phenylpurine-1-β-D-ribofuranoside-3',5'-cyclic boranophosphate, Rp-isomer (Rp-6-Phe-cPuMPB, #175)

Triphenylphosphine (Sigma-Aldrich) and palladium acetate (Sigma-Aldrich) were dissolved in dry dimethylformamide and heated for 15 min. at 50° C. to form an active red catalyst as described by Andrei et al., *Org. Biomol. Chem.*, 5, 2070-2080 (2007).

1 μmol of Rp-6-Cl-cAMPB (example 42) and 10 μl of phenyl-tri-n-butylstannane (Sigma-Aldrich) were dissolved in 50 µl of dimethylformamide, 5 µl of the freshly prepared catalyst were added and the whole mixture was heated for 1 h at 85° C.

Rp-6-Phe-cPuMPB was isolated as main product from the dark brown solution by semipreparative high pressure liquid chromatography (purity 99.2%) on reversed phase silica (20 Vol.-% acetonitrile, 20 mM triethylammonium formate buffer, pH 7, 2 ml/min., 289 nm) with a yield of 24.5%.

$C_{16}H_{18}BN_4O_5P$; MW 388.13 (free acid)
UV: $\lambda_{max}$: 289 nm, $\epsilon$20.000
HPLC: 4:68 min.
ESI-MS (+): m/z 490 [M+TEA+H]$^+$
ESI-MS (−): m/z 387 [M−H]$^-$→373 [M-BH$_3$–H]$^-$→195 [6-Phe-Pu–H]$^-$

80) 6-Chloropurine-2'-O-(imidazolylcarbamoyl)-1-β-D-ribofuranoside-3',5'-cyclic boranophosphate, Rp-isomer (Rp-6-Cl-2'-IC-cPuMPB, #135)

10 µmol of Rp-6-Cl-cPuMPB, sodium salt (example 42), were dissolved in 1 ml of dry dimethylformamide and 50 mg of carbonyldiimidazole (Sigma-Aldrich) were added. The progress of the reaction was followed by HPLC (RP-18, 30 Vol.-% acetonitrile, 20 mM triethylammonium formate buffer, 1.5 ml/min., UV detection at 263 nm). After completion of the reaction, the raw Rp-6-Cl-2'-IC-cPuMPB was isolated and purified by preparative liquid chromatography (99.3%) on RP-18 reversed phase silica with the same eluent as the corresponding triethyl ammonium salt; yield 87.4%.

$C_{14}H_{15}BClN_6O_6P$; MW 440.55 (free acid)
UV: $\lambda_{max}$: 263 nm, $\epsilon$8.900
HPLC: 2:57 min.
ESI-MS (+): m/z 643/645 [M+2TEA+H]$^+$→441 [M+H]$^+$
ESI-MS (−): m/z 439/441 [M−H]$^-$→425 [M-BH$_3$–H]$^-$→153 [6-Cl—Pu–H]$^-$

81) 6-Chloropurine-2'-O-(6-aminohexylcarbamoyl)-1-β-D-ribofuranoside-3',5'-cyclic boranophosphate, Rp-isomer (Rp-2'-AHC-6-Cl-cPuMPB, #137)

5 µmol of Rp-6-Cl-2'-IC-cPuMPB, triethylammonium salt (example 80), was dissolved in dry dimethylformamide (Sigma-Aldrich) and 15 mg of 1,6-diaminohexane (Sigma-Aldrich) were added. The solution was stirred at RT while the coupling progress was followed by HPLC (RP-18, 15 Vol.-% acetonitrile, 20 mM triethylammonium formate buffer, 1 ml/min., UV detection at 264 nm), monitoring the decrease of the Rp-6-Cl-2'-IC-cPuMPB signal at 6:32 min. After 0.5 h the starting material had disappeared and a new product signal had risen at 1:73 min.; yield 89%.

The raw Rp-2'-AHC-6-Cl-cPuMPB was isolated and purified by preparative reversed phase chromatography up to 99.1% as the corresponding triethyl ammonium salt, using 15 Vol.-% acetonitrile, 20 mM triethylammonium formate buffer at 1.5 ml/min.; yield 78.3%.

$C_{17}H_{27}BClN_6O_6P$; MW 488.68 (free acid)
UV: $\lambda_{max}$: 263 nm, $\epsilon$8.900
HPLC: 1:73 min.
ESI-MS (+): m/z 590/592 [M+TEA+H]$^+$→576 [M-BH$_3$+H]$^+$
ESI-MS (−): m/z 487/489 [M−H]$^-$→345 [M-AHC–H]$^-$; 153 [6-Cl—Pu–H]$^-$

82) 2-(6-Aminohexylamino)adenosine-3',5'-cyclic boranophosphate, Rp-isomer (Rp-2-AHA-cAMPB, #187)

To 1 µmol of Rp-2-Cl-cAMPB (example 70) in 100 µl of water 10 mg of 1,6-diaminohexane (Sigma-Aldrich) were added and the closed vial was heated for 24 h at 99° C.

The product signal (54.7%) was isolated by semipreparative high pressure liquid chromatography on RP-18 reversed phase silica (25 Vol.-% acetonitrile, 20 mM triethylammonium formate buffer, pH 7, 1 ml/min., UV detection at 258 nm) as triethylammonium salt with a purity of 99.7%.

$C_{16}H_{29}BN_7O_5P$; MW 441.23 (free acid)
UV: $\lambda_{max}$: 258 nm, $\epsilon$12.600
HPLC: 2:33 min.
ESI-MS (+): m/z 543 [M+TEA+H]$^+$→442 [M−TEA+H]$^+$→426 [M-BH$_3$+H]$^+$→250 [2-AHA-A+H]$^+$
ESI-MS (−): m/z 440 [M−H]$^-$→426 [M-BH$_3$–H]$^-$→248 [2-AHA-A–H]$^-$

83) 2-Diethylaminoadenosine-3',5'-cyclic boranophosphate, Rp-isomer (Rp-2-DEA-cAMPB, #193)

To 1 µmol of Rp-2-Cl-cAMPB (example 70) in 100 µl of dimethylformamide 10 µl of diethylamine (Sigma-Aldrich) were added and the closed vial was heated for 24 h at 99° C.

The product signal (42.1%) was isolated by semipreparative high pressure liquid chromatography on RP-18 reversed phase silica (20 Vol.-% acetonitrile, 20 mM triethylammonium formate buffer, pH 7, 2 ml/min., UV detection at 262 nm) as triethylammonium salt with a purity of 99.7%.

$C_{14}H_{24}BN_6O_5P$; MW 398.17 (free acid)
UV: $\lambda_{max}$: 262 nm, $\epsilon$13.000
HPLC: 3:15 min.
ESI-MS (+): m/z 500 [M+TEA+H]$^+$→486 [M-BH$_3$+H]$^+$
ESI-MS (−): m/z 397 [M−H]$^-$→383 [M-BH$_3$–H]$^-$→205 [2-DEA-A–H]$^-$

84) 8-Bromo-2'-O-(imidazolylcarbamoyl)adenosine-3',5'-cyclic boranophosphate, Rp-isomer (Rp-8-Br-2'-IC-cAMPB, #007)

1 µmol of Rp-8-Br-cAMPB, sodium salt (example 1), was dissolved in 100 µl of dry dimethylformamide and 5 mg of carbonyldiimidazole (Sigma-Aldrich) were added. The progress of the reaction was followed by HPLC (RP-18, 25 Vol.-% acetonitrile, 20 mM triethylammonium formate buffer, 2 ml/min., UV detection at 264 nm). After completion of the reaction, the raw Rp-8-Br-2'-IC-cAMPB was isolated and purified up to 91.8% by preparative liquid chromatography on RP-18 reversed phase silica with the same eluent as the corresponding triethyl ammonium salt, yield 74.2%.

$C_{14}H_{15}BBrN_7O_6P$; MW 499.01 (free acid)
UV: $\lambda_{max}$: 264 nm, $\epsilon$17.000
HPLC: 3:38 min.
ESI-MS (+): m/z 601/603 [M+TEA+H]$^+$→587 [M-BH$_3$+H]$^+$
702/704 [M+2TEA+H]$^+$→601 [M+TEA+H]$^+$
ESI-MS (−): m/z 498/500 [M−H]$^-$→484 [M-BH$_3$–H]$^-$→212 [8-Br-A–H]$^-$

85) 8-(4-Chlorophenylthio)guanosine-3',5'-cyclic boranophosphate, Sp-isomer (Sp-8-pCPT-cGMPB, #242)

Sp-8-pCPT-cAMPB was prepared by nucleophilic substitution of the 8-bromo function of 1 µmol of Sp-8-Br-cAMPB, sodium salt (example 6), with excessive 4-chlorothiophenol (Fluka) and diisopropylethylamine (Hünig's base, Sigma-Aldrich) in 500 µl propanol-2 at 99° C. in a sealed plastic vial for 24 h.

The progress of the reaction was followed by HPLC (RP-18, 25 Vol.-% acetonitrile, 20 mM triethylammonium formate buffer, 2.5 ml/min., UV detection at 260 and 276 nm). Using the same eluent, Sp-8-pCPT-cGMPB was isolated and purified by preparative reversed phase chromatography as the corresponding triethyl ammonium salt, purity 98.5%, yield 72%.

$C_{16}H_{18}ClBN_5O_6PS$; MW 485.65 (free acid)
UV: $\lambda_{max}$: 276 nm, $\epsilon$21.500
HPLC: 10:27 min.
ESI-MS (+): m/z 587 [M+TEA+H]$^+$→573 [M-BH$_3$+H]$^+$→294 [8-pCPT-G+H]$^+$
ESI-MS (−): m/z 484/486 [M−H]$^-$→470 [M-BH$_3$−H]$^-$→292 [8-pCPT-G−H]$^-$

86) 2'-O-(8-[5-Carboxytetramethylrhodaminyl]amino-3,6-dioxaoctylcarbamoyl)-8-bromo-guanosine-3',5'-cyclic boranophosphate, Sp-isomer (Sp-2'-TAMRA-ADOC-8-Br-cGMPB, #230)

0.1 µmol of Sp-2'-ADOC-8-Br-cGMPB, triethylammonium salt (example 19), was dissolved in 10 mM aqueous hydrogencarbonate (Merck) and 3 mg of 5-carboxytetramethylrhodamine, succinimidyl ester (ChemPep, Wellington, Fla., USA) were added. The solution was stirred at RT while the coupling progress was followed by HPLC (RP-18, 25 Vol.-% acetonitrile, 20 mM triethylammonium formate buffer, 2 ml/min., UV 260 nm), monitoring the decrease of the Sp-2'-ADOC-8-Br-cGMPB signal at 1:03 min. After 0.5 h the starting material had disappeared and a new product signal had risen at 2:55 min.; yield 53%.

The red, fluorescent Sp-2'-TAMRA-ADOC-8-Br-cGMPB was isolated and purified by preparative reversed phase chromatography as the corresponding triethyl ammonium salt, using 25 Vol.-% acetonitrile, 20 mM triethylammonium formate buffer at 1.5 ml/min., purity 92.3% by HPLC.

$C_{42}H_{49}BBrN_9O_{13}P$; MW 1009.59 (free acid)
UV: $\lambda_{max}$: 543 nm, $\epsilon$95.000 (MeOH)
HPLC: 2:55 min.
ESI-MS (+): m/z 1110/1112 [M+TEA+H]$^+$
ESI-MS (−): m/z 1007/1009 [M−H]$^-$→940 [?−H]$^-$

87) 2'-O-(Imidazolylcarbamoyl)cytidine-3',5'-cyclic boranophosphate, Rp-isomer (Rp-2'-IC-cCMPB, #265)

10 µmol of Rp-cCMPB, sodium salt (example 67), was dissolved in 1 ml of dry dimethylformamide and 50 mg of carbonyldiimidazole (Sigma-Aldrich) were added. The progress of the reaction was followed by HPLC (RP-18, 15 Vol.-% acetonitrile, 20 mM triethylammonium formate buffer, 1 ml/min., UV detection at 270 nm). After completion of the reaction, the raw Rp-2'-IC-cCMPB (89.7%) was isolated and purified by preparative liquid chromatography on RP-18 reversed phase silica with the same eluent as the corresponding triethyl ammonium salt, purity 94.4%.

$C_{13}H_{17}BN_5O_7P$; MW 397.09 (free acid)
UV: $\lambda_{max}$: 270 nm, $\epsilon$9.000
HPLC: 4:25 min.
ESI-MS (+): m/z 499 [M+TEA+H]$^+$→485 [M-BH$_3$+H]$^+$ 600 [M+2TEA+H]$^-$→499 [M+TEA+H]$^+$
ESI-MS (−): m/z 396 [M−H]$^-$→382 [M-BH$_3$−H]$^-$

88) 2'-O-(4-Aminobutylcarbamoyl)cytidine-3',5'-cyclic boranophosphate, Rp-isomer (Rp-2'-ABC-cCMPB, #267)

5 µmol of Rp-2'-IC-cCMPB, triethylammonium salt (example 87), was dissolved in 500 µl of dry dimethylformamide and 20 µl of 1,4-diaminobutane (Merck, Darmstadt, Germany) were added. The solution was stirred at RT while the coupling progress was followed by HPLC (RP-18, 15 Vol.-% acetonitrile, 20 mM triethylammonium formate buffer, 1 ml/min., UV 270 nm), monitoring the decrease of the Rp-8-Br-2'-IC-cGMPB signal at 4:25 min. After 0.5 h the starting material had disappeared and a new product signal had risen at 2:58 min.

The raw Rp-2'-ABC-cCMPB was isolated and purified by preparative reversed phase chromatography as the corresponding triethyl ammonium salt, using 15 Vol.-% acetonitrile, 20 mM triethylammonium formate buffer at 1.0 ml/min.; yield 80%.

$C_{14}H_{25}BN_5O_7P$; MW 417.17 (free acid)
UV: $\lambda_{max}$: 270 nm, $\epsilon$9.000
HPLC: 2:58 min.
ESI-MS (+): m/z 418 [M+H]$^+$→404 [M-BH$_3$+H]$^+$
ESI-MS (−): m/z 416 [M−H]$^-$→402 [M-BH$_3$−H]$^-$

89) 2'-O-(4-Aminobutylcarbamoyl)cytidine-3',5'-cyclic boranophosphate, Rp-isomer, immobilised to agarose (Rp-2'-ABC-cCMPB-Agarose, #269)

4 µmol of Rp-2'-ABC-cCMPB, triethylammonium salt (example 88) was coupled to 1 ml of N-hydroxysuccinimide-activated Sepharose Fast Flow (Pharmacia, Erlangen, Germany) in dry dimethylsulfoxide via the endstanding primary ω-amino group in position of the 2'-ribose moiety. 5 µl of diisopropylethylamine (Hünig's base, Sigma-Aldrich) were added and the coupling progress was followed by HPLC (RP-18, 15 Vol.-% acetonitrile, 20 mM triethylammonium formate buffer, 1 ml/min., UV 270 nm), monitoring the decrease of the Rp-2'-ABC-cCMPB signal at 2:58 min. After 1 h of gentle shaking at RT one equivalent of ethanolamine (Fluka) was added in order to block all non-reacted active sites. Subsequently, the gel was filtered off, washed with propanol-2 and phosphate buffer and stored in phosphate buffer containing 0.01% sodium azide for preservation.

Rp-2'-ABC-cCMPB-Agarose ligand density: approx. 0.4 µmol/100 µl of settled gel

90) 2'-O-(6-Carboxypentylcarbamoyl)cytidine-3',5'-cyclic boranophosphate, Rp-isomer (Rp-2'-CPC-cCMPB, #273)

4 µmol of Rp-2'-IC-cCMPB, triethylammonium salt (example 87), was dissolved in 1 ml of water and an excess of 20 mg of 6-aminohexanoic acid (Sigma) were added. The solution was stirred at RT while the coupling progress was followed by HPLC (RP-18, 15 Vol.-% acetonitrile, 20 mM triethylammonium formate buffer, 1 ml/min., UV 270 nm), monitoring the decrease of the Rp-2'-IC-cCMPB signal at 4:25 min. After 24 h the starting material had nearly disappeared and a new product signal had risen at 2:95 min.

The raw Rp-2'-CPC-cCMPB was isolated and purified by preparative reversed phase chromatography as the corresponding triethyl ammonium salt, using 15 Vol.-% acetonitrile, 20 mM triethylammonium formate buffer at 1.0 ml/min.; yield 93%, purity >99.5%

$C_{16}H_{26}BN_4O_9P$; MW 460.19 (free acid)
UV: $\lambda_{max}$: 270 nm, $\epsilon$9.000
HPLC: 3:15 min.
ESI-MS (+): m/z 562 [M+2TEA+H]$^+$→548 [M-BH$_3$+H]$^+$→447 [548-TEA+H]$^+$
ESI-MS (−): m/z 459 [M−H]$^-$→445 [M-BH$_3$−H]$^-$ 481 [M+Na−H]$^-$

91) 2-Thioadenosine-3',5'-cyclic boranophosphate, Sp-isomer (Sp-2-SH-cAMPB, #196)

Sp-2-SH-cAMPB was prepared by nucleophilic substitution of the chlorine atom in position 2 of the adenine nucleobase of 1 µmol Sp-2-Cl-cAMPB, sodium salt (example 71), in presence of 10 µl of Hünig's base (Sigma), with a saturated solution of sodium hydrogen sulfide (Fluka) in 100 µl of dimethylformamide at 90° C. in a sealed plastic vial for 24 h.

The progress of the reaction was followed by HPLC (RP-18, 15 Vol.-% acetonitrile, 20 mM triethylammonium formate buffer, 1.5 ml/min., UV detection at 262 and 286 nm). Using the same eluent, Sp-2-SH-cAMPB was isolated and purified (99.3%) by preparative reversed phase chromatography as the corresponding triethyl ammonium salt in 53% yield.

$C_{10}H_{15}BN_5O_5PS$; MW 359.11 (free acid)
UV: $\lambda_{max}$: 286 nm, ∈20.600
HPLC: 2:84 min.
ESI-MS (+): m/z 461[M+TEA+H]$^+$→447 [M-BH$_3$+H]$^+$
ESI-MS (−): m/z 358 [M−H]$^-$→344 [M-BH$_3$−H]$^-$→166 [2-SH-A−H]$^-$

92) 2-(2-Hydroxyethylthio)adenosine-3',5'-cyclic boranophosphate, Sp-isomer (Sp-2-HET-cAMPB, #198)

Sp-2-HET-cAMPB was prepared by nucleophilic substitution of the chlorine atom in position 2 of the adenine nucleobase of 1 µmol Sp-2-Cl-cAMPB, sodium salt (example 71), in presence of 10 µl of ethyldiisopropylamine (Sigma), with an excess of 20 µl of mercaptoethanol (Fluka) in 100 µl of dimethylformamide at 90° C. in a sealed plastic vial for 24 h.

The progress of the reaction was followed by HPLC (RP-18, 20 Vol.-% acetonitrile, 20 mM triethylammonium formate buffer, 1.5 ml/min., UV detection at 262 and 286 nm). Using the same eluent, Sp-2-HET-cAMPB was isolated and purified (>99%) by preparative reversed phase chromatography as the corresponding triethyl ammonium salt in 44% yield.

$C_{12}H_{13}BN_5O_6PS$; MW 403.16 (free acid)
UV: $\lambda_{max}$: 273 nm, ∈14.500
HPLC: 3:88 min.
ESI-MS (+): m/z 606 [M+2TEA+H]$^+$→592 [M-BH$_3$+H]$^+$
ESI-MS (−): m/z 402 [M−H]$^-$→388 [M-BH$_3$−H]$^-$→210 [2-HET-A−H]$^-$

93) 6-(N,N-Dimethylaminocarbonyl)purine-1-β-D-ribofuranoside-3',5'-cyclic boranophosphate, Sp-isomer (Sp-6-DMAC-cPuMPB, #177)

Triphenylphosphine (Sigma-Aldrich) and palladium acetate (Sigma-Aldrich) were dissolved in dry dimethylformamide and heated for 15 min. at 50° C. to form an active red catalyst as described by Andrei et al., Org. Biomol. Chem., 5, 2070-2080 (2007).

1 µmol of Sp-6-Cl-cAMPB (example 43) and 10 µl of trimethylsilyl-tri-n-butylstannane (Sigma-Aldrich) were dissolved in 50 µl of dimethylformamide, 5 µl of the freshly prepared catalyst was added and the whole mixture heated for 1 h at 85° C. Two new product signals at 2:28 and 2:78 minutes rose, which were identified by mass spectrometry to be Sp-cPuMPB and Sp-6-DMAC-cPuMPB, respectively.

Sp-6-DMAC-cPuMPB was isolated as main product from the dark brown solution by semipreparative high pressure liquid chromatography on reversed phase silica (RP-18, Vol.-% acetonitrile, 20 mM triethylammonium formate buffer, pH 7, 2 ml/min., 263 nm) with a yield of 19.3% and a purity of 99.6%.

$C_{13}H_{19}BN_5O_6P$; MW 383.11 (free acid)
UV: $\lambda_{max}$: 271 nm
HPLC: 2:78 min.
ESI-MS (+): m/z 559 [357+2TEA+H]$^+$
ESI-MS (−): m/z 382 [M−H]$^-$→311 [M-DMAC-H]$^-$

94) 6-Azidopurine-1-β-D-ribofuranoside-3',5'-cyclic boranophosphate, Rp-isomer Rp-6-N$_3$-cPuMPB #179)

A solution of 1 µmol of Rp-6-Cl-cPuMPB (example 42) in dimethylformamide was treated with a saturated solution of sodium azide (Fluka) in dimethylformamide at 80° C. for 5 minutes. Rp-6-N$_3$-cPuMPB was quantitatively formed at 3:07 min. and could be isolated by preparative column chromatography on reversed phase silica (RP-18, 25 Vol.-% acetonitrile, 20 mM triethylammonium formate buffer, 1 ml/min., pH 7).

$C_{10}H_{13}BN_7O_5P$; MW 353.04 (free acid)
UV: $\lambda_{max}$: 290 nm
HPLC: 3:07 min.
ESI-MS (+): m/z 398 [M+2Na+H]$^+$→356 [M+2Na—BH$_3$—N$_2$+H]$^+$
m/z 455 [M+TEA+H]$^+$
m/z 556 [M+2TEA+H]$^+$→455 [M+TEA+H]$^+$
ESI-MS (−): m/z 352 [M−H]$^-$→338 [M-BH$_3$-H]$^-$
324 [M-N$_2$-H]$^-$
310 [M-BH$_3$—N$_2$-H]$^-$

95) 8-Bromo-2'-phenoxythiocarbonyladenosine-3', 5'-cyclic boranophosphate, Sp-isomer (Sp-8-Br-2'-PTC-cAMPB, #306)

A solution of 5 µmol of Sp-8-Br-cAMPB (example 2) in 2 ml of dry dichloromethane was treated with 2.5 mg of dimethylaminopyridine (Aldrich) and 1.4 µl of phenoxythiocarbonyl chloride (Fluka) for 16 h at RT under argon. The decrease of the starting material at 1:62 min was followed by HPLC (RP-18, 20 Vol.-% acetonitrile, 20 mM triethylammonium formate buffer, 1.5 ml/min., pH 7 at 259 nm).

The peak for Sp-8-Br-2'-PTC-cAMPB at 2:69 min was isolated by semipreparative column chromatography on reversed phase silica (RP-18, 40 Vol.-% acetonitrile, 20 mM triethylammonium formate buffer, 1.5 ml/min., pH 7), yield 87.6%.

$C_{17}H_{18}BBrN_5O_6PS$; MW 542.11
UV: $\lambda_{max}$: 259 nm
HPLC: 2:69 min.
ESI-MS (+): m/z 643/645 [M+2TEA+H]$^+$→629 [M+2TEA-BH$_3$+H]$^+$
ESI-MS (−): m/z 540/542 [M−H]$^-$→526 [M-BH$_3$-H]$^-$→212 [8-Br-A−H]$^+$

96) 2'-Deoxyadenosine-3',5'-cyclic boranophosphate, Sp-isomer (Sp-2'-cdAMPB, #122)

4 µmol of Sp-8-Br-2'-PTC-cAMPB, triethylammonium salt (example 94) was dissolved in 2 ml of dry dioxane and treated with 3 mg of azo-bis(isobutyronitrile) (Aldrich), and 10 µl of tris(trimethyl)silane (Fluka) at 80° C. for 1 h. The decrease of the starting material at 2:58 min. was followed by HPLC (RP-18, 40 Vol.-% acetonitrile, 20 mM triethyl-ammonium formate buffer, 1.5 ml/min., pH 7 at 259 nm).

The product peak at 3:31 min. (37.6% HPLC) was isolated by semipreparative column chromatography on reversed phase silica (RP-18, 15 Vol.-% acetonitrile, 20 mM triethylammonium formate buffer, 1.5 ml/min., pH 7) and turned out to be Sp-cdAMPB. Under these experimental conditions also dehalogenation had taken place.

$C_{10}H_{15}BN_5O_4P$; MW 311.05
UV: $\lambda_{max}$: 259 nm
HPLC: 3:31 min.
ESI-MS (+): m/z 514 [M+2TEA+H]$^+$→413 [M+TEA+H]$^+$
ESI-MS (−): m/z 310 [M−H]$^-$→296 [M−BH$_3$−H]$^-$→134 [B—H]$^+$ Stability Experiments Degradation Example 1

In order to check out the stability of the boranophosphates described in this invention towards oxidising conditions in comparison to the corresponding phosphorothioates, 0.1 µmol of the sodium salts of each, Rp-8-bromoadenosine-3',5'-cyclic boranophosphate (Rp-8-Br-cAMPB, example 1), Sp-8-bromoadenosine-3',5'-cyclic boranophosphate (Sp-8-Br-cAMPB, example 2), Rp-8-bromoadenosine-3',5'-cyclic phosphorothioate (Rp-8-Br-cAMPS, Biolog) and Sp-8-bromoadenosine-3',5'-cyclic phosphorothioate (Sp-8-Br-cAMPS, Biolog) were dissolved in 100 µl of eluent and the mixture was analyzed by HPLC (RP-18, 11% acetonitrile, 20 mM triethylammonium formate buffer, pH 6.1, 1.5 ml/min, UV 258 nm). The following elution profile was recorded: Rp-8-Br-cAMPS (5:13 min.)<Sp-8-Br-cAMPS (7:23 min.)<Sp-8-Br-cAMPB (9:13 min.)<Rp-8-Br-cAMPB (11:99 min.).

Subsequently, aqueous hydrogen peroxide (Merck) was added in small portions while the stability of the four compounds was permanently monitored over time.

10 µl of H$_2$O$_2$ (0.3%) as well as 10 µl of 3% H$_2$O$_2$ were added to no effect.

After further addition of 10 µl of 30% H$_2$O$_2$ the signals for the phosphorothioate analogues Rp- and Sp-8-Br-cAMPS began to decrease, while both boranophosphates showed no detectable decomposition. After two hours at RT both phosphorothioate signals were completely vanished while the signals for Rp- and Sp-8-Br-cAMPB had lost only 35% area.

From this experiment the half-life of cyclic boranophosphates versus that of the corresponding phosphorothioates appears to be considerably longer, approx. by a factor of 10.

FIG. 1 depicts the result of the degradation example 1 with hydrogen peroxide. Oxidation of cyclic boranophosphates (Rp-8-Br-cAMPB; Sp-8-Br-cAMPB) versus cyclic phosphorothioates (Rp-8-Br-cAMPS; Sp-8-Br-cAMPS).

Degradation Example 2

In a subsequent experiment it was tested whether a substitution of the adenine nucleobase with a bulky group would influence oxidative stability of cyclic boranophosphates substantially.

Thus, 0.05 µmol of the Rp-isomer of 8-(4-chlorophenyl-thio)adenosine-3',5'-cyclic boranophosphate (Rp-8-pCPT-cAMPB, example 9), was treated stepwise with 5 µl portions of 30% aqueous hydrogen peroxide solution (Merck) every 30 min. The oxidation process was monitored by reversed phase HPLC (RP-18, 25 Vol.-% acetonitrile, 20 mM triethylammonium formate buffer, pH 6.1, 2 ml/min, UV 280 nm). As a control the corresponding cyclic nucleotide with phosphorothioate modification (Sp-8-pCPT-cAMPS, Biolog) was added. In summary, 15 µl peroxide, were applied.

Right from the start the signal for Sp-8-pCPT-cAMPS was decreasing and a new peak with shorter retention time appeared, which was identified as the corresponding oxidised compound 8-pCPT-cAMP by both, mass spectrometry and authentic material (Biolog). After 1.5 hours at RT Sp-8-pCPT-cAMPS was degraded by more than 50% while the peak for Rp-8-pCPT-cAMPB had still 79% of the original area, and a final control after 18 hours showed that still 30% of the cyclic boranophosphate were present, while the phosphorothioate signal was completely vanished from the chromatogram.

TABLE 2

Oxidation of Rp-8-pCPT-cAMPB versus the corresponding cyclic phosphorothioate (Sp-8-pCPT-CAMPS) by hydrogen peroxide; quantification by HPLC.

| Time (h) | Sp-8-pCPT-CAMPS (HPLC Area %) | Rp-8-pCPT-cAMPB (HPLC Area %) |
|---|---|---|
| 0.00 | 100 | 100 |
| 0.50 | 81.7 | 87.51 |
| 1.00 | 57.47 | 82.89 |
| 1.50 | 45.71 | 79.25 |
| 18.00 | 0 | 29.56 |

Degradation Example 3

It was also investigated whether the higher stability of the boranophosphate-modified cyclic nucleotides disclosed, towards peroxide—as observed for 8-Br-cAMPB and 8-pCPT-cAMPB—could be confirmed for analogues additionally modified at the 2'-hydroxyl group as well.

Thus, 0.1 µmol of the Rp-isomer of 8-(4-chlorophenyl-thio)-2'-O-methyladenosine-3',5'-cyclic boranophosphate (Rp-8-pCPT-2'-O-Me-cAMPB, example 44), dissolved in 300 µl of water, was treated stepwise with 2 µl portions of 30% aqueous hydrogen peroxide solution (Merck). The oxidation process was monitored again by reversed phase HPLC (RP-18, 30 Vol.-% acetonitrile, 20 mM triethylammonium formate buffer, pH 8.3, 2 ml/min, UV 282 nm). As a control, the corresponding cyclic nucleotide with phosphorothioate modification (Sp-8-pCPT-2'-O-Me-cAMPS, Biolog) was added. In summary, 20 µl peroxide, were applied.

Figure 2:
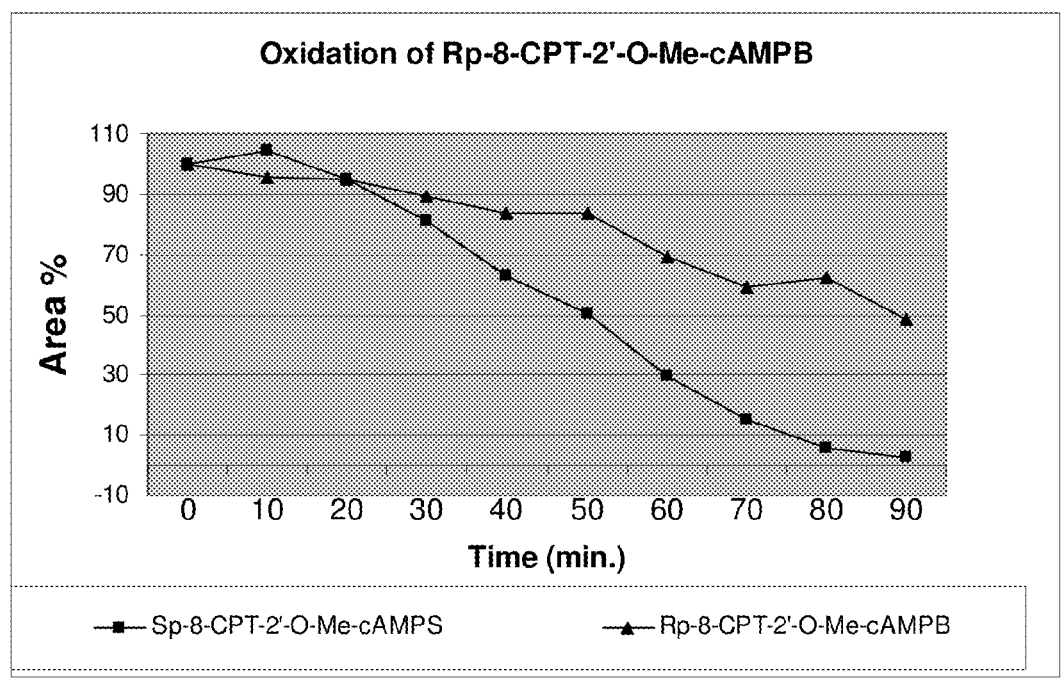
FIG. 2 depicts the result of degradation example 3 with hydrogen peroxide.

FIG. 2 depicts the result of degradation example 3 with hydrogen peroxide. Oxidation of a cyclic boranophosphate with bulky group in position 8 of the adenine nucleobase and additional modification in position 2' of the ribose moiety (Rp-8-pCPT-2'-O-Me-cAMPB) versus the corresponding cyclic phosphorothioate (Sp-8-pCPT-2'-O-Me-cAMPS).

Again, the signal for Sp-8-pCPT-2'-O-Me-cAMPS at 3:40 min. was decreasing with every new peroxide addition and a new peak with shorter retention time at 2:24 min. appeared, which was identified as the corresponding oxidised compound 8-pCPT-2'-O-Me-cAMP by both, mass spectrometry and authentic material (Biolog). After 90 min. at RT Sp-8-pCPT-2'-O-Me-cAMPS was completely degraded while the peak for Rp-8-pCPT-2'-O-Me-cAMPB at 8:22 min. had still 50% of the original area.

Degradation Example 4

In a comparable experiment, the Sp-isomer of 8-benzyl-thio-2'-O-methyladenosine-3',5'-cyclic boranophosphate (Sp-8-BT-2'-O-Me-cAMPB, example 45), dissolved in water, was treated stepwise with µl portions of 30% aqueous hydrogen peroxide solution (Merck). As a control, the corresponding cyclic nucleotide with phosphorothioate modification (Rp-8-BT-2'-O-Me-cAMPS, Biolog) had been added. The oxidation process was monitored by reversed phase HPLC (RP-18, 30 Vol.-% acetonitrile, 20 mM triethylammonium formate buffer, pH 8.3, 2 ml/min, UV 282 nm). The areas of both peaks were recorded, integrated and compared (Tab. 2).

As expected, the signal for Rp-8-BT-2'-O-Me-cAMPS at 2:54 min. was decreasing under peroxide addition and a new peak with shorter retention time at 2:34 min. appeared (8-BT-2'-O-Me-cAMP). After 3 hours at RT Rp-8-BT-2'-O-Me-cAMPS was nearly completely degraded while the peak for Sp-8-BT-2'-O-Me-cAMPB at 7:21 min. had still 73% of the original area.

TABLE 3

Oxidation of Sp-8-BT-2'-O—Me-cAMPB by hydrogen peroxide versus the corresponding cyclic phosphorothioate (Rp-8-BT-2'-O—Me-cAMPS); quantification by HPLC as ratio of area percentages.

| Time (min) | Peak Area Ratio Rp-8-BT-2'-O—Me-cAMPS versus Sp-8-BT-2'-O—Me-cAMPB | |
|---|---|---|
| 0 | 1.00:1 | $H_2O_2$ |
| 14 | 0.97:1 | |
| 22 | 0.93:1 | |
| 40 | 0.91:1 | |
| 48 | 0.88:1 | |
| 62 | 0.70:1 | $H_2O_2$ |
| 72 | 0.62:1 | |
| 82 | 0.63:1 | |
| 91 | 0.58:1 | |
| 118 | 0.43:1 | $H_2O_2$ |
| 139 | 0.36:1 | |
| 155 | 0.30:1 | $H_2O_2$ |
| 165 | 0.26:1 | |
| 174 | 0.22:1 | |
| 234 | 0.11:1 | |

Degradation Example 5

In another experiment it was investigated whether the higher stability of boranophosphate-modified cyclic nucleotides towards peroxide as observed for different 8- and 2'-modified structures could be confirmed for analogues modified at position 6 of the purine nucleobase as well.

Thus, the cyclic boranophosphate 6-chloropurine-1-β-D-ribofuranoside-3',5'-cyclic boranophosphate, Rp-isomer (Rp-6-Cl-cPuMPB, example 42) together with the corresponding phosphorothioate 6-chloropurine-1-β-D-ribofuranoside-3',5'-cyclic phosphorothioate, Sp-isomer (Sp-6-Cl-cPuMPS, Biolog) as a control were treated repeatedly with µl doses of 30% aqueous hydrogen peroxide (Merck). During one hour, oxidative degradation was monitored by HPLC (RP-18, 15 Vol.-% acetonitrile, 20 mM triethylammonium formate buffer, pH 6.5, 2 ml/min., UV 263 nm) and corresponding peak areas were recorded, integrated and compared (Tab. 3).

TABLE 4

Oxidation of Rp-6-Cl-cPuMPB by hydrogen peroxide versus the corresponding cyclic phosphorothioate (Sp-6-Cl-cPuMPS); quantification by HPLC as ratio of area percentages.

| Time (min) | Peak Area Ratio Sp-6-Cl-cPuMPS versus Rp-6-Cl-cPuMPB |
|---|---|
| 0 | 1.00:1 |
| 5 | 0.95:1 |
| 20 | 0.93:1 |
| 30 | 0.86:1 |
| 45 | 0.80:1 |
| 60 | 0.63:1 |

Again, the signal for Sp-6-Cl-cPuMPS at 2:48 min. was decreasing under peroxide addition and a new peak with shorter retention time (6-Cl-cPuMP) at 1:32 min. appeared, After 1 hour at RT Sp-6-Cl-cPuMPS had been considerably degraded (37%), while the peak for the cyclic boranophosphate Rp-6-Cl-cPuMPB at 3:77 min. had still 93% of the original area.

Degradation Example 6

In another experiment it was investigated whether the higher stability of boranophosphate-modified cyclic nucleotides towards peroxide as observed for different 6-, 8- and 2'-modified structures could be confirmed for analogues modified at position 2 of the purine nucleobase as well.

Thus, 0.1 µmol of the cyclic boranophosphate 2-chloroadenosine-3',5'-cyclic boranophosphate, Sp-isomer (Sp-2-Cl-cAMPB, example 71) and 0.1 µmol of the corresponding phosphorothioate 2-chloroadenosine-3',5'-cyclic phosphorothioate, Rp-isomer (Rp-2-Cl-cAMPS, Biolog) as a control, were each dissolved in 100 µl of water, combined and treated with 10 µl of 30% aqueous hydrogen peroxide (Merck), and another 10 µl after one hour. During 2.5 hours, oxidative degradation was monitored by HPLC (RP-18, 15 Vol.-% acetonitrile, 20 mM triethylammonium formate buffer, pH 6.5, 1.5 ml/min., UV 262 nm). Corresponding peak areas were recorded, integrated and compared (Tab. 5).

TABLE 5

Oxidation of Sp-2-Cl-cAMPB by hydrogen peroxide versus the corresponding cyclic phosphorothioate (Rp-2-Cl-cAMPS); quantification by HPLC as ratio of area percentages.

| Time (min) | Peak Area Ratio Rp-2-Cl-CAMPS versus Sp-2-Cl-cAMPB | |
|---|---|---|
| 0 | 1.00:1 | $H_2O_2$ |
| 10 | 0.76:1 | |
| 30 | 0.52:1 | |
| 60 | 0.39:1 | $H_2O_2$ |
| 90 | 0.29:1 | |
| 120 | 0.22:1 | |
| 150 | 0.19:1 | |

The signal for Sp-2-Cl-cAMPS at 3:74 min. was decreasing under peroxide addition and a new peak with shorter retention time (2-Cl-cAMP) at 2:35 min. appeared. After 1 hour at RT Sp-2-Cl-cAMPS had been considerably degraded (22%), while the peak for the cyclic boranophosphate Rp-2-Cl-cAMPB at 6:84 min. had still 90% of the original area.

Degradation Example 7

In order to demonstrate, that the higher stability of cyclic boranophosphates described in this invention is independent also from the type of nucleobase, a cyclic boranophosphate with pyrimidine nucleobase cytidine-3',5'-cyclic boranophosphate, Rp-isomer (Rp-cCMPB, example 67) was treated with 5 subsequent portions of aqueous peroxide (30% $H_2O_2$, Merck) and compared to the corresponding phosphorothioate cytidine-3',5'-cyclic phosphorothioate, Sp-isomer (Sp-cCMPS, Biolog) as a control.

TABLE 6

Oxidation of Sp-cCMPB by hydrogen peroxide versus the corresponding cyclic phosphorothioate (Rp-cCMPS); quantification by HPLC as ratio of area percentages.

| Time [min] | Rp-cCMPB (HPLC Area %) | Sp-cCMPS (HPLC Area %) |
|---|---|---|
| 0 | 100 | 100 |
| 10 | 99 | 94 |
| 20 | 98 | 85 |
| 34 | 96 | 69 |
| 65 | 91 | 46 |
| 81 | 84 | 23 |
| 92 | 78 | 14 |
| 98 | 79 | 13 |

The degradation experiment was monitored by HPLC (RP-18, 15 Vol.-% acetonitrile, 20 mM triethylammonium formate buffer, pH 6.5, 1 ml/min., UV 270 nm) and peak areas were recorded.

Degradation Example 8

While Sp-cCMPS at 2:62 min. was rapidly oxidized, the corresponding boranophosphate Rp-cCMPB at 3:18 min. showed considerably higher resistance.

Finally, with the Sp-isomer of 8-bromoguanosine-3',5'-cyclic boranophosphate (Sp-8-Br-cGMPB, example 6) also the oxidative stability of a cyclic boranophosphate with a modified guanine nucleobase was investigated and again compared to the corresponding phosphorothioate Rp-8-bromoguanosine-3',5'-cyclic phosphorothioate (Rp-8-Br-cGMPS, Biolog).

Both compounds were treated together with two 10 µl doses of 30% aqueous hydrogen peroxide (Merck). During more than four hours, oxidative degradation was monitored by HPLC (RP-18, 15 Vol.-% acetonitrile, 20 mM triethylammonium formate buffer, pH 6.5, 1.5 ml/min., UV 263 nm) and corresponding peak areas were recorded and compared (Tab. 7).

TABLE 7

Oxidation of Sp-8-Br-cGMPB by hydrogen peroxide versus the corresponding cyclic phosphorothioate (Rp-8-Br-cGMPS); quantification by HPLC as ratio of area percentages.

| Time (min) | Peak Area Ratio Rp-8-Br-cGMPS versus Sp-8-Br-cGMPB | |
|---|---|---|
| 0 | 1.00:1 | $H_2O_2$ |
| 15 | 0.94:1 | |
| 30 | 0.92:1 | |
| 45 | 0.83:1 | $H_2O_2$ |
| 60 | 0.78:1 | |
| 90 | 0.71:1 | |
| 120 | 0.63:1 | |
| 150 | 0.58:1 | |
| 180 | 0.50:1 | |
| 225 | 0.26:1 | |
| 250 | 0.24:1 | |

The signal for Sp-8-Br-cGMPS at 2:36 min. was decreasing rapidly under peroxide addition and a new peak with shorter retention time (8-Br-cGMP) at 1:80 min. appeared. After 1 hour at RT Rp-8-Br-cGMPS had been considerably degraded (15%), while the peak for the cyclic boranophosphate Sp-8-Br-cGMPB at 3:53 min. had still 65% of the original area.

Thus the surprising oxidative stability of the chemical structures disclosed by this invention is solely due to the unique properties of the cyclic 3',5' boranophosphate moiety, and therefore is independent from any structural modifications at other parts of the nucleotide, such as nucleobase or ribose. The considerably increased stability principally holds true for both diastereomers, where, according to FIG. 2, a comparison leaves the axial Rp-isomer as slightly more resistant compared to the equatorial Sp-isomer.

As a rule, both isomers of the cyclic boranophosphates described in this invention are always much more stable against oxidation compared to structures with corresponding phosphorothioate modification, which is a clear advantage for their use as signal transduction reagents and for therapeutic applications, respectively.

Dimerisation, described in literature as a side reaction during oxidation of phosphorothioates from corresponding disulfides, has not been observed at all with the cyclic boranophosphates described in this invention.

Degradation Example 9

Finally, resistance of compounds according this invention towards phosphodiesterases was tested.

For this purpose 0.1 µmol of Rp-8-bromoadenosine-3',5'-cyclic boranophosphate (example 1) and Sp-8-bromoadenosine-3',5'-cyclic boranophosphate (example 1) were dissolved in TRIS buffer pH 7.2 containing calcium chloride and calmodulin and incubated with PDE type I from bovine brain (Sigma-Aldrich) at 37° C. Activity of the enzyme was checked by hydrolysis of cyclic AMP. Stability was monitored by HPLC (RP-18, 11 Vol.-% propanol-2, 20 mM TEAF buffer, pH 6.8, 1 ml/min., UV 264 nm). For both compounds even after 8 days no degradation was detected. At that time, cyclic AMP was still hydrolysed immediately when added to the system, demonstrating that the PDE was active after this prolonged incubation time. This strategy of testing PDE performance was applied accordingly in degradation examples 10 and 11.

In a second set of experiments and under similar conditions, PDE-stability of boranophosphates according to the invention was tested in direct comparison to their respective phosphorothioate analogues. For this purpose, preferentially the axially modified isomers were selected, since it is well-known in the literature that phosphorothioates with this conformation are sometimes still tolerated by PDEs for hydrolysis (although at considerably reduced velocity), whereas equatorially modified analogues are totally stable anyhow.

Thus, Rp-8-Br-cAMPB (example 1) and Sp-8-Br-cAMPS (Biolog, Bremen/Germany) were incubated with PDE 1 from bovine heart (Sigma-Aldrich) and monitored by HPLC as described above.

While Sp-8-Br-cAMPS (3:57 min.) was degraded with a half life of approx. 50 h (bovine heart), the Rp-8-Br-cAMPB (4:39 min.) disclosed within this invention (example 1), was completely stable, even after 8 days of incubation time. The same result was received when PDE 1 from bovine brain was used.

Degradation Example 10

Another comparison between a cyclic boranophosphate disclosed within this invention and its corresponding phosphorothioate version was performed with Rp-2'-O-Me-cAMPB (example 7) and Sp-2'-O-Me-cAMPS (Biolog, Bremen/Germany). While the phosphorothioate-modified Sp-2'-O-Me-cAMPS was hydrolysed with half lifes of 30 h (PDE 1, bovine heart) and 6 h (PDE 1, bovine brain), respectively, Rp-2'-O-Me-cAMPB was stable over the whole assay period towards both PDE 1 subtypes. The same results were obtained for Sp-2'-O-Me-cAMPB (example 8).

Degradation Example 11

Next, stability of the disclosed boranophosphates against PDE IV (A4B, Houslay lab, Glasgow/Scotland) was tested in similar experiments as described above.

Both, Rp-8-Br-cAMPB as well as Rp-2'-O-Me-cAMPB were completely stable over several days, while cAMP as a control was hydrolysed with a half life of only 5 min.

As a result, the cyclic boranophosphates disclosed here are completely stable towards three hydrolysing enzymes, which is a clear advantage over phosphorothioate-modified structures, where at least the axial Sp-isomers are still subject to degradation.

Obviously, also chemical stability of the boranophosphates according to the invention in water is very high, since over the whole PDE assay period no indications of decomposition were detected.

Biological Activity of Boranophosphate-Modified Cyclic Nucleotides

The cyclic phosphate moiety in cyclic AMP and cyclic GMP is the distinguishing unique characteristic to obtain high specificity for their corresponding receptors such as protein kinases, Epac proteins or ion channels, in presence of a plethora of other nucleotide recognizing receptor proteins.

Any modifications at this sensitive part thus have substantial impact on the orientation within the binding site of a receptor and can lead to a broad spectrum of different effects, ranging from strong agonistic behaviour to inactivity, or from partial to full antagonism.

Since in cyclic boranophosphates, as disclosed by this invention, either the axial or the equatorial exocyclic oxygen atom is substituted by a borano group, the electronic properties compared to a genuine cyclic phosphate are considerably changed and biological effects cannot be predicted.

Therefore, both, axially and equatorially modified cyclic boranophosphates, have been tested on typical receptor proteins for cyclic AMP and cyclic GMP, in order to find out, how the changed molecular moiety is accepted by the different binding sites and whether cyclic boranophosphate analogues, as described by this invention, can be valuable tools for the modulation of second messenger-controlled signaling pathways.

Activity Example 1

In a first experiment, the biological activity of the Rp- and Sp-isomer of 8-bromoadenosine-3',5'-cyclic boranophosphate (examples 1 and 2) has been tested with the holoenzyme of protein kinase A type I alpha (FIGS. 3 and 4) using a standard photometric assay (Cook, P. F.; Neville, M. E., Jr.; Vrana, K. E.; Hartl, F. T. and Roskoski, R., Jr., *Biochemistry* 21, 5794-5799 (1982)).

Figure 3:
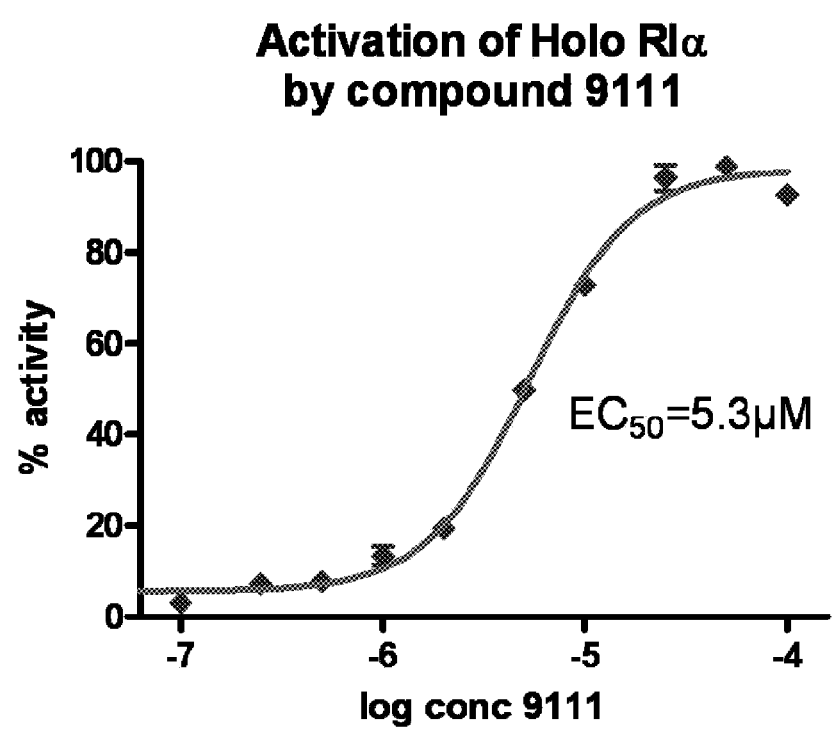
FIG. 3 depicts the activation profile of Rp-8-Br-cAMPB (9111, example 1) on protein kinase A type I alpha holoenzyme.

FIG. 3 depicts the activation profile of Rp-8-Br-cAMPB (9111, example 1) on protein kinase A type I alpha holoenzyme.

Figure 4:
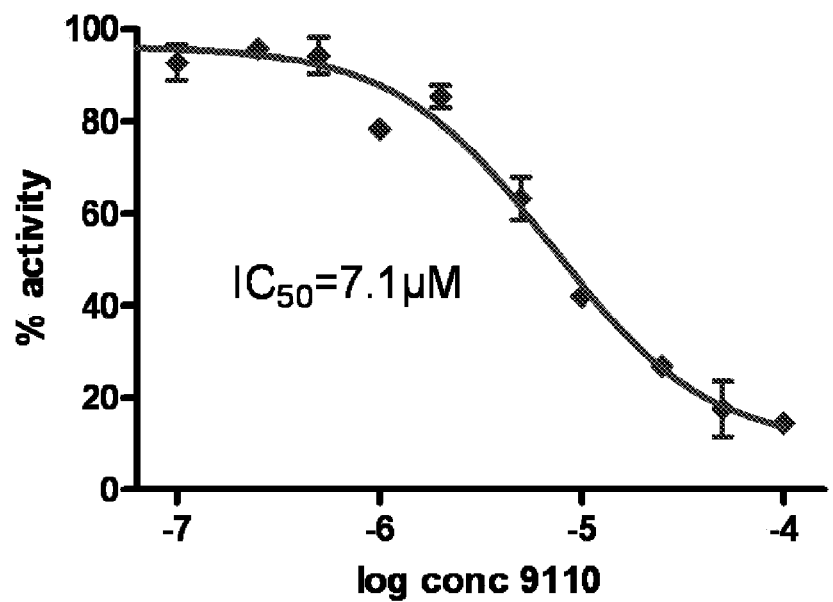
FIG. 4 depicts the inhibition profile of Sp-8-Br-cAMPB (9110, example 2) on protein kinase A type I alpha holoenzyme.

FIG. 4 depicts the inhibition profile of Sp-8-Br-cAMPB (9110, example 2) on protein kinase A type I alpha holoenzyme.

Surprisingly, the chromatographically slower eluting diastereomer with a $^{31}$P-NMR shift of 96.2 ppm leads to kinase activation, while the corresponding other isomer (fast eluting, 91.1 ppm) inhibits the enzyme. This strikingly mirrors the properties of diastereomeric cyclic phosphorothioates towards that receptor, where axially modified structures are kinase agonists, while equatorially modified congeners are inhibitors. However, this similarity could not have been predicted since the electronic and spacial properties of a borane moiety compared to a thiol are quite different. However, from this result it can be deducted that the agonistic cyclic boranophosphate isomer with a 96.2 ppm shift must carry its borane in axial position and is hence the Rp-isomer, while the corresponding inhibitory structure has an equatorially modified phosphate and is thus Sp-configurated. This important finding has been applied on all structures disclosed by this invention. The absolute conformation, however, remains to be determined by x-ray crystallographic analysis.

Activity Example 2

As a control, two boranophosphate analogues with a 2'-O-methyl modification (Rp-2'-O-Me-cAMPB and Sp-2'-O-Me-cAMPB, examples 7 & 8) have been tested by the same type of assay with protein kinase A type I alpha as well. Cyclic AMP analogues with a modified 2'-OH group usually do not activate the receptor, since this position is essential for any potential agonist to be recognized by the kinase (Houge, G., Steinberg, R. A., Øgreid, D. & Døskeland, S. O., *J. Biol. Chem.* 265, 19507-19516 (1990)).

Figure 5:
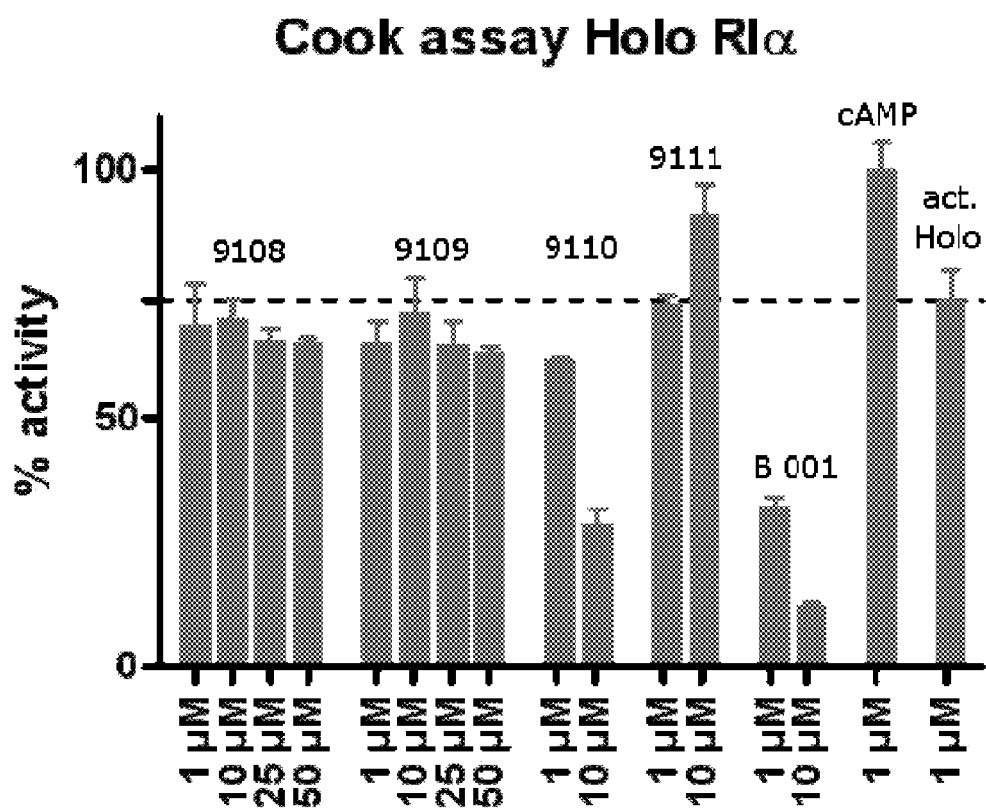
FIG. 5 also demonstrates the inhibitory potential of an equatorially modified cyclic boranophosphate (Sp-8-Br-cAMPB, example 2), very similar to the corresponding phosphorothioate (Rp-8-Br-cAMPS, Biolog)

Consequently, neither Rp- nor Sp-2'-O-Me-cAMPB did modulate the kinase in any way, as can be seen from FIG. 5

FIG. 5 depicts the activity overview of four different cyclic boranophosphate analogues with protein kinase A type I alpha holoenzyme. 9108: Sp-2'-O-Me-cAMPB; 9109: Rp-2'-O-Me-cAMPB; 9110: Sp-8-Br-cAMPB; 9111: Rp-8-Br-cAMPB; controls: B 001: Rp-8-Br-cAMPS. Control: cAMP. "Cook Assay" with Holoenzyme RIα.

Thus, with respect to a free 2'-hydroxy group necessary for protein kinase A kinase recognition, nucleotides with cyclic boranophosphates, as disclosed here, behave like ordinary phosphates or phosphorothioates as well.

FIG. 5 also demonstrates the inhibitory potential of an equatorially modified cyclic boranophosphate (Sp-8-Br-cAMPB, example 2), very similar to the corresponding phosphorothioate (Rp-8-Br-cAMPS, Biolog). Also, the agonistic property of Rp-8-Br-cAMPB (example 1) is shown.

Activity Example 3

In another similar experiment the properties of Rp- and Sp-8-Br-cAMPB towards protein kinase A type II a were investigated in the photometric assay (Cook, P. F., Neville, M. E., Jr., Vrana, K. E., Hartl, F. T. and Roskoski, R., Jr., *Biochemistry* 21, 5794-5799 (1982))

Figure 6:
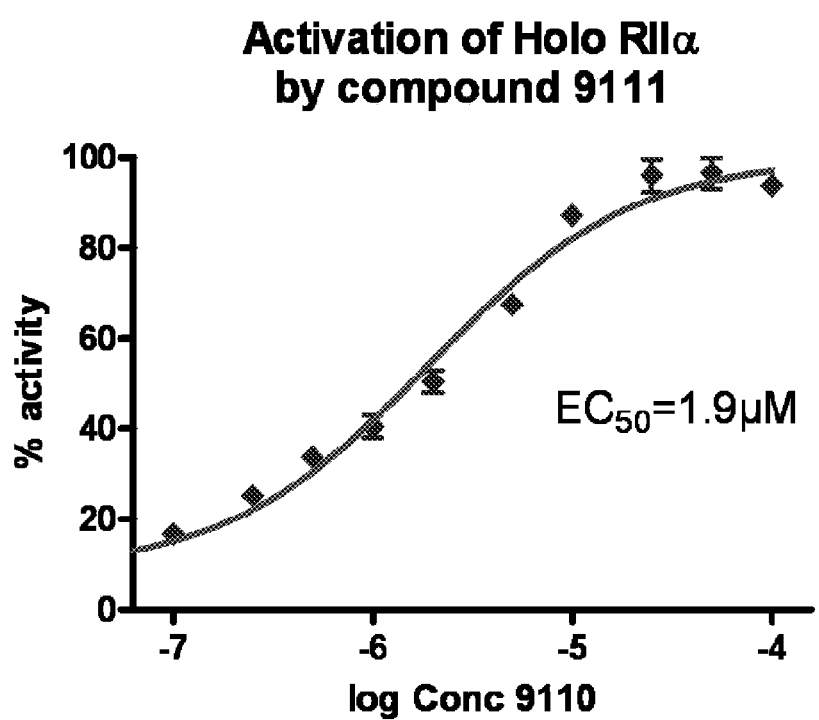
FIG. 6 depicts the activation profile of Rp-8-Br-cAMPB (9111, example 1) on protein kinase A type II alpha holoenzyme.

FIG. 6 depicts the activation profile of Rp-8-Br-cAMPB (9111, example 1) on protein kinase A type II alpha holoenzyme.

Figure 7:
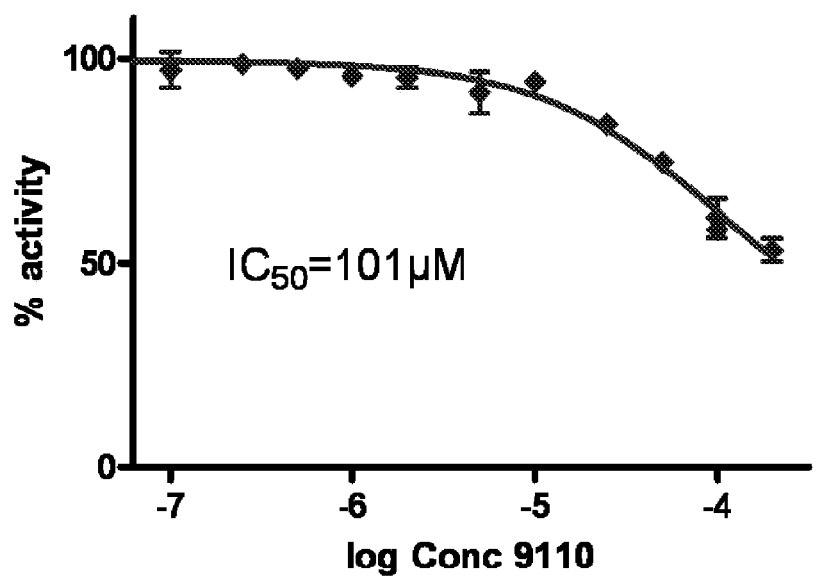
FIG. 7 depicts the inhibition profile of Sp-8-Br-cAMPB (9110, example 2) on protein kinase A type II alpha holoenzyme.

FIG. 7 depicts the inhibition profile of Sp-8-Br-cAMPB (9110, example 2) on protein kinase A type II alpha holoenzyme.

Surprisingly, Rp-8-Br-cAMPB (example 2) shows even higher activation potential for type II of the kinase (FIG. 6), and is thus an isozyme-selective agonist with only marginally lower potency compared to the phosphorothioate Sp-8-Br-cAMPS with an $EC_{50}$ of 0.71 µM (data not shown).

Interestingly, the corresponding Sp-8-Br-cAMPB, is only moderately antagonistic for type II of the kinase and thus an isozyme-selective antagonist which prefers type I over type II by a factor of 14.

Summing up, the properties of boranophosphate isomers of cyclic AMP towards protein kinase A isozyme resemble those that can be obtained with the corresponding phosphorothioates, however, there are considerable differences with respect to selectivity and isozyme specificity, respectively.

Activity Example 4

Figure 8:
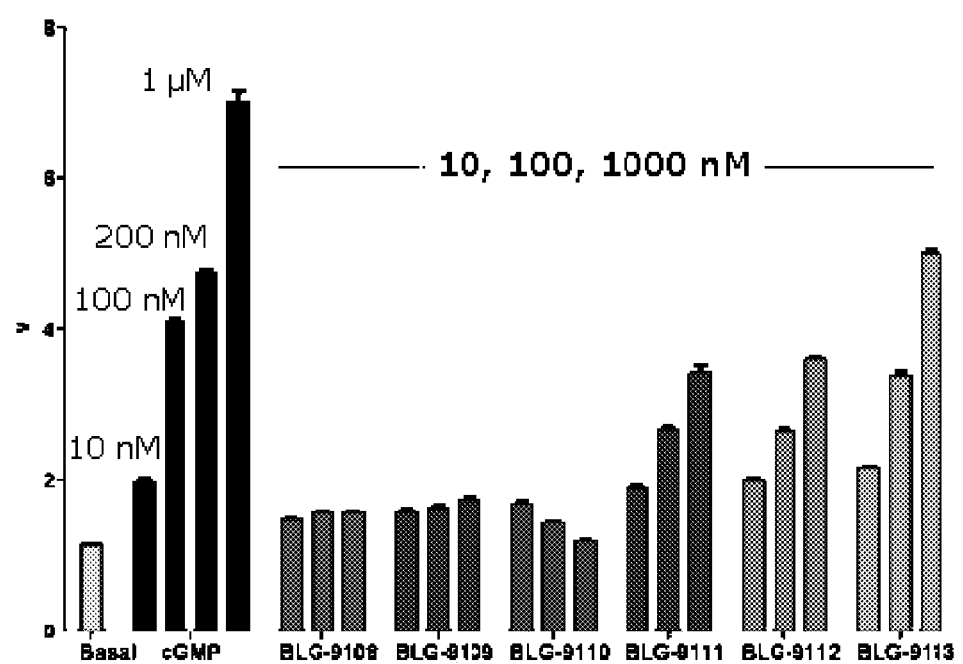
FIG. 8 depicts the activity ($\mu$mol $\times$min$^{-1}\times$mg$^{-1}$) overview of six different cyclic boranophosphate analogues with protein kinase G type I at 10 nM, 100 nM and 1 $\mu$M.
Figure 9:
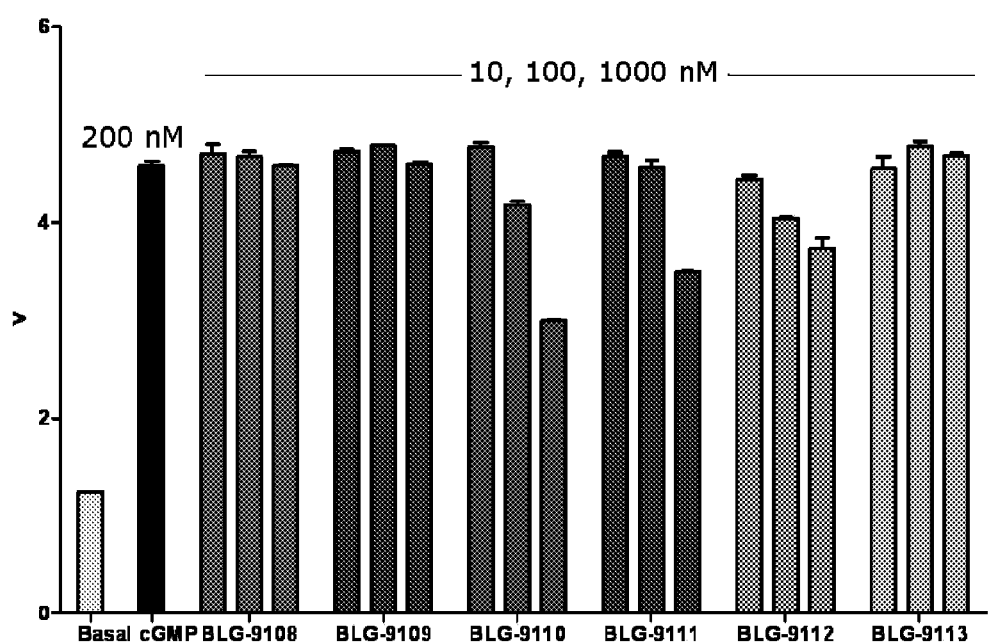
FIG. 9 depicts the inhibitory potential of six different cyclic boranophosphate analogues at 10 nM, 100 nM and 1 $\mu$M to counter-act with protein kinase G type I $\alpha$, activated by cGMP (200 nM)

Next, the activity profile of some cyclic boranophosphates disclosed in this invention has also been investigated on protein kinase G I α (FIGS. 8 and 9). Potential activatory potential towards the enzyme has been determined by a standard phosphotransferyl assay protocol according to Dostmann et al. (Dostmann, W. R.; Nickl, C.; Thiel, S.; Tsigelny, I.; Frank, R.; and Tegge, W. J., Pharmacol. Ther., 82, 373-387 (1999). FIG. 8 depicts the activity (µmol×min$^{-1}$×mg$^{-1}$) overview of six different cyclic boranophosphate analogues with protein kinase G type I at 10 nM, 100 nM and 1 µM. BLG-9108: Rp-2'-O-Me-cAMPB; BLG-9109: Sp-2'-O-Me-cAMPB; BLG-9110: Sp-8-Br-cAMPB; BLG-9111: Rp-8-Br-cAMPB; BLG-9112: Sp-8-Br-cGMPB; BLG-9113: Rp-8-Br-cGMPB; control: cyclic GMP.

The ability of cyclic boranophosphates disclosed in this invention to suppress kinase activity of basal and cGMP-stimulated enzyme has been determined by a method described by Taylor et al. (Taylor, M. S.; Okwuchukwua-sanya, C.; Nickl, C. K.; Tegge, W., Mol. Pharmacol., 65, 1111-1119 (2004). FIG. 9 depicts the inhibitory potential of six different cyclic boranophosphate analogues at 10 nM, 100 nM and 1 µM to counter-act with protein kinase G type I α, activated by cGMP (200 nM). BLG-9108: Rp-2'-O-Me-cAMPB; BLG-9109: Sp-2'-O-Me-cAMPB; BLG-9110: Sp-8-Br-cAMPB; BLG-9111: Rp-8-Br-cAMPB; BLG-9112: Sp-8-Br-cGMPB; BLG-9113: Rp-8-Br-cGMPB; control: cGMP. v=µmol×min$^{-1}$×mg$^{-1}$ While analogues with modified 2'-position were inactive again, compounds with a guanine nucleobase, e.g. Rp- and Sp-8-Br-cGMPB (examples 5 & 6) showed agonistic and antagonistic properties, respectively. Again, the borane in axial position (Rp-8-Br-cGMPB) activated the kinase while the equatorially modified isomer (Sp-8-Br-cGMPB) isomer showed antagonistic potential.

This surprising result could have not been predicted on its own as well, however, it fits to the data received with protein kinase A, as described above.

Generally, it can be concluded as a rule, that cyclic boranophosphates as disclosed by this invention, will activate protein kinase isozymes A and G whenever they carry the borane modification in axial position (Rp-isomers), and will have inhibitory potential, if the borano group is in equatorial position (Sp-isomers). As observed and described with phosphorothioate-modified cyclic nucleotides it is solely the cyclic phosphate that decides upon the agonistic or antagonistic properties, while the purine nucleobase brings specification within the various binding proteins. The nucleobase can be varied extremely broad, tolerating even benzimidazole and its analogues (Genieser, H.-G.; Winkler, E.; Butt, E.; Zorn, M.; Schulz, S.; Iwitzki, F.; Stormann, R.; Jastorff, B.; Døskeland, S. O.; Øgreid, D.; Ruchaud, S.; Lanotte, M.; Carbohydrate Res., 234, 217-235 (1992)).

Interestingly and unforeseen, structures with an adenine nucleobase (Rp-8-Br-cAMPB; Sp-8-Br-cAMPB) seem to modulate protein kinase G as well and were as potent or even better as guanine related compounds. This needs more attention, and is probably one example, where the cyclic boranophosphates differ from corresponding phosphorothioates.

Activity Example 5

Also the potential interaction of the compounds disclosed in this invention with the EPAC protein was analyzed. In contrast to protein kinases, EPAC tolerates certain modifications of the 2'-hydroxy group.

For these experiments the EPAC receptor protein (Jena Bioscience, Jena, Germany) has been immobilized to the activated surface of a chip and its binding properties towards compounds according to this invention were analyzed by surface plasmon resonance spectroscopy using a Biacore instrument (Biaffin AG, Kassel, Germany) (FIGS. 10-13).

Figure 10:
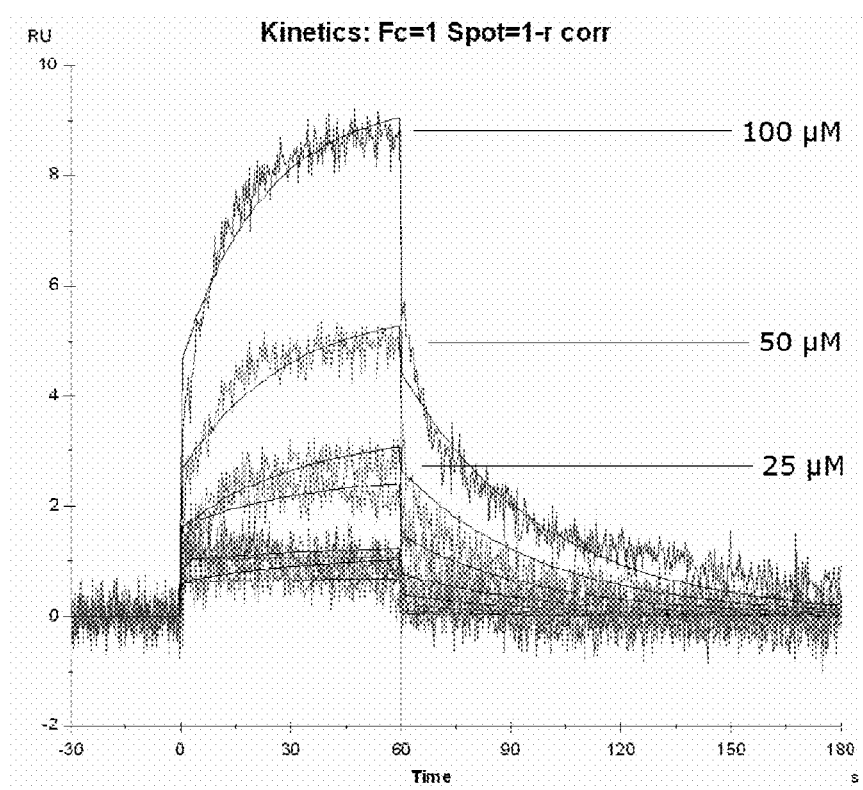
FIG. 10 depicts the binding profile of Rp-2'-O-Me-cAMPB (example 7) on immobilized EPAC.

FIG. 10 depicts the binding profile of Rp-2'-O-Me-cAMPB (example 7) on immobilized EPAC.

Figure 11:
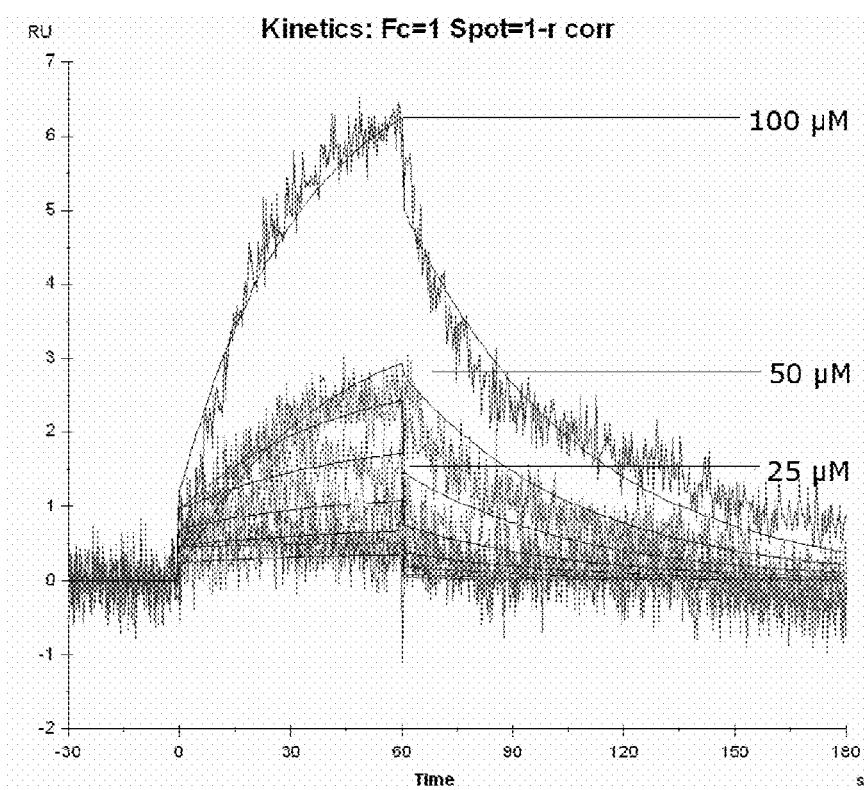
FIG. 11 depicts the Binding profile of Sp-2'-O-Me-cAMPB (example 8) on immobilized EPAC.

FIG. 11 depicts the Binding profile of Sp-2'-O-Me-cAMPB (example 8) on immobilized EPAC.

Figure 12:
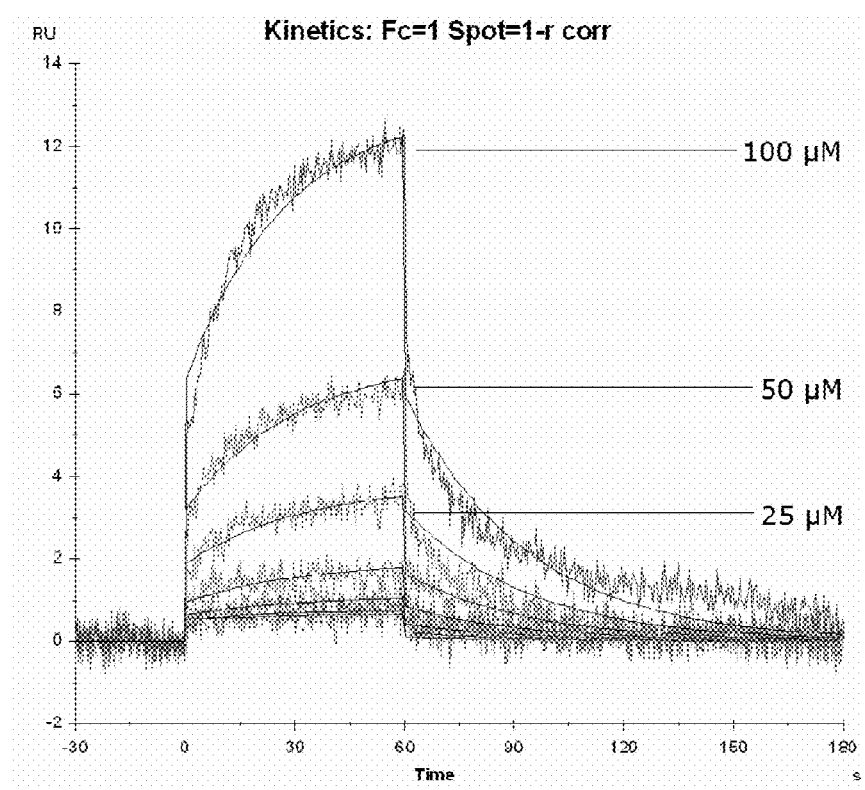
FIG. 12 depicts the binding profile of Sp-8-Br-cAMPB (example 2) on immobilized EPAC.

FIG. 12 depicts the binding profile of Sp-8-Br-cAMPB (example 2) on immobilized EPAC.

Figure 13:
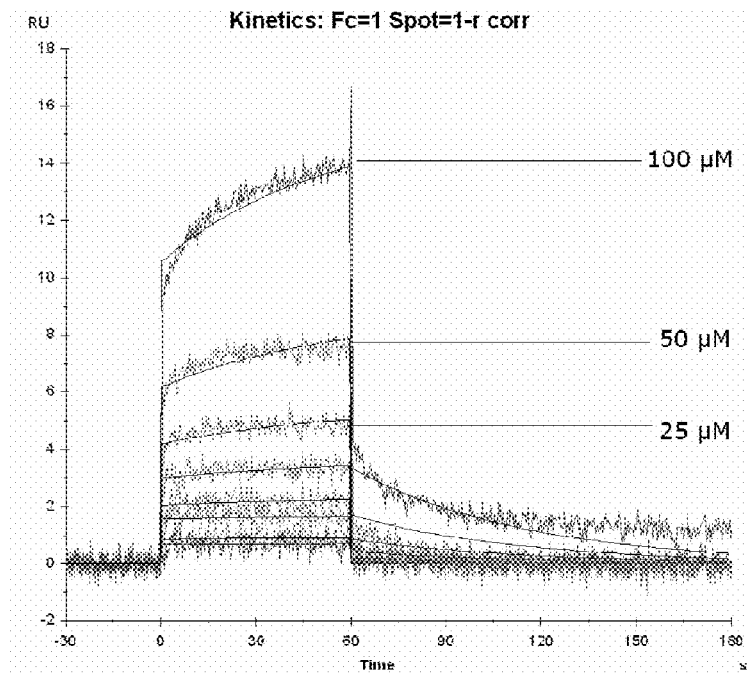
FIG. 13 depicts the binding profile of Rp-8-Br-cAMPB (example 1) on immobilized EPAC.

FIG. 13 depicts the binding profile of Rp-8-Br-cAMPB (example 1) on immobilized EPAC.

Here, both diastereomers of 8-Br-cAMPB (example 1 and 2) and of 2'-O-cAMPB (examples 7 and 8) were tested.

As a result, all four analogues bind to EPAC, however, obviously with quite different profiles.

Activity Example 6

In another fluorescence-based test (Rehmann, H., Methods Enzymol., 407, 159-173 (2006)), further data were raised for the EPAC protein and compared with cyclic AMP.

Rp-8-Br-cAMPB (example 1), Rp- and Sp-8-Br-2'-O-Me-cAMPB (examples 34 and 35), Rp- and Sp-8-pCPT-2'-O-Me cAMPB (examples 43 and 44) as well as Rp- and Sp-8-BT-2'-O-Me-cAMPB (examples 45 and 46) were tested.

Especially the Rp-configurated analogues turned out to be moderate or even good activators of the EPAC protein (FIG. 14), while the Sp-isomers were more or less inactive (not all data shown).

Figure 14:
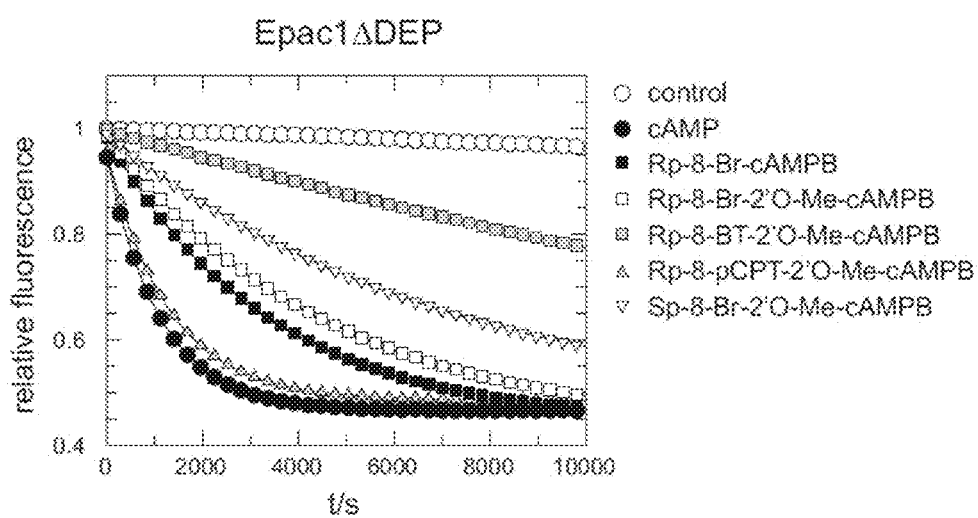
FIG. 14 depicts the activation of the EPAC protein by cyclic boranophosphate analogues.

FIG. 14 depicts the activation of the EPAC protein by cyclic boranophosphate analogues. The exchange activity of the EPAC protein was monitored as a decrease in fluorescence over time.

This behaviour is again quite similar to various other cyclic AMP analogues, especially to those with phosphorothioate modification. Indeed, the corresponding phosphorothioate-modified structures gave rather similar results with the EPAC protein (data not shown).

Thus, nucleotides with cyclic boranophosphate modification according to the invention, can modulate EPAC proteins and the activation potentials of their Rp- and Sp-diastereomers resemble those achieved with phosphorothioate modification.

Activity Example 7

Next, the effects of cyclic nucleotide boranophosphates, disclosed in this invention, on olfactory cyclic nucleotide-gated ion channels in clamps of oocyte cell membrane patches were investigated.

For the experiments, oocytes were obtained and prepared as described previously (Biskup, C. et al., Nature 446, 440-443 (2007)). In brief, oocytes were obtained by partial ovariectomy from adult females of Xenopus laevis anaesthesized with 0.3% 3-aminobenzoic acid ethyl ester (Sigma). The oocytes were treated for 60-90 min with 1.2 mg/ml collagenase (Type I, Sigma) and separated manually. 40-70 nl of a solution containing cRNA encoding bovine CNGA2 channels (accession No. X55010) was injected, and the oocytes were incubated at 18° C. in Barth medium until they were used for the experiments within 3-6 days after injection. Immediately prior to the experiments the vitelline membrane of the oocytes was removed.

Currents were recorded in inside-out patches with the patch-clamp technique. The patch pipettes were pulled from quartz tubing (outer diameter 1.0 mm, inner diameter 0.7 mm) using a laser puller (P-2000, Sutter Instrument, Novato, Calif.). The pipette resistance was 0.8-2.5 MΩ. Recording was performed with an Axopatch 200B amplifier (Molecular Devices, Sunnyvale, Calif.). All experiments were performed with the same recording solution in the bath and the pipette containing (in mM) 150 KCl, 1 EGTA, 5 HEPES. pH was adjusted to 7.4 with KOH.

Measurements were controlled and data were collected with the ISO3 setup (MFK, Niedernhausen, Germany). The sampling rate was 5 kHz (filter 2 kHz). To test for possible background channel activity, each excised patch was first exposed to a solution containing no cyclic nucleotides. Then the maximum current was activated with free cyclic adenosine monophosphate (500 mM cAMP (Trudeau, J. Biol. Chem. 278, 18705-18708 (2003)). Currents were measured at voltages of −50 mV and +50 mV.

Figure 15:
FIG. 15 A-C depict the agonistic activity of Rp-8-Br-cAMPB on CNGA2 channels.
Figure 15:
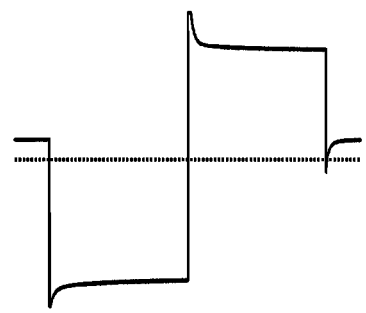
Figure 15:
Figure 15:
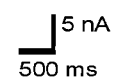

FIGS. 15 A-C depict the agonistic activity of Rp-8-Br-cAMPB on CNGA2 channels. Currents were recorded in a patch containing CNGA2 channels. The patch membrane was clamped subsequently from 0 mV to −50 mV, +50 mV and back to 0 mV. (A) Currents measured in the absence of cAMP and Rp-8-Br-cAMPB. (B) Currents measured at a saturating cAMP concentration of 500 μM. (C) Current measured in the presence of 500 μM Rp-8-Br-cAMPB.

In the absence of cAMP no current was observed (FIG. 15 A), showing that no endogenous channels could be activated by voltage steps to −50 mV and +50 mV. However, a current could be recorded in the presence of cAMP (FIG. 15 B). In this experiment, saturating cAMP concentrations of 500 μM were used and the current elicited by −50 mV and +50 mV pulses reached maximal values. In contrast, Rp-8-Br-cAMPB (example 1) activated the CNGA2 channels at a concentration of 500 μM only slightly (FIG. 15 C). At −50 mV the current reached only 7±1% (mean±SEM) of its maximal value; at +50 mV the current reached only 14±4% of its maximal value (n=3).

Activity Example 8

To test if Rp-8-Br-cAMPB was a competitive antagonist, it was applied in the presence of cAMP. Comparison of the current observed at 50 μM cAMP in the presence and the absence of Rp-8-Br-cAMPB showed that the compound does not inhibit channel activation by cAMP (data not shown).

Thus, surprisingly, Rp-8-Br-cAMPB with its axial borano modification is a selective agonist of protein kinase A with negligible activation and no inhibition potential for olfactory CNG ion channels.

Figure 16:
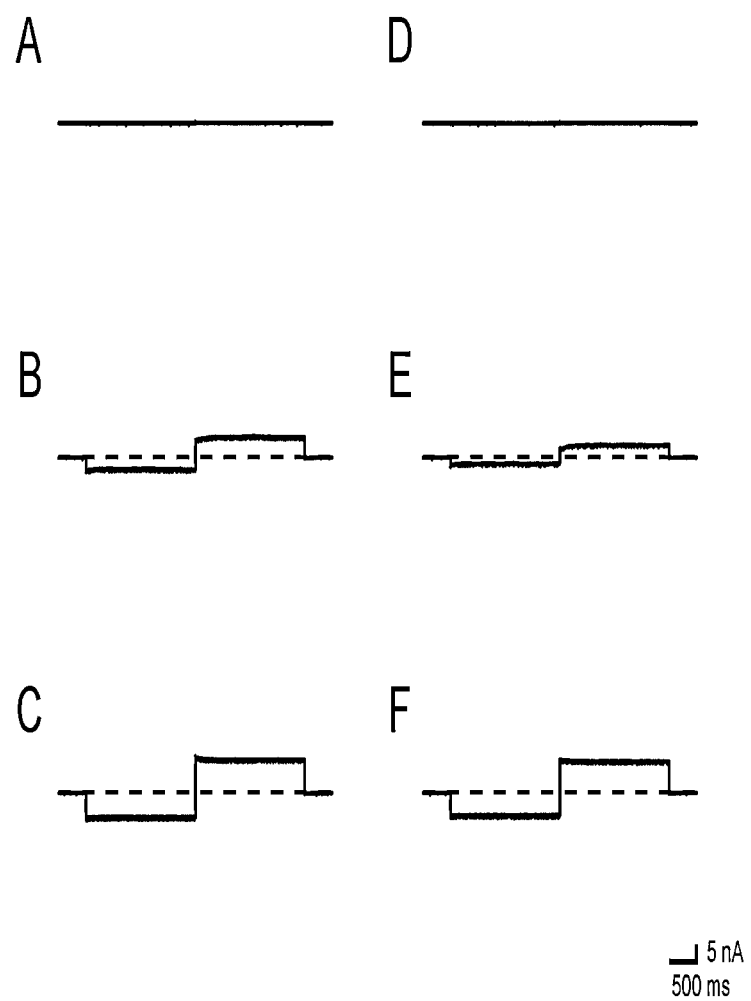
FIG. 16 A-F depict the antagonistic activity of Sp-8-Br-cAMPB on CNGA2 channels.

FIGS. 16 A-F depict the antagonistic activity of Sp-8-Br-cAMPB on CNGA2 channels. Currents were recorded in a patch containing CNGA2 channels. The patch membrane was clamped subsequently from 0 mV to −50 mV, +50 mV and back to 0 mV. (A-C) Currents measured in (A) the absence and in the presence of (B) 50 μM and (C) 500 μM cAMP. (D) Currents measured in the presence of 100 μM Sp-8-Br-cAMPB and in the absence of cAMP (E-F) Currents measured in the presence of 50 μM Sp-8-Br-cAMPB and in the presence of (E) 50 μM and (F) 500 M cAMP.

Under the concentrations tested (up to 100 μM) Sp-8-Br-cAMPB (example 2) did not show any intrinsic activity on CNGA2 channels (FIG. 16 D). It has, however, the potential to inhibit CNGA2 channels competitively. Currents observed in the presence of 50 μM cAMP (FIG. 16 B) are considerably reduced in the presence of Sp-8-Br-cAMPB (FIG. 16 E). Current amplitudes were 34±9% at −50 mV and 48±11% at +50 mV (n=9) of the amplitudes observed in the absence of Sp-8-Br-cAMPB.

Thus Sp-8-Br-cAMPB (example 2) is able to block the current induced by cyclic AMP and is thus a competitive antagonist for channel activation (FIG. 16 A-F).

This result resembles earlier observations by Kramer and Tibbs (R. N. Kramer and G. R. Tibbs, J. Neurosci., 16, 1285-1293 (1996)) with Rp- and Sp-cyclic nucleotide phosphorothioates, where the equatorial Rp-isomer is an inhibitor and the axial Sp-Isomer an activator of the olfactory channel. In contrast to phosphorothioates, however, the agonistic property of Rp-8-Br-cAMPB (example 1) is very small, which could thus lead to a valuable new agonistic analogue tool to discriminate between protein kinase A and olfactory CNG channels.

Finally, concerning the effects of cyclic nucleotides with boranophosphate modification, as disclosed in this invention, on biological systems, it is concluded, that these new compounds are principally biologically active. They bind to, activate or inhibit, respectively, the typical receptor proteins of the parent natural cyclic nucleotides cyclic AMP and cyclic GMP, and—besides some interesting exceptions—often act very similar to regular cyclic nucleotides or to the cyclic phosphorothioate diastereomers. However, they are much more stable against oxidation and chemical hydrolysis, have much higher lipophilicity and both, the axial and the equatorial isomer are completely resistant towards phosphodiesterases, at least against the ubiquitous types I and IV.

By additional modification of the nucleobase or the ribose moiety, special properties such as fluorescence or certain specificities can be further introduced into nucleotides with cyclic boranophosphate modification, however, the principal nature of the biological effect (activation, inhibition, inactivity) is mainly governed by the diastereomeric orientation of the borane, as disclosed here.

By introducing a triester function at the borano phosphate, interesting prodrugs of cyclic boranophosphates, as disclosed by this invention, can be obtained, having considerably improved membrane permeability due to the masked negative charge, and which release the biologically active parent structure upon either metabolic degradation by esterases or by chemical hydrolysis. Such prodrugs are already known for phosphorothioates, but unfortunately these structures form potent oxidised by-products during hydrolysis, which—e.g. in case of an equatorially modified phosphate with its corresponding inhibitory potential, counteract against the desired biological effect. Thus, the AM ester of the well known phosphorothioate-based kinase inhibitor Rp-cAMPS is completely useless, since it develops the kinase activator cyclic AMP upon metabolic degradation in biological systems.

Therefore, an especially valuable prodrug is a triester structure of a cyclic boranophosphate with antagonistic Sp-configuration (e.g. example 4), since, it could release the intact cyclic boranophosphate without remarkable side products from oxidation.

The same holds true when it comes to the use of immobilized cyclic nucleotides as ligands for affinity chromatography. Here, immobilized Rp-cAMPS is used for affinity chromatography of the holoenzyme of protein kinase A. However, due to oxidation processes the affinity column ligands tend to change into immobilized cyclic AMP which will lead to activation of the kinase and hence to separated regulatory and catalytic subunits. In addition, normal cyclic phosphates without any modification at phosphorus are good substrates for phosphodiesterases, which will quickly hydrolyze the cyclic phosphate and thus open up the chance for a broad variety of nucleases to further destroy the ligand, especially when cyclic nucleotide binding proteins are searched within crude cell extracts.

Affinity ligands from cyclic boranophosphates, as disclosed by this invention, have the great advantage that the first metabolic step, necessary for degradation of cyclic nucleotides, is blocked by two different mechanisms: First, they are stable against direct attack by phosphodiesterases and second, they are also stable against oxidation which would make resulting normal cyclic phosphates vulnerable against PDE degradation.

By blocking the hydrogen bonding capability of the 2'-hydroxy group of the ribose moiety, e.g. by a 2'-O-methyl group, valuable reagents for the discrimination between protein kinase A isozymes and the EPAC proteins can be obtained. Cyclic Boranophosphates with 2'-O-methyl modification, as disclosed by this invention, combine this highly valuable discriminatory potential with high oxidative stability and membrane permeability, and are thus promising lead structures for medical treatment of diseases connected to EPAC.

Concluding, the structures disclosed in this invention are highly valuable reagent tools for modulation of the signaling pathways of the second messenger molecules cyclic AMP, cyclic GMP and the pyrimidine cNMPs, and hence are prospective candidates for drug development to fight diseases caused by corresponding second messenger misregulation as well.

The invention claimed is:
1. A compound having the structural formula (I) or (II)

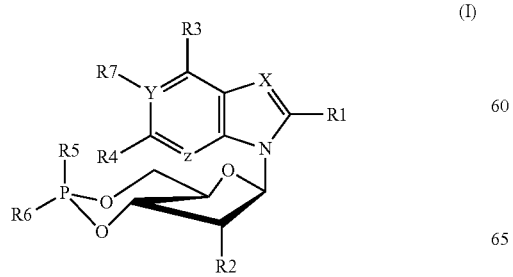

(I)

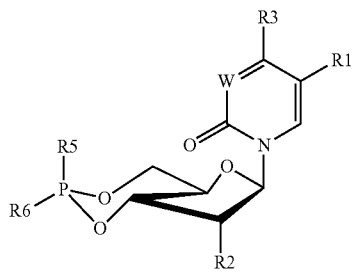

(II)

wherein:
W, X, Z can be independently from each other N or CH;
Y can be N or C,
R1 can be independently H, halogen, azido, cyano, acyl, aracyl, nitro, alkyl, aryl, aralkyl, amido-alkyl, amido-aryl, amido-aralkyl, NH-carbamoyl-alkyl, NH-carbamoyl-aryl, NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR8R9, or SiR10R11R12 wherein R8, R9, R10, R11, R12 independently from each other can be H, alkyl, or aryl, aralkyl;
R2 can be independently H, halogen, azido, acyl, aracyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR13R14, or O—SiR15R16R17, wherein R13, R14, R15, R16, R17, independently from each other can be H, alkyl, aryl, or aralkyl;
R3 can be independently H, halogen, azido, cyano, acyl, aracyl, nitro, alkyl, aryl, aralkyl, amido-alkyl, amido-aryl, amido-aralkyl, NH-carbamoyl-alkyl, NH-carbamoyl-aryl, NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR18R19, SiR20R21R22, or NH-carbamoyl-R23R24 wherein R18, R19, R20, R21, R22, R23, R24 independently from each other can be H, alkyl, aryl, or aralkyl;
R4 can be independently H, halogen, azido, cyano, acyl, aracyl, nitro, alkyl, aryl, aralkyl, amido-alkyl, amido-aryl, amido-aralkyl, NH-carbamoyl-alkyl, NH-carbamoyl-aryl, NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, SeH, Se-alkyl, Se-aryl, Se-aralkyl, NR25R26, or SiR27R28R29 wherein R25, R26, R27, R28, R29 independently from each other can be H, alkyl, aryl, or aralkyl;
R7 can be independently H, amino, alkyl, nitro, N-oxide or absent, or can form together with R3, Y and the C bridging Y and R3 an imidazole ring which can be unsubstituted or substituted with alkyl, aryl or aralkyl or, can form together with R4 an imidazole ring which can be unsubstituted or substituted with alkyl, aryl or aralkyl; and wherein
R5 is a borano (BH$_3$), methylborano, dimethylborano or cyanoborano (BH$_2$CN) group and R6 is H, azido, acyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, SH, S-alkyl, S-aryl, S-aralkyl, SeH, Se-alkyl, Se-aryl, Se-aralkyl or NR30R31, wherein R30, R31 independently from each other can be H, alkyl, aryl, or aralkyl; or R5 is H, azido, acyl, nitro, alkyl, aryl, aralkyl, amido-alkyl, amido-aryl, amido-aralkyl, O-carbamoyl-alkyl, O-carbamoyl-aryl, O-carbamoyl-aralkyl, OH, O-alkyl, O-aryl, O-aralkyl, O-acyl, SH, S-alkyl, S-aryl, S-aralkyl, SeH, Se-alkyl, Se-aryl, Se-aralkyl or NR32R33, wherein R32, R33 independently from each other can be H, alkyl, aryl, or aralkyl; and R6 is a borano (BH$_3$), methylborano, dimethylborano or cyanoborano (BH$_2$CN) group;

and salts and/or hydrates thereof, wherein the compound of formula (I) or (II) can optionally be isotopically or radioactively labeled, be labeled with a dye or be immobilized;

with the proviso that the compound of formula (I) and (II) is not selected from the group consisting of N$^6$-benzoyl-2'-tert.-butyldimethylsilyladenosine-3',5'-cyclic boranophosphate, cyanoethyl ester, Rp-/Sp-isomer, 2'-tert.-butyldimethylsilyladenosine-3',5'-cyclic boranophosphate, cyanoethyl ester, Rp-/Sp-isomer, adenosine-3',5'-cyclic boranophosphate, Rp-/Sp-isomer, thymidine-3',5'-cyclic cyanoboranophosphate, Rp-/Sp-isomer, N$^6$-benzoyl-2'-tert.-butyldimethylsilyladenosine-3',5'-cyclic cyanoboranophosphate, Rp-/Sp-isomer, 2'-tert.-butyldimethylsilyladenosine-3',5'-cyclic cyanoboranophosphate, Rp-/Sp-isomer, adenosine-3',5'-cyclic cyanoboranophosphate, Rp-/Sp-isomer, 5-fluoro-2'-deoxyuridine-3',5'-cyclic boranophosphate, 4-nitrophenyl ester, Rp-/Sp-isomer, 5-fluoro-2'-deoxyuridine-3',5'-cyclic boranophosphate, Rp-/Sp-isomer, 5-fluoro-2'-deoxyuridine-3',5'-cyclic boranophosphorothioate, Rp-/Sp-isomer, thymidine-3',5'-cyclic boranophosphate, cyanoethyl ester, Rp-/Sp-isomer, thymidine-3',5'-cyclic boranophosphate, 4-nitrophenyl ester, Rp-/Sp-isomer, thymidine-3',5'-cyclic boranophosphate, Rp-/Sp-isomer and thymidine-3',5'-cyclic boranophosphorothioate, Rp-/Sp-isomer.

2. The compound of claim 1, wherein

R1 is H, halogen, azido, nitro, alkyl, aryl, OH, O-alkyl, O-aryl, SH, S-alkyl, S-aryl, S-aralkyl, S-benzyl, amino, NH-alkyl, NH-benzyl, NH-aryl, Se-aryl, NR8R9 or SiR10R11R12 wherein R8, R9, R10, R11, R12 are alkyl; and/or R2 is H, halogen, azido, amino, alkylamino, O-carbamoyl-alkyl, O-carbamoyl-aryl, O-carbamoyl-aralkyl, OH, O-alkyl, O-aryl, O-aralkyl, O-acyl, O-aracyl, SH, S-alkyl or OSiR15R16R17 wherein R15, R16, R17 are alkyl; and/or R3 is H, halogen, acyl, aracyl, nitro, alkyl, aryl, aralkyl, amido-alkyl, amido-aryl, amido-aralkyl, amino, NH-alkyl, NH-aryl, NH-aralkyl, NH-carbamoyl-alkyl, NH-carbamoyl-aryl,NH-carbamoyl-aralkyl, OH, O-alkyl, O-aryl, O-aralkyl, O-acyl, O-aracyl, SH, S-alkyl, S-aryl, S-aralkyl, S-acyl, S-aracyl, NR18R19 or SiR2OR21R22 wherein R18, R19, R20, R21, R22 are alkyl and/or R4 is H, halogen, azido, acyl, aracyl, nitro, alkyl, aryl, aralkyl, amido-alkyl, amido-aryl, amido-aralkyl, NH-carbamoyl-alkyl, NH-carbamoyl-aryl, NH-carbamoyl-aralkyl, OH, O-alkyl, O-aryl, O-aralkyl, SH, S-alkyl, S-aryl, S-aralkyl, amino, alkylamino, NR25R26 or SiR27R28R29 wherein R25, R26, R27, R28, R29 are alkyl; and/or R5 is a borano (BH$_3$) or cyanoborano (BH$_2$CN) group; and R6 is H, acyl, alkyl, aryl, aralkyl, OH, O-alkyl, O-aryl, O-aralkyl, O-acyl, SH, S-alkyl, S-aryl, S-aralkyl, amino, NH-alkyl, H-aryl, N-aralkyl or NR30R31, wherein R30, R31 are alkyl or R6 is a borano (BH$_3$) or cyanoborano (BH$_2$CN) group; and R5 is H, acyl, alkyl, aryl, aralkyl, OH, O-alkyl, O-aryl, O-aralkyl, O-acyl, SH, S-alkyl, S-aryl, S-aralkyl, amino, NH-alkyl, H-aryl, N-aralkyl or NR32R33, wherein R32, R33 are alkyl; and/or R7 is H, halogen, alkyl, nitro, N-oxide or absent.

3. The compound of claim 1, wherein

R1 is H, F, Cl, Br, I, azido, nitro, 2-furyl, 3-furyl, 2-bromo-5-furyl, 2-thienyl, 3-thienyl, allyl, trifluoromethyl, phenyl, OH, methoxy, ethoxy, n-propoxy, n-butoxy, benzyloxy, 4-methylbenzyloxy, 4-methoxybenzyloxy, 4-fluorobenzyloxy, 4-chlorobenzyloxy, 4-bromobenzyloxy, phenyloxy, SH, methylthio, ethylthio, n-propylthio, n-butylthio, n-pentylthio, n-hexylthio, isopropylthio, 2-hydroxyethylthio, 2-aminoethylthio, 2-carboxyethylthio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, cyclohexylthio, benzylthio, 4-azidobenzylthio, phenylthio, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 4-nitrophenylthio, 2-aminophenylthio, 3-aminophenylthio, 4-aminophenylthio, phenylethylamino, 3-phenyl-propylamino, 2-methoxyphenylthio, 3-methoxyphenylthio, 4-methoxyphenylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,3-dichlorophenylthio, 2,4-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio, 2,6-dichlorophenylthio, 4-isopropyloxyphenylthio, 4-methylthiophenylthio, 4-azidophenylthio, 4-methylcumarinyl, naphtyl-2-thio, 4-azidophenacylthio, benzimidazolyl-2-thiobenzothiazolylthio, pyridinylthio, amino, methylamino, n-hexylamino, 2-aminoethylamino, 6-aminohexylamino, 5-amino-3-oxopentylamino, 8-amino-3,6-dioxaoctylamino, 19-amino-4,7,10,13,16-pentaoxanonadecylamino, 17-amino-9-azaheptadecylamino, 2-carboxyethylamino, 4-(N-methylanthranoyl)aminobutylamino, cyclopropylamino, cyclopentylamino, cyclohexylamino, dimethylamino, diethylamino, morpholino, piperidino, piperazino, benzylamino, 4-azidobenzylamino, anilino, 4-azidoanilino or phenylseleno; and/or R2 is H, F, Cl, Br, amino, alkylamino, O-(2-aminoethylcarbamoyl), O-(3-aminopropylcarbamoyl), O-(4-amino-n-butylcarbamoyl), O-(6-aminohexylcarbamoyl), O-(8-amino-3,6-dioxaoctylaminocarbamoyl), O-(19-amino-4,7,10,13,16-pentaoxanonadecylaminocarbamoyl), O-(17-amino-9-aza-heptadecylaminocarbamoyl), O-(6-carboxyhexylcarbamoyl), OH, methyloxy, ethyloxy, n-propyloxy, n-butyloxy, isobutyloxy, methoxyethyloxy, acyloxymethyloxy, 4-nitrobenzyloxymethyloxy, benzyloxy, O-acetyl, O-propionyl, O-n-butyryl, O-isobutyryl, O-n-hexanoyl, O-n-octanoyl, O-succinyl, O-anthraniloyl, O—(N-methylanthraniloyl), O-benzoyl, O-(4-benzoylbenzoyl), O-triflyl, O-toluolsulfonyl, O-dansyl, methylthio, O-trimethylsilyl, O-triethylsilyl, O-tert. butyldimethylsilyl or O-triisopropylsilyloxymethyl; and/or R3 is H, F, Cl, Br, I, azido, acetyl, butyryl, benzoyl, nitro, methyl, ethyl, n-propyl, trifluoromethyl, 2-furyl, 2-thienyl, phenyl, benzyl, amidomethyl, amidoethyl, amido-n-propyl, amido-n-butyl, amidoisobutyl, benzoyl, 4-benzoylbenzoyl, amino, NH-methyl, NH-ethyl, NH-n-propyl, NH-tert.-butyl, NH-(2-aminoethyl), NH-n-(6-aminohexyl), NH-(8-amino-3,6-dioxaoctyl), NH-(6-carboxy-n-hexyl), NH-cyclohexyl, N,N-dimethyl, N,N-diethyl, N,N-di-n-propyl, N,N-diisopropyl, N-piperidinyl, N-piperazinyl, NH-benzyl, NH-phenyl, NH-4-azidophenyl, NH-phenylethyl, NH-phenylpropyl, NH-tert.-butylcarbamoyl, NH-phenylcarbamoyl, OH, methyloxy, ethyloxy, propyloxy, n-hexyloxy, 6-amino-n-hexyloxy, phenyloxy, benzyloxy, methylcarbonyloxy, benzoyloxy, SH, methylthio, ethylthio, propylthio, n-hexylthio, 6-amino-n-hexylthio, 4-bromo-2,3-dioxobutylthio, phenylthio, benzylthio, trimethylsilyl, triethylsilyl or tert. butyldimethylsilyl; and/or R4 is H, F, Cl, Br, I, nitro, methyl, ethyl, n-propyl, n-hexyl, 6-amino-n-hexyl, trifluoromethyl, phenyl, 4-N,N-dimethylaminophenyl, benzyl, 4-azidobenzyl, amido-n-butyl, amidoisobutyl, amido(6-amino-n-hexyl), amidobenzoyl, OH, methyloxy, n-hexyloxy, phenyloxy, benzyloxy, SH, methylthio, ethylthio, 6-amino-n-hexylthio, phenylthio, 4-azidophenylthio, benzylthio, 4-azidobenzylthio, amino, methylamino, 2-aminoethylamino, n-hexylamino, 6-amino-n-hexylamino, 8-amino-3,6-dioxaoctylamino, dimethylamino, piperidino, piperazino, trimethylsilyl, triethylsilyl or tert. butyldimethylsilyl; and/or R5 is a borano ($BH_3$) or cyanoborano ($BH_2CN$) group and R6 is H, methyl, ethyl, phenyl, benzyl, OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, acetyloxy, propionyloxy, benzoyloxy, SH, methylthio, acetoxymethylthio, cyanoethylthio, phenylthio, benzylthio, amino, methylamino, dimethylamino, piperidino, anilino or benzylamino or R6 is a borano ($BH_3$) or cyanoborano ($BH_2CN$) group and R5 is H, methyl, ethyl, phenyl, benzyl, OH, methyloxy, ethyloxy, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, acetyloxy, propionyloxy, benzoyloxy, SH, methylthio, acetoxymethylthio, cyanoethylthio, phenylthio, benzylthio, amino, methylamino, dimethylamino, piperidino, anilino or benzylamino; and/or R7 is Cl, methyl, nitro, N-oxide or absent.

4. The compound of claim 1, wherein

R1 is H, F, Cl, Br, azido, nitro, 2-furyl, allyl, trifluoromethyl, phenyl, OH, methoxy, benzyloxy, phenyloxy, SH, methylthio, n-hexylthio, 2-hydroxyethylthio, 2-aminoethylthio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, phenylthio, benzylthio, 4-azidobenzylthio, 4-chlorophenylthio, 4-nitrophenylthio, 2-aminophenylthio, 4-methoxyphenylthio, 4-methylphenylthio, 2,3,5,6-tetrafluorophenylthio, 4-hydroxyphenylthio, 2,4-dichlorophenylthio, 4-azidophenylthio, 4-methylcumarinyl, 4-azidophenacylthio, 4-isopropylphenylthio, pyridinylthio, amino, methylamino, n-hexylamino, 6-aminohexylamino, 5-amino-3-oxopentylamino, 8-amino-3,6-dioxaoctylamino, 17-amino-9-aza-heptadecylamino, 19-amino-4,7,10,13,16-pentaoxanonadecylamino, 4-(N-methylanthranoyl)aminobutylamino, cyclohexylamino, dimethylamino, diethylamino, morpholino, piperidino, piperazino, benzylamino, 4-azidobenzylamino, anilino, 4-azidoanilino or phenylseleno; and/or R2 is H, F, O-(2-aminoethylcarbamoyl), O-(6-aminohexylcarbamoyl), O-(8-amino-3,6-dioxaoctylaminocarbamoyl), O-(6-carboxyhexylcarbamoyl), OH, O-methyl, O-ethyl, O-n-propyl, O-n-butyl, O-n-butyryl, O-n-octanoyl, O-succinyl, O-anthraniloyl, O—(N-methylanthraniloyl), O-(4-benzoylbenzoyl), O-triflyl, O-dansyl, methylthio, O-trimethylsilyl or O-triethylsilyl; and/or R3 is H, F, Cl, Br, I, azido, nitro, methyl, 2-furyl, 2-thienyl, phenyl, benzyl, amidoethyl, amido-n-propyl, amido-n-butyl, amidoisobutyl, benzoyl, 4-benzoylbenzoyl, amino, NH-methyl, NH-tert.-butyl, NH-(2-aminoethyl), NH-n-(6-aminohexyl), NH-(8-amino-3,6-dioxaoctyl), NH-(6-carboxy-n-hexyl), N,N-dimethyl, N,N-diethyl, N,N-di-n-propyl, N,N-diisopropyl, N-piperidinyl, N-piperazinyl, NH-benzyl, NH-phenyl, NH-tert.-butylcarbamoyl, NH-phenylcarbamoyl; OH, methyloxy, n-hexyloxy, 6-amino-n-hexyloxy, phenyloxy, benzyloxy, SH, ethylthio, 2-aminoethylthio, n-hexylthio, 6-amino-n-hexylthio, 4-bromo-2,3-dioxobutylthio, phenylthio, benzylthio, trimethylsilyl or triethylsilyl; and/or R4 is H, F, Cl, Br, I, methyl, n-hexyl, 6-amino-n-hexyl, phenyl, benzyl, amido-n-butyl, amidoisobutyl, amido(6-amino-n-hexyl), amidobenzoyl, OH, SH, methylthio, ethylthio, 6-amino-n-hexylthio, phenylthio, benzylthio, 4-azidobenzylthio, amino, methylamino, 2-aminoethylamino, 6-amino-n-hexylamino, 8-amino-3,6-dioxaoctylamino, dimethylamino, piperidino, piperazino, trimethylsilyl or tert. butyldimethylsilyl; and/or R5 is a borano ($BH_3$) or cyanoborano ($BH_2CN$) group and R6 is H, methyl, ethyl, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, SH, methylthio, acetoxymethylthio, cyanoethylthio, phenylthio, benzylthio, amino, methylamino, dimethylamino, piperidino, anilino or benzylamino; or R6 is a borano (BH$_3$) or cyanoborano (BH$_2$CN) group and R5 is H, methyl, ethyl, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, phenyloxy, benzyloxy, SH, methylthio, acetoxymethylthio, cyanoethylthio, phenylthio, benzylthio, amino, methylamino, dimethylamino, piperidino, anilino or benzylamino; and/or R7 is Cl, methyl, nitro, N-oxide or absent.

5. The compound of claim 1, wherein

R1 is H, F, Cl, Br, azido, 2-furyl, allyl, phenyl, OH, SH, 2-aminoethylthio, [2-[(fluoresceinylthioureido)amino] ethyl]thio, benzylthio, 4-azidobenzylthio, 4-chlorophenylthio, 2-aminophenylthio, 4-methoxyphenylthio, 4-hydroxyphenylthio, 4-azidophenylthio, amino, methylamino, n-hexylamino, 6-aminohexylamino, 19-amino-4,7,10,13,16-pentaoxanonadecylamino, diethylamino, piperidino or 4-azidoanilino; and/or R2 is H, O-(2-aminoethylcarbamoyl), O-(6-aminohexylcarbamoyl), O-(8-amino-3,6-dioxaoctylaminocarbamoyl), OH, O-methyl, O-ethyl, O-n-butyryl, O-succinyl, O-anthraniloyl, O—(N-methylanthraniloyl), O-dansyl, O-(4-benzoylbenzoyl), methylthio or O-trimethylsilyl; and/or R3 is H, F, Cl, Br, I, nitro, 2-furyl, phenyl, benzyl, amidoethyl, amido-n-butyl, amidoisobutyl, benzoyl, 4-benzoylbenzoyl, amino, NH-methyl, NH-tert.-butyl, NH-(2-aminoethyl), NH-n-(6-aminohexyl), NH-(8-amino-3,6-dioxaoctyl), NH-(6-carboxy-n-hexyl), N,N-dimethyl, N,N-diethyl, N,N-di-n-propyl, N,N-diisopropyl, NH-tert-butyl, NH-benzyl, NH-phenyl, NH-tert-butylcarbamoyl, OH, O-methyl, O-(6-amino-n-hexyl), SH, ethylthio, 6-amino-n-hexylthio, phenylthio, benzylthio or trimethylsilyl; and/or R4 is H, F, Cl, phenyl, benzyl, amido-n-butyl, amidoisobutyl, amido(6-amino-n-hexyl), amidobenzoyl, OH, SH, methylthio, 2-aminoethylthio, 6-amino-n-hexylthio, phenylthio, benzylthio, 4-azidobenzylthio, 4-bromo-2,3-dioxobutylthio, amino, methylamino, 2-aminoethylamino, 6-amino-n-hexylamino, 8-amino-3,6-dioxaoctylamino, dimethylamino, piperidino, piperazino, trimethylsilyl or tert. butyldimethylsilyl; and/or R5 is a borano (BH$_3$) or cyanoborano (BH$_2$CN) group and R6 is H, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, benzyloxy, SH, methylthio, acetoxymethylthio, methylamino, dimethylamino, piperidino or anilino; or R6 is a borano (BH$_3$) or cyanoborano (BH$_2$CN) group and R5 is H, OH, cyanoethyloxy, acetoxymethyloxy, pivaloyloxymethyloxy, methoxymethyloxy, propionyloxymethyloxy, butyryloxymethyloxy, acetoxyethyloxy, acetoxybutyloxy, acetoxyisobutyloxy, benzyloxy, SH, methylthio, acetoxymethylthio, methylamino, dimethylamino, piperidino or anilino; and/or R7 is Cl, methyl or absent.

6. The compound of claim 1, wherein

R1 is H, F, Cl, Br, azido, 2-furyl, phenyl, OH, SH, 2-aminoethylthio, benzylthio, 4-chlorophenylthio, methylamino, 6-aminohexylamino or piperidino; and/or R2 is H, O-(2-aminoethylcarbamoyl), O-(6-aminohexylcarbamoyl), OH, O-methyl, O-n-butyryl, O-succinyl, O—(N-methylanthraniloyl), O-dansyl or O-trimethylsilyl; and/or R3 is H, F, Cl, nitro, phenyl, amido-n-butyl, amidoisobutyl, benzoyl, 4-benzoylbenzoyl, amino, NH-tert.-butyl, NH-(2-aminoethyl), NH-n-(6-aminohexyl), N,N-dimethyl, N,N-di-n-propyl, N,N-diisopropyl, NH-benzyl, NH-phenyl, NH-tert-butylcarbamoyl, OH, 6-amino-n-hexyloxy, SH, ethylthio, 6-amino-n-hexylthio, phenylthio or benzylthio; and/or R4 is H, F, Cl, methyl, amido-n-butyl, amido(6-amino-n-hexyl), OH, SH, methylthio, 2-aminoethylthio, 6-amino-n-hexylthio, amino, methylamino, 2-aminoethylamino, 6-amino-n-hexylamino or dimethylamino; and/or R5 is a borano (BH$_3$) group and R6 is OH, cyanoethyloxy, acetoxymethyloxy, pivaloyloxymethyloxy, methoxymethyloxy, propionyloxymethyloxy, butyryloxymethyloxy, SH, acetoxymethylthio, methylamino, dimethylamino or piperidino; or R6 is a borano (BH$_3$) group and R5 is OH, cyanoethyloxy, acetoxymethyloxy, pivaloyloxymethyloxy, methoxymethyloxy, propionyloxymethyloxy, butyryloxymethyloxy, SH, acetoxymethylthio, methylamino, dimethylamino or piperidino; and/or R7 is Cl, methyl or absent.

7. The compound of claim 1, wherein R1 is H, Br, azido, OH, 2-aminoethylthio, benzylthio, 4-chlorophenylthio, 6-aminohexylamino or piperidino;

R2 is H, O-(2-aminoethylcarbamoyl), O-(6-aminohexylcarbamoyl), OH, O-methyl, O-n-butyryl, O-succinyl or O—(N-methylanthraniloyl);

R3 is H, Cl, amido-n-butyl, benzoyl, amino, NH-(2-aminoethyl), NH-n-(6-aminohexyl), N,N-dimethyl, NH-benzyl, NH-phenyl, NH-tert.-butylcarbamoyl, OH, 6-amino-n-hexyloxy, SH, 6-amino-n-hexylthio, phenylthio or benzylthio;

R4 is H, Cl, amido-n-butyl, OH, SH, methylthio, 2-aminoethylthio, 6-amino-n-hexylthio, amino, methylamino, 2-aminoethylamino, 6-amino-n-hexylamino or dimethylamino; and/or R5 is a borano (BH$_3$) group and R6 is OH, cyanoethyloxy, acetoxymethyloxy or pivaloyloxymethyloxy; or R6 is a borano (BH$_3$) group and R5 is OH, cyanoethyloxy, acetoxymethyloxy or pivaloyloxymethyloxy; and/or R7 is Cl, methyl or absent.

8. The compound of claim 1, wherein one of R5 and R6 is BH$_3$ or BH$_2$CN and the other of R5 and R6 is OH or SH.

9. The compound of claim 1, wherein R5 is BH$_3$ or BH$_2$CN.

10. The compound of claim 1, wherein R6 is BH$_3$ or BH$_2$CN.

11. The compound of claim 1 selected from the group consisting of

| Compound | Formula # |
|---|---|
| 8-Bromoadenosine-3',5'-cyclic boranophosphate, Rp-isomer | 001 |
| 8-Bromoadenosine-3',5'-cyclic boranophosphate, Sp-isomer | 002 |
| 8-Bromoadenosine-3',5'-cyclic boranophosphate, 2-cyanoethyl ester, Rp-isomer | 003 |
| 8-Bromoadenosine-3',5'-cyclic boranophosphate, 2-cyanoethyl ester, Sp-isomer | 004 |
| 8-Bromoadenosine-3',5'-cyclic boranophosphate, Rp-isomer, acetoxymethyl ester | 005 |
| 8-Bromoadenosine-3',5'-cyclic boranophosphate, Sp-isomer, acetoxymethyl ester | 006 |
| 8-Bromo-2'-O-(imidazoylcarbamoyl)adenosine-3',5'-cyclic boranophosphate, Rp-isomer | 007 |
| 8-Bromo-2'-O-(imidazoylcarbamoyl)adenosine-3',5'-cyclic boranophosphate, Sp-isomer | 008 |
| 8-Bromo-2'-O-(N-methylanthraniloyl)adenosine-3',5'-cyclic boranophosphate, Rp-isomer | 009 |
| 8-Bromo-2'-O-(N-methylanthraniloyl)adenosine-3',5'-cyclic boranophosphate, Sp-isomer | 010 |
| 8-Bromo-2'-O-monosuccinyladenosine-3',5'-cyclic boranophosphate, Rp-isomer | 011 |
| 8-Bromo-2'-O-monosuccinyladenosine-3',5'-cyclic boranophosphate, Sp-isomer | 012 |
| 8-Chloroadenosine-3',5'-cyclic boranophosphate, Rp-isomer | 013 |
| 8-Chloroadenosine-3',5'-cyclic boranophosphate, Sp-isomer | 014 |
| 8-Hydroxyadenosine-3',5'-cyclic boranophosphate, Rp-isomer | 015 |
| 8-Hydroxyadenosine-3',5'-cyclic boranophosphate, Sp-isomer | 016 |
| 8-Thioadenosine-3',5'-cyclic boranophosphate, Rp-isomer | 017 |
| 8-Thioadenosine-3',5'-cyclic boranophosphate, Sp-isomer | 018 |
| 8-Azidoadenosine-3',5'-cyclic boranophosphate, Rp-isomer | 019 |
| 8-Azidoadenosine-3',5'-cyclic boranophosphate, Sp-isomer | 020 |
| 8-Aminoadenosine-3',5'-cyclic boranophosphate, Rp-isomer | 021 |
| 8-Aminoadenosine-3',5'-cyclic boranophosphate, Sp-isomer | 022 |
| 8-(2-Aminoethylamino)adenosine-3',5'-cyclic boranophosphate, Rp-isomer | 023 |
| 8-(2-Aminoethylamino)adenosine-3',5'-cyclic boranophosphate, Sp-isomer | 024 |
| 8-(6-Aminohexylamino)adenosine-3',5'-cyclic boranophosphate, Rp-isomer | 025 |
| 8-(6-Aminohexylamino)adenosine-3',5'-cyclic boranophosphate, Sp-isomer | 026 |
| 8-(6-Aminohexylamino)adenosine-3',5'-cyclic boranophosphate, Rp-isomer, immobilized to agarose | 027 |
| 8-(6-Aminohexylamino)adenosine-3',5'-cyclic boranophosphate, Sp-isomer, immobilized to agarose | 028 |
| 8-(19-Amino-4,7,10,13,16-pentaoxanonadecylamino)adenosine-3',5'-cyclic boranophosphate, Rp-isomer | 029 |
| 8-(19-Amino-4,7,10,13,16-pentaoxanonadecylamino)adenosine-3',5'-cyclic boranophosphate, Sp-isomer | 030 |
| 8-Diethylaminoadenosine-3',5'-cyclic boranophosphate, Rp-isomer | 031 |
| 8-Diethylaminoadenosine-3',5'-cyclic boranophosphate, Sp-isomer | 032 |
| 8-Cyclopentylamino adenosine-3',5'-cyclic boranophosphate, Rp-isomer | 033 |
| 8-Cyclopentylamino adenosine-3',5'-cyclic boranophosphate, Sp-isomer | 034 |
| 8-Piperidinoadenosine-3',5'-cyclic boranophosphate, Rp-isomer | 035 |
| 8-Piperidinoadenosine-3',5'-cyclic boranophosphate, Sp-isomer | 036 |
| 8-Piperazinoadenosine-3',5'-cyclic boranophosphate, Rp-isomer | 037 |
| 8-Piperazinoadenosine-3',5'-cyclic boranophosphate, Sp-isomer | 038 |
| 8-Benzylaminoadenosine-3',5'-cyclic boranophosphate, Rp-isomer | 039 |
| 8-Benzylaminoadenosine-3',5'-cyclic boranophosphate, Sp-isomer | 040 |
| 8-Ethyloxyadenosine-3',5'-cyclic boranophosphate, Rp-isomer | 041 |
| 8-Ethyloxyadenosine-3',5'-cyclic boranophosphate, Sp-isomer | 042 |
| 8-Phenoxyadenosine-3',5'-cyclic boranophosphate, Rp-isomer | 043 |
| 8-Phenoxyadenosine-3',5'-cyclic boranophosphate, Sp-isomer | 044 |
| 8-Benzyloxyadenosine-3',5'-cyclic boranophosphate, Rp-isomer | 045 |
| 8-Benzyloxyadenosine-3',5'-cyclic boranophosphate, Sp-isomer | 046 |
| 8-n-Hexylthioadenosine-3',5'-cyclic boranophosphate, Rp-isomer | 047 |
| 8-n-Hexylthioadenosine-3',5'-cyclic boranophosphate, Sp-isomer | 048 |
| 8-(2-Aminoethylthio)adenosine-3',5'-cyclic boranophosphate, Rp-isomer | 049 |
| 8-(2-Aminoethylthio)adenosine-3',5'-cyclic boranophosphate, Sp-isomer | 050 |
| 8-(2-Aminophenylthio)adenosine-3',5'-cyclic boranophosphate, Rp-isomer | 051 |
| 8-(2-Aminophenylthio)adenosine-3',5'-cyclic boranophosphate, Sp-isomer | 052 |
| 8-(4-Chlorophenylthio)adenosine-3',5'-cyclic boranophosphate, Rp-isomer | 053 |
| 8-(4-Chlorophenylthio)adenosine-3',5'-cyclic boranophosphate, Sp-isomer | 054 |
| 8-(2-Naphtylthio)adenosine-3',5'-cyclic boranophosphate, Rp-isomer | 055 |
| 8-(2-Naphtylthio)adenosine-3',5'-cyclic boranophosphate, Sp-isomer | 056 |
| 8-(2-Furyl)adenosine-3',5'-cyclic boranophosphate, Rp-isomer | 057 |
| 8-(2-Furyl)adenosine-3',5'-cyclic boranophosphate, Sp-isomer | 058 |
| 8-(2-Furyl)adenosine-3',5'-cyclic boranophosphate, Rp-isomer, pivaloyloxymethyl ester | 059 |
| 8-(2-Furyl)adenosine-3',5'-cyclic boranophosphate, Sp-isomer, pivaloyloxymethyl ester | 060 |
| 8-Phenyladenosine-3',5'-cyclic boranophosphate, Rp-isomer | 061 |
| 8-Phenyladenosine-3',5'-cyclic boranophosphate, Sp-isomer | 062 |

-continued

| Compound | Formula # |
|---|---|
| 8-Phenyladenosine-3',5'-cyclic boranophosphate, Rp-isomer, acetoxymethyl ester | 063 |
| 8-Phenyladenosine-3',5'-cyclic boranophosphate, Sp-isomer, acetoxymethyl ester | 064 |
| 8-Bromo-2'-O-methyladenosine-3',5'-cyclic boranophosphate, Rp-isomer | 065 |
| 8-Bromo-2'-O-methyladenosine-3',5'-cyclic boranophosphate, Sp-isomer | 066 |
| 8-Bromo-2'-O-methyladenosine-3',5'-cyclic boranophosphate, 2-cyanoethyl ester, Rp-isomer | 067 |
| 8-Bromo-2'-O-methyladenosine-3',5'-cyclic boranophosphate, 2-cyanoethyl ester, Sp-isomer | 068 |
| 8-Hydroxy-2'-O-methyladenosine-3',5'-cyclic boranophosphate, Rp-isomer | 069 |
| 8-Hydroxy-2'-O-methyladenosine-3',5'-cyclic boranophosphate, Sp-isomer | 070 |
| 8-Benzylthio-2'-O-methyladenosine-3',5'-cyclic boranophosphate, Rp-isomer | 071 |
| 8-Benzylthio-2'-O-methyladenosine-3',5'-cyclic boranophosphate, Sp-isomer | 072 |
| 8-Benzylthio-2'-O-methyladenosine-3',5'-cyclic boranophosphate, Rp-isomer, acetoxymethyl ester | 073 |
| 8-Benzylthio-2'-O-methyladenosine-3',5'-cyclic boranophosphate, Sp-isomer, acetoxym ethyl ester | 074 |
| 8-(4-Chlorophenylthio)-2'-O-methyladenosine-3',5'-cyclic boranophosphate, Rp-isomer | 075 |
| 8-(4-Chlorophenylthio)-2'-O-methyladenosine-3',5'-cyclic boranophosphate, Sp-isomer | 076 |
| 8-(4-Chlorophenylthio)-2'-O-methyladenosine-3',5'-cyclic boranophosphate, Rp-isomer, acetoxymethyl ester | 077 |
| 8-(4-Chlorophenylthio)-2'-O-methyladenosine-3',5'-cyclic boranophosphate, Sp-isomer, acetoxymethyl ester | 078 |
| 8-(4-Methoxyphenylthio)-2'-O-methyladenosine-3',5'-cyclic boranophosphate, Rp-isomer | 079 |
| 8-(4-Methoxyphenylthio)-2'-O-methyladenosine-3',5'-cyclic boranophosphate, Sp-isomer | 080 |
| 8-(4-Methoxyphenylthio)-2'-O-methyladenosine-3',5'-cyclic boranophosphate, Rp-isomer, acetoxymethyl ester | 081 |
| 8-(4-Methoxyphenylthio)-2'-O-methyladenosine-3',5'-cyclic boranophosphate, Sp-isomer, acetoxymethyl ester | 082 |
| 8-(6-Aminohexylamino)-2'-O-methyladenosine-3',5'-cyclic boranophosphate, Rp-isomer; immobilised to agarose | 083 |
| 8-(6-Aminohexylamino)-2'-O-methyladenosine-3',5'-cyclic boranophosphate, Sp-isomer; immobilised to agarose | 084 |
| 2'-O-Methyladenosine-3',5'-cyclic boranophosphate, Rp-isomer | 085 |
| 2'-O-Methyladenosine-3',5'-cyclic boranophosphate, Sp-isomer | 086 |
| 2'-O-Methyladenosine-3',5'-cyclic boranophosphate, 2-cyanoethylester, Rp-isomer | 087 |
| 2'-O-Methyladenosine-3',5'-cyclic boranophosphate, 2-cyanoethylester, Sp-isomer | 088 |
| 2'-O-Methylinosine-3',5'-cyclic boranophosphate, Rp-isomer | 089 |
| 2'-O-Methylinosine-3',5'-cyclic boranophosphate, Sp-isomer | 090 |
| 2'-O-Methyl-$N^6$-monobutyryladenosine-3',5'-cyclic boranophosphate, Rp-isomer | 091 |
| 2'-O-Methyl-$N^6$-monobutyryladenosine-3',5'-cyclic boranophosphate, Sp-isomer | 092 |
| Adenosine-3',5'-cyclic boranophosphate, Rp-isomer, acetoxymethyl ester | 093 |
| Adenosine-3',5'-cyclic boranophosphate, Sp-isomer, acetoxymethyl ester | 094 |
| $N^6$-Monobutyryladenosine-3',5'-cyclic boranophosphate, Rp-isomer | 095 |
| $N^6$-Monobutyryladenosine-3',5'-cyclic boranophosphate, Sp-isomer | 096 |
| $N^6$-,2'-O-Dibutyryladenosine-3',5'-cyclic boranophosphate, Rp-isomer | 097 |
| $N^6$-,2'-O-Dibutyryladenosine-3',5'-cyclic boranophosphate, Sp-isomer | 098 |
| $N^6$-,2'-O-Dibutyryladenosine-3',5'-cyclic boranophosphate, Rp-isomer, acetoxymethyl ester | 099 |
| $N^6$-,2'-O-Dibutyryladenosine-3',5'-cyclic boranophosphate, Sp-isomer, acetoxymethyl ester | 100 |
| $N^6$-Mono-tert. butylcarbamoyladenosine-3',5'-cyclic boranophosphate, Rp-isomer | 101 |
| $N^6$-Mono-tert. butylcarbamoyladenosine-3',5'-cyclic boranophosphate, Sp-isomer | 102 |
| $N^6$-Benzoyladenosine-3',5'-cyclic boranophosphate, Rp-isomer | 103 |
| $N^6$-Benzoyladenosine-3',5'-cyclic boranophosphate, Sp-isomer | 104 |
| $N^6$-Benzoyladenosine-3',5'-cyclic boranophosphate, Rp-isomer, acetoxymethyl ester | 105 |
| $N^6$-Benzoyladenosine-3',5'-cyclic boranophosphate, Sp-isomer, acetoxymethyl ester | 106 |
| 2'-O-(N-Methylanthraniloyl)adenosine-3',5'-cyclic boranophosphate, Rp-isomer | 107 |
| 2'-O-(N-Methylanthraniloyl)adenosine-3',5'-cyclic boranophosphate, Sp-isomer | 108 |

| Compound | Formula # |
| --- | --- |
| 2'-O-([Fluoresceinyl]aminohexylcarbamoyl)adenosine-3',5'-cyclic boranophosphate, Rp-isomer | 109 |
| 2'-O-([Fluoresceinyl]aminohexylcarbamoyl)adenosine-3',5'-cyclic boranophosphate, Sp-isomer | 110 |
| 2'-O-Monosuccinyladenosine-3',5'-cyclic boranophosphate, Rp-isomer | 111 |
| 2'-O-Monosuccinyladenosine-3',5'-cyclic boranophosphate, Sp-isomer | 112 |
| 2'-O-Monosuccinyladenosine-3',5'-cyclic boranophosphate, Rp-isomer, tyrosylmethylester | 113 |
| 2'-O-Monosuccinyladenosine-3',5'-cyclic boranophosphate, Sp-isomer, tyrosylmethylester | 114 |
| 2'-O-(2-Aminoethylcarbamoyl)adenosine-3',5'-cyclic boranophosphate, Rp-isomer | 115 |
| 2'-O-(2-Aminoethyl carbamoyl)adenosine-3',5'-cyclic boranophosphate, Sp-isomer | 116 |
| 2'-O-(6-Aminohexylcarbamoyl)adenosine-3',5'-cyclic boranophosphate, Rp-isomer | 117 |
| 2'-O-(6-Aminohexylcarbamoyl)adenosine-3',5'-cyclic boranophosphate, Sp-isomer | 118 |
| 2'-O-(6-Aminohexylcarbamoyl)adenosine-3',5'-cyclic boranophosphate, Rp-isomer; immobilised to agarose | 119 |
| 2'-O-(6-Aminohexylcarbamoyl)adenosine-3',5'-cyclic boranophosphate, Sp-isomer; immobilised to agarose | 120 |
| 2'-Deoxyadenosine-3',5'-cyclic boranophosphate, Rp-isomer | 121 |
| 2'-Deoxyadenosine-3',5'-cyclic boranophosphate, Sp-isomer | 122 |
| 2'-Deoxyadenosine-3',5'-cyclic boranophosphate, Rp-isomer, acetoxymethyl ester | 123 |
| 2'-Deoxyadenosine-3',5'-cyclic boranophosphate, Sp-isomer, acetoxymethyl ester | 124 |
| 2'-Amino-2'-deoxyadenosine-3',5'-cyclic boranophosphate, Rp-isomer | 125 |
| 2'-Amino-2'-deoxyadenosine-3',5'-cyclic boranophosphate, Sp-isomer | 126 |
| 2'-Fluoro-2'-deoxyadenosine-3',5'-cyclic boranophosphate, Rp-isomer | 127 |
| 2'-Fluoro-2'-deoxyadenosine-3',5'-cyclic boranophosphate, Sp-isomer | 128 |
| 6-Chloropurine-1-β-D-ribofuranoside-3',5'-cyclic boranophosphate, Rp-isomer | 129 |
| 6-Chloropurine-1-β-D-ribofuranoside-3',5'-cyclic boranophosphate, Sp-isomer | 130 |
| 6-Chloropurine-1-β-D-ribofuranoside-3',5'-cyclic boranophosphate, 2-cyanoethylester, Rp-isomer | 131 |
| 6-Chloropurine-1-β-D-ribofuranoside-3',5'-cyclic boranophosphate, 2-cyanoethylester, Sp-isomer | 132 |
| 6-Chloropurine-1-β-D-2'-O-trimethylsilylribofuranoside-3',5'-cyclic boranophosphate, Rp-isomer | 133 |
| 6-Chloropurine-1-β-D-2'-O-trimethylsilylribofuranoside-3',5'-cyclic boranophosphate, Sp-isomer | 134 |
| 6-Chloropurine-1-β-D-2'-O-(imidazolylcarbamoyl)ribofuranoside-3',5'-cyclic boranophosphate, Rp-isomer | 135 |
| 6-Chloropurine-1-β-D-2'-O-(imidazolylcarbamoyl)ribofuranoside-3',5'-cyclic boranophosphate, Sp-isomer | 136 |
| 6-Chloropurine-1-β-D-2'-O-(6-aminohexylcarbamoyl) ribofuranoside-3',5'-cyclic boranophosphate, Rp-isomer | 137 |
| 6-Chloropurine-1-β-D-2'-O-(6-aminohexylcarbamoyl) ribofuranoside-3',5'-cyclic boranophosphate, Sp-isomer | 138 |
| Inosine-3',5'-cyclic boranophosphate, Rp-isomer | 139 |
| Inosine-3',5'-cyclic boranophosphate, Sp-isomer | 140 |
| 6-Methoxypurine-1-β-D-ribofuranoside-3',5'-cyclic boranophosphate, Rp-isomer | 141 |
| 6-Methoxypurine-1-β-D-ribofuranoside-3',5'-cyclic boranophosphate, Sp-isomer | 142 |
| 6-Benzyloxypurine-1-β-D-ribofuranosyl-3',5'-cyclic boranophosphate, Rp-isomer | 143 |
| 6-Benzyloxypurine-1-β-D-ribofuranosyl-3',5'-cyclic boranophosphate, Sp-isomer | 144 |
| $N^6$-(2-Aminoethyl)adenosine-3',5'-cyclic boranophosphate, Rp-isomer | 145 |
| $N^6$-(2-Aminoethyl)adenosine-3',5'-cyclic boranophosphate, Sp-isomer | 146 |
| $N^6$-(2-Aminoethyl)adenosine-3',5'-cyclic boranophosphate, Rp-isomer; immobilised to agarose | 147 |
| $N^6$-(2-Aminoethyl)adenosine-3',5'-cyclic boranophosphate, Sp-isomer; immobilised to agarose | 148 |
| $N^6$-(6-Aminohexyl)adenosine-3',5'-cyclic boranophosphate, Rp-isomer | 149 |
| $N^6$-(6-Aminohexyl)adenosine-3',5'-cyclic boranophosphate, Sp-isomer | 150 |
| $N^6,N^6$-Dimethyladenosine-3',5'-cyclic boranophosphate, Rp-isomer | 151 |
| $N^6,N^6$-Dimethyladenosine-3',5'-cyclic boranophosphate, Sp-isomer | 152 |
| $N^6,N^6$-Di-n-propyladenosine-3',5'-cyclic boranophosphate, Rp-isomer | 153 |
| $N^6,N^6$-Di-n-propyladenosine-3',5'-cyclic boranophosphate, Sp-isomer | 154 |
| $N^6,N^6$-Di-n-propyladenosine-3',5'-cyclic boranophosphate, Rp-isomer, acetoxymethyl ester | 155 |

| Compound | Formula # |
|---|---|
| N⁶,N⁶-Di-n-propyladenosine-3',5'-cyclic boranophosphate, Sp-isomer, acetoxymethyl ester | 156 |
| N⁶-Cycloheptyladenosine-3',5'-cyclic boranophosphate, Rp-isomer | 157 |
| N⁶-Cycloheptyladenosine-3',5'-cyclic boranophosphate, Sp-isomer | 158 |
| N⁶-Benzyladenosine-3',5'-cyclic boranophosphate, Rp-isomer | 159 |
| N⁶-Benzyladenosine-3',5'-cyclic boranophosphate, Sp-isomer | 160 |
| N⁶-Benzyladenosine-3',5'-cyclic boranophosphate, Rp-isomer, acetoxymethyl ester | 161 |
| N⁶-Benzyladenosine-3',5'-cyclic boranophosphate, Sp-isomer, acetoxymethyl ester | 162 |
| N⁶-Phenyladenosine-3',5'-cyclic boranophosphate, Rp-isomer | 163 |
| N⁶-Phenyladenosine-3',5'-cyclic boranophosphate, Sp-isomer | 164 |
| 8-(4-Chlorophenylthio)-N⁶-phenyladenosine-3',5'-cyclic boranophosphate, Rp-isomer | 165 |
| 8-(4-Chlorophenylthio)-N⁶-phenyladenosine-3',5'-cyclic boranophosphate, Sp-isomer | 166 |
| 6-Thiopurine-1-β-D-ribofuranoside-3',5'-cyclic boranophosphate, Rp-isomer | 167 |
| 6-Thiopurine-1-β-D-ribofuranoside-3',5'-cyclic boranophosphate, Sp-isomer | 168 |
| 6-Thiopurine-1-β-D-ribofuranoside-3',5'-cyclic boranophosphate, 2-cyanoethylester, Rp-isomer | 169 |
| 6-Thiopurine-1-β-D-ribofuranoside-3',5'-cyclic boranophosphate, 2-cyanoethylester, Sp-isomer | 170 |
| 6-(2-Aminoethylthio)purine-1-β-D-ribofuranosyl-3',5'-cyclic boranophosphate, Rp-isomer | 171 |
| 6-(2-Aminoethylthio)purine-1-β-D-ribofuranosyl-3',5'-cyclic boranophosphate, Sp-isomer | 172 |
| 6-Phenylthiopurine-1-β-D-ribofuranoside-3',5'-cyclic boranophosphate, Rp-isomer | 173 |
| 6-Phenylthiopurine-1-β-D-ribofuranoside-3',5'-cyclic boranophosphate, Sp-isomer | 174 |
| 6-Phenylpurine-1-β-D-ribofuranoside-3',5'-cyclic boranophosphate, Rp-isomer | 175 |
| 6-Phenylpurine-1-β-D-ribofuranoside-3',5'-cyclic boranophosphate, Sp-isomer | 176 |
| 6-(N,N-Dimethylaminocarbonyl)purine-1-β-D-ribofuranoside-3',5'-cyclic borano-phosphate, Rp-isomer | 177 |
| 6-(N,N-Dimethylaminocarbonyl)purine-1-β-D-ribofuranoside-3',5'-cyclic borano-phosphate, Sp-isomer | 178 |
| 6-Azidopurine-1-β-D-ribofuranoside-3',5'-cyclic borano-phosphate, Rp-isomer | 179 |
| 6-Azidopurine-1-β-D-ribofuranoside-3',5'-cyclic borano-phosphate, Sp-isomer | 180 |
| Purine-1-β-D-ribofuranoside-3',5'-cyclic boranophosphate, Rp-isomer | 181 |
| Purine-1-β-D-ribofuranoside-3',5'-cyclic boranophosphate, Sp-isomer | 182 |
| 2-Chloroadenosine-3',5'-cyclic boranophosphate, Rp-isomer | 183 |
| 2-Chloroadenosine-3',5'-cyclic boranophosphate, Sp-isomer | 184 |
| 2-Chloroadenosine-3',5'-cyclic boranophosphate, 2-cyanoethyl ester, Rp-isomer | 185 |
| 2-Chloroadenosine-3',5'-cyclic boranophosphate, 2-cyanoethyl ester, Sp-isomer | 186 |
| 2-(2-Aminoethylamino)adenosine-3',5'-cyclic boranophosphate, Rp-isomer | 187 |
| 2-(2-Aminoethylamino)adenosine-3',5'-cyclic boranophosphate, Sp-isomer | 188 |
| 2-(6-Aminohexyl)adenosine-3',5'-cyclic boranophosphate, Rp-isomer | 189 |
| 2-(6-Aminohexyl)adenosine-3',5'-cyclic boranophosphate, Sp-isomer | 190 |
| 2-(6-Aminohexylamino)adenosine-3',5'-cyclic boranophosphate, Rp-isomer; immobilised to agarose | 191 |
| 2-(6-Aminohexylamino)adenosine-3',5'-cyclic boranophosphate, Sp-isomer; immobilised to agarose | 192 |
| 2-N,N-Diethylaminoadenosine-3',5'-cyclic boranophosphate, Rp-isomer | 193 |
| 2-N,N-Diethylaminoadenosine-3',5'-cyclic boranophosphate, Sp-isomer | 194 |
| 2-Thioadenosine-3',5'-cyclic boranophosphate, Rp-isomer | 195 |
| 2-Thioadenosine-3',5'-cyclic boranophosphate, Sp-isomer | 196 |
| 2-(2-Hydroxyethylthioadenosine-3',5'-cyclic boranophosphate, Rp-isomer 2- | 197 |
| 2-(2-Hydroxyethylthioadenosine-3',5'-cyclic boranophosphate, Sp-isomer- | 198 |
| 2-Chloro-8-methylaminoadenosine-3',5'-cyclic boranophosphate, Rp-isomer | 199 |
| 2-Chloro-8-methylaminoadenosine-3',5'-cyclic boranophosphate, Sp-isomer | 200 |
| 2-Chloro-8-hexylaminoadenosine-3',5'-cyclic boranophosphate, Rp-isomer | 201 |
| 2-Chloro-8-hexylaminoadenosine-3',5'-cyclic boranophosphate, Sp-isomer | 202 |
| Guanosine-3',5'-cyclic boranophosphate, Rp-isomer | 203 |
| Guanosine-3',5'-cyclic boranophosphate, Sp-isomer | 204 |
| Guanosine-3',5'-cyclic boranophosphate, Rp-isomer, acetoxymethyl ester | 205 |
| Guanosine-3',5'-cyclic boranophosphate, Sp-isomer, acetoxymethyl ester | 206 |

-continued

| Compound | Formula # |
|---|---|
| 2'-O-Monosuccinylguanosine-3',5'-cyclic boranophosphate, Rp-isomer | 207 |
| 2'-O-Monosuccinylguanosine-3',5'-cyclic boranophosphate, Sp-isomer | 208 |
| 2'-O-Monosuccinylguanosine-3',5'-cyclic boranophosphate, Rp-isomer, tyrosylmethylester | 209 |
| 2'-O-Monosuccinylguanosine-3',5'-cyclic boranophosphate, Sp-isomer, tyrosylmethylester | 210 |
| 2'-O-(2-Aminoethylcarbamoyl)guanosine-3',5'-cyclic boranophosphate, Rp-isomer | 211 |
| 2'-O-(2-Aminoethylcarbamoyl)guanosine-3',5'-cyclic boranophosphate, Sp-isomer | 212 |
| 2'-O-(6-Aminohexylcarbamoyl)guanosine-3',5'-cyclic boranophosphate, Rp-isomer | 213 |
| 2'-O-(6-Aminohexylcarbamoyl)guanosine-3',5'-cyclic boranophosphate, Sp-isomer | 214 |
| 2'-O-([Fluoresceinyl]aminohexylcarbamoyl)guanosine-3',5'-cyclic boranophosphate, Rp-isomer | 215 |
| 2'-O-([Fluoresceinyl]aminohexylcarbamoyl)guanosine-3',5'-cyclic boranophosphate, Sp-isomer | 216 |
| 2'-O-(6-Aminohexylcarbamoyl)guanosine-3',5'-cyclic boranophosphate, Rp-isomer; immobilised to agarose | 217 |
| 2'-O-(6-Aminohexylcarbamoyl)guanosine-3',5'-cyclic boranophosphate, Sp-isomer; immobilised to agarose | 218 |
| 8-Bromoguanosine-3',5'-cyclic boranophosphate, Rp-isomer | 219 |
| 8-Bromoguanosine-3',5'-cyclic boranophosphate, Sp-isomer | 220 |
| 8-Bromoguanosine-3',5'-cyclic boranophosphate, 2-cyanoethyl ester, Rp-isomer | 221 |
| 8-Bromoguanosine-3',5'-cyclic boranophosphate, 2-cyanoethyl ester, Sp-isomer | 222 |
| 8-Bromo-2'-O-(imidazoylcarbamoyl)guanosine-3',5'-cyclic boranophosphate, Rp-isomer | 223 |
| 8-Bromo-2'-O-(imidazoylcarbamoyl)guanosine-3',5'-cyclic boranophosphate, Sp-isomer | 224 |
| 2'-O-(8-Amino-3,6-dioxaoctylcarbamoyl)-8-bromoguanosine-3',5'-cyclic boranophosphate, Rp-isomer | 225 |
| 2'-O-(8-Amino-3,6-dioxaoctylcarbamoyl)-8-bromoguanosine-3',5'-cyclic boranophosphate, Sp-isomer | 226 |
| 2'-O-(8-Amino-3,6-dioxaoctylcarbamoyl)-8-bromoguanosine-3',5'-cyclic boranophosphate, Rp-isomer; immobilised to agarose | 227 |
| 2'-O-(8-Amino-3,6-dioxaoctylcarbamoyl)-8-bromoguanosine-3',5'-cyclic boranophosphate, Sp-isomer; immobilised to agarose | 228 |
| 2'-O-(8-[Tetramethylrhodaminyl]amino-3,6-dioxaoctylcarbamoyl)-8-bromo-guanosine-3',5'-cyclic boranophosphate, Rp-isomer | 229 |
| 2'-O-(8-[Tetramethylrhodaminyl]amino-3,6-dioxaoctylcarbamoyl)-8-bromo-guanosine-3',5'-cyclic boranophosphate, Sp-isomer | 230 |
| 2'-O-(N-Methylanthraniloyl)guanosine-3',5'-cyclic boranophosphate, Rp-isomer | 231 |
| 2'-O-(N-Methylanthraniloyl)guanosine-3',5'-cyclic boranophosphate, Sp-isomer | 232 |
| 8-Nitroguanosine-3',5'-cyclic boranophosphate, Rp-isomer | 233 |
| 8-Nitroguanosine-3',5'-cyclic boranophosphate, Sp-isomer | 234 |
| 8-(2-Aminoethylthio)guanosine-3',5'-cyclic boranophosphate, Rp-isomer | 235 |
| 8-(2-Aminoethylthio)guanosine-3',5'-cyclic boranophosphate, Sp-isomer | 236 |
| 8-(2-Aminoethylthio)guanosine-3',5'-cyclic boranophosphate, Rp-isomer; immobilised to agarose | 237 |
| 8-(2-Aminoethylthio)guanosine-3',5'-cyclic boranophosphate, Sp-isomer; immobilised to agarose | 238 |
| 8-(6-Aminohexylamino)guanosine-3',5'-cyclic boranophosphate, Rp-isomer | 239 |
| 8-(6-Aminohexylamino)guanosine-3',5'-cyclic boranophosphate, Sp-isomer | 240 |
| 8-(4-Chlorophenylthio)guanosine-3',5'-cyclic boranophosphate, Rp-isomer | 241 |
| 8-(4-Chlorophenylthio)guanosine-3',5'-cyclic boranophosphate, Sp-isomer | 242 |
| 8-(4-Chlorophenylthio)guanosine-3',5'-cyclic boranophosphate, Rp-isomer, acetoxymethyl ester | 243 |
| 8-(4-Chlorophenylthio)guanosine-3',5'-cyclic boranophosphate, Sp-isomer, acetoxymethyl ester | 244 |
| 2-(6-Aminohexyl)guanosine-3',5'-cyclic boranophosphate, Rp-isomer; immobilised to agarose | 245 |
| 2-(6-Aminohexyl)guanosine-3',5'-cyclic boranophosphate, Sp-isomer; immobilised to agarose | 246 |
| 8-Phenylguanosine-3',5'-cyclic boranophosphate, Rp-isomer | 247 |
| 8-Phenylguanosine-3',5'-cyclic boranophosphate, Sp-isomer | 248 |
| 2-Aminopurine-1-β-D-ribofuranoside-3',5'-cyclic boranophosphate, Rp-isomer | 249 |
| 2-Aminopurine-1-β-D-ribofuranoside-3',5'-cyclic boranophosphate, Sp-isomer | 250 |
| Xanthosine-3',5'-cyclic boranophosphate, Rp-isomer | 251 |
| Xanthosine-3',5'-cyclic boranophosphate, Sp-isomer | 252 |
| Xanthosine-3',5'-cyclic boranophosphate, Rp-isomer, acetoxymethyl ester | 253 |

-continued

| Compound | Formula # |
|---|---|
| Xanthosine-3',5'-cyclic boranophosphate, Sp-isomer, acetoxymethyl ester | 254 |
| 2'-Deoxyguanosine-3',5'-cyclic boranophosphate, Rp-isomer | 255 |
| 2'-Deoxyguanosine-3',5'-cyclic boranophosphate, Sp-isomer | 256 |
| 2'-Deoxyguanosine-3',5'-cyclic boranophosphate, Rp-isomer, acetoxymethyl ester | 257 |
| 2'-Deoxyguanosine-3',5'-cyclic boranophosphate, Sp-isomer, acetoxymethyl ester | 258 |
| Cytidine-3',5'-cyclic boranophosphate, Rp-isomer | 259 |
| Cytidine-3',5'-cyclic boranophosphate, Sp-isomer | 260 |
| Cytidine-3',5'-cyclic boranophosphate, 2-cyanoethyl ester, Rp-isomer | 261 |
| Cytidine-3',5'-cyclic boranophosphate, 2-cyanoethyl ester, Sp-isomer | 262 |
| Cytidine-3',5'-cyclic boranophosphate, Rp-isomer, acetoxymethyl ester | 263 |
| Cytidine-3',5'-cyclic boranophosphate, Sp-isomer, acetoxymethyl ester | 264 |
| 2'-O-(Imidazolylcarbamoyl)cytidine-3',5'-cyclic boranophosphate, Rp-isomer | 265 |
| 2'-O-(Imidazolylcarbamoyl)cytidine-3',5'-cyclic boranophosphate, Sp-isomer | 266 |
| 2'-O-(4-Aminobutylaminocarbamoyl)cytidine-3',5'-cyclic boranophosphate, Rp-isomer | 267 |
| 2'-O-(4-Aminobutylaminocarbamoyl)cytidine-3',5'-cyclic boranophosphate, Sp-isomer | 268 |
| 2'-O-(4-Aminobutylaminocarbamoyl)cytidine-3',5'-cyclic boranophosphate, Rp-isomer; immobilised to agarose | 269 |
| 2'-O-(4-Aminobutylaminocarbamoyl)cytidine-3',5'-cyclic boranophosphate, Sp-isomer; immobilised to agarose | 270 |
| 2'-(N-Methylanthraniloyl)cytidine-3',5'-cyclic boranophosphate, Rp-isomer | 271 |
| 2'-(N-Methylanthraniloyl)cytidine-3',5'-cyclic boranophosphate, Sp-isomer | 272 |
| 2'-O-(6-Carboxypentylcarbamoyl)cytidine-3',5'-cyclic boranophosphate, Rp-isomer | 273 |
| 2'-O-(6-Carboxypentylcarbamoyl)cytidine-3',5'-cyclic boranophosphate, Sp-isomer | 274 |
| Uridine-3',5'-cyclic boranophosphate, Rp-isomer | 275 |
| Uridine-3',5'-cyclic boranophosphate, Sp-isomer | 276 |
| Uridine-3',5'-cyclic boranophosphate, Rp-isomer, acetoxymethyl ester | 277 |
| Uridine-3',5'-cyclic boranophosphate, Sp-isomer, acetoxymethyl ester | 278 |
| 7-Deazaadenosine-3',5'-cyclic boranophosphate, Rp-isomer | 279 |
| 7-Deazaadenosine-3',5'-cyclic boranophosphate, Sp-isomer | 280 |
| 7-Deazaadenosine-3',5'-cyclic boranophosphate, Rp-isomer, acetoxymethyl ester | 281 |
| 7-Deazaadenosine-3',5'-cyclic boranophosphate, Sp-isomer, acetoxymethyl ester | 282 |
| 7-Deazaguanosine-3',5'-cyclic boranophosphate, Rp-isomer | 283 |
| 7-Deazaguanosine-3',5'-cyclic boranophosphate, Sp-isomer | 284 |
| Adenosine-1-N-oxide-3',5'-cyclic boranophosphate, Rp-isomer | 285 |
| Adenosine-1-N-oxide-3',5'-cyclic boranophosphate, Sp-isomer | 286 |
| 1,$N^6$-Ethenoadenosine-3',5'-cyclic boranophosphate, Rp-isomer | 287 |
| 1,$N^6$-Ethenoadenosine-3',5'-cyclic boranophosphate, Sp-isomer | 288 |
| 1,$N^6$-Ethenoadenosine-3',5'-cyclic boranophosphate, Rp-isomer, acetoxymethyl ester | 289 |
| 1,$N^6$-Ethenoadenosine-3',5'-cyclic boranophosphate, Sp-isomer, acetoxymethyl ester | 290 |
| 8-Azido-1,$N^6$-ethenoadenosine-3',5'-cyclic boranophosphate, Rp-isomer | 291 |
| 8-Azido-1,$N^6$-ethenoadenosine-3',5'-cyclic boranophosphate, Sp-isomer | 292 |
| 8-Bromo-β-phenyl-1,$N^6$-ethenoguanosine-3',5'-cyclic boranophosphate, Rp-isomer | 293 |
| 8-Bromo-β-phenyl-1,$N^6$-ethenoguanosine-3',5'-cyclic boranophosphate, Sp-isomer | 294 |
| 4-Nitrobenzimidazole-1-β-D-ribofuranoside-3',5'-cyclic boranophosphate, Rp-isomer | 295 |
| 4-Nitrobenzimidazole-1-β-D-ribofuranoside-3',5'-cyclic boranophosphate, Sp-isomer | 296 |
| 5,6-Dimethylbenzimidazole-1-β-D-ribofuranoside-3',5'-cyclic boranophosphate, Rp-isomer | 297 |
| 5,6-Dimethylbenzimidazole-1-β-D-ribofuranoside-3',5'-cyclic boranophosphate, Sp-isomer | 298 |
| 5,6-Dimethylbenzimidazole-1-β-D-ribofuranoside-3',5'-cyclic boranophosphate, Rp-isomer, acetoxymethyl ester | 299 |
| 5,6-Dimethylbenzimidazole-1-β-D-ribofuranoside-3',5'-cyclic boranophosphate, Sp-isomer, acetoxymethyl ester | 300 |
| 5,6-Dichlorobenzimidazole-1-β-D-ribofuranoside-3',5'-cyclic boranophosphate, Rp-isomer | 301 |
| 5,6-Dichlorobenzimidazole-1-β-D-ribofuranoside-3',5'-cyclic boranophosphate, Sp-isomer | 302 |
| 5,6-Dichlorobenzimidazole-1-β-D-ribofuranoside-3',5'-cyclic boranophosphate, Rp-isomer, acetoxymethyl ester | 303 |
| 5,6-Dichlorobenzimidazole-1-β-D-ribofuranoside-3',5'-cyclic boranophosphate, Sp-isomer, acetoxymethyl ester | 304 |

| Compound | Formula # |
|---|---|
| 8-Bromo-2'-phenoxythiocarbonyladenosine-3',5'-cyclic boranophosphate, Rp-isomer | 305 |
| and | |
| 8-Bromo-2'-phenoxythiocarbonyladenosine-3',5'-cyclic boranophosphate, Sp-isomer. | 306 |

12. A medicament comprising a compound according to claim 1.

13. A pharmaceutical composition, comprising one or more of the compounds according to claim 1 and one or more pharmaceutically acceptable excipients.

14. A method for treating a disease selected from the group consisting of cardiovascular diseases, cancer, diabetes, asthma cystic fibrosis, dekubitus, adipositas, proliferative skin diseases, cellulite, erectile dysfunction, immunodeficiency, neurodegenerative diseases, spinal cord injuries, paralysis, kidney failure, alzheimer's disease, mood disorders, aging processes, gout, dental disease, periodontal disease, memory disorders and learning disorders comprising administering a compound according to claim 1 to a human.

15. A reagent for signal transductions research, comprising a compound according to claim 1.

16. A biological research method comprising the step of modulating protein kinases A and G, EPAC (exchange protein directly activated by cyclic AMP) isozymes, CNG (cyclic nucleotide gated) ion channels, CAP (catabolite activated protein) proteins, cyclic nucleotide-responsive phosphodiesterases, GAF (cGMP-specific phosphodiesterases, adenylyl cyclases and formate hydrogen lyase system activator) domains, transporter systems or other cyclic nucleotide-regulated binding proteins or isozymes thereof, wherein in said method a compound according to claim 1 is applied as a modulator.

17. An immobilized, hydrolysis-and oxidation-resistant ligand for affinity chromatography, for antibody production or for diagnostic applications on chip surfaces, wherein said ligand comprises a compound according to claim 1.

18. An organ transplantation storage solution comprising a compound according to claim 1.

* * * * *

UNITED STATES PATENT AND TRADEMARK OFFICE
CERTIFICATE OF CORRECTION

PATENT NO. : 9,487,553 B2
APPLICATION NO. : 14/008337
DATED : November 8, 2016
INVENTOR(S) : Hans-Gottfried Genieser It is certified that error appears in the above-identified patent and that said Letters Patent is hereby corrected as shown below:

On the Title Page

(54) should be changed as follows:

Reads:
BORANOPHOSPHATE ANALOGUES OF CYCLIC NUCLEOTIDES

Should read:
NEW BORANOPHOSPHATE ANALOGUES OF CYCLIC NUCLEOTIDES

Signed and Sealed this
Third Day of October, 2017

Joseph Matal
*Performing the Functions and Duties of the*
*Under Secretary of Commerce for Intellectual Property and*
*Director of the United States Patent and Trademark Office*